(12) United States Patent
Giampietro et al.

(10) Patent No.: US 11,332,452 B2
(45) Date of Patent: May 17, 2022

(54) PESTICIDAL COMPOSITIONS AND METHODS

(71) Applicant: CORTEVA AGRISCIENCE LLC, Indianapolis, IN (US)

(72) Inventors: Natalie C. Giampietro, Carmel, IN (US); Andrew Ward, Canton, MI (US); Gary D. Crouse, Noblesville, IN (US); Thomas C. Sparks, Greenfield, IN (US); Thomas J. Barton, Indianapolis, IN (US); Lindsey G. Horty, Indianapolis, IN (US); David A. Demeter, Fishers, IN (US)

(73) Assignee: CORTEVA AGRISCIENCE LLC, Indianapolis, IN (US)

( * ) Notice: Subject to any disclaimer, the term of this patent is extended or adjusted under 35 U.S.C. 154(b) by 0 days.

(21) Appl. No.: 17/263,928

(22) PCT Filed: Jan. 30, 2020

(86) PCT No.: PCT/US2020/015800
§ 371 (c)(1),
(2) Date: Jan. 28, 2021

(87) PCT Pub. No.: WO2020/163146
PCT Pub. Date: Aug. 13, 2020

(65) Prior Publication Data
US 2021/0276963 A1 Sep. 9, 2021

Related U.S. Application Data

(60) Provisional application No. 62/800,587, filed on Feb. 4, 2019.

(51) Int. Cl.
*C07D 277/48* (2006.01)
*C07D 277/54* (2006.01)
*A01N 47/36* (2006.01)

(52) U.S. Cl.
CPC ........... *C07D 277/54* (2013.01); *A01N 47/36* (2013.01); *C07D 277/48* (2013.01)

(58) Field of Classification Search
CPC .. C07D 277/54; C07D 277/48; C07D 417/00; A01N 47/36; A01N 47/28
See application file for complete search history.

(56) References Cited

U.S. PATENT DOCUMENTS

| 4,378,357 A | 3/1983 | Miller et al. |
| 9,661,854 B2 | 5/2017 | Giampietro et al. |
| 9,783,532 B2 | 10/2017 | Giampietro et al. |
| 2021/0071025 A1* | 3/2021 | Horn ........................ B41M 5/41 |

FOREIGN PATENT DOCUMENTS

| EP | WO 2014/160031 A1 | 10/2014 | |
| WO | WO2019215099 | * 11/2019 | |
| WO | WO-2019215099 A1 * | 11/2019 | ............. C09D 11/50 |

OTHER PUBLICATIONS

Registry No. 1623749-94-9. STN Database [online]. Chemical Abstract Service. [Entered STN:Sep. 19, 2014]. (Year: 2014).*
Registry No. 1607326-57-7. STN Database [online]. Chemical Abstract Service. [Entered STN: May 20, 2014]. (Year: 2014).*
WO 2020/163146 International Preliminary Report on Patentability, dated Aug. 10, 2021, Foreign Counterpart to U.S. Appl. No. 17/263,928.

* cited by examiner

*Primary Examiner* — Amanda L. Aguirre

(57) ABSTRACT

This disclosure relates to the field of molecules having pesticidal utility against pests in phyla Nematoda, Arthropoda, and/or Mollusca, processes to produce such molecules and intermediates used in such processes, compositions containing such molecules, and processes of using such molecules against such pests. These molecules may be used, for example, as nematicides, acaricides, insecticides, miticides, and/or molluscicides. This document discloses molecules having the structure of Formula A.

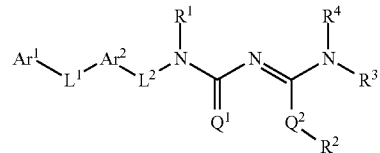

7 Claims, No Drawings

PESTICIDAL COMPOSITIONS AND METHODS

CROSS REFERENCE TO RELATED APPLICATIONS

This application claims the benefit of U.S. Provisional Patent Application Ser. No. 62/800,587 filed Feb. 4, 2019, which is expressly incorporated by reference herein.

FIELD OF THE INVENTION

The invention disclosed in this document is related to the field of pesticides and their use in controlling pests.

BACKGROUND OF THE INVENTION

Pests cause millions of human deaths around the world each year. Furthermore, there are more than ten thousand species of pests that cause losses in agriculture. These agricultural losses amount to billions of U.S. dollars each year. Termites cause damage to various structures such as homes. These termite damage losses amount to billions of U.S. dollars each year. As a final note, many stored food pests eat and adulterate stored food. These stored food losses amount to billions of U.S. dollars each year, but more importantly, deprive people of needed food.

There is an acute need for new pesticides. Insects are developing resistance to pesticides in current use. Hundreds of insect species are resistant to one or more pesticides.

The development of resistance to some of the older pesticides, such as DDT, the carbamates, and the organophosphates, is well known. But resistance has even developed to some of the newer pesticides. Therefore, a need exists for new pesticides and particularly for pesticides that have new modes of action.

SUMMARY OF THE INVENTION

In one aspect, provided are molecules having the structure of Formula A:

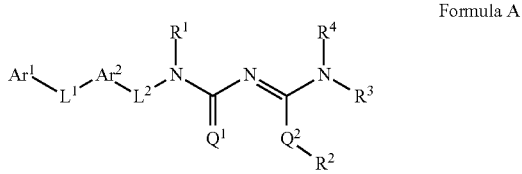

Formula A wherein:
(A) $Ar^1$ is selected from
(1) furanyl, phenyl, pyridazinyl, pyridyl, pyrimidinyl, thienyl, or
(2) substituted furanyl, substituted phenyl, substituted pyridazinyl, substituted pyridyl, substituted pyrimidinyl, or substituted thienyl,
  wherein said substituted furanyl, substituted phenyl, substituted pyridazinyl, substituted pyridyl, substituted pyrimidinyl, and substituted thienyl have one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n(C_3$-$C_8$ cycloalkyl), $S(=O)_n(C_3$-$C_8$ halocycloalkyl), $S(=O)_n(C_1$-$C_8$ alkyl), $S(=O)_n(C_1$-$C_8$ haloalkyl), $OSO_2(C_1$-$C_8$ alkyl), $OSO_2(C_1$-$C_8$ haloalkyl), $C(=O)NR^xR^y$, $(C_1$-$C_8$ alkyl)$NR^xR^y$, $C(=O)C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)O($C_1$-$C_8$ alkyl), $(C_1$-$C_8$ alkyl)S$(=O)_n(C_1$-$C_8$ alkyl), $(C_1$-$C_8$ alkyl)OC$(=O)(C_1$-$C_8$ alkyl), $(C_1$-$C_8$ alkyl)OC$(=O)O(C_1$-$C_8$ alkyl), $C(=O)(C_1$-$C_8$ alkyl)C$(=O)O(C_1$-$C_8$ alkyl), $(C_1$-$C_8$ alkyl)C$(=O)O(C_1$-$C_8$ alkyl), $(C_1$-$C_8$ alkyl)C$(=O)(C_1$-$C_8$ alkyl), $(C_1$-$C_8$ alkyl)phenyl, $(C_1$-$C_8$ alkyl)-O-phenyl, phenyl, phenoxy, $Si(C_1$-$C_8$ alkyl)$_3$, or $S(=O)_n NR^xR^y$, or (Het-1),
  wherein each alkyl, haloalkyl, cycloalkyl, halocycloalkyl, alkoxy, haloalkoxy, alkenyl, cycloalkenyl, haloalkenyl, alkynyl, phenyl, phenoxy, and (Het-1) substituent may be optionally substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n(C_3$-$C_8$ cycloalkyl), $S(=O)_n(C_3$-$C_8$ halocycloalkyl), $S(=O)_n(C_1$-$C_8$ alkyl), $S(=O)_n(C_1$-$C_8$ haloalkyl), $OSO_2(C_1$-$C_8$ alkyl), $OSO_2(C_1$-$C_8$ haloalkyl), $C(=O)NR^xR^y$, $(C_1$-$C_8$ alkyl)$NR^xR^y$, $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)O($C_1$-$C_8$ alkyl), $(C_1$-$C_8$ alkyl)S$(=O)_n(C_1$-$C_8$ alkyl), $(C_1$-$C_8$ alkyl)OC$(=O)(C_1$-$C_8$ alkyl), $(C_1$-$C_8$ alkyl)OC$(=O)O(C_1$-$C_8$ alkyl), $C(=O)(C_1$-$C_8$ alkyl)C$(=O)O(C_1$-$C_8$ alkyl), $(C_1$-$C_8$ alkyl)C$(=O)OC_1$-$C_8$ alkyl), $(C_1$-$C_8$ alkyl)C$(=O)(C_1$-$C_8$ alkyl), $(C_1$-$C_8$ alkyl)phenyl, $(C_1$-$C_8$ alkyl)-O-phenyl, phenyl, phenoxy, $Si(C_1$-$C_8$ alkyl)$_3$, $S(=O)_n NR^xR^y$, or (Het-1);
(B) $Ar^2$ is selected from
(1) furanyl, phenyl, pyridazinyl, pyridyl, pyrimidinyl, thienyl, or
(2) substituted furanyl, substituted phenyl, substituted pyridazinyl, substituted pyridyl, substituted pyrimidinyl, or substituted thienyl,
  wherein said substituted furanyl, substituted phenyl, substituted pyridazinyl, substituted pyridyl, substituted pyrimidinyl, and substituted thienyl, have one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n(C_3$-$C_8$ cycloalkyl), $S(=O)_n(C_3$-$C_8$ halocycloalkyl), $S(=O)_n(C_1$-$C_8$ alkyl), $S(=O)_n(C_1$-$C_8$ haloalkyl), $OSO_2(C_1$-$C_8$ alkyl), $OSO_2(C_1$-$C_8$ haloalkyl), $C(=O)NR^xR^y$, $(C_1$-$C_8$ alkyl)$NR^xR^y$, $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)O($C_1$-$C_8$ alkyl), $(C_1$-$C_8$ alkyl)S$(=O)_n(C_1$-$C_8$ alkyl), $(C_1$-$C_8$ alkyl)OC$(=O)(C_1$-$C_8$ alkyl), $(C_1$-$C_8$ alkyl)OC$(=O)O(C_1$-$C_8$ alkyl), $C(=O)(C_1$-$C_8$ alkyl)C$(=O)O(C_1$-$C_8$ alkyl), $(C_1$-$C_8$ alkyl)C$(=O)O(C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, phenoxy, Si($C_1$-$C_8$ alkyl)$_3$, S(=O)$_n$NR$^x$R$^y$, or (Het-1), wherein each alkyl, haloalkyl, cycloalkyl, halocycloalkyl, alkoxy, haloalkoxy, alkenyl, cycloalkenyl, haloalkenyl, alkynyl, phenyl, phenoxy, and (Het-1) substituent may be optionally substituted with one or more substituents independently selected from H, F, Cl, Br, I, CN, OH, SH, NO$_2$, oxo, thioxo, NR$^x$R$^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), OSO$_2$($C_1$-$C_8$ alkyl), OSO$_2$($C_1$-$C_8$ haloalkyl), C(=O)NR$^x$R$^y$, ($C_1$-$C_8$ alkyl)NR$^x$R$^y$, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, phenoxy, Si($C_1$-$C_8$ alkyl)$_3$, S(=O)$_n$NR$^x$R$^y$, or (Het-1);

(C) R$^1$ is selected from H, CN, OH, SH, NO$_2$, oxo, thioxo, NR$^x$R$^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), OSO$_2$($C_1$-$C_8$ alkyl), OSO$_2$($C_1$-$C_8$ haloalkyl), C(=O)NR$^x$R$^y$, ($C_1$-$C_8$ alkyl)NR$^x$R$^y$, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, and ($C_1$-$C_8$ alkyl)-O-phenyl, phenyl, phenoxy, Si($C_1$-$C_8$ alkyl)$_3$, S(=O)$_n$NR$^x$R$^y$, or (Het-1), wherein each alkyl, haloalkyl, cycloalkyl, halocycloalkyl, alkoxy, haloalkoxy, alkenyl, cycloalkenyl, haloalkenyl, alkynyl, phenyl, phenoxy, and (Het-1) may be optionally substituted with one or more substituents independently selected from H, F, Cl, Br, I, CN, OH, SH, NO$_2$, oxo, thioxo, NR$^x$R$^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), OSO$_2$($C_1$-$C_8$ alkyl), OSO$_2$($C_1$-$C_8$ haloalkyl), C(=O)NR$^x$R$^y$, ($C_1$-$C_8$ alkyl)NR$^x$R$^y$, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, and ($C_1$-$C_8$ alkyl)-O-phenyl, phenyl, phenoxy, Si($C_1$-$C_8$ alkyl)$_3$, S(=O)$_n$NR$^x$R$^y$, or (Het-1);

(D) R$^2$ is selected from (F), H, $C_1$-$C_8$ alkyl, $C_3$-$C_8$ cycloalkyl, $C_2$-$C_8$ alkenyl, $C_2$-$C_8$ alkynyl, C(=O)($C_1$-$C_8$ alkyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)phenyl, ($C_1$-$C_8$ alkyl)-O-phenyl, C(=O)(Het-1), (Het-1), ($C_1$-$C_8$ alkyl)-(Het-1), ($C_1$-$C_8$ alkyl)-C(=O)—($C_1$-$C_8$ alkyl), ($C_1$-$C_8$ alkyl)-OC(=O)—($C_1$-$C_8$ alkyl), ($C_1$-$C_8$ alkyl)-O—C(=O)O—($C_1$-$C_8$ alkyl), ($C_1$-$C_8$ alkyl)-O—C(=O)NR$^x$R$^y$, ($C_1$-$C_8$ alkyl)-C(=O)N(R$^x$)($C_1$-$C_8$ alkyl)-(Het-1), ($C_1$-$C_8$ alkyl)-C(=O)(Het-1), ($C_1$-$C_8$ alkyl)-C(=O)N(R$^x$)($C_1$-$C_8$ alkyl)N(R$^y$)C(=O)OH, ($C_1$-$C_8$ alkyl)-C(=O)N(R$^x$)($C_1$-$C_8$ alkyl)N(R$^x$)(R$^y$), ($C_1$-$C_8$ alkyl)-C(=O)N(R$^x$)($C_1$-$C_8$ alkyl)N(R$^y$)C(=O)O—($C_1$-$C_8$ alkyl), ($C_1$-$C_8$ alkyl)-C(=O)N(R$^x$)($C_1$-$C_8$ alkyl)(N(R$^y$)C(=O)O—($C_1$-$C_8$ alkyl)C(=O)OH, ($C_1$-$C_8$ alkyl)-C(=O)(Het-1)C(=O)O—($C_1$-$C_8$ alkyl), ($C_1$-$C_8$ alkyl)-OC(=O)O—($C_1$-$C_8$ alkyl), ($C_1$-$C_8$ alkyl)-OC(=O)—($C_1$-$C_8$ alkyl), ($C_1$-$C_8$ alkyl)-OC(=O)—($C_3$-$C_8$ cycloalkyl), ($C_1$-$C_8$ alkyl)-OC(=O)-(Het-1), ($C_1$-$C_8$ alkyl)-OC(=O)—($C_1$-$C_8$ alkyl)N(R$^x$)C(=O)O—($C_1$-$C_8$ alkyl), ($C_1$-$C_8$ alkyl)-NR$^x$R$^y$, ($C_1$-$C_8$ alkyl)-S-(Het-1), ($C_1$-$C_8$ alkyl)S(=O)$_n$(Het-1), or ($C_1$-$C_8$ alkyl)-O-(Het-1), wherein each alkyl, cycloalkyl, phenyl, and (Het-1) are optionally substituted with one or more substituents independently selected from H, F, Cl, Br, I, CN, OH, SH, NO$_2$, oxo, thioxo, NR$^x$R$^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), OSO$_2$($C_1$-$C_8$ alkyl), OSO$_2$($C_1$-$C_8$ haloalkyl), C(=O)H, C(=O)OH, C(=O)NR$^x$R$^y$, ($C_1$-$C_8$ alkyl)NR$^x$R$^y$, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, phenoxy, Si($C_1$-$C_8$ alkyl)$_3$, S(=O)$_n$NR$^x$R$^y$, or (Het-1);

(E) R$^3$ is selected from (F), H, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), OSO$_2$($C_1$-$C_8$ alkyl), OSO$_2$($C_1$-$C_8$ haloalkyl), C(=O)H, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, ($C_1$-$C_8$ alkyl)phenyl, ($C_1$-$C_8$ alkyl)-O-phenyl, C(=O)(Het-1), (Het-1), ($C_1$-$C_8$ alkyl)-(Het-1), ($C_1$-$C_8$ alkyl)-C(=O)—($C_1$-$C_8$ alkyl), ($C_1$-$C_8$ alkyl)-OC(=O)—($C_1$-$C_8$ alkyl), ($C_1$-$C_8$ alkyl)-O—C(=O)O—($C_1$-$C_8$ alkyl), ($C_1$-$C_8$ alkyl)-O—C(=O)NR$^x$R$^y$, ($C_1$-$C_8$ alkyl)-C(=O)N(R$^x$)($C_1$-$C_8$ alkyl)-(Het-1), ($C_1$-$C_8$ alkyl)-C(=O)(Het-1), (C₁-C₈ alkyl)-C(=O)N(Rˣ)(C₁-C₈ alkyl)N(Rʸ)C(=O)OH, (C₁-C₈ alkyl)-C(=O)N(Rˣ)(C₁-C₈ alkyl)N(Rˣ)(Rʸ), (C₁-C₈ alkyl)-C(=O)N(Rˣ)(C₁-C₈ alkyl)N(Rʸ)C(=O)O—(C₁-C₈ alkyl), (C₁-C₈ alkyl)-C(=O)N(Rˣ)(C₁-C₈ alkyl)N(Rʸ)C(=O)O—(C₁-C₈ alkyl)C(=O)OH, (C₁-C₈ alkyl)-C(=O)(Het-1)C(=O)O—(C₁-C₈ alkyl), (C₁-C₈ alkyl)-OC(=O)O—(C₁-C₈ alkyl), (C₁-C₈ alkyl)-OC(=O)—(C₁-C₈ alkyl), (C₁-C₈ alkyl)-OC(=O)—(C₃-C₈ cycloalkyl), (C₁-C₈ alkyl)-OC(=O)-(Het-1), (C₁-C₈ alkyl)-OC(=O)—(C₁-C₈ alkyl)N(Rˣ)C(=O)O—(C₁-C₈ alkyl), (C₁-C₈ alkyl)-NRˣRʸ, (C₁-C₈ alkyl)-S-(Het-1), (C₁-C₈ alkyl)S(=O)ₙ(Het-1), or (C₁-C₈ alkyl)-O-(Het-1), wherein each alkyl, haloalkyl, cycloalkyl, halocycloalkyl, cycloalkoxy, halocycloalkoxy, alkoxy, haloalkoxy, alkenyl, cycloalkenyl, haloalkenyl, alkynyl, phenyl, and (Het-1), are optionally substituted with one or more substituents independently selected from H, F, Cl, Br, I, CN, OH, SH, NO₂, oxo, thioxo, C₁-C₈ alkyl, C₁-C₈ haloalkyl, C₃-C₈ cycloalkyl, C₃-C₈ halocycloalkyl, C₃-C₈ cycloalkoxy, C₃-C₈ halocycloalkoxy, C₁-C₈ alkoxy, C₁-C₈ haloalkoxy, C₂-C₈ alkenyl, C₃-C₈ cycloalkenyl, C₂-C₈ haloalkenyl, C₂-C₈ alkynyl, S(=O)ₙ(C₃-C₈ cycloalkyl), S(=O)ₙ(C₃-C₈ halocycloalkyl), S(=O)ₙ(C₁-C₈ alkyl), S(=O)ₙ(C₁-C₈ haloalkyl), OSO₂(C₁-C₈ alkyl), OSO₂(C₁-C₈ haloalkyl), C(=O)H, C(=O)OH, C(=O)(C₁-C₈ alkyl), C(=O)O(C₁-C₈ alkyl), C(=O)(C₁-C₈ haloalkyl), C(=O)O(C₁-C₈ haloalkyl), C(=O)(C₃-C₈ cycloalkyl), C(=O)O(C₃-C₈ cycloalkyl), C(=O)(C₂-C₈ alkenyl), C(=O)O(C₂-C₈ alkenyl), (C₁-C₈ alkyl)O(C₁-C₈ alkyl), (C₁-C₈ alkyl)S(=O)ₙ(C₁-C₈ alkyl), (C₁-C₈ alkyl)OC(=O)(C₁-C₈ alkyl), (C₁-C₈ alkyl)OC(=O)O(C₁-C₈ alkyl), C(=O)(C₁-C₈ alkyl)C(=O)O(C₁-C₈ alkyl), (C₁-C₈ alkyl)C(=O)O(C₁-C₈ alkyl), (C₁-C₈ alkyl)C(=O)(C₁-C₈ alkyl), (C₁-C₈ alkyl)phenyl, (C₁-C₈ alkyl)-O-phenyl, phenyl, halophenyl, phenoxy, and (Het-1);

(F) R² and R³ may be a 1- to 4-membered saturated or unsaturated, hydrocarbyl link, which may contain one or more heteroatoms selected from nitrogen, sulfur, and oxygen, and together with (Q²)(C)(N) forms a 4- to 7-membered cyclic structure, wherein said hydrocarbyl link may optionally be substituted with one or more substituents independently selected from H, F, Cl, Br, I, CN, OH, SH, NO₂, oxo, thioxo, NRˣRʸ, C₁-C₈ alkyl, C₁-C₈ haloalkyl, C₃-C₈ cycloalkyl, C₃-C₈ halocycloalkyl, C₃-C₈ cycloalkoxy, C₃-C₈ halocycloalkoxy, C₁-C₈ alkoxy, C₁-C₈ haloalkoxy, C₂-C₈ alkenyl, C₃-C₈ cycloalkenyl, C₂-C₈ haloalkenyl, C₂-C₈ alkynyl, S(=O)ₙ(C₃-C₈ cycloalkyl), S(=O)ₙ(C₃-C₈ halocycloalkyl), S(=O)ₙ(C₁-C₈ alkyl), S(=O)ₙ(C₁-C₈ haloalkyl), OSO₂(C₁-C₈ alkyl), OSO₂(C₁-C₈ haloalkyl), C(=O)H, C(=O)(C₁-C₈ alkyl), C(=O)O(C₁-C₈ alkyl), C(=O)(C₁-C₈ haloalkyl), C(=O)O(C₁-C₈ haloalkyl), C(=O)(C₃-C₈ cycloalkyl), C(=O)O(C₃-C₈ cycloalkyl), C(=O)(C₂-C₈ alkenyl), C(=O)O(C₂-C₈ alkenyl), (C₁-C₈ alkyl)O(C₁-C₈ alkyl), (C₁-C₈ alkyl)S(=O)ₙ(C₁-C₈ alkyl), (C₁-C₈ alkyl)OC(=O)(C₁-C₈ alkyl), (C₁-C₈ alkyl)OC(=O)O(C₁-C₈ alkyl), C(=O)(C₁-C₈ alkyl)C(=O)O(C₁-C₈ alkyl), (C₁-C₈ alkyl)C(=O)O(C₁-C₈ alkyl), (C₁-C₈ alkyl)C(=O)(C₁-C₈ alkyl), (C₁-C₈ alkyl)phenyl, (C₁-C₈ alkyl)-O-phenyl, phenyl, substituted phenyl, phenoxy, or (Het-1);

(G) R⁴ is selected from C₃-C₈ cycloalkyl, phenyl, (C₁-C₈ alkyl)phenyl, (C₁-C₈ alkyl)-O-phenyl, (C₂-C₈ alkenyl)-O-phenyl, (Het-1), (C₁-C₈ alkyl)-(Het-1), (C₁-C₈ alkyl)-O-(Het-1), wherein the C₃-C₈ cycloalkyl, phenyl, (C₁-C₈ alkyl)phenyl, (C₁-C₈ alkyl)-O-phenyl, (C₂-C₈ alkenyl)-O-phenyl, (Het-1), (C₁-C₈ alkyl)-(Het-1), or (C₁-C₈ alkyl)-O-(Het-1) may be optionally substituted with one or more substituents independently selected from H, F, Cl, Br, I, CN, OH, SH, NO₂, oxo, thioxo, NRˣRʸ, C₁-C₈ alkyl, C₁-C₈ haloalkyl, C₃-C₈ cycloalkyl, C₃-C₈ halocycloalkyl, C₃-C₈ cycloalkoxy, C₃-C₈ halocycloalkoxy, C₁-C₈ alkoxy, C₁-C₈ haloalkoxy, C₂-C₈ alkenyl, C₃-C₈ cycloalkenyl, C₂-C₈ haloalkenyl, C₂-C₈ alkynyl, S(=O)ₙ(C₃-C₈ cycloalkyl), S(=O)ₙ(C₃-C₈ halocycloalkyl), S(=O)ₙ(C₁-C₈ alkyl), S(=O)ₙ(C₁-C₈ haloalkyl), OSO₂(C₁-C₈ alkyl), OSO₂(C₁-C₈ haloalkyl), C(=O)(C₁-C₈ alkyl), C(=O)O(C₁-C₈ alkyl), C(=O)(C₁-C₈ haloalkyl), C(=O)O(C₁-C₈ haloalkyl), C(=O)(C₃-C₈ cycloalkyl), C(=O)O(C₃-C₈ cycloalkyl), C(=O)(C₂-C₈ alkenyl), C(=O)O(C₂-C₈ alkenyl), (C₁-C₈ alkyl)O(C₁-C₈ alkyl), (C₁-C₈ alkyl)O(C₁-C₈ haloalkyl), (C₁-C₈ alkyl)S(=O)ₙ(C₁-C₈ alkyl), (C₁-C₈ alkyl)OC(=O)(C₁-C₈ alkyl), (C₁-C₈ alkyl)OC(=O)O(C₁-C₈ alkyl), C(=O)(C₁-C₈ alkyl)C(=O)O(C₁-C₈ alkyl), (C₁-C₈ alkyl)C(=O)O(C₁-C₈ alkyl), (C₁-C₈ alkyl)C(=O)(C₁-C₈ alkyl), (C₁-C₈ alkyl)phenyl, (C₁-C₈ alkyl)-O-phenyl, phenyl, phenoxy, Si(C₁-C₈ alkyl)₃, S(=O)ₙNRˣRʸ, or (Het-1), or wherein two adjacent substituents form a 5- or 6-membered saturated or unsaturated, hydrocarbyl link, which may contain one or more heteroatoms selected from nitrogen, sulfur, and oxygen, and such ring is optionally substituted with one or more substituents selected from H, F, Cl, Br, I, CN, OH, SH, NO₂, NRˣRʸ, C₁-C₆ alkyl, C₁-C₆ haloalkyl, C₁-C₆ alkoxy, C₁-C₆ haloalkoxy, S(=O)ₙ(C₁-C₆ alkyl), S(=O)ₙ(C₁-C₆ haloalkyl), phenyl, and oxo;

(H) L¹ is a linker selected from the group consisting of:

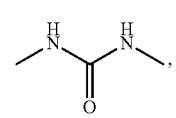
L¹-1

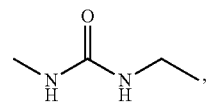
L¹-2

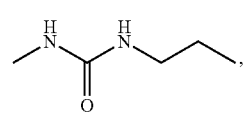
L¹-3

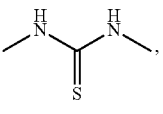
L¹-4

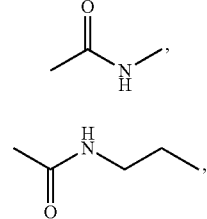
L¹-5

L¹-6

L¹-7

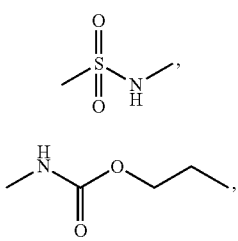
L¹-8

-continued

L¹-9: [structure: methyl carbamate fragment]

L¹-10: [structure: N-methyl acetone amine with C=O]

L¹-11: [structure with R⁵ on C=N-NH]

L¹-12: [structure: hydrazide fragment]

L¹-13: [structure: acetohydrazide fragment]

wherein R⁵ is selected from H, $C_1$-$C_8$ alkyl, $C_1$-$C_8$ haloalkyl, $C_1$-$C_8$ alkoxy, $C_1$-$C_8$ haloalkoxy, phenyl, and substituted phenyl, wherein said substituted phenyl has one or more substituents selected from H, F, Cl, Br, I, CN, NO₂, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_3$-$C_8$ halocycloalkenyl, and $C_2$-$C_8$ alkynyl;

(I) $L^2$ is linker selected from
(1) a bond,
(2) —$CR^6R^7$—$CR^8R^9$—, or
(3) —$CR^6$=$CR^8$—, wherein each of $R^6$, $R^7$, $R^8$, and $R^9$ is selected from H, F, Cl, Br, I, CN, OH, SH, NO₂, oxo, thioxo, $NR^xR^y$, $C_1$-$C_8$ alkyl, $C_1$-$C_8$ haloalkyl, $C_1$-$C_8$ alkoxy, $C_1$-$C_8$ haloalkoxy, $C_2$-$C_8$ alkenyl, $C_2$-$C_8$ haloalkenyl, $C_2$-$C_8$ alkynyl, $C_2$-$C_8$ haloalkynyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_3$-$C_8$ cycloalkenyl, $C_3$-$C_8$ halocycloalkenyl, C(=O)($C_1$-$C_6$ alkyl), C(=O)O($C_1$-$C_6$ alkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), S(=O)ₙ($C_3$-$C_8$ cycloalkyl), S(=O)ₙ($C_3$-$C_8$ halocycloalkyl), phenyl, or phenoxy, or $R^6$ and $R^8$ together can optionally form a 3- to 7-membered ring which may contain C=O, C=S, N, S or O, and is optionally substituted with H, OH, F, Cl, Br, I, CN, NO₂, $NR^xR^y$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_3$-$C_6$ cycloalkenyl, $C_2$-$C_6$ alkynyl, $C_3$-$C_6$ cycloalkynyl, S(=O)ₙ($C_1$-$C_6$ alkyl), S(=O)ₙ($C_1$-$C_6$ haloalkyl), OSO₂($C_1$-$C_6$ alkyl), OSO₂($C_1$-$C_6$ haloalkyl), C(=O)H, C(=O)OH, C(=O)$NR^xR^y$, ($C_1$-$C_6$ alkyl)$NR^xR^y$, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, phenoxy, and Het-1;

(J) $Q^1$ is selected from O or S;
(K) $Q^2$ is selected from O or S;
(L) $R^x$ and $R^y$ are independently selected from H, OH, SH, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)ₙ($C_3$-$C_8$ cycloalkyl), S(=O)ₙ($C_3$-$C_8$ halocycloalkyl), S(=O)ₙ ($C_1$-$C_8$ alkyl), S(=O)ₙ($C_1$-$C_8$ haloalkyl), OSO₂($C_1$-$C_8$ alkyl), OSO₂($C_1$-$C_8$ haloalkyl), C(=O)H, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)ₙ($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, ($C_1$-$C_8$ alkyl)phenyl, ($C_1$-$C_8$ alkyl)-O-phenyl, C(=O)(Het-1), (Het-1), ($C_1$-$C_8$ alkyl)-(Het-1), ($C_1$-$C_8$ alkyl)-C(=O)—($C_1$-$C_8$ alkyl), ($C_1$-$C_8$ alkyl)-OC(=O)—($C_1$-$C_8$ alkyl), ($C_1$-$C_8$ alkyl)-O—C(=O)O—($C_1$-$C_8$ alkyl), ($C_1$-$C_8$ alkyl)-C(=O)(Het-1), ($C_1$-$C_8$ alkyl)-C(=O)(Het-1)C(=O)O—($C_1$-$C_8$ alkyl), ($C_1$-$C_8$ alkyl)-OC(=O)O—($C_1$-$C_8$ alkyl), ($C_1$-$C_8$ alkyl)-OC(=O)—($C_1$-$C_8$ alkyl), ($C_1$-$C_8$ alkyl)-OC(=O)—($C_3$-$C_8$ cycloalkyl), ($C_1$-$C_8$ alkyl)-OC(=O)-(Het-1), ($C_1$-$C_8$ alkyl)-S-(Het-1), ($C_1$-$C_8$ alkyl)S(=O)ₙ(Het-1), or ($C_1$-$C_8$ alkyl)-O-(Het-1), wherein each alkyl, haloalkyl, cycloalkyl, halocycloalkyl, cycloalkoxy, halocycloalkoxy, alkoxy, haloalkoxy, alkenyl, cycloalkenyl, haloalkenyl, alkynyl, phenyl, and (Het-1), are optionally substituted with one or more substituents independently selected from H, F, Cl, Br, I, CN, OH, SH, NO₂, oxo, thioxo, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)ₙ($C_3$-$C_8$ cycloalkyl), S(=O)ₙ($C_3$-$C_8$ halocycloalkyl), S(=O)ₙ($C_1$-$C_8$ alkyl), S(=O)ₙ($C_1$-$C_8$ haloalkyl), OSO₂($C_1$-$C_8$ alkyl), OSO₂($C_1$-$C_8$ haloalkyl), C(=O)H, C(=O)OH, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)ₙ($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, halophenyl, phenoxy, and (Het-1), or $R^x$ and $R^y$ together can optionally form a 5- to 7-membered saturated or unsaturated cyclic group which may contain one or more heteroatoms selected from nitrogen, sulfur, and oxygen, and where said cyclic group may be substituted with H, F, Cl, Br, I, CN, OH, SH, NO₂, oxo, thioxo, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)ₙ($C_3$-$C_8$ cycloalkyl), S(=O)ₙ($C_3$-$C_8$ halocycloalkyl), S(=O)ₙ($C_1$-$C_8$ alkyl), S(=O)ₙ($C_1$-$C_8$ haloalkyl), OSO₂($C_1$-$C_8$ alkyl), OSO₂($C_1$-$C_8$ haloalkyl), C(=O)($C_1$-$C_8$ alkyl), C(=O)O($C_1$-$C_8$ alkyl), C(=O)($C_1$-$C_8$ haloalkyl), C(=O)O ($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$ ($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, substituted phenyl, phenoxy, and (Het-1);

(M) (Het-1) is a 5- or 6-membered, saturated or unsaturated, heterocyclic ring, containing one or more heteroatoms independently selected from nitrogen, sulfur or oxygen, wherein said heterocyclic ring may also be substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), $OSO_2$($C_1$-$C_8$ alkyl), $OSO_2$($C_1$-$C_8$ haloalkyl), C(=O)$NR^xR^y$, ($C_1$-$C_8$ alkyl)$NR^xR^y$, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, and phenoxy, wherein each alkyl, cycloalkyl, alkoxy, alkenyl, alkynyl, phenyl, and phenoxy may be optionally substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), $OSO_2$($C_1$-$C_8$ alkyl), $OSO_2$($C_1$-$C_8$ haloalkyl), C(=O)H, C(=O)$NR^xR^y$, ($C_1$-$C_8$ alkyl)$NR^xR^y$, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, and phenoxy; and (N) n is each individually 0, 1, or 2.

In some embodiments, the molecules provided have the structure of Formula One, Formula Two, Formula Three:

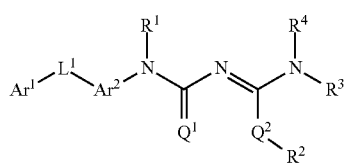

Formula One

Formula Two

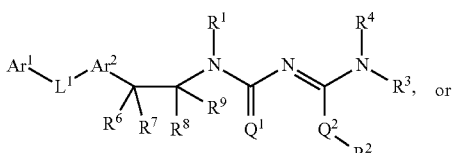

Formula Three wherein:

(A) $Ar^1$ is a phenyl or substituted phenyl having one or more substituents independently selected from H, $C_1$-$C_6$ alkyl, $C_1$-$C_6$ haloalkyl, $C_1$-$C_6$ alkoxy, and $C_1$-$C_6$ haloalkoxy;

(B) $Ar^2$ is a phenyl or a substituted phenyl having one or more substituents independently selected from H, F, Cl, Br, I, CN, $NO_2$, $NR^xR^y$, OH, $C_1$-$C_6$ alkyl, $C_1$-$C_6$ haloalkyl, $C_1$-$C_6$ alkoxy, and $C_1$-$C_6$ haloalkoxy;

(C) $R^1$ is H, $C_1$-$C_6$ alkyl, $C_3$-$C_6$ cycloalkyl, or $C_2$-$C_6$ alkenyl, wherein said alkyl, cycloalkyl, or alkenyl is optionally substituted with a $C_1$-$C_6$ alkoxy, $C_1$-$C_6$ haloalkoxy, $C_3$-$C_6$ cycloalkyl, or $C_3$-$C_6$ halocycloalkyl;

(D) $R^2$ is selected from (F), H, $C_1$-$C_6$ alkyl, $C_1$-$C_6$ haloalkyl, or $C_2$-$C_6$ alkenyl, wherein said alkyl, haloalkyl, or alkenyl is optionally substituted with a $C_3$-$C_6$ cycloalkyl or $C_1$-$C_6$ alkoxy;

(E) $R^3$ is selected from (F), H, $C_1$-$C_6$ alkyl, $C_1$-$C_6$ haloalkyl, or $C_2$-$C_6$ alkenyl, wherein said alkyl, haloalkyl, or alkenyl is optionally substituted with a $C_3$-$C_6$ cycloalkyl or $C_1$-$C_6$ alkoxy;

(F) $R^2$ and $R^3$ may be a 1- to 4-membered saturated or unsaturated, hydrocarbyl link, which may contain one or more heteroatoms selected from nitrogen, sulfur, and oxygen, and together with ($Q^2$)(C)(N) forms a 4- to 7-membered cyclic structure, wherein said hydrocarbyl link may optionally be substituted with one or more substituents independently selected from H, F, Cl, Br, I, CN, OH, SH, $NO_2$, $NR^xR^y$, oxo, $C_1$-$C_6$ alkyl, $C_1$-$C_6$ haloalkyl, $C_1$-$C_6$ alkoxy, $C_1$-$C_6$ haloalkoxy, S($C_1$-$C_6$ alkyl), S($C_1$-$C_6$ haloalkyl), phenyl, and oxo;

(G) $R^4$ is phenyl or (Het-1), wherein the phenyl or (Het-1) may be optionally substituted with one or more substituents independently selected from H, F, Cl, Br, I, CN, OH, SH, $NO_2$, $NR^xR^y$, $C_1$-$C_6$ alkyl, $C_1$-$C_6$ haloalkyl, $C_2$-$C_6$ alkenyl, $C_2$-$C_6$ haloalkenyl, $C_1$-$C_6$ alkoxy, $C_1$-$C_6$ haloalkoxy, $C_3$-$C_6$ cycloalkyl, $C_3$-$C_6$ halocycloalkyl, S(=O)($C_1$-$C_6$ alkyl), S(=O)($C_1$-$C_6$ haloalkyl), ($C_1$-$C_8$ alkyl)O($C_1$-$C_8$ alkyl), ($C_1$-$C_8$ alkyl)O($C_1$-$C_8$ haloalkyl), phenyl, and oxo, or wherein two adjacent substituents form a 5- or 6-membered saturated or unsaturated, hydrocarbyl link, which may contain one or more heteroatoms selected from nitrogen, sulfur, and oxygen, and such ring is optionally substituted with one or more substituents selected from H, F, Cl, Br, I, CN, OH, SH, $NO_2$, $NR^xR^y$, $C_1$-$C_6$ alkyl, $C_1$-$C_6$ haloalkyl, $C_1$-$C_6$ alkoxy, $C_1$-$C_6$ haloalkoxy, S(=O)$_n$($C_1$-$C_6$ alkyl), S(=O)$_n$($C_1$-$C_6$ haloalkyl), phenyl, and oxo;

(H) L¹ is a linker selected from the group consisting of:

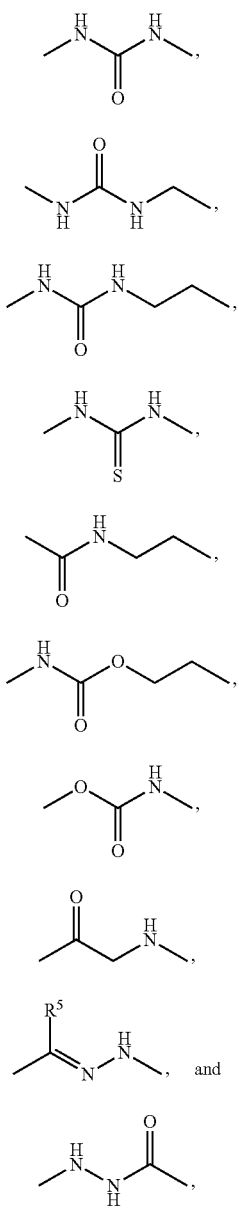

wherein R⁵ is selected from H, $C_1$-$C_8$ alkyl, $C_1$-$C_8$ haloalkyl, $C_1$-$C_8$ alkoxy, $C_1$-$C_8$ haloalkoxy, phenyl, and substituted phenyl, wherein said substituted phenyl has one or more substituents selected from H, F, Cl, Br, I, CN, NO₂, NR$^x$R$^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_3$-$C_8$ halocycloalkenyl, and $C_2$-$C_8$ alkynyl;

(I1) Each R⁶ and R⁸ is selected from H, F, Cl, Br, I, CN, oxo, $C_1$-$C_6$ alkyl, $C_1$-$C_6$ alkoxy, $C_1$-$C_6$ haloalkoxy, $C_2$-$C_6$ alkenyl, $C_2$-$C_6$ haloalkenyl, $C_2$-$C_6$ alkynyl, $C_1$-$C_6$ haloalkyl, $C_3$-$C_6$ cycloalkyl, $C_3$-$C_6$ cycloalkenyl, $C_3$-$C_6$ halocycloalkyl, and phenyl, or R⁶ and R⁸ together can optionally form a 3- to 7-membered saturated or unsaturated ring which may contain C=O, C=S, N, S or O, and is optionally substituted with H, OH, F, Cl, Br, I, $C_1$-$C_6$ alkyl, $C_1$-$C_6$ haloalkyl, $C_1$-$C_6$ alkoxy, $C_1$-$C_6$ haloalkoxy, phenyl, phenoxy, and Het-1;

(I2) Each R⁷ and R⁹ is selected from H, F, Cl, Br, I, CN, oxo, $C_1$-$C_6$ alkyl, $C_1$-$C_6$ alkoxy, $C_1$-$C_6$ haloalkoxy, $C_2$-$C_6$ alkenyl, $C_2$-$C_6$ haloalkenyl, $C_2$-$C_6$ alkynyl, $C_1$-$C_6$ haloalkyl, $C_3$-$C_6$ cycloalkyl, $C_3$-$C_6$ cycloalkenyl, $C_3$-$C_6$ halocycloalkyl, and phenyl;

(J) Q¹ is O;

(K) Q² is S;

(L) R$^x$ and R$^y$ are independently selected from H, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ alkynyl, and phenyl; and (M) (Het-1) is a 5- or 6-membered, saturated or unsaturated, heterocyclic ring, containing one or more heteroatoms independently selected from nitrogen, sulfur or oxygen, wherein said heterocyclic ring may also be substituted with one or more substituents independently selected from H, F, Cl, Br, I, CN, OH, SH, NO₂, NR$^x$R$^y$, $C_1$-$C_6$ alkyl, $C_1$-$C_6$ haloalkyl, $C_1$-$C_6$ alkoxy, $C_1$-$C_6$ haloalkoxy, ($C_1$-$C_8$ alkyl)O($C_1$-$C_8$ alkyl), ($C_1$-$C_8$ alkyl)O($C_1$-$C_8$ haloalkyl), S(=O)$_n$($C_1$-$C_6$ alkyl), S(=O)$_n$($C_1$-$C_6$ haloalkyl), phenyl, and oxo.

In one embodiment, Ar¹ is substituted phenyl having one or more substituents independently selected from OCF₃, OCF₂CF₃, and CF₃. In another embodiment, Ar² is phenyl.

In another embodiment, R² and R³ may be a 1- to 4-membered saturated or unsaturated, hydrocarbyl link, which may contain one or more heteroatoms selected from nitrogen, sulfur, and oxygen, and together with (Q²)(C)(N) forms a 5-membered saturated or unsaturated ring containing zero, one, or two C=O, and such ring is optionally substituted with H, OH, F, Cl, Br, I, CN, oxo, $C_1$-$C_6$ alkyl, $C_1$-$C_6$ haloalkyl, $C_1$-$C_6$ alkoxy, $C_1$-$C_6$ haloalkoxy, phenyl or phenoxy.

In another embodiment, R⁴ is substituted phenyl with one or more substituents independently selected from H, OH, F, Cl, Br, I, $C_1$-$C_6$ alkyl, $C_1$-$C_6$ haloalkyl, $C_2$-$C_6$ alkenyl, $C_2$-$C_6$ haloalkenyl, ($C_1$-$C_6$ alkyl)O($C_1$-$C_6$ alkyl), ($C_1$-$C_6$ alkyl)O ($C_1$-$C_6$ haloalkyl), ($C_1$-$C_6$ alkyl)S(=O)$_n$($C_1$-$C_6$ alkyl), $C_3$-$C_6$ cycloalkyl, $C_3$-$C_6$ halocycloalkyl, $C_1$-$C_6$ alkoxy, or $C_1$-$C_6$ haloalkoxy, or wherein two adjacent substituents form a 5- or 6-membered saturated or unsaturated, hydrocarbyl link, which may contain one or more heteroatoms selected from nitrogen, sulfur, and oxygen, and wherein said hydrocarbyl link may optionally be substituted with one or more substituents independently selected from H, F, Cl, Br, I, CN, OH, SH, NO₂, NR$^x$R$^y$, $C_1$-$C_6$ alkyl, $C_1$-$C_6$ haloalkyl, $C_1$-$C_6$ alkoxy, $C_1$-$C_6$ haloalkoxy, S($C_1$-$C_6$ alkyl), S($C_1$-$C_6$ haloalkyl), phenyl, and oxo.

In another aspect, provided is a process to apply a molecule provided herein. The process comprises applying a molecule provided herein, to an area to control a pest, in an amount sufficient to control such pest. In one embodiment, the pest is beet armyworm (BAW), cabbage looper (CL), or green peach aphid (GPA).

In another aspect, provided is a molecule that is a pesticidally acceptable acid addition salt, a salt derivative, a solvate, or an ester derivative, of a molecule provided herein. In another aspect, provided is a molecule provided herein wherein at least one H is ²H or at least one C is ¹⁴C. In another aspect, provided is a composition comprising a molecule provided herein and at least one other compound having insecticidal, herbicidal, acaricidal, nematicidal, or fungicidal activity. In another aspect, provided is a composition comprising a molecule provided herein and a seed.

In another aspect, provided is a process comprising applying a molecule provided herein to a genetically modified plant or a genetically-modified seed, which has been genetically modified to express one or more specialized traits. In another aspect, provided is a process comprising: orally administering or topically applying a molecule provided herein, to a non-human animal, to control endoparasites, ectoparasites, or both.

DETAILED DESCRIPTION OF THE INVENTION

The examples given for the substituents are (except for halo) non-exhaustive and must not be construed as limiting the invention disclosed in this document.

Definitions

"Alkenyl" means an acyclic, unsaturated (at least one carbon-carbon double bond), branched or unbranched, substituent consisting of carbon and hydrogen, for example, vinyl, allyl, butenyl, pentenyl, hexenyl, heptenyl, octenyl, nonenyl, and decenyl.

"Alkenyloxy" means an alkenyl further consisting of a carbon-oxygen single bond, for example, allyloxy, butenyloxy, pentenyloxy, hexenyloxy, heptenyloxy, octenyloxy, nonenyloxy, and decenyloxy.

"Alkoxy" means an alkyl further consisting of a carbon-oxygen single bond, for example, methoxy, ethoxy, propoxy, isopropoxy, 1-butoxy, 2-butoxy, isobutoxy, tert-butoxy, pentoxy, 2-methylbutoxy, 1,1-dimethylpropoxy, hexoxy, heptoxy, octoxy, nonoxy, and decoxy.

"Alkyl" means an acyclic, saturated, branched or unbranched, substituent consisting of carbon and hydrogen, for example, methyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, and decyl.

"Alkynyl" means an acyclic, unsaturated (at least one carbon-carbon triple bond, and any double bonds), branched or unbranched, substituent consisting of carbon and hydrogen, for example, ethynyl, propargyl, butynyl, pentynyl, hexynyl, heptynyl, octynyl, nonynyl, and decynyl.

"Alkynyloxy" means an alkynyl further consisting of a carbon-oxygen single bond, for example, pentynyloxy, hexynyloxy, heptynyloxy, octynyloxy, nonynyloxy, and decynyloxy.

"Aryl" means a cyclic, aromatic substituent consisting of hydrogen and carbon, for example, phenyl, naphthyl, and biphenyl.

"Cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, cycloheptenyl, cyclooctenyl, cyclodecenyl, norbornenyl, bicyclo[2.2.2]octenyl, tetrahydronaphthyl, hexahydronaphthyl, and octahydronaphthyl.

"Cycloalkenyloxy" means a cycloalkenyl further consisting of a carbon-oxygen single bond, for example, cyclobutenyloxy, cyclopentenyloxy, cyclohexenyloxy, cycloheptenyloxy, cyclooctenyloxy, cyclodecenyloxy, norbornenyloxy, and bicyclo[2.2.2]octenyloxy.

"Cycloalkyl" means a monocyclic or polycyclic, saturated substituent consisting of carbon and hydrogen, for example, cyclopropyl, cyclobutyl, cyclopentyl, cyclohexyl, cycloheptyl, cyclooctyl, cyclodecyl, norbornyl, bicyclo[2.2.2]octyl, and decahydronaphthyl.

"Cycloalkoxy" means a cycloalkyl further consisting of a carbon-oxygen single bond, for example, cyclopropyloxy, cyclobutyloxy, cyclopentyloxy, cyclohexyloxy, cycloheptyloxy, cyclooctyloxy, cyclodecyloxy, norbornyloxy, and bicyclo[2.2.2]octyloxy.

"Halo" means fluoro, chloro, bromo, and iodo.

"Haloalkyl" means an alkyl further consisting of, from one to the maximum possible number of, identical or different, halos, for example, fluoromethyl, difluoromethyl, trifluoromethyl, 1-fluoromethyl, 2-fluoroethyl, 2,2,2-trifluoroethyl, chloromethyl, trichloromethyl, and 1,1,2,2-tetrafluoroethyl.

"Heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen, for example, benzofuranyl, benzoisothiazolyl, benzoisoxazolyl, benzoxazolyl, benzothienyl, benzothiazolyl cinnolinyl, furanyl, indazolyl, indolyl, imidazolyl, isoindolyl, isoquinolinyl, isothiazolyl, isoxazolyl, 1,3,4-oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, 1,2,3,4-tetrazolyl, thiazolinyl, thiazolyl, thienyl, 1,2,3-triazinyl, 1,2,4-triazinyl, 1,3,5-triazinyl, 1,2,3-triazolyl, and 1,2,4-triazolyl.

Compounds

The compounds of this invention have the structure of Formula A:

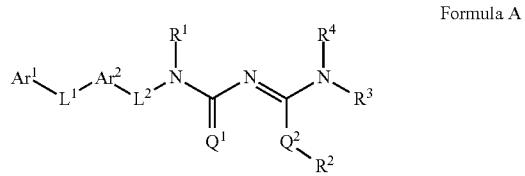

Formula A wherein:

(A) $Ar^1$ is selected from (1) furanyl, phenyl, pyridazinyl, pyridyl, pyrimidinyl, thienyl, or (2) substituted furanyl, substituted phenyl, substituted pyridazinyl, substituted pyridyl, substituted pyrimidinyl, or substituted thienyl, wherein said substituted furanyl, substituted phenyl, substituted pyridazinyl, substituted pyridyl, substituted pyrimidinyl, and substituted thienyl have one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n(C_3$-$C_8$ cycloalkyl), $S(=O)_n(C_3$-$C_8$ halocycloalkyl), $S(=O)_n(C_1$-$C_8$ alkyl), $S(=O)_n(C_1$-$C_8$ haloalkyl), $OSO_2(C_1$-$C_8$ alkyl), $OSO_2(C_1$-$C_8$ haloalkyl), $C(=O)NR^xR^y$, $(C_1$-$C_8$ alkyl)$NR^xR^y$, $C(=O)C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(=O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)$C(=O)(C_1$-$C_8$ alkyl), $(C_1$-$C_8$ alkyl)phenyl, $(C_1$-$C_8$ alkyl)-O-phenyl, phenyl, phenoxy, $Si(C_1$-$C_8$ alkyl)$_3$, or $S(=O)_nNR^xR^y$, or (Het-1), wherein each alkyl, haloalkyl, cycloalkyl, halocycloalkyl, alkoxy, haloalkoxy, alkenyl, cycloalkenyl, haloalkenyl, alkynyl, phenyl, phenoxy, and (Het-1) substituent may be optionally substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n(C_3$-$C_8$ cycloalkyl), $S(=O)_n(C_3$-$C_8$ halocycloalkyl), $S(=O)_n(C_1$-$C_8$ alkyl), $S(=O)_n(C_1$-$C_8$ haloalkyl), $OSO_2(C_1$-$C_8$ alkyl), $OSO_2(C_1$-$C_8$ haloalkyl), $C(=O)NR^xR^y$, $(C_1$-$C_8$ alkyl)$NR^xR^y$, $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)O($C_1$-$C_8$ alkyl), $(C_1$-$C_8$ alkyl)S$(=O)_n(C_1$-$C_8$ alkyl), $(C_1$-$C_8$ alkyl)OC$(=O)(C_1$-$C_8$ alkyl), $(C_1$-$C_8$ alkyl)OC$(=O)O(C_1$-$C_8$ alkyl), $C(=O)(C_1$-$C_8$ alkyl)C$(=O)O(C_1$-$C_8$ alkyl), $(C_1$-$C_8$ alkyl)C$(=O)OC_1$-$C_8$ alkyl), $(C_1$-$C_8$ alkyl)C$(=O)(C_1$-$C_8$ alkyl), $(C_1$-$C_8$ alkyl)phenyl, $(C_1$-$C_8$ alkyl)-O-phenyl, phenyl, phenoxy, Si($C_1$-$C_8$ alkyl)$_3$, $S(=O)$, $NR^xR^y$, or (Het-1);

(B) $Ar^2$ is selected from (1) furanyl, phenyl, pyridazinyl, pyridyl, pyrimidinyl, thienyl, or (2) substituted furanyl, substituted phenyl, substituted pyridazinyl, substituted pyridyl, substituted pyrimidinyl, or substituted thienyl, wherein said substituted furanyl, substituted phenyl, substituted pyridazinyl, substituted pyridyl, substituted pyrimidinyl, and substituted thienyl, have one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n(C_3$-$C_8$ cycloalkyl), $S(=O)_n(C_3$-$C_8$ halocycloalkyl), $S(=O)_n(C_1$-$C_8$ alkyl), $S(=O)_n(C_1$-$C_8$ haloalkyl), $OSO_2(C_1$-$C_8$ alkyl), $OSO_2(C_1$-$C_8$ haloalkyl), $C(=O)NR^xR^y$, $(C_1$-$C_8$ alkyl)$NR^xR^y$, $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)O($C_1$-$C_8$ alkyl), $(C_1$-$C_8$ alkyl)S$(=O)_n(C_1$-$C_8$ alkyl), $(C_1$-$C_8$ alkyl)OC$(=O)(C_1$-$C_8$ alkyl), $(C_1$-$C_8$ alkyl)OC$(=O)O(C_1$-$C_8$ alkyl), $C(=O)(C_1$-$C_8$ alkyl)C$(=O)O(C_1$-$C_8$ alkyl), $(C_1$-$C_8$ alkyl)C$(=O)O(C_1$-$C_8$ alkyl), $(C_1$-$C_8$ alkyl)C$(=O)(C_1$-$C_8$ alkyl), $(C_1$-$C_8$ alkyl)phenyl, $(C_1$-$C_8$ alkyl)-O-phenyl, phenyl, phenoxy, Si($C_1$-$C_8$ alkyl)$_3$, $S(=O)_n NR^xR^y$, or (Het-1), wherein each alkyl, haloalkyl, cycloalkyl, halocycloalkyl, alkoxy, haloalkoxy, alkenyl, cycloalkenyl, haloalkenyl, alkynyl, phenyl, phenoxy, and (Het-1) substituent may be optionally substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n(C_3$-$C_8$ cycloalkyl), $S(=O)_n(C_3$-$C_8$ halocycloalkyl), $S(=O)_n(C_1$-$C_8$ alkyl), $S(=O)_n(C_1$-$C_8$ haloalkyl), $OSO_2(C_1$-$C_8$ alkyl), $OSO_2(C_1$-$C_8$ haloalkyl), $C(=O)NR^xR^y$, $(C_1$-$C_8$ alkyl)$NR^xR^y$, $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)O($C_1$-$C_8$ alkyl), $(C_1$-$C_8$ alkyl)S$(=O)_n(C_1$-$C_8$ alkyl), $(C_1$-$C_8$ alkyl)OC$(=O)(C_1$-$C_8$ alkyl), $(C_1$-$C_8$ alkyl)OC$(=O)O(C_1$-$C_8$ alkyl), $C(=O)(C_1$-$C_8$ alkyl)C$(=O)O(C_1$-$C_8$ alkyl), $(C_1$-$C_8$ alkyl)C$(=O)O(C_1$-$C_8$ alkyl), $(C_1$-$C_8$ alkyl)C$(=O)(C_1$-$C_8$ alkyl), $(C_1$-$C_8$ alkyl)phenyl, and $(C_1$-$C_8$ alkyl)-O-phenyl, phenyl, phenoxy, Si($C_1$-$C_8$ alkyl)$_3$, $S(=O)_n NR^xR^y$, or (Het-1);

(C) $R^1$ is selected from H, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(=O)_n(C_3$-$C_8$ cycloalkyl), $S(=O)_n(C_3$-$C_8$ halocycloalkyl), $S(=O)_n(C_1$-$C_8$ alkyl), $S(=O)_n(C_1$-$C_8$ haloalkyl), $OSO_2(C_1$-$C_8$ alkyl), $OSO_2(C_1$-$C_8$ haloalkyl), $C(=O)NR^xR^y$, $(C_1$-$C_8$ alkyl)$NR^xR^y$, $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)O($C_1$-$C_8$ alkyl), $(C_1$-$C_8$ alkyl)S$(=O)_n(C_1$-$C_8$ alkyl), $(C_1$-$C_8$ alkyl)OC$(=O)(C_1$-$C_8$ alkyl), $(C_1$-$C_8$ alkyl)OC$(=O)O(C_1$-$C_8$ alkyl), $C(=O)(C_1$-$C_8$ alkyl)C$(=O)O(C_1$-$C_8$ alkyl), $(C_1$-$C_8$ alkyl)C$(=O)O(C_1$-$C_8$ alkyl), $(C_1$-$C_8$ alkyl)C$(=O)(C_1$-$C_8$ alkyl), $(C_1$-$C_8$ alkyl)phenyl, and $(C_1$-$C_8$ alkyl)-O-phenyl, phenyl, phenoxy, Si($C_1$-$C_8$ alkyl)$_3$, $S(=O)_n NR^xR^y$, or (Het-1);

(D) $R^2$ is selected from (F), H, $C_1$-$C_8$ alkyl, $C_3$-$C_8$ cycloalkyl, $C_2$-$C_8$ alkenyl, $C_2$-$C_8$ alkynyl, $C(=O)(C_1$-$C_8$ alkyl), $(C_1$-$C_8$ alkyl)O($C_1$-$C_8$ alkyl), $(C_1$-$C_8$ alkyl)S$(=O)_n(C_1$-$C_8$ alkyl), $(C_1$-$C_8$ alkyl)phenyl, $(C_1$-$C_8$ alkyl)-O-phenyl, $C(=O)$(Het-1), (Het-1), $(C_1$-$C_8$ alkyl)-(Het-1), $(C_1$-$C_8$ alkyl)-C$(=O)$—$(C_1$-$C_8$ alkyl), $(C_1$-$C_8$ alkyl)-OC$(=O)$—$(C_1$-$C_8$ alkyl), $(C_1$-$C_8$ alkyl)-O—C$(=O)O$—$(C_1$-$C_8$ alkyl), $(C_1$-$C_8$ alkyl)-O—C$(=O)NR^xR^y$, $(C_1$-$C_8$ alkyl)-C$(=O)N(R^x)(C_1$-$C_8$ alkyl)-(Het-1), $(C_1$-$C_8$ alkyl)-C$(=O)$(Het-1), $(C_1$-$C_8$ alkyl)-C$(=O)N(R^x)(C_1$-$C_8$ alkyl)$N(R^y)C(=O)OH$, $(C_1$-$C_8$ alkyl)-C$(=O)N(R^x)(C_1$-$C_8$ alkyl)$N(R^x)(R^y)$, $(C_1$-$C_8$ alkyl)-C$(=O)N(R^x)(C_1$-$C_8$ alkyl)$N(R^y)C(=O)O$—$(C_1$-$C_8$ alkyl), $(C_1$-$C_8$ alkyl)-C$(=O)N(R^x)(C_1$-$C_8$ alkyl)$(N(R^y)C(=O)O$—$(C_1$-$C_8$ alkyl)C$(=O)OH$, $(C_1$-$C_8$ alkyl)-C$(=O)$ (Het-1)C(=O)O—($C_1$-$C_8$ alkyl), ($C_1$-$C_8$ alkyl)-OC(=O)O—($C_1$-$C_8$ alkyl), ($C_1$-$C_8$ alkyl)-OC(=O)—($C_1$-$C_8$ alkyl), ($C_1$-$C_8$ alkyl)-OC(=O)—($C_3$-$C_8$ cycloalkyl), ($C_1$-$C_8$ alkyl)-OC(=O)-(Het-1), ($C_1$-$C_8$ alkyl)-OC(=O)—($C_1$-$C_8$ alkyl)N($R^x$)C(=O)O—($C_1$-$C_8$ alkyl), ($C_1$-$C_8$ alkyl)-$NR^xR^y$, ($C_1$-$C_8$ alkyl)-S-(Het-1), ($C_1$-$C_8$ alkyl)S(=O)$_n$(Het-1), or ($C_1$-$C_8$ alkyl)-O-(Het-1), wherein each alkyl, cycloalkyl, phenyl, and (Het-1) are optionally substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), $OSO_2$($C_1$-$C_8$ alkyl), $OSO_2$($C_1$-$C_8$ haloalkyl), C(=O)H, C(=O)OH, C(=O)$NR^xR^y$, ($C_1$-$C_8$ alkyl)$NR^xR^y$, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, phenoxy, Si($C_1$-$C_8$ alkyl)$_3$, S(=O)$_n$$NR^xR^y$, or (Het-1);

(E) $R^3$ is selected from (F), H, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), $OSO_2$($C_1$-$C_8$ alkyl), $OSO_2$($C_1$-$C_8$ haloalkyl), C(=O)H, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, ($C_1$-$C_8$ alkyl)phenyl, ($C_1$-$C_8$ alkyl)-O-phenyl, C(=O)(Het-1), (Het-1), ($C_1$-$C_8$ alkyl)-(Het-1), ($C_1$-$C_8$ alkyl)-C(=O)—($C_1$-$C_8$ alkyl), ($C_1$-$C_8$ alkyl)-OC(=O)—($C_1$-$C_8$ alkyl), ($C_1$-$C_8$ alkyl)-O—C(=O)O—($C_1$-$C_8$ alkyl), ($C_1$-$C_8$ alkyl)-O—C(=O)$NR^xR^y$, ($C_1$-$C_8$ alkyl)-C(=O)N($R^x$)($C_1$-$C_8$ alkyl)-(Het-1), ($C_1$-$C_8$ alkyl)-C(=O)(Het-1), ($C_1$-$C_8$ alkyl)-C(=O)N($R^x$)($C_1$-$C_8$ alkyl)N($R^y$)C(=O)OH, ($C_1$-$C_8$ alkyl)-C(=O)N($R^x$)($C_1$-$C_8$ alkyl)N($R^x$)($R^y$), ($C_1$-$C_8$ alkyl)-C(=O)N($R^x$)($C_1$-$C_8$ alkyl)N($R^y$)C(=O)O—($C_1$-$C_8$ alkyl), ($C_1$-$C_8$ alkyl)-C(=O)N($R^x$)($C_1$-$C_8$ alkyl)(N($R^y$)C(=O)O—($C_1$-$C_8$ alkyl)C(=O)OH, ($C_1$-$C_8$ alkyl)-C(=O)(Het-1)C(=O)O—($C_1$-$C_8$ alkyl), ($C_1$-$C_8$ alkyl)-OC(=O)O—($C_1$-$C_8$ alkyl), ($C_1$-$C_8$ alkyl)-OC(=O)—($C_1$-$C_8$ alkyl), ($C_1$-$C_8$ alkyl)-OC(=O)—($C_3$-$C_8$ cycloalkyl), ($C_1$-$C_8$ alkyl)-OC(=O)-(Het-1), ($C_1$-$C_8$ alkyl)-OC(=O)—($C_1$-$C_8$ alkyl)N($R^x$)C(=O)O—($C_1$-$C_8$ alkyl), ($C_1$-$C_8$ alkyl)-$NR^xR^y$, ($C_1$—C alkyl)-S-(Het-1), ($C_1$-$C_8$ alkyl)S(=O)$_n$(Het-1), or ($C_1$-$C_8$ alkyl)-O-(Het-1), wherein each alkyl, haloalkyl, cycloalkyl, halocycloalkyl, cycloalkoxy, halocycloalkoxy, alkoxy, haloalkoxy, alkenyl, cycloalkenyl, haloalkenyl, alkynyl, phenyl, and (Het-1), are optionally substituted with one or more substituents independently selected from H, F, Cl, Br, I, CN, OH, SH, $NO_2$, oxo, thioxo, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), $OSO_2$($C_1$-$C_8$ alkyl), $OSO_2$($C_1$-$C_8$ haloalkyl), C(=O)H, C(=O)OH, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, halophenyl, phenoxy, and (Het-1);

(F) $R^2$ and $R^3$ may be a 1- to 4-membered saturated or unsaturated, hydrocarbyl link, which may contain one or more heteroatoms selected from nitrogen, sulfur, and oxygen, and together with ($Q^2$)(C)(N) forms a 4- to 7-membered cyclic structure, wherein said hydrocarbyl link may optionally be substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), $OSO_2$($C_1$-$C_8$ alkyl), $OSO_2$($C_1$-$C_8$ haloalkyl), C(=O)H, C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, substituted phenyl, phenoxy, or (Het-1);

(G) $R^4$ is selected from $C_3$-$C_8$ cycloalkyl, phenyl, ($C_1$-$C_8$ alkyl)phenyl, ($C_1$-$C_8$ alkyl)-O-phenyl, ($C_2$-$C_8$ alkenyl)-O-phenyl, (Het-1), ($C_1$-$C_8$ alkyl)-(Het-1), ($C_1$-$C_8$ alkyl)-O-(Het-1), wherein the $C_3$-$C_8$ cycloalkyl, phenyl, ($C_1$-$C_8$ alkyl)phenyl, ($C_1$-$C_8$ alkyl)-O-phenyl, ($C_2$-$C_8$ alkenyl)-O-phenyl, (Het-1), ($C_1$-$C_8$ alkyl)-(Het-1), or ($C_1$-$C_8$ alkyl)-O-(Het-1) may be optionally substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S(=O)$_n$($C_3$-$C_8$ cycloalkyl), S(=O)$_n$($C_3$-$C_8$ halocycloalkyl), S(=O)$_n$($C_1$-$C_8$ alkyl), S(=O)$_n$($C_1$-$C_8$ haloalkyl), $OSO_2$($C_1$-$C_8$ alkyl), $OSO_2$($C_1$-$C_8$ haloalkyl), C(=O)($C_1$-$C_8$ alkyl), C(=O)O($C_1$-$C_8$ alkyl), C(=O)($C_1$-$C_8$ haloalkyl), C(=O)O($C_1$-$C_8$ haloalkyl), C(=O)($C_3$-$C_8$ cycloalkyl), C(=O)O($C_3$-$C_8$ cycloalkyl), C(=O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)O($C_1$-$C_8$ haloalkyl), ($C_1$-$C_8$ alkyl)S(=O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(=O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(=O)($C_1$-$C_8$ alkyl), ($C_1$-$C_8$ alkyl)phenyl, ($C_1$-$C_8$ alkyl)-O-phenyl, phenyl, phenoxy, Si($C_1$-$C_8$ alkyl)$_3$, S(=O)$_n$$NR^xR^y$, or (Het-1), or wherein two adjacent substituents form a 5- or 6-membered saturated or unsaturated, hydrocarbyl link, which may contain one or more heteroatoms selected from nitrogen, sulfur, and oxygen, and such ring is optionally substituted with one or more substituents selected from H, F, Cl, Br, I, CN, OH, SH, NO$_2$, NR$^x$R$^y$, C$_1$-C$_6$ alkyl, C$_1$-C$_6$ haloalkyl, C$_1$-C$_6$ alkoxy, C$_1$-C$_6$ haloalkoxy, S(=O)(C$_1$-C$_6$ alkyl), S(=O)(C$_1$-C$_6$ haloalkyl), phenyl, and oxo;

(H) L$^1$ is a linker selected from the group consisting of:

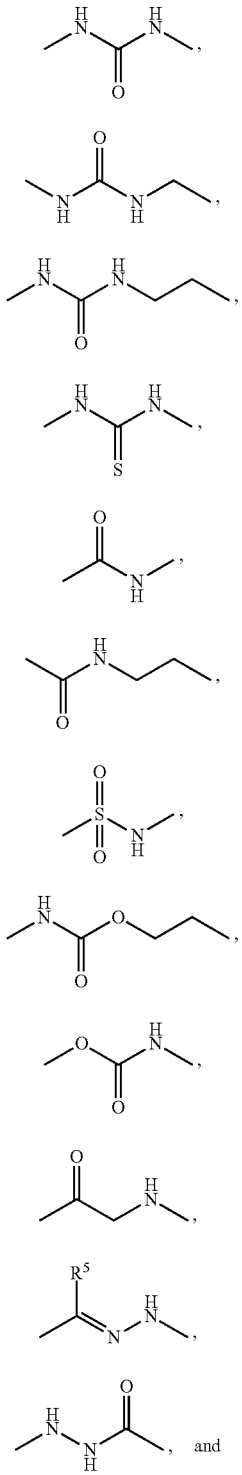

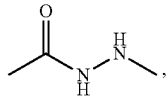

wherein R$^5$ is selected from H, C$_1$-C$_8$ alkyl, C$_1$-C$_8$ haloalkyl, C$_1$-C$_8$ alkoxy, C$_1$-C$_8$ haloalkoxy, phenyl and substituted phenyl, wherein said substituted phenyl has one or more substituents selected from H, F, Cl, Br, I, CN, NO$_2$, NR$^x$R$^y$, C$_1$-C$_8$ alkyl, C$_1$-C$_8$ haloalkyl, C$_3$-C$_8$ cycloalkyl, C$_3$-C$_8$ halocycloalkyl, C$_3$-C$_8$ cycloalkoxy, C$_3$-C$_8$ halocycloalkoxy, C$_1$-C$_8$ alkoxy, C$_1$-C$_8$ haloalkoxy, C$_2$-C$_8$ alkenyl, C$_3$-C$_8$ cycloalkenyl, C$_2$-C$_8$ haloalkenyl, C$_3$-C$_8$ halocycloalkenyl, and C$_2$-C$_8$ alkynyl;

(I) L$^2$ is linker selected from
(1) a bond,
(2) —CR$^6$R$^7$—CR$^8$R$^9$—, or
(3) —CR$^6$=CR$^8$—,
wherein each of R$^6$, R$^7$, R$^8$, and R$^9$ is selected from H, F, Cl, Br, I, CN, OH, SH, NO$_2$, oxo, thioxo, NR$^x$R$^y$, C$_1$-C$_8$ alkyl, C$_1$-C$_8$ haloalkyl, C$_1$-C$_8$ alkoxy, C$_1$-C$_8$ haloalkoxy, C$_2$-C$_8$ alkenyl, C$_2$-C$_8$ haloalkenyl, C$_2$-C$_8$ alkynyl, C$_2$-C$_8$ haloalkynyl, C$_3$-C$_8$ cycloalkyl, C$_3$-C$_8$ halocycloalkyl, C$_3$-C$_8$ cycloalkoxy, C$_3$-C$_8$ halocycloalkoxy, C$_3$-C$_8$ cycloalkenyl, C$_3$-C$_8$ halocycloalkenyl, C(=O)(C$_1$-C$_6$ alkyl), C(=O)O (C$_1$-C$_6$ alkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), S(=O)$_n$ (C$_3$-C$_8$ cycloalkyl), S(=O)$_n$(C$_3$-C$_8$ halocycloalkyl), phenyl, or phenoxy, or R$^6$ and R$^8$ together can optionally form a 3- to 7-membered ring which may contain C=O, C=S, N, S or O, and is optionally substituted with H, OH, F, Cl, Br, I, CN, NO$_2$, NR$^x$R$^y$, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_3$-C$_6$ cycloalkenyl, C$_2$-C$_6$ alkynyl, C$_3$-C$_6$ cycloalkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)OH, C(=O)NR$_x$R$_y$, (C$_1$-C$_6$ alkyl)NR$_x$R$_y$, C(=O)(C$_1$-C$_6$ alkyl), C(=O)O(C$_1$-C$_6$ alkyl), C(=O)(C$_1$-C$_6$ haloalkyl), C(=O)O (C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, phenoxy, and Het-1;

(J) Q$^1$ is selected from O or S;
(K) Q$^2$ is selected from O or S;
(L) R$^x$ and R$^y$ are independently selected from H, OH, SH, C$_1$-C$_8$ alkyl, C$_1$-C$_8$ haloalkyl, C$_3$-C$_8$ cycloalkyl, C$_3$-C$_8$ halocycloalkyl, C$_3$-C$_8$ cycloalkoxy, C$_3$-C$_8$ halocycloalkoxy, C$_1$-C$_8$ alkoxy, C$_1$-C$_8$ haloalkoxy, C$_2$-C$_8$ alkenyl, C$_3$-C$_8$ cycloalkenyl, C$_2$-C$_8$ haloalkenyl, C$_2$-C$_8$ alkynyl, S(=O)$_n$ (C$_3$-C$_8$ cycloalkyl), S(=O)$_n$(C$_3$-C$_8$ halocycloalkyl), S(=O)$_n$ (C$_1$-C$_8$ alkyl), S(=O)$_n$(C$_1$-C$_8$ haloalkyl), OSO$_2$ (C$_1$-C$_8$ alkyl), OSO$_2$(C$_1$-C$_8$ haloalkyl), C(=O)H, C(=O) (C$_1$-C$_8$ alkyl), C(=O)O(C$_1$-C$_8$ alkyl), C(=O)(C$_1$-C$_8$ haloalkyl), C(=O)O(C$_1$-C$_8$ haloalkyl), C(=O)(C$_3$-C$_8$ cycloalkyl), C(=O)O(C$_3$-C$_8$ cycloalkyl), C(=O)(C$_2$-C$_8$ alkenyl), C(=O)O(C$_2$-C$_8$ alkenyl), (C$_1$-C$_8$ alkyl)O(C$_1$-C$_8$ alkyl), (C$_1$-C$_8$ alkyl)S(=O)$_n$(C$_1$-C$_8$ alkyl), (C$_1$-C$_8$ alkyl)OC (=O)(C$_1$-C$_8$ alkyl), (C$_1$-C$_8$ alkyl)OC(=O)O(C$_1$-C$_8$ alkyl), C(=O)(C₁-C₈ alkyl)C(=O)O(C₁-C₈ alkyl), (C₁-C₈ alkyl)C(=O)O(C₁-C₈ alkyl), (C₁-C₈ alkyl)C(=O)(C₁-C₈ alkyl), (C₁-C₈ alkyl)phenyl, (C₁-C₈ alkyl)-O-phenyl, phenyl, (C₁-C₈ alkyl)phenyl, (C₁-C₈ alkyl)-O-phenyl, C(=O)(Het-1), (Het-1), (C₁-C₈ alkyl)-(Het-1), (C₁-C₈ alkyl)-C(=O)—(C₁-C₈ alkyl), (C₁-C₈ alkyl)-OC(=O)—(C₁-C₈ alkyl), (C₁-C₈ alkyl)-O—C(=O)O—(C₁-C₈ alkyl), (C₁-C₈ alkyl)-C(=O)(Het-1), (C₁-C₈ alkyl)-C(=O)(Het-1)C(=O)O—(C₁-C₈ alkyl), (C₁-C₈ alkyl)-OC(=O)O—(C₁-C₈ alkyl), (C₁-C₈ alkyl)-OC(=O)—(C₁-C₈ alkyl), (C₁-C₈ alkyl)-OC(=O)—(C₃-C₈ cycloalkyl), (C₁-C₈ alkyl)-OC(=O)-(Het-1), (C₁-C₈ alkyl)-S-(Het-1), (C₁-C₈ alkyl)S(=O)ₙ(Het-1), or (C₁-C₈ alkyl)-O-(Het-1), wherein each alkyl, haloalkyl, cycloalkyl, halocycloalkyl, cycloalkoxy, halocycloalkoxy, alkoxy, haloalkoxy, alkenyl, cycloalkenyl, haloalkenyl, alkynyl, phenyl, and (Het-1), are optionally substituted with one or more substituents independently selected from H, F, Cl, Br, I, CN, OH, SH, NO₂, oxo, thioxo, C₁-C₈ alkyl, C₁-C₈ haloalkyl, C₃-C₈ cycloalkyl, C₃-C₈ halocycloalkyl, C₃-C₈ cycloalkoxy, C₃-C₈ halocycloalkoxy, C₁-C₈ alkoxy, C₁-C₈ haloalkoxy, C₂-C₈ alkenyl, C₃-C₈ cycloalkenyl, C₂-C₈ haloalkenyl, C₂-C₈ alkynyl, S(=O)ₙ(C₃-C₈ cycloalkyl), S(=O)ₙ(C₃-C₈ halocycloalkyl), S(=O)ₙ(C₁-C₈ alkyl), S(=O)ₙ(C₁-C₈ haloalkyl), OSO₂(C₁-C₈ alkyl), OSO₂(C₁-C₈ haloalkyl), C(=O)H, C(=O)OH, C(=O)(C₁-C₈ alkyl), C(=O)O(C₁-C₈ alkyl), C(=O)(C₁-C₈ haloalkyl), C(=O)O(C₁-C₈ haloalkyl), C(=O)(C₃-C₈ cycloalkyl), C(=O)O(C₃-C₈ cycloalkyl), C(=O)(C₂-C₈ alkenyl), C(=O)O(C₂-C₈ alkenyl), (C₁-C₈ alkyl)O(C₁-C₈ alkyl), (C₁-C₈ alkyl)S(=O)ₙ(C₁-C₈ alkyl), (C₁-C₈ alkyl)OC(=O)(C₁-C₈ alkyl), (C₁-C₈ alkyl)OC(=O)O(C₁-C₈ alkyl), C(=O)(C₁-C₈ alkyl)C(=O)O(C₁-C₈ alkyl), (C₁-C₈ alkyl)C(=O)O(C₁-C₈ alkyl), (C₁-C₈ alkyl)C(=O)(C₁-C₈ alkyl), (C₁-C₈ alkyl)phenyl, (C₁-C₈ alkyl)-O-phenyl, phenyl, halophenyl, phenoxy, and (Het-1), or Rˣ and Rʸ together can optionally form a 5- to 7-membered saturated or unsaturated cyclic group which may contain one or more heteroatoms selected from nitrogen, sulfur, and oxygen, and where said cyclic group may be substituted with H, F, Cl, Br, I, CN, OH, SH, NO₂, oxo, thioxo, C₁-C₈ alkyl, C₁-C₈ haloalkyl, C₃-C₈ cycloalkyl, C₃-C₈ halocycloalkyl, C₃-C₈ cycloalkoxy, C₃-C₈ halocycloalkoxy, C₁-C₈ alkoxy, C₁-C₈ haloalkoxy, C₂-C₈ alkenyl, C₃-C₈ cycloalkenyl, C₂-C₈ haloalkenyl, C₂-C₈ alkynyl, S(=O)ₙ(C₃-C₈ cycloalkyl), S(=O)ₙ(C₃-C₈ halocycloalkyl), S(=O)ₙ(C₁-C₈ alkyl), S(=O)ₙ(C₁-C₈ haloalkyl), OSO₂(C₁-C₈ alkyl), OSO₂(C₁-C₈ haloalkyl), C(=O)(C₁-C₈ alkyl), C(=O)O(C₁-C₈ alkyl), C(=O)(C₁-C₈ haloalkyl), C(=O)O(C₁-C₈ haloalkyl), C(=O)(C₃-C₈ cycloalkyl), C(=O)O(C₃-C₈ cycloalkyl), C(=O)(C₂-C₈ alkenyl), C(=O)O(C₂-C₈ alkenyl), (C₁-C₈ alkyl)O(C₁-C₈ alkyl), (C₁-C₈ alkyl)S(=O)ₙ (C₁-C₈ alkyl), (C₁-C₈ alkyl)OC(=O)(C₁-C₈ alkyl), (C₁-C₈ alkyl)OC(=O)O(C₁-C₈ alkyl), C(=O)(C₁-C₈ alkyl)C(=O)O(C₁-C₈ alkyl), (C₁-C₈ alkyl)C(=O)O(C₁-C₈ alkyl), (C₁-C₈ alkyl)C(=O)(C₁-C₈ alkyl), (C₁-C₈ alkyl)phenyl, (C₁-C₈ alkyl)-O-phenyl, phenyl, substituted phenyl, phenoxy, and (Het-1);

(M) (Het-1) is a 5- or 6-membered, saturated or unsaturated, heterocyclic ring, containing one or more heteroatoms independently selected from nitrogen, sulfur or oxygen, wherein said heterocyclic ring may also be substituted with one or more substituents independently selected from H, F, Cl, Br, I, CN, OH, SH, NO₂, oxo, thioxo, NRˣRʸ, C₁-C₈ alkyl, C₁-C₈ haloalkyl, C₃-C₈ cycloalkyl, C₃-C₈ halocycloalkyl, C₃-C₈ cycloalkoxy, C₃-C₈ halocycloalkoxy, C₁-C₈ alkoxy, C₁-C₈ haloalkoxy, C₂-C₈ alkenyl, C₃-C₈ cycloalkenyl, C₂-C₈ haloalkenyl, C₂-C₈ alkynyl, S(=O)ₙ(C₃-C₈ cycloalkyl), S(=O)ₙ(C₃-C₈ halocycloalkyl), S(=O)ₙ(C₁-C₈ alkyl), S(=O)ₙ(C₁-C₈ haloalkyl), OSO₂(C₁-C₈ alkyl), OSO₂(C₁-C₈ haloalkyl), C(=O)NRˣRʸ, (C₁-C₈ alkyl)NRˣRʸ, C(=O)(C₁-C₈ alkyl), C(=O)O(C₁-C₈ alkyl), C(=O)(C₁-C₈ haloalkyl), C(=O)O(C₁-C₈ haloalkyl), C(=O)(C₃-C₈ cycloalkyl), C(=O)O(C₃-C₈ cycloalkyl), C(=O)(C₂-C₈ alkenyl), C(=O)O(C₂-C₈ alkenyl), (C₁-C₈ alkyl)O(C₁-C₈ alkyl), (C₁-C₈ alkyl)S(=O)ₙ(C₁-C₈ alkyl), (C₁-C₈ alkyl)OC(=O)(C₁-C₈ alkyl), (C₁-C₈ alkyl)OC(=O)O(C₁-C₈ alkyl), C(=O)(C₁-C₈ alkyl)C(=O)O(C₁-C₈ alkyl), (C₁-C₈ alkyl)C(=O)O(C₁-C₈ alkyl), (C₁-C₈ alkyl)C(=O)(C₁-C₈ alkyl), (C₁-C₈ alkyl)phenyl, (C₁-C₈ alkyl)-O-phenyl, phenyl, and phenoxy, wherein each alkyl, cycloalkyl, alkoxy, alkenyl, alkynyl, phenyl, and phenoxy may be optionally substituted with one or more substituents independently selected from H, F, Cl, Br, I, CN, OH, SH, NO₂, oxo, thioxo, NRˣRʸ, C₁-C₈ alkyl, C₁-C₈ haloalkyl, C₃-C₈ cycloalkyl, C₃-C₈ halocycloalkyl, C₃-C₈ cycloalkoxy, C₃-C₈ halocycloalkoxy, C₁-C₈ alkoxy, C₁-C₈ haloalkoxy, C₂-C₈ alkenyl, C₃-C₈ cycloalkenyl, C₂-C₈ haloalkenyl, C₂-C₈ alkynyl, S(=O)ₙ(C₃-C₈ cycloalkyl), S(=O)ₙ(C₃-C₈ halocycloalkyl), S(=O)ₙ(C₁-C₈ alkyl), S(=O)ₙ(C₁-C₈ haloalkyl), OSO₂(C₁-C₈ alkyl), OSO₂(C₁-C₈ haloalkyl), C(=O)H, C(=O)NRˣRʸ, (C₁-C₈ alkyl)NRˣRʸ, C(=O)(C₁-C₈ alkyl), C(=O)O(C₁-C₈ alkyl), C(=O)(C₁-C₈ haloalkyl), C(=O)O(C₁-C₈ haloalkyl), C(=O)(C₃-C₈ cycloalkyl), C(=O)O(C₃-C₈ cycloalkyl), C(=O)(C₂-C₈ alkenyl), C(=O)O(C₂-C₈ alkenyl), (C₁-C₈ alkyl)O(C₁-C₈ alkyl), (C₁-C₈ alkyl)S(=O)ₙ(C₁-C₈ alkyl), (C₁-C₈ alkyl)OC(=O)(C₁-C₈ alkyl), (C₁-C₈ alkyl)OC(=O)O(C₁-C₈ alkyl), C(=O)(C₁-C₈ alkyl)C(=O)O(C₁-C₈ alkyl), (C₁-C₈ alkyl)C(=O)O(C₁-C₈ alkyl), (C₁-C₈ alkyl)C(=O)(C₁-C₈ alkyl), (C₁-C₈ alkyl)phenyl, (C₁-C₈ alkyl)-O-phenyl, phenyl, and phenoxy; and (N) n is each individually 0, 1, or 2.

In one embodiment, Ar¹ is phenyl or substituted phenyl having one or more substituents independently selected from H, C₁-C₆ alkyl, C₁-C₆ haloalkyl, C₁-C₆ alkoxy, and C₁-C₆ haloalkoxy.

In another embodiment, L¹ is a linker selected from the group consisting of:

L¹-1

L¹-2

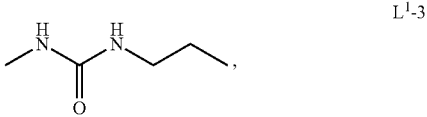

L¹-3

L¹-4

L¹-6

L¹-8: [structure: methyl carbamate ethyl ester fragment]

L¹-9: [structure: methyl carbamate fragment]

L¹-10: [structure: N-methyl aminoacetone fragment]

L¹-11: [structure: hydrazone with R⁵]

and

L¹-12: [structure: acetyl methylhydrazide fragment]

wherein $R^5$ is selected from H, $C_1$-$C_8$ alkyl, $C_1$-$C_8$ haloalkyl, $C_1$-$C_8$ alkoxy, $C_1$-$C_8$ haloalkoxy, phenyl, and substituted phenyl, wherein said substituted phenyl has one or more substituents selected from H, F, Cl, Br, I, CN, $NO_2$, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_3$-$C_8$ halocycloalkenyl, and $C_2$-$C_8$ alkynyl.

In another embodiment, $Ar^2$ is phenyl or a substituted phenyl having one or more substituents independently selected from H, F, Cl, Br, I, CN, $C_1$-$C_6$ alkyl, $C_1$-$C_6$ haloalkyl, $C_1$-$C_6$ haloalkoxy, and $C_1$-$C_6$ alkoxy.

In another embodiment, $R^2$ and $R^3$ are independently selected from H, $C_1$-$C_6$ alkyl, $C_1$-$C_6$ haloalkyl, $C_2$-$C_6$ alkenyl.

In another embodiment, $R^2$ and $R^3$ may be a 1- to 4-membered saturated or unsaturated, hydrocarbyl link, which may contain one or more heteroatoms selected from nitrogen, sulfur, and oxygen, and together with $(Q^2)(C)(N)$ forms a 5- to 7-membered cyclic structure, wherein said hydrocarbyl link is optionally substituted with H, OH, F, Cl, Br, I, CN, $NO_2$, oxo, $C_1$-$C_6$ alkyl, $C_1$-$C_6$ alkoxy, $C_1$-$C_6$ haloalkyl, $C_1$-$C_6$ haloalkoxy, phenyl, phenoxy, or (Het-1), wherein (Het-1) is a 5- or 6-membered, saturated or unsaturated, heterocyclic ring, containing one or more heteroatoms independently selected from nitrogen, sulfur and oxygen.

In another embodiment, $R^2$ and $R^3$ may be a hydrocarbyl link, wherein said hydrocarbyl link may be substituted with H, oxo, OH, F, Cl, Br, I, $C_1$-$C_6$ alkyl, $C_1$-$C_6$ haloalkyl, $C_1$-$C_6$ alkoxy, or $C_1$-$C_6$ haloalkoxy.

In another embodiment, $R^4$ is phenyl optionally substituted with one or more substituents independently selected from H, OH, F, Cl, Br, I, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, $C_2$-$C_6$ haloalkenyl, $C_3$-$C_6$ cycloalkyl, $C_3$-$C_6$ halocycloalkyl, $NR^xR^y$, ($C_1$-$C_8$ alkyl)O($C_1$-$C_8$ alkyl), or ($C_1$-$C_8$ alkyl)O($C_1$-$C_8$ haloalkyl).

In another embodiment, $Ar^1$ is substituted phenyl having one or more substituents independently selected from $OCF_3$, $OCF_2CF_3$, and $CF_3$.

In another embodiment, $Ar^2$ is phenyl.

In another embodiment, $Ar^2$ is substituted phenyl having one or more substituents independently selected from H, F, Cl, Br, I, CN, $C_1$-$C_6$ alkyl, $C_1$-$C_6$ haloalkyl, $C_1$-$C_6$ alkoxy, and $C_1$-$C_6$ haloalkoxy.

In another embodiment, $R^2$ is H or $C_1$-$C_6$ alkyl.

In another embodiment, $R^3$ is H or $C_1$-$C_6$ alkyl.

In another embodiment, each $R^6$, $R^7$, $R^8$, or $R^9$ is independently H, F, Cl, or $C_1$-$C_6$ alkyl.

In another embodiment, each $R^6$, $R^7$, $R^8$, or $R^9$ is independently H or a $C_1$-$C_6$ alkyl.

In another embodiment, each of $R^2$ and $R^3$ is independently H or a $C_1$-$C_6$ alkyl.

In another embodiment, $R^2$ and $R^3$ is a hydrocarbyl link, wherein said hydrocarbyl link is $CH_2C(=O)$, $CHBrC(=O)$, $CHFC(=O)$, $CHClC(=O)$, $CH(CH_3)C(O)$, $C(CH_3)_2C(O)$, $CH_2CH(OH)$, $CH_2CH_2$, $CH_2CH(CH_3)$, or $CH=CH$.

In another embodiment, $R^4$ is substituted phenyl with one or more H, OH, F, Cl, Br, I, $C_1$-$C_6$ alkyl, $C_1$-$C_6$ haloalkyl, $C_1$-$C_6$ alkoxy, $C_1$-$C_6$ haloalkoxy, $NR^xR^y$, ($C_1$-$C_8$ alkyl)O ($C_1$-$C_8$ alkyl), or ($C_1$-$C_8$ alkyl)O($C_1$-$C_8$ haloalkyl.

In another embodiment, the molecule has a structure selected from compounds listed in Table 1 below:

TABLE 1

Structures for Compounds

A1: [structure of compound A1]

TABLE 1-continued
Structures for Compounds
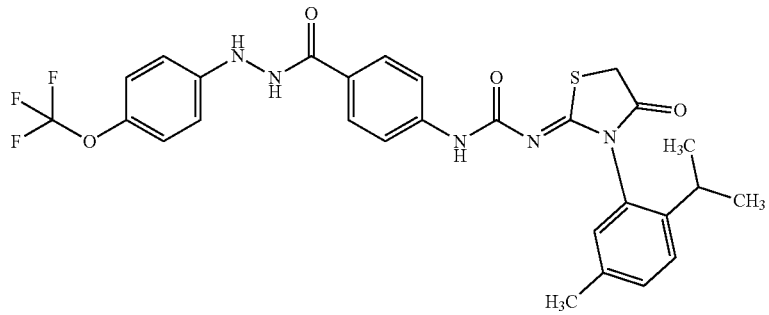 [SMILES: Cc1ccc(C(C)C)c(N2C(=O)CS/C2=N\C(=O)Nc2ccc(C(=O)NNc3ccc(OC(F)(F)F)cc3)cc2)c1]
A2
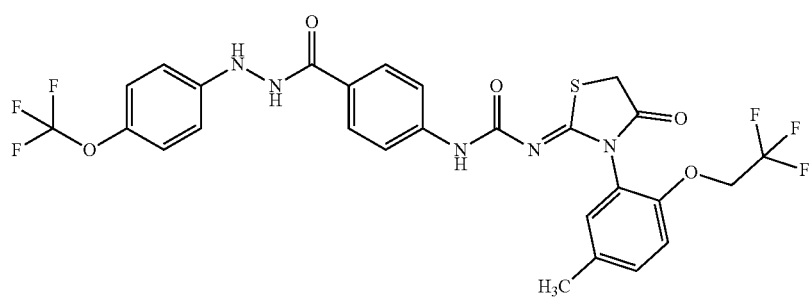 [SMILES: Cc1ccc(OCC(F)(F)F)c(N2C(=O)CS/C2=N\C(=O)Nc2ccc(C(=O)NNc3ccc(OC(F)(F)F)cc3)cc2)c1]
A3
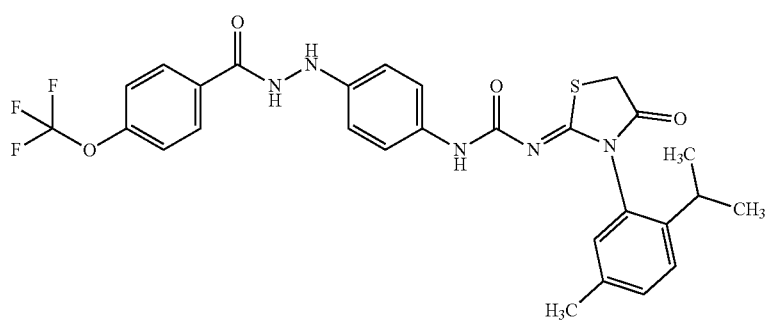 [SMILES: Cc1ccc(C(C)C)c(N2C(=O)CS/C2=N\C(=O)Nc2ccc(NNC(=O)c3ccc(OC(F)(F)F)cc3)cc2)c1]
A4
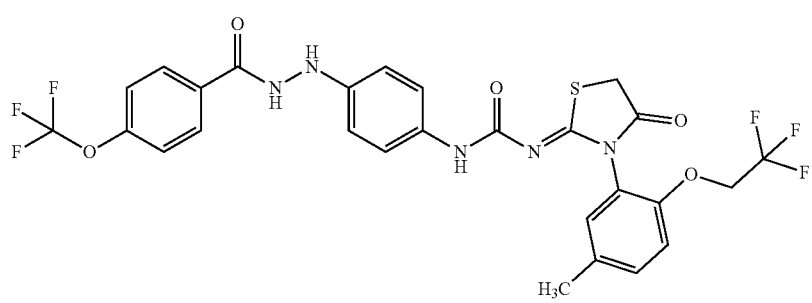
A5
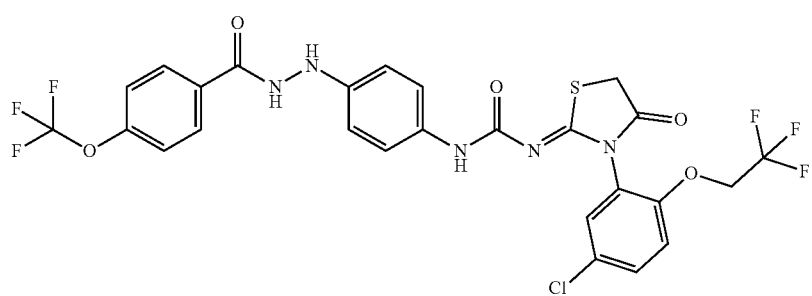 [SMILES: O=C(/N=C1\SCC(=O)N1c1cc(Cl)ccc1OCC(F)(F)F)Nc1ccc(NNC(=O)c2ccc(OC(F)(F)F)cc2)cc1]
A6

TABLE 1-continued

Structures for Compounds

| | |
|---|---|
| (structure) | A7 |
| (structure) | A8 |
| (structure) | A9 |
| (structure) | A10 |
| (structure) | A11 |

TABLE 1-continued
Structures for Compounds
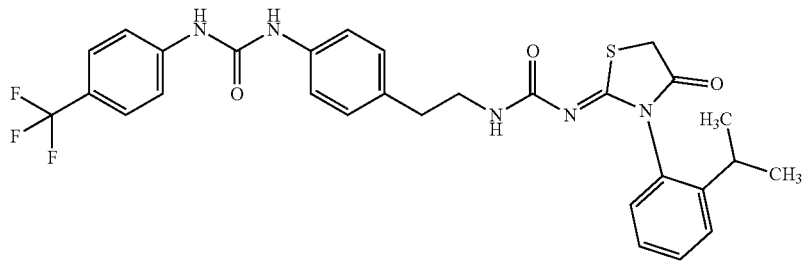 [SMILES: CC(C)c1ccccc1N1C(=O)CS/C1=N\C(=O)NCCc1ccc(NC(=O)Nc2ccc(C(F)(F)F)cc2)cc1]
A12
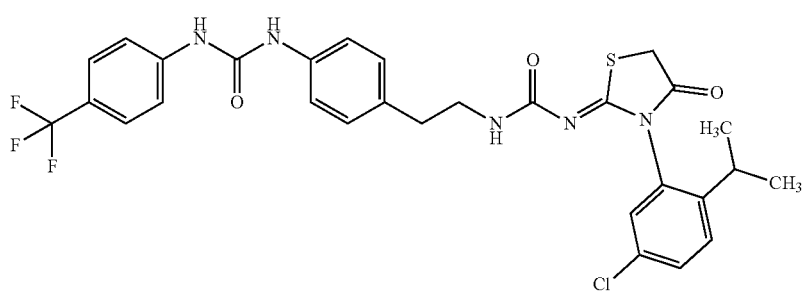 [SMILES: CC(C)c1ccc(Cl)cc1N1C(=O)CS/C1=N\C(=O)NCCc1ccc(NC(=O)Nc2ccc(C(F)(F)F)cc2)cc1]
A13
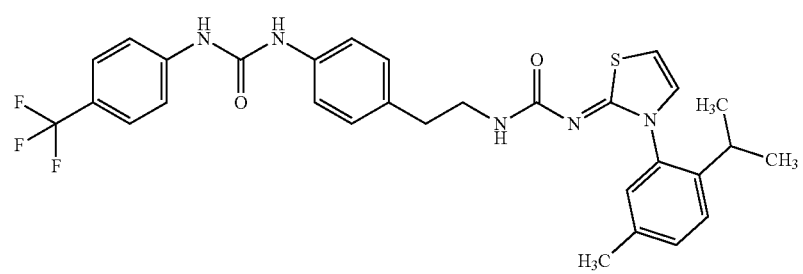 [SMILES: Cc1ccc(C(C)C)c(-n2ccs/c2=N\C(=O)NCCc2ccc(NC(=O)Nc3ccc(C(F)(F)F)cc3)cc2)c1]
A14
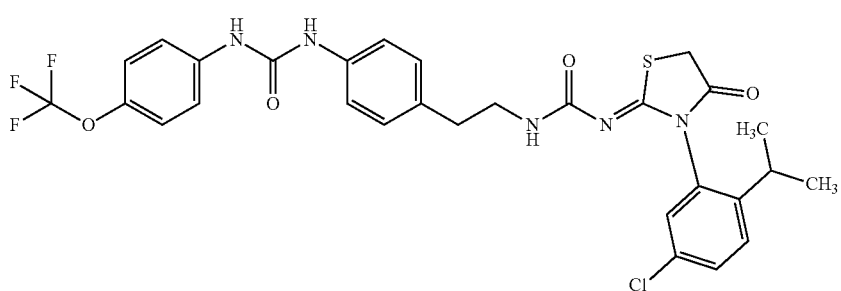 [SMILES: CC(C)c1ccc(Cl)cc1N1C(=O)CS/C1=N\C(=O)NCCc1ccc(NC(=O)Nc2ccc(OC(F)(F)F)cc2)cc1]
A15
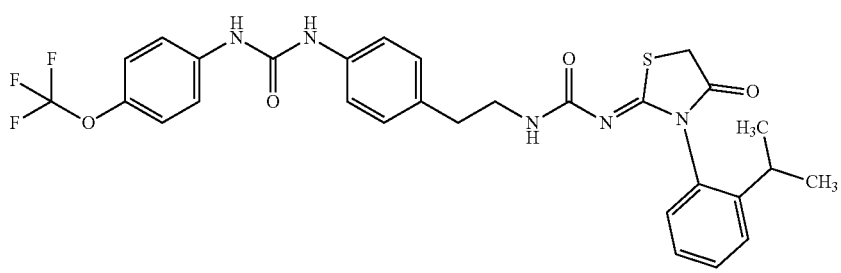 [SMILES: CC(C)c1ccccc1N1C(=O)CS/C1=N\C(=O)NCCc1ccc(NC(=O)Nc2ccc(OC(F)(F)F)cc2)cc1]
A16

TABLE 1-continued
Structures for Compounds
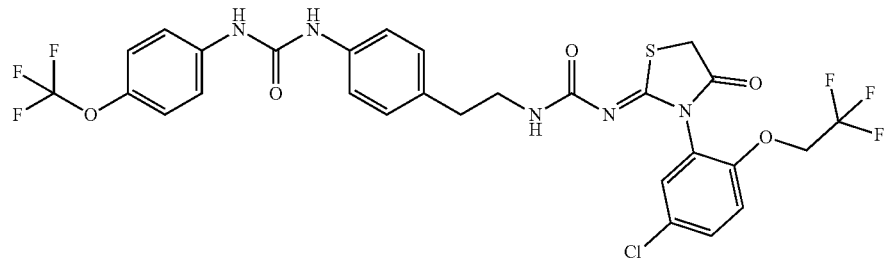 [SMILES: O=C(/N=C1\SCC(=O)N1c1cc(Cl)ccc1OCC(F)(F)F)NCCc1ccc(NC(=O)Nc2ccc(OC(F)(F)F)cc2)cc1]
A17
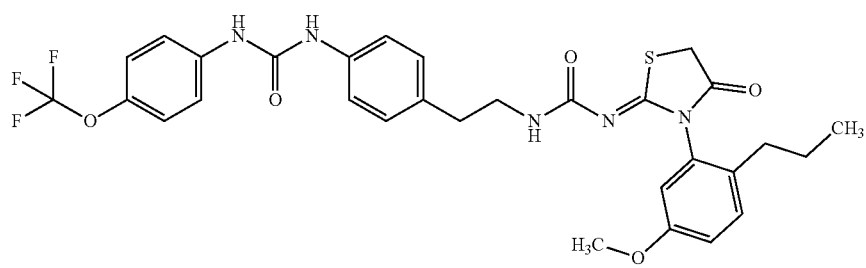 [SMILES: CCCc1ccc(OC)cc1N1C(=O)CS/C1=N\C(=O)NCCc1ccc(NC(=O)Nc2ccc(OC(F)(F)F)cc2)cc1]
A18
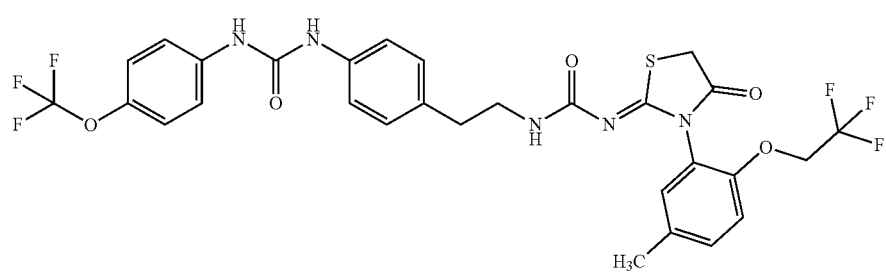 [SMILES: Cc1ccc(OCC(F)(F)F)c(N2C(=O)CS/C2=N\C(=O)NCCc2ccc(NC(=O)Nc3ccc(OC(F)(F)F)cc3)cc2)c1]
A19
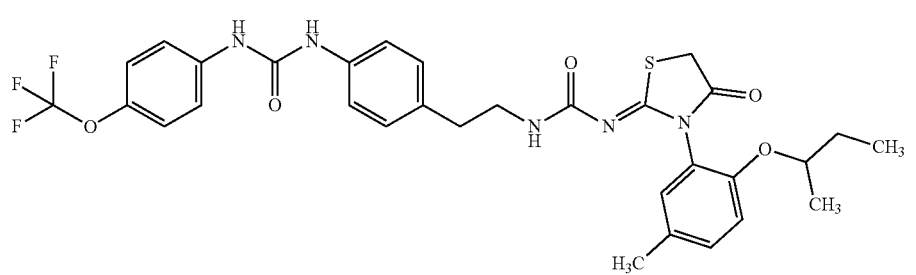 [SMILES: CCC(C)Oc1ccc(C)cc1N1C(=O)CS/C1=N\C(=O)NCCc1ccc(NC(=O)Nc2ccc(OC(F)(F)F)cc2)cc1]
A20
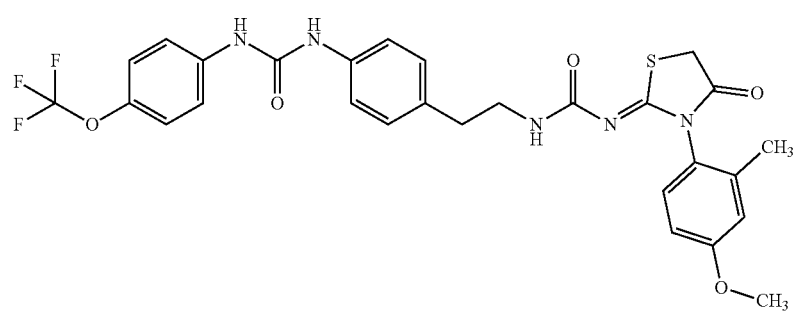 [SMILES: COc1ccc(N2C(=O)CS/C2=N\C(=O)NCCc2ccc(NC(=O)Nc3ccc(OC(F)(F)F)cc3)cc2)c(C)c1]
A21

TABLE 1-continued
Structures for Compounds
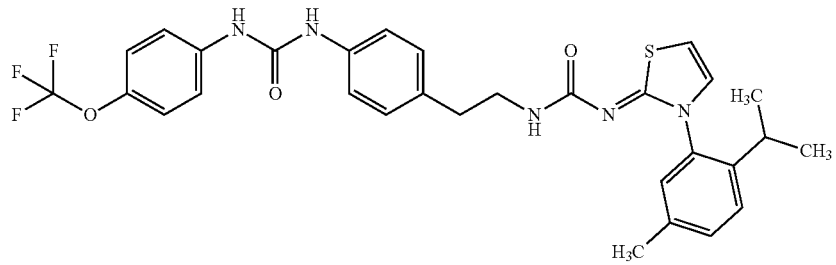 [SMILES: Cc1ccc(C(C)C)c(-n2ccs/c2=N\C(=O)NCCc2ccc(NC(=O)Nc3ccc(OC(F)(F)F)cc3)cc2)c1]
A22
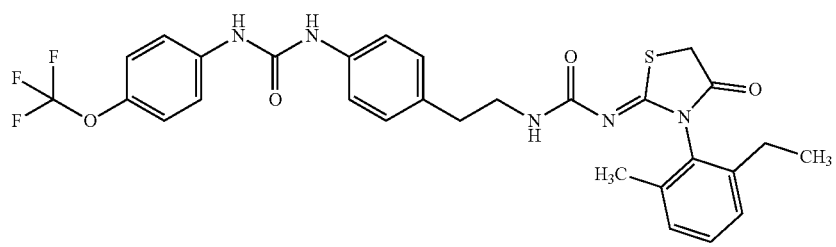 [SMILES: CCc1cccc(C)c1N1C(=O)CS/C1=N\C(=O)NCCc1ccc(NC(=O)Nc2ccc(OC(F)(F)F)cc2)cc1]
A23
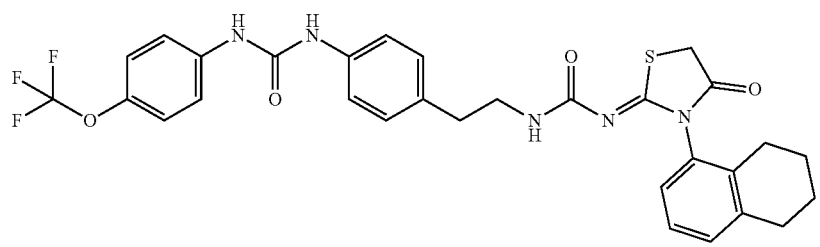 [SMILES: O=C(/N=C1\SCC(=O)N1c1cccc2c1CCCC2)NCCc1ccc(NC(=O)Nc2ccc(OC(F)(F)F)cc2)cc1]
A24
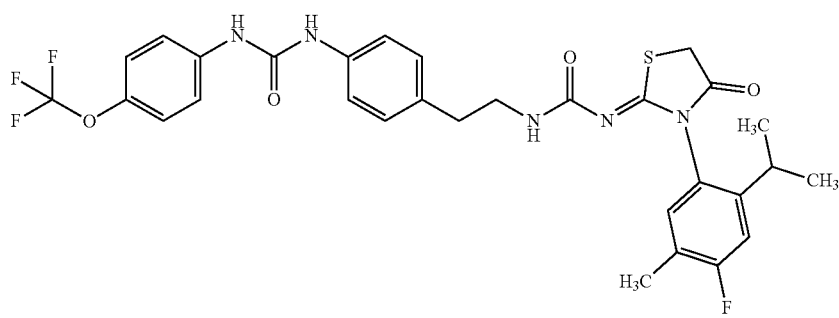 [SMILES: Cc1cc(N2C(=O)CS/C2=N\C(=O)NCCc2ccc(NC(=O)Nc3ccc(OC(F)(F)F)cc3)cc2)c(C(C)C)cc1F]
A25
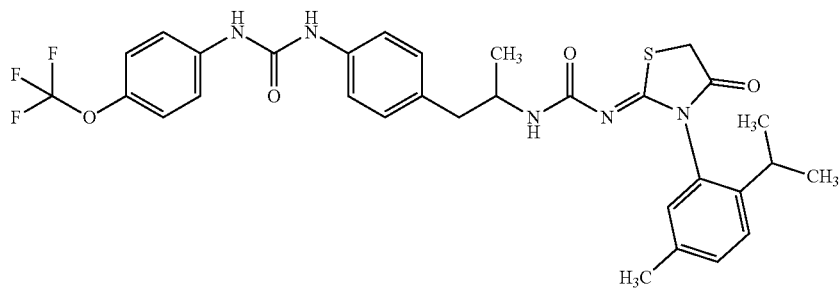 [SMILES: Cc1ccc(C(C)C)c(N2C(=O)CS/C2=N\C(=O)NC(C)Cc2ccc(NC(=O)Nc3ccc(OC(F)(F)F)cc3)cc2)c1]
A26

TABLE 1-continued

Structures for Compounds

A27

A28

A29

A30

A31

TABLE 1-continued

Structures for Compounds

A32

A33

A34

A35

A36

A37

TABLE 1-continued
Structures for Compounds
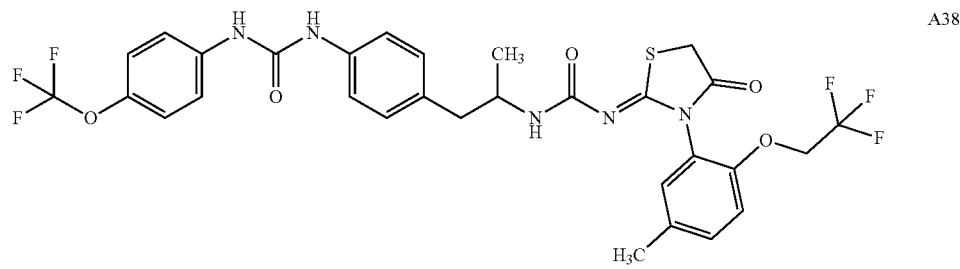
A38
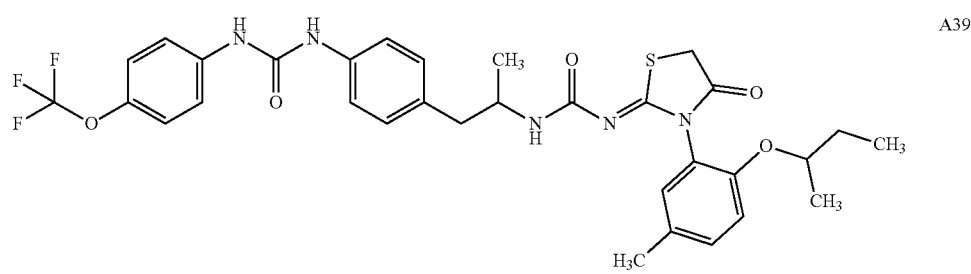
A39
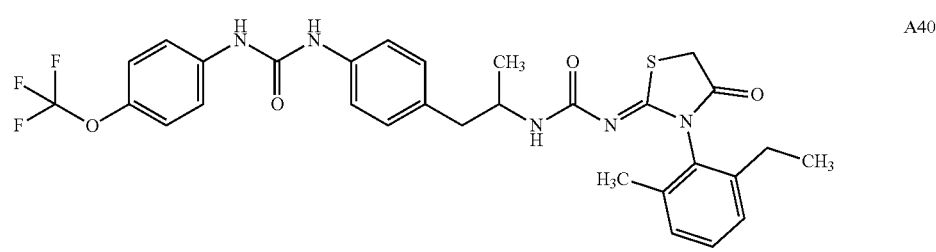
A40
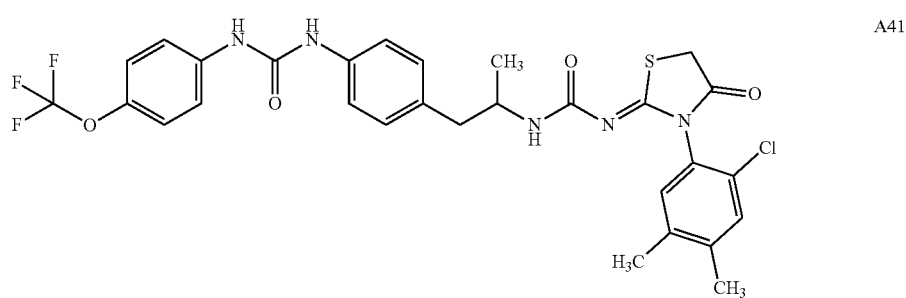
A41
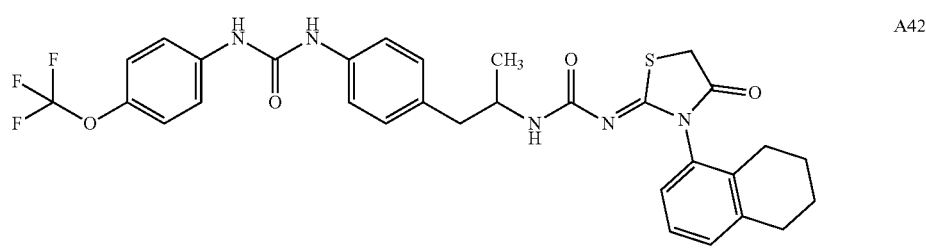
A42

TABLE 1-continued
Structures for Compounds
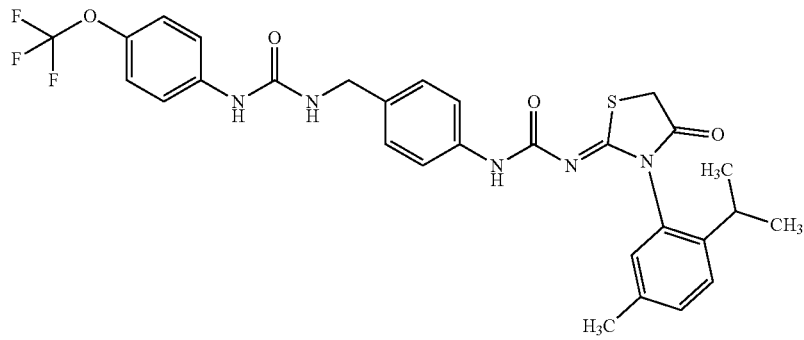 [SMILES: Cc1ccc(C(C)C)c(N2C(=O)CS/C2=N\C(=O)Nc2ccc(CNC(=O)Nc3ccc(OC(F)(F)F)cc3)cc2)c1]
A43
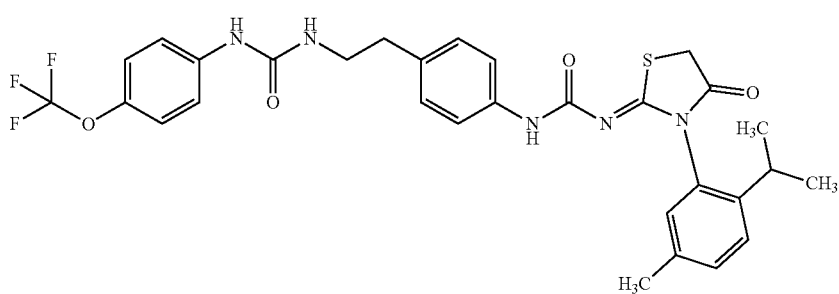 [SMILES: Cc1ccc(C(C)C)c(N2C(=O)CS/C2=N\C(=O)Nc2ccc(CCNC(=O)Nc3ccc(OC(F)(F)F)cc3)cc2)c1]
A44
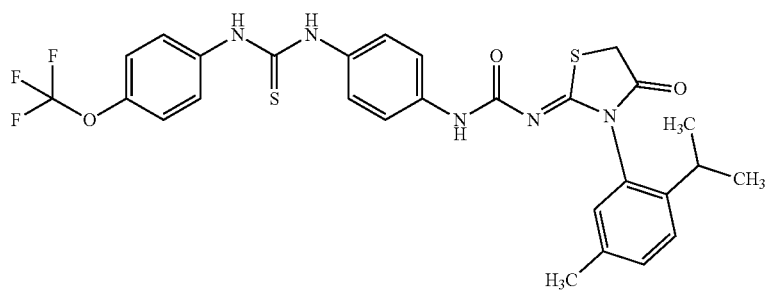
A45
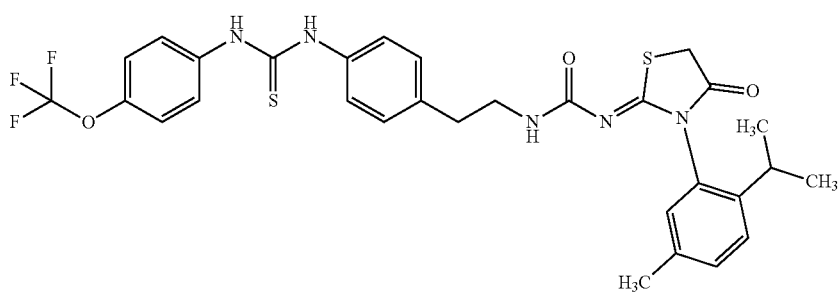 [SMILES: Cc1ccc(C(C)C)c(N2C(=O)CS/C2=N\C(=O)NCCc2ccc(NC(=S)Nc3ccc(OC(F)(F)F)cc3)cc2)c1]
A46
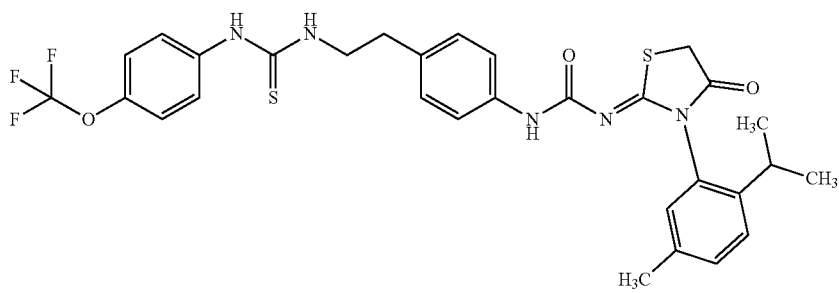 [SMILES: Cc1ccc(C(C)C)c(N2C(=O)CS/C2=N\C(=O)Nc2ccc(CCNC(=S)Nc3ccc(OC(F)(F)F)cc3)cc2)c1]
A47

TABLE 1-continued
Structures for Compounds
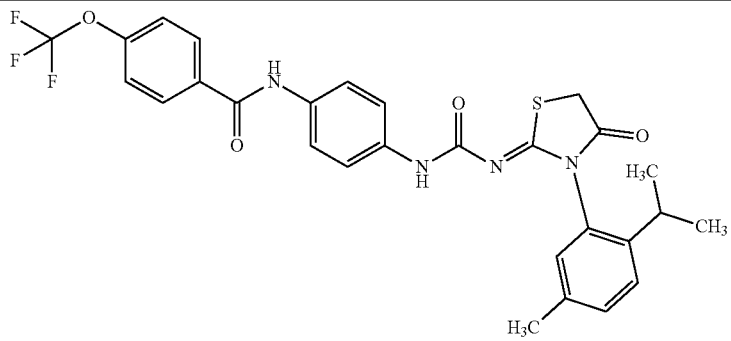
A48
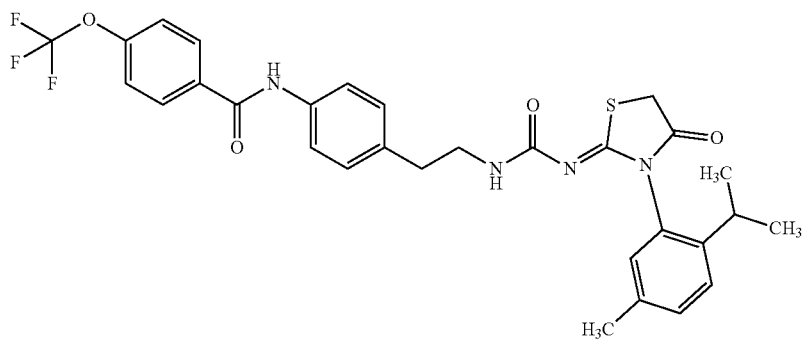 [SMILES: Cc1ccc(C(C)C)c(N2C(=O)CS/C2=N\C(=O)NCCc2ccc(NC(=O)c3ccc(OC(F)(F)F)cc3)cc2)c1]
A49
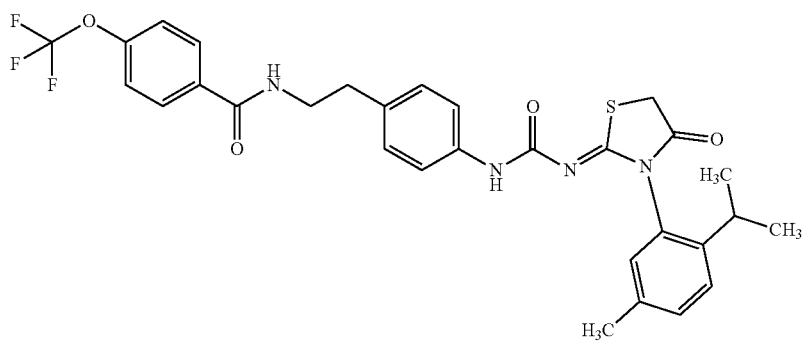 [SMILES: Cc1ccc(C(C)C)c(N2C(=O)CS/C2=N\C(=O)Nc2ccc(CCNC(=O)c3ccc(OC(F)(F)F)cc3)cc2)c1]
A50
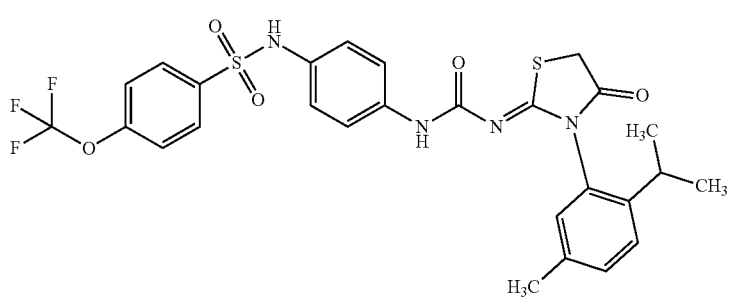 [SMILES: Cc1ccc(C(C)C)c(N2C(=O)CS/C2=N\C(=O)Nc2ccc(NS(=O)(=O)c3ccc(OC(F)(F)F)cc3)cc2)c1]
A51
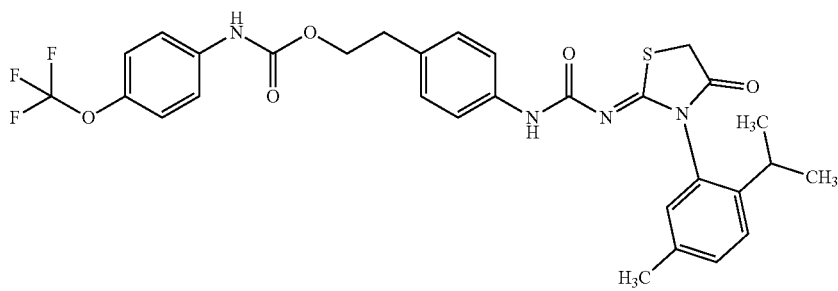 [SMILES: Cc1ccc(C(C)C)c(N2C(=O)CS/C2=N\C(=O)Nc2ccc(CCOC(=O)Nc3ccc(OC(F)(F)F)cc3)cc2)c1]
A52

TABLE 1-continued

Structures for Compounds

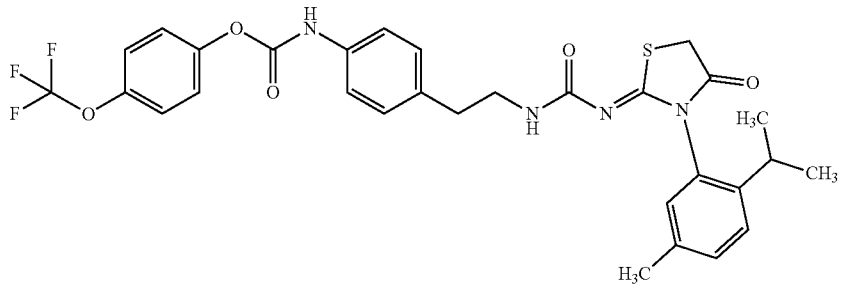 [SMILES: Cc1ccc(C(C)C)c(N2C(=O)CS/C2=N\C(=O)NCCc2ccc(NC(=O)Oc3ccc(OC(F)(F)F)cc3)cc2)c1]

A53

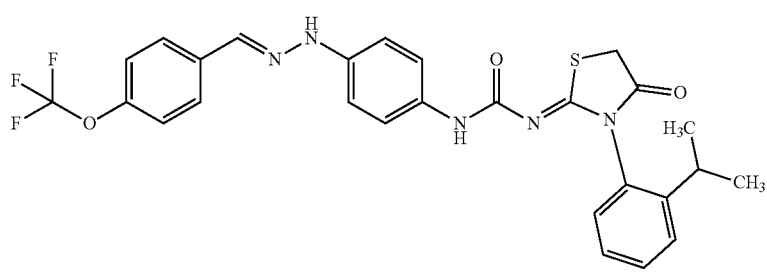 [SMILES: CC(C)c1ccccc1N1C(=O)CS/C1=N\C(=O)Nc1ccc(N/N=C/c2ccc(OC(F)(F)F)cc2)cc1]

A54

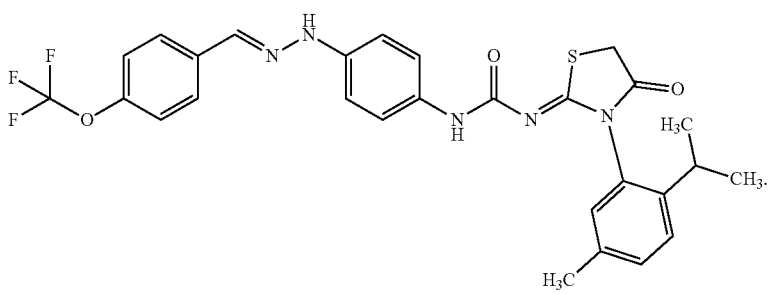 [SMILES: Cc1ccc(C(C)C)c(N2C(=O)CS/C2=N\C(=O)Nc2ccc(N/N=C/c3ccc(OC(F)(F)F)cc3)cc2)c1]

A55

The compounds 1-1, wherein $Ar^1$, $L^1$, $Ar^2$, $R^1$, $R^2$, $R^3$, $R^4$, $Q^1$, and $Q^2$ are as previously disclosed, can be generated by reaction of an aryl electrophile $Ar^1$-$E^1$ 1-3, wherein $Ar^1$ is as previously disclosed and $E^1$ is an electrophile such as an α-haloketone, an isocyanate, an isothiocyanate, or an acid chloride with an aryl amine 1-2, wherein $Ar^2$, $R^1$, $R^2$, $R^3$, $R^4$, $Q^1$, and $Q^2$ are as previously disclosed, in a polar solvent such as methanol, tetrahydrofuran, or acetonitrile, with or without the addition of a base, such as cesium carbonate and N,N-diisopropylethylamine as in step a of Scheme 1. Alternatively, the compounds 1-1, wherein $Ar^1$, $L^1$, $Ar^2$, $R^1$, $R^2$, $R^3$, $R^4$, $Q^1$, and $Q^2$ are as previously disclosed, can be generated by reaction of a nucleophile such an aryl alcohol 1-5, wherein $Ar^1$ is as previously disclosed, with an activated amine intermediate 1-4, wherein $Ar^2$, $R^1$, $R^2$, $R^3$, $R^4$, $Q^1$, and $Q^2$ are as previously disclosed and A is an activated group, in a polar, aprotic solvent, such as acetonitrile and in the presence of bases such as N,N-diisopropylethylamine and cesium carbonate as in step c of Scheme 1. The activated amine intermediate 1-4, wherein $Ar^2$, $R^1$, $R^2$, $R^3$, $R^4$, $Q^1$, and $Q^2$ are as previously disclosed and A is an activated group, can be generated by treatment of the aryl amine 1-2 with an activating agent such as bis(2,5-dioxopyrrolidin-1-yl) carbonate or 4-nitrophenyl carbonochloridate in a polar, aprotic solvent, such as tetrahydrofuran (Scheme 1, step b).

Scheme 1

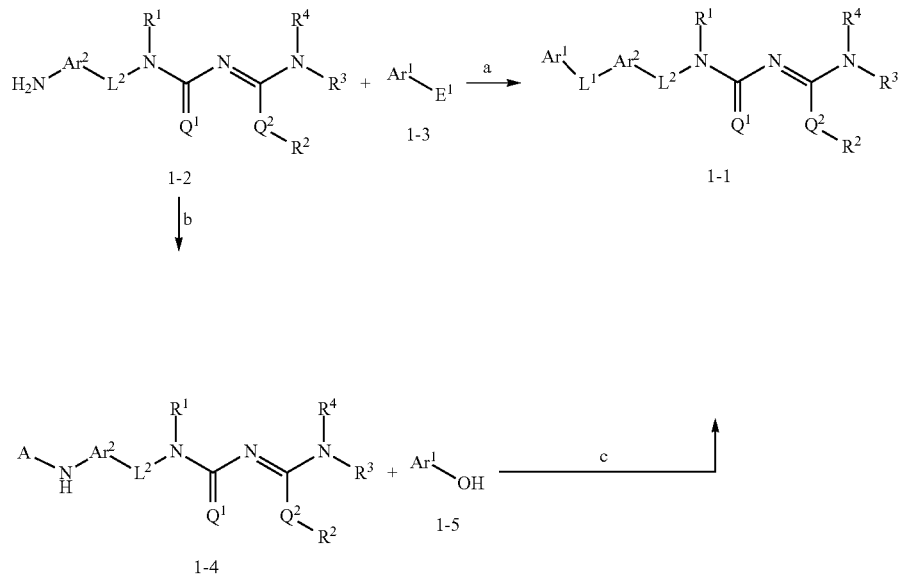

The compounds 2-1, wherein $Ar^1$, $L^1$, $Ar^2$, $R^1$, $R^2$, $R^3$, $R^4$, $Q^1$, and $Q^2$ are as previously disclosed, can be generated in either one or two steps from an aryl amine 2-2, wherein $Ar^1$, $L^1$, and $Ar^2$ are as previously disclosed. In the one-step method, the activated amine 2-3, wherein $Ar^1$, $L^1$, and $Ar^2$ are as previously disclosed and A is an activated group, is formed in situ by reaction of the aryl amine 2-2 with an activating agent such as bis(2,5-dioxopyrrolidin-1-yl) carbonate in the presence of a base, such as N,N-diisopropylethylamine, in a polar, aprotic solvent such as acetonitrile, and then is allowed to react with imine 2-4, wherein $R^1$, $R^2$, $R^3$, $R^4$, $Q^1$, and $Q^2$ are as previously disclosed, as in step a of Scheme 2. In the two-step method, the activated amine intermediate 2-3, wherein $Ar^1$, $L^1$, and $Ar^2$ are as previously disclosed and A is an activated group, can be generated and isolated by treatment of the aryl amine 2-2 with an activating agent such as 4-nitrophenyl carbonochloridate in a polar, aprotic solvent, such as acetonitrile (Scheme 2, step b) and subsequently reacted with imine 2-4, wherein $R^1$, $R^2$, $R^3$, $R^4$, $Q^1$, and $Q^2$ are as previously disclosed, in a polar, aprotic solvent, such as acetonitrile and in the presence of bases such as N,N-diisopropylethylamine and cesium carbonate as in step c of Scheme 2.

The compounds 3-1, wherein $Ar^1$, $L^1$, $Ar^2$, $R^1$, $R^2$, $R^3$, $R^4$, $Q^1$, and $Q^2$ are as previously disclosed, can be generated in a three-step, one-pot sequence by submitting an acyl azide 3-2, wherein $Ar^1$, $L^1$, and $Ar^2$ are as previously disclosed, to Curtius rearrangment conditions to generate an isocyanate in a polar, aprotic solvent such as acetonitrile at a temperature of about 75 to about 85° C., as in step a of Scheme 3. The isocyanate is allowed to react with a thiourea 3-3, wherein $R^4$ is as previously disclosed, in the presence of a base such as cesium carbonate at about room temperature (Scheme 3, step b). The formation of a ring including $R^2$ and $R^3$ can be accomplished by reaction with an alkylating agent, such as methyl bromoacetate, in a mixed polar solvent system, such as acetonitrile-ethanol and in the presence of sodium acetate at a temperature of about 50 to about 70° C., to afford compound 3-1, wherein $Ar^1$, $L^1$, $Ar^2$, $R^1$, $R^2$, $R^3$, $R^4$, $Q^1$, and $Q^2$ are as previously disclosed (Scheme 3, step c). In the two-step, one-pot method, an acyl azide 3-2, wherein $Ar^1$, $L^1$, and $Ar^2$ are as previously disclosed, is submitted to Curtius rearrangment conditions to generate an isocyanate in a polar, aprotic solvent such as acetonitrile at a temperature of about 75 to about 85° C., as in step a of Scheme 4. The isocyanate is reacted with imine 3-4, wherein $R^2$, $R^3$, $R^4$, and $Q^2$ are as previously disclosed, as in step d of Scheme 3, to Scheme 2

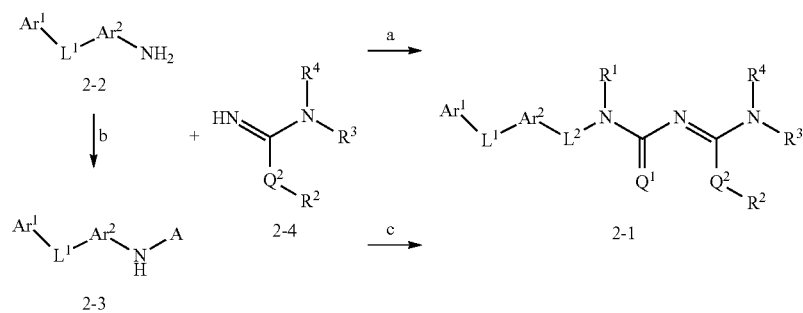

afford compound 3-1, wherein $Ar^1$, $L^1$, $Ar^2$, $R^1$, $R^2$, $R^3$, $R^4$, $Q^1$, and $Q^2$ are as previously disclosed.

Scheme 3

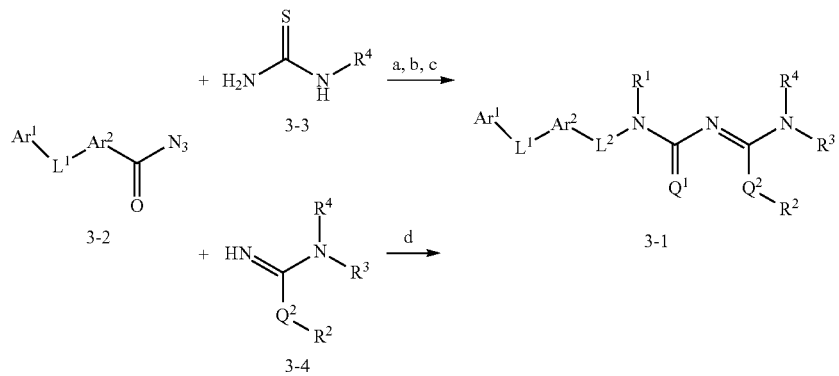

The compounds 4-1, wherein $Ar^1$, $L^1$, $Ar^2$, $R^1$, $R^2$, $R^3$, $R^4$, $Q^1$, and $Q^2$ are as previously disclosed, can be generated in two steps by reaction of tert-butyl aminobenzoate 4-2, wherein $Ar^2$ and $L^2$ are as previously disclosed, with an activating agent, such as triphosgene or bis(2,5-dioxopyrrolidin-1-yl) carbonate, in the presence of a base, such as N,N-diisopropylethylamine, in an aprotic solvent such as dichloromethane or acetonitrile as in Scheme 4, step a. To the mixture is then added an imine 4-3, wherein $R^2$, $R^3$, $R^4$, and $Q^2$ are as previously disclosed, to provide the tert-butyl ester of 4-4, as in step b of Scheme 4. The ester is removed by treatment with an acid, such as hydrogen chloride in dioxane or neat trifluoroacetic acid to provide the acid 4-4, wherein $Ar^2$, $R^1$, $R^2$, $R^3$, $R^4$, $Q^1$, and $Q^2$ are as previously disclosed (Scheme 4, step c). The acid 4-4 is treated with an activating agent, such as (benzotriazol-1-yloxy)tripyrrolidinophosphonium hexafluorophosphate (PyBOP) in an aprotic solvent, such as dichloromethane, in the presence of a base such as N,N-diisopropylethylamine, and an aryl hydrazine or hydrazine hydrochloride 4-5, wherein $Ar^1$ is as previously disclosed, to furnish compound 4-1, wherein $Ar^1$, $L^1$, $Ar^2$, $R^1$, $R^2$, $R^3$, $R^4$, $Q^1$, and $Q^2$ are as previously disclosed.

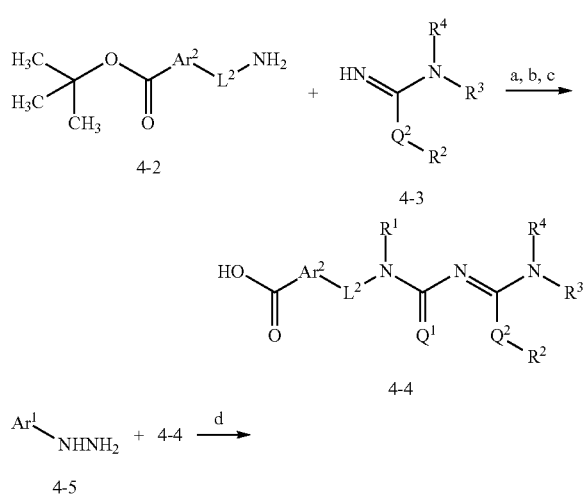

-continued

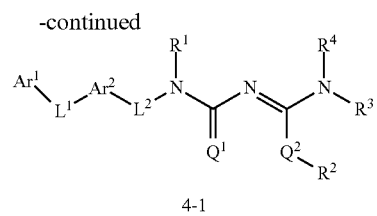

Acid and Salt Derivatives and Solvates

The compounds disclosed in this invention can be in the form of pesticidally acceptable acid addition salts.

By way of non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids.

Additionally, by way of non-limiting example, an acid function can form salts including those derived from alkali or alkaline earth metals and those derived from ammonia and amines. Examples of preferred cations include sodium, potassium, magnesium, and aminium cations.

The salts are prepared by contacting the free base form with a sufficient amount of the desired acid to produce a salt. The free base forms may be regenerated by treating the salt with a suitable dilute aqueous base solution such as dilute aqueous sodium hydroxide (NaOH), potassium carbonate, ammonia, and sodium bicarbonate. As an example, in many cases, a pesticide is modified to a more water soluble form e.g. 2,4-dichlorophenoxy acetic acid dimethyl amine salt is a more water soluble form of 2,4-dichlorophenoxy acetic acid, a well-known herbicide.

The compounds disclosed in this invention can also form stable complexes with solvent molecules that remain intact after the non-complexed solvent molecules are removed from the compounds. These complexes are often referred to as "solvates."

Stereoisomers

Certain compounds disclosed in this document can exist as one or more stereoisomers. The various stereoisomers include geometric isomers, diastereomers, and enantiomers. Thus, the compounds disclosed in this invention include racemic mixtures, individual stereoisomers, and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials, or by conventional resolution procedures.

Pests

In another embodiment, the invention disclosed in this document can be used to control pests.

In another embodiment, the invention disclosed in this document can be used to control pests of the Phylum Nematoda.

In another embodiment, the invention disclosed in this document can be used to control pests of the Phylum Arthropoda.

In another embodiment, the invention disclosed in this document can be used to control pests of the Subphylum Chelicerata.

In another embodiment, the invention disclosed in this document can be used to control pests of the Class Arachnida.

In another embodiment, the invention disclosed in this document can be used to control pests of the Subphylum Myriapoda.

In another embodiment, the invention disclosed in this document can be used to control pests of the Class Symphyla.

In another embodiment, the invention disclosed in this document can be used to control pests of the Subphylum Hexapoda.

In another embodiment, the invention disclosed in this document can be used to control pests of the Class Insecta.

In another embodiment, the invention disclosed in this document can be used to control Coleoptera (beetles). A non-exhaustive list of these pests includes, but is not limited to, *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhorned beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turfgrass *Ataenius*), *Atomaria linearis* (pygmy mangold beetle), *Aulacophora* spp., *Bothynoderes punctiventris* (beet root weevil), *Bruchus* spp. (weevils), *Bruchus pisorum* (pea weevil), *Cacoesia* spp., *Callosobruchus maculatus* (southern cow pea weevil), *Carpophilus hemipteras* (dried fruit beetle), *Cassida vittata, Cerosterna* spp., *Cerotoma* spp. (chrysomeids), *Cerotoma trifurcata* (bean leaf beetle), *Ceutorhynchus* spp. (weevils), *Ceutorhynchus assimilis* (cabbage seedpod weevil), *Ceutorhynchus napi* (cabbage curculio), *Chaetocnema* spp. (chrysomelids), *Colaspis* spp. (soil beetles), *Conoderus scalaris, Conoderus stigmosus, Conotrachelus nenuphar* (plum curculio), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leafcutting weevil), *Dermestes lardarius* (larder beetle), *Dermestes maculates* (hide beetle), *Diabrotica* spp. (chrysolemids), *Epilachna varivestis* (Mexican bean beetle), *Faustinus cubae, Hylobius pales* (pales weevil), *Hypera* spp. (weevils), *Hypera postica* (alfalfa weevil), *Hyperdoes* spp. (Hyperodes weevil), *Hypothenemus hampei* (coffee berry beetle), *Ips* spp. (engravers), *Lasioderma serricorne* (cigarette beetle), *Leptinotarsa decemlineata* (Colorado potato beetle), *Liogenys fuscus, Liogenys suturalis, Lissorhoptrus oryzophilus* (rice water weevil), *Lyctus* spp. (wood beetles/powder post beetles), *Maecolaspis joliveti, Megascelis* spp., *Melanotus communis, Meligethes* spp., *Meligethes aeneus* (blossom beetle), *Melolontha melolontha* (common European cockchafer), *Oberea brevis, Oberea linearis, Oryctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae, Pantomorus* spp. (weevils), *Phyllophaga* spp. (May/June beetle), *Phyllophaga cuyabana, Phyllotreta* spp. (chrysomelids), *Phynchites* spp., *Popillia japonica* (Japanese beetle), *Prostephanus truncates* (larger grain borer), *Rhizopertha dominica* (lesser grain borer), *Rhizotrogus* spp. (European chafer), *Rhynchophorus* spp. (weevils), *Scolytus* spp. (wood beetles), *Shenophorus* spp. (Billbug), *Sitona lineatus* (pea leaf weevil), *Sitophilus* spp. (grain weevils), *Sitophilus granaries* (granary weevil), *Sitophilus oryzae* (rice weevil), *Stegobium* paniceum (drugstore beetle), *Tribolium* spp. (flour beetles), *Tribolium castaneum* (red flour beetle), *Tribolium confusum* (confused flour beetle), *Trogoderma variabile* (warehouse beetle), and *Zabrus tenebioides*.

In another embodiment, the invention disclosed in this document can be used to control Dermaptera (earwigs).

In another embodiment, the invention disclosed in this document can be used to control Dictyoptera (cockroaches). A non-exhaustive list of these pests includes, but is not limited to, *Blattella germanica* (German cockroach), *Blatta orientalis* (oriental cockroach), *Parcoblatta pennylvanica, Periplaneta americana* (American cockroach), *Periplaneta australoasiae* (Australian cockroach), *Periplaneta brunnea* (brown cockroach), *Periplaneta fuliginosa* (smokybrown cockroach), *Pyncoselus suninamensis* (Surinam cockroach), and *Supella longipalpa* (brownbanded cockroach).

In another embodiment, the invention disclosed in this document can be used to control Diptera (true flies). A non-exhaustive list of these pests includes, but is not limited to, *Aedes* spp. (mosquitoes), *Agromyza frontella* (alfalfa blotch leafminer), *Agromyza* spp. (leaf miner flies), *Anastrepha* spp. (fruit flies), *Anastrepha suspensa* (Caribbean fruit fly), *Anopheles* spp. (mosquitoes), *Batrocera* spp. (fruit flies), *Bactrocera cucurbitae* (melon fly), *Bactrocera dorsalis* (oriental fruit fly), *Ceratitis* spp. (fruit flies), *Ceratitis capitata* (Mediterranean fruit fly), *Chrysops* spp. (deer flies), *Cochlomyia* spp. (screwworms), *Contarinia* spp. (gall midges), *Culex* spp. (mosquitoes), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis* (little house fly), *Fannia scalaris* (latrine fly), Gasterophilus intestinalis (horse bot fly), *Gracillia perseae, Haematobia irritans* (horn fly), *Hylemyia* spp. (root maggots), *Hypoderma lineatum* (common cattle grub), *Liriomyza* spp. (leafminer flies), *Liriomyza brassica* (serpentine leafminer), *Melophagus ovinus* (sheep ked), *Musca* spp. (muscid flies), *Musca autumnalis* (face fly), *Musca domestica* (housefly), *Oestrus ovis* (sheep bot fly), *Oscinella frit* (frit fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies), and *Tipula* spp. (crane flies).

In another embodiment, the invention disclosed in this document can be used to control Hemiptera (true bugs). A non-exhaustive list of these pests includes, but is not limited to, *Acrosternum hilare* (green stink bug), *Blissus leucopterus* (chinch bug), *Calocoris norvegicus* (potato mirid), *Cimex hemipterus* (tropical bed bug), *Cimex lectularius* (bed bug), *Dagbertus fasciatus*, *Dichelops furcatus*, *Dysdercus suturellus* (cotton stainer), *Edessa meditabunda*, *Eurygaster maura* (cereal bug), *Euschistus heros*, *Euschistus servus* (brown stink bug), *Helopeltis antonii*, *Helopeltis theivora* (tea blight plantbug), *Lagynotomus* spp. (stink bugs), *Leptocorisa oratorius*, *Leptocorisa varicornis*, *Lygus* spp. (plant bugs), *Lygus hesperus* (western tarnished plant bug), *Maconellicoccus hirsutus*, *Neurocolpus longirostris*, *Nezara viridula* (southern green stink bug), *Phytocoris* spp. (plant bugs), *Phytocoris californicus*, *Phytocoris relativus*, *Piezodorus guildingi*, *Poecilocapsus lineatus* (fourlined plant bug), *Psallus vaccinicola*, *Pseudacysta perseae*, *Scaptocoris castanea*, and *Triatoma* spp. (bloodsucking conenose bugs/kissing bugs).

In another embodiment, the invention disclosed in this document can be used to control Homoptera (aphids, scales, whiteflies, leafhoppers). A non-exhaustive list of these pests includes, but is not limited to, *Acrythosiphon pisum* (pea aphid), *Adelges* spp. (adelgids), *Aleurodes proletella* (cabbage whitefly), *Aleurodicus disperses*, *Aleurothrixus floccosus* (woolly whitefly), *Aluacaspis* spp., *Amrasca bigutella bigutella*, *Aphrophora* spp. (leafhoppers), *Aonidiella aurantii* (California red scale), *Aphis* spp. (aphids), *Aphis gossypii* (cotton aphid), *Aphis pomi* (apple aphid), *Aulacorthum solani* (foxglove aphid), *Bemisia* spp. (whiteflies), *Bemisia argentifolii*, *Bemisia tabaci* (sweetpotato whitefly), *Brachycolus noxius* (Russian aphid), *Brachycorynella asparagi* (asparagus aphid), *Brevennia rehi*, *Brevicoryne brassicae* (cabbage aphid), *Ceroplastes* spp. (scales), *Ceroplastes rubens* (red wax scale), Chionaspis spp. (scales), *Chrysomphalus* spp. (scales), *Coccus* spp. (scales), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata*, *Metopolophium dirhodum* (rose grain aphid), *Mictis longicornis*, *Myzus persicae* (green peach aphid), *Nephotettix* spp. (leafhoppers), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape *phylloxera*), Physokermes *piceae* (spruce bud scale), *Planococcus* spp. (mealybugs), *Pseudococcus* spp. (mealybugs), *Pseudococcus brevipes* (pineapple mealybug), *Quadraspidiotus perniciosus* (San Jose scale), *Rhapalosiphum* spp. (aphids), *Rhapalosiphum maida* (corn leaf aphid), *Rhapalosiphum padi* (oat bird-cherry aphid), *Saissetia* spp. (scales), *Saissetia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (bandedwing whitefly), *Unaspis* spp. (scales), *Unaspis yanonensis* (arrowhead scale), and Zulia entreriana.

In another embodiment, the invention disclosed in this document can be used to control Hymenoptera (ants, wasps, and bees). A non-exhaustive list of these pests includes, but is not limited to, *Acromyrrmex* spp., *Athalia rosae*, *Atta* spp. (leafcutting ants), *Camponotus* spp. (carpenter ants), *Diprion* spp. (sawflies), *Formica* spp. (ants), *Iridomyrmex humilis* (Argentine ant), *Monomorium* ssp., *Monomorium minumum* (little black ant), *Monomorium pharaonis* (Pharaoh ant), *Neodiprion* spp. (sawflies), *Pogonomyrmex* spp. (harvester ants), *Polistes* spp. (paper wasps), *Solenopsis* spp. (fire ants), *Tapoinoma sessile* (odorous house ant), *Tetranomorium* spp. (pavement ants), *Vespula* spp. (yellow jackets), and *Xylocopa* spp. (carpenter bees).

In another embodiment, the invention disclosed in this document can be used to control Isoptera (termites). A non-exhaustive list of these pests includes, but is not limited to, *Coptotermes* spp., *Coptotermes curvignathus*, *Coptotermes frenchii*, *Coptotermes formosanus* (Formosan subterranean termite), *Cornitermes* spp. (nasute termites), *Cryptotermes* spp. (drywood termites), *Heterotermes* spp. (desert subterranean termites), *Heterotermes aureus*, *Kalotermes* spp. (drywood termites), *Incisitermes* spp. (drywood termites), *Macrotermes* spp. (fungus growing termites), *Marginitermes* spp. (drywood termites), *Microcerotermes* spp. (harvester termites), *Microtermes obesi*, *Procornitermes* spp., *Reticulitermes* spp. (subterranean termites), *Reticulitermes banyulensis*, *Reticulitermes grassei*, *Reticulitermes flavipes* (eastern subterranean termite), *Reticulitermes hageni*, *Reticulitermes hesperus* (western subterranean termite), *Reticulitermes santonensis*, *Reticulitermes speratus*, *Reticulitermes tibialis*, *Reticulitermes virginicus*, *Schedorhinotermes* spp., and *Zootermopsis* spp. (rotten-wood termites).

In another embodiment, the invention disclosed in this document can be used to control Lepidoptera (moths and butterflies). A non-exhaustive list of these pests includes, but is not limited to, *Achoea janata*, *Adoxophyes* spp., *Adoxophyes orana*, *Agrotis* spp. (cutworms), *Agrotis ipsilon* (black cutworm), *Alabama argillacea* (cotton leafworm), *Amorbia cuneana*, *Amyelosis transitella* (navel orangeworm), *Anacamptodes defectaria*, *Anarsia lineatella* (peach twig borer), *Anomis sabulfera* (jute looper), *Anticarsia gemmatalis* (velvetbean caterpillar), *Archips argyrospila* (fruit tree leafroller), *Archips* rosana (rose leaf roller), *Argyrotaenia* spp. (tortricid moths), *Argyrotaenia citrana* (orange *tortrix*), *Autographa gamma*, *Bonagota cranaodes*, *Borbo cinnara* (rice leaf folder), *Bucculatrix thurberiella* (cotton leaf perforator), *Caloptilia* spp. (leaf miners), *Capua reticulana*, *Carposina niponensis* (peach fruit moth), *Chilo* spp., *Chlumetia transversa* (mango shoot borer), *Choristoneura rosaceana* (oblique banded leaf roller), *Chrysodeixis* spp., *Cnaphalocerus medinalis* (grass leafroller), Colas spp., *Conpomorpha cramerella*, *Cossus cossus* (carpenter moth), *Crambus* spp. (Sod webworms), *Cydia funebrana* (plum fruit moth), *Cydia molesta* (oriental fruit moth), *Cydia nignicana* (pea moth), *Cydia pomonella* (codling moth), *Darna diducta*, *Diaphania* spp. (stem borers), *Diatraea* spp. (stalk borers), *Diatraea saccharalis* (sugarcane borer), *Diatraea graniosella* (southwestern corn borer), *Earias* spp. (bollworms), *Earias insulata* (Egyptian bollworm), *Earias vitella* (rough northern bollworm), *Ecdytopopha aurantianum*, *Elasmopalpus lignosellus* (lesser cornstalk borer), *Epiphysias postruttana* (light brown apple moth), *Ephestia* spp. (flour moths), *Ephestia cautella* (almond moth), *Ephestia elutella* (tobacco moth), *Ephestia kuehniella* (Mediterranean flour moth), *Epimeces* spp., *Epinotia aporema*, *Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Grapholita molesta* (oriental fruit moth), *Hedylepta indicata* (bean leaf webber), *Helicoverpa* spp. (noctuid moths), *Helicoverpa armigera*

(cotton bollworm), *Helicoverpa zea* (bollworm/corn earworm), *Heliothis* spp. (noctuid moths), *Heliothis virescens* (tobacco budworm), *Hellula undalis* (cabbage webworm), *Indarbela* spp. (root borers), *Keiferia lycopersicella* (tomato pinworm), *Leucinodes orbonalis* (eggplant fruit borer), *Leucoptera malifoliella, Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyonetia clerkella* (apple leaf miner), Mahasena *corbetti* (oil palm bagworm), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia, Pandemis cerasana* (common currant *tortrix*), *Pandemis heparana* (brown apple *tortrix*), *Papilio demodocus, Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella, Phyllonorycter* spp. (leafminers), *Pieris rapae* (imported cabbageworm), *Plathypena scabra, Plodia interpunctella* (Indian meal moth), *Plutella xylostella* (diamondback moth), *Polychrosis viteana* (grape berry moth), *Prays endocarpa, Prays oleae* (olive moth), *Pseudaletia* spp. (noctuid moths), *Pseudaletia unipunctata* (armyworm), *Pseudoplusia includens* (soybean looper), *Rachiplusia nu, Scirpophaga incertulas, Sesamia* spp. (stemborers), *Sesamia inferens* *selliella* (webbing clothes moth), *Trichoplusia ni* (cabbage looper), *Tuta absoluta, Yponomeuta* spp., *Zeuzera coffeae* (red branch borer), and *Zeuzera pyrina* (leopard moth).

In another embodiment, the invention disclosed in this document can be used to control Mallophaga (chewing lice). A non-exhaustive list of these pests includes, but is not limited to, *Bovicola ovis* (sheep biting louse), *Menacanthus stramineus* (chicken body louse), and *Menopon gallinea* (common hen louse).

In another embodiment, the invention disclosed in this document can be used to control Orthoptera (grasshoppers, locusts, and crickets). A non-exhaustive list of these pests includes, but is not limited to, *Anabrus simplex* (Mormon cricket), Gryllotalpidae (mole crickets), *Locusta migratoria, Melanoplus* spp. (grasshoppers), *Microcentrum retinerve* (angular winged katydid), *Pterophylla* spp. (katydids), chistocerca *gregaria, Scudderia furcata* (fork tailed bush katydid), and *Valanga* nigricorni.

In another embodiment, the invention disclosed in this document can be used to control Phthiraptera (sucking lice). A non-exhaustive list of these pests includes, but is not limited to, *Haematopinus* spp. (cattle and hog lice), *Linognathus ovillus* (sheep louse), *Pediculus humanus* capitis (human body louse), *Pediculus humanus humanus* (human body lice), and *Pthirus pubis* (crab louse), In another embodiment, the invention disclosed in this document can be used to control Siphonaptera (fleas). A non-exhaustive list of these pests includes, but is not limited to, *Ctenocephalides canis* (dog flea), *Ctenocephalides felis* (cat flea), and *Pulex irritans* (human flea).

In another embodiment, the invention disclosed in this document can be used to control Thysanoptera (*thrips*). A non-exhaustive list of these pests includes, but is not limited to, *Frankliniella fusca* (tobacco *thrips*), *Frankliniella occidentalis* (western flower *thrips*), *Frankliniella shultzei Frankliniella williamsi* (corn *thrips*), *Heliothrips haemorrhaidalis* (greenhouse *thrips*), *Riphiphorothrips cruentatus,* *Scirtothrips* spp., *Scirtothrips citri* (citrus *thrips*), *Scirtothrips dorsalis* (yellow tea *thrips*), *Taeniothrips rhopalantennalis*, and *Thrips* spp.

In another embodiment, the invention disclosed in this document can be used to control Thysanura (bristletails). A non-exhaustive list of these pests includes, but is not limited to, *Lepisma* spp. (silverfish) and *Thermobia* spp. (firebrats).

In another embodiment, the invention disclosed in this document can be used to control Acarina (mites and ticks). A non-exhaustive list of these pests includes, but is not limited to, *Acarapsis woodi* (tracheal mite of honeybees), *Acarus* spp. (food mites), *Acarus siro* (grain mite), *Aceria mangiferae* (mango bud mite), Aculops spp., Aculops *lycopersici* (tomato russet mite), Aculops pelekasi, *Aculus* pelekassi, *Aculus schlechtendali* (apple rust mite), *Amblyomma americanum* (lone star tick), *Boophilus* spp. (ticks), *Brevipalpus* obovatus (privet mite), *Brevipalpus phoenicis* (red and black flat mite), *Demodex* spp. (mange mites), *Dermacentor* spp. (hard ticks), *Dermacentor variabilis* (American dog tick), *Dermatophagoides pteronyssinus* (house dust mite), Eotetranycus spp., *Eotetranychus carpini* (yellow spider mite), Epitimerus spp., *Eriophyes* spp., *Ixodes* spp. (ticks), Metatetranycus spp., Notoedres *cati, Oligonychus* spp., *Oligonychus* coffee, *Oligonychus* ilicus (southern red mite), *Panonychus* spp., *Panonychus citri* (citrus red mite), *Panonychus ulmi* (European red mite), Phyllocoptruta *oleivora* (citrus rust mite), Polyphagotarsonemun *latus* (broad mite), *Rhipicephalus sanguineus* (brown dog tick), Rhizoglyphus spp. (bulb mites), Sarcoptes *scabiei* (itch mite), Tegolophus perseaflorae, *Tetranychus* spp., *Tetranychus urticae* (two-spotted spider mite), and *Varroa destructor* (honey bee mite).

In another embodiment, the invention disclosed in this document can be used to control Nematoda (nematodes). A non-exhaustive list of these pests includes, but is not limited to, Aphelenchoides spp. (bud and leaf & pine wood nematodes), Belonolaimus spp. (sting nematodes), Criconemella spp. (ring nematodes), Dirofilaria *immitis* (dog heartworm), Ditylenchus spp. (stem and bulb nematodes), *Heterodera* spp. (cyst nematodes), *Heterodera zeae* (corn cyst nematode), Hirschmanniella spp. (root nematodes), Hoplolaimus spp. (lance nematodes), Meloidogyne spp. (root knot nematodes), Meloidogyne *incognita* (root knot nematode), Onchocerca *volvulus* (hook-tail worm), Pratylenchus spp. (lesion nematodes), Radopholus spp. (burrowing nematodes), and Rotylenchus renformis (kidney-shaped nematode).

In another embodiment, the invention disclosed in this document can be used to control Symphyla (symphylans). A non-exhaustive list of these pests includes, but is not limited to, *Scutigerella immaculata.*

Neonicotinoid-resistant insect is known in the art (see for example WO 2012/141754 A2). Compounds of the subject invention disclosed herein have the advantage of being superior or at least equal to insecticide activity against such neonicotinoid-resistant insect as compared to previously disclosed compounds. In some embodiments, the neonicotinoid-resistant insect has resistance to at least one of the insecticides selected from the group consisting of acetamiprid, clothianidin, dinotefuran, flupyradifurone (BYI 02960), imidacloprid, imidaclothiz, nitenpyram, thiacloprid, thiamethoxam, and combinations thereof. In other embodiments, the combination between the compounds of the subject invention and a second pesticide can be used for controlling such neonicotinoid-resistant insect. In further embodiments, the second pesitide is selected from the group consisting of acetamiprid, clothianidin, dinotefuran, flupyradifurone (BYI 02960), imidacloprid, imidaclothiz, nitenpyram, thiacloprid, and thiamethoxam.

Mixtures

The invention disclosed in this document can also be used with various insecticides, both for reasons of economy and synergy. Such insecticides include, but are not limited to, antibiotic insecticides, macrocyclic lactone insecticides (for example, avermectin insecticides, milbemycin insecticides, and spinosyn insecticides), arsenical insecticides, botanical insecticides, carbamate insecticides (for example, benzofuranyl methylcarbamate insecticides, dimethylcarbamate insecticides, oxime carbamate insecticides, and phenyl methylcarbamate insecticides), diamide insecticides, desiccant insecticides, dinitrophenol insecticides, fluorine insecticides, formamidine insecticides, fumigant insecticides, inorganic insecticides, insect growth regulators (for example, chitin synthesis inhibitors, juvenile hormone mimics, juvenile hormones, moulting hormone agonists, moulting hormones, moulting inhibitors, precocenes, and other unclassified insect growth regulators), nereistoxin analogue insecticides, nicotinoid insecticides (for example, nitroguanidine insecticides, nitromethylene insecticides, and pyridylmethylamine insecticides), organochlorine insecticides, organophosphorus insecticides, oxadiazine insecticides, oxadiazolone insecticides, phthalimide insecticides, pyrazole insecticides, pyrethroid insecticides, pyrimidinamine insecticides, pyrrole insecticides, tetramic acid insecticides, tetronic acid insecticides, thiazole insecticides, thiazolidine insecticides, thiourea insecticides, urea insecticides, as well as, other unclassified insecticides.

Some of the particular insecticides that can be employed beneficially in combination with the invention disclosed in this document include, but are not limited to, the following 1,2-dichloropropane, 1,3-dichloropropene, abamectin, acephate, acetamiprid, acethion, acetoprole, acrinathrin, acrylonitrile, acynonapyr, afidopyropen, afoxolaner, alanycarb, aldicarb, aldoxycarb, aldrin, allethrin, allosamidin, allyxycarb, alpha-cypermethrin, alpha-endosulfan, amidithion, aminocarb, amiton, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, benzpyrimoxan, beta-cyfluthrin, beta-cypermethrin, bifenthrin, bioallethrin, bioethanomethrin, biopermethrin, bioresmethrin, bistrifluron, borax, boric acid, broflanilide, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chlorantraniliprole, chlorbicyclen, chlordane, chlordecone, chlordimeform, chlorethoxyfos, chlorfenapyr, chlorfenvinphos, chlorfluazuron, chlormephos, chloroform, chloropicrin, chloroprallethrin, chlorphoxim, chlorprazophos, chlorpyrifos, chlorpyrifos-methyl, chlorthiophos, chromafenozide, cinerin I, cinerin II, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclaniliprole, cyclethrin, cyclobutrifluram, cycloprothrin, cycloxaprid, cyetpyrafen, cyfluthrin, cyhalothrin, cyhalodiamide, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicloromezotiaz, dicresyl, dicrotophos, dicyclanil, dieldrin, diflubenzuron, dilor, dimefluthrin, dimefox, dimetan, dimethoate, dimethrin, dimethylvinphos, dimetilan, dimpropyridaz, dinex, dinoprop, dinosam, dinotefuran, diofenolan, dioxabenzofos, dioxacarb, dioxathion, disulfoton, dithicrofos, d-limonene, DNOC, doramectin, ecdysterone, emamectin, EMPC, empenthrin, endosulfan, endothion, endrin, EPN, epofenonane, eprinomectin, epsilon-metofluthrin, epsilon-momfluorothrin, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, flufiprole, fluhexafon, flupentiofenox, flupyradifurone, flupyrimin, fluralaner, fluvalinate, fluxametamide, fonofos, formetanate, formothion, formparanate, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imidaclothiz, imiprothrin, indoxacarb, iodomethane, IPSP, isazofos, isobenzan, isocarbophos, isocycloseram, isodrin, isofenphos, isoprocarb, isoprothiolane, isothioate, isoxathion, ivermectin, jasmolin I, jasmolin II, jodfenphos, juvenile hormone I, juvenile hormone II, juvenile hormone III, kappa-bifenthrin, kappa-tefluthrin, kelevan, kinoprene, lambda-cyhalothrin, lead arsenate, lepimectin, leptophos, lindane, lirimfos, lotilaner, lufenuron, lythidathion, malathion, malonoben, mazidox, mecarbam, mecarphon, menazon, meperfluthrin, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methylchloroform, methylene chloride, metofluthrin, metolcarb, metoxadiazone, mevinphos, mexacarbate, milbemectin, milbemycin oxime, mipafox, mirex, momfluorothrin, monocrotophos, morphothion, moxidectin, naftalofos, naled, naphthalene, nicotine, nifluridide, nitenpyram, nithiazine, nitrilacarb, novaluron, noviflumuron, omethoate, oxamyl, oxazosulfyl, oxydemeton-methyl, oxydeprofos, oxydisulfoton, paichongding, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluthrin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sarolaner, sophamide, spinetoram, spinosad, spiromesifen, spiropidion, spirotetramat, sulcofuron, sulfoxaflor, sulfluramid, sulfotep, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, tetraniliprole, tetrachlorantraniliprole, theta-cypermethrin, thiacloprid, thiamethoxam, thicrofos, thiocarboxime, thiocyclam, thiodicarb, thiofanox, thiometon, thiosultap, thuringiensin, tolfenpyrad, tralomethrin, transfluthrin, transpermethrin, triarathene, triazamate, triazophos, trichlorfon, trichlormetaphos-3, trichloronat, trifenofos, triflumezopyrim, triflumuron, trimethacarb, triprene, tyclopyrazoflor, vamidothion, vaniliprole, XMC, xylylcarb, zeta-cypermethrin, zolaprofos, and α-ecdysone.

Additionally, any combination of the above insecticides can be used.

The invention disclosed in this document can also be used, for reasons of economy and synergy, with acaricides, algicides, antifeedants, avicides, bactericides, bird repellents, chemosterilants, fungicides, herbicide safeners, herbicides, insect attractants, insect repellents, mammal repellents, mating disrupters, molluscicides, plant activators, plant growth regulators, rodenticides, synergists, defoliants, desiccants, disinfectants, semiochemicals, and virucides (these categories not necessarily mutually exclusive).

Synergistic Mixtures

The invention disclosed in this document can be used with other compounds such as the ones mentioned under the heading "Mixtures" to form synergistic mixtures where the mode of action of the compounds in the mixtures are the same, similar, or different.

Examples of mode of actions include, but are not limited to: acetylcholinesterase inhibitor; sodium channel modulator; chitin biosynthesis inhibitor; GABA-gated chloride channel antagonist; GABA- and glutamate-gated chloride channel agonist; acetylcholine receptor agonist; MET I inhibitor; Mg-stimulated ATPase inhibitor; nicotinic acetylcholine receptor; Midgut membrane disrupter; oxidative phosphorylation disrupter, and ryanodine receptor (RyRs).

Additionally, the following compounds are known as synergists and can be used with the invention disclosed in this document: piperonyl butoxide, piprotal, propyl isome, sesamex, sesamolin, and sulfoxide.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions.

Pesticides are applied most often as aqueous suspensions or emulsions prepared from concentrated formulations of such pesticides. Such water-soluble, water-suspendable, or emulsifiable formulations, are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually chosen from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and nonionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and nonionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums, may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They are used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one nonionic lipophilic surface-active agent, (2) at least one nonionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use this embodiment will be referred to as "OIWE".

Other Formulation Components

Generally, the invention disclosed in this document when used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of a particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, nonionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Nonionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The type of surfactants usually used for solubilization are nonionics: sorbitan monooleates; sorbitan monooleate ethoxylates; and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often nonionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, ULV (ultra low volume) formulations, and to a lesser extent granular formulations. Sometimes mixtures of solvents are used. The first main groups of solvents are aliphatic paraffinic oils such as kerosene or refined paraffins. The second main group and the most common comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, e.g. bentonite; magnesium aluminum silicate; and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazalin-3-one (BIT).

The presence of surfactants, which lower interfacial tension, often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane while the non-silicone anti-foam agents are water-insoluble oils, such as octanol and nonanol, or silica. In both cases, the function of the anti-foam agent is to displace the surfactant from the air-water interface.

Applications

The actual amount of pesticide to be applied to loci of pests is generally not critical and can readily be determined by those skilled in the art. In general, concentrations from about 0.01 grams of pesticide per hectare to about 5000 grams of pesticide per hectare are expected to provide good control.

The locus to which a pesticide is applied can be any locus inhabited by any pest, for example, vegetable crops, fruit and nut trees, grapevines, ornamental plants, domesticated animals, the interior or exterior surfaces of buildings, and the soil around buildings. Controlling pests generally means that pest populations, activity, or both, are reduced in a locus. This can come about when: pest populations are repulsed from a locus; when pests are incapacitated in or around a locus; or pests are exterminated, in whole or in part, in or around a locus. Of course a combination of these results can occur. Generally, pest populations, activity, or both are desirably reduced more than fifty percent, preferably more than 90 percent.

Generally, with baits, the baits are placed in the ground where, for example, termites can come into contact with the bait. Baits can also be applied to a surface of a building, (horizontal, vertical, or slant surface) where, for example, ants, termites, cockroaches, and flies, can come into contact with the bait.

Because of the unique ability of the eggs of some pests to resist pesticides repeated applications may be desirable to control newly emerged larvae.

Systemic movement of pesticides in plants may be utilized to control pests on one portion of the plant by applying the pesticides to a different portion of the plant. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement or any other beneficial traits. Furthermore, such seed treatments with the invention disclosed in this document can further enhance the ability of a plant to better withstand stressful growing conditions. This results in a healthier, more vigorous plant, which can lead to higher yields at harvest time.

It should be readily apparent that the invention can be used with plants genetically transformed to express specialized traits, such as *Bacillus thuringiensis* or other insecticidal toxins, or those expressing herbicide resistance, or those with "stacked" foreign genes expressing insecticidal toxins, herbicide resistance, nutrition-enhancement or any other beneficial traits.

The invention disclosed in this document is suitable for controlling endoparasites and ectoparasites in the veterinary medicine sector or in the field of animal keeping. Compounds are applied in a known manner, such as by oral administration in the form of, for example, tablets, capsules, drinks, granules, by dermal application in the form of, for example, dipping, spraying, pouring on, spotting on, and dusting, and by parenteral administration in the form of, for example, an injection.

The invention disclosed in this document can also be employed advantageously in livestock keeping, for example, cattle, sheep, pigs, chickens, and geese. Suitable formulations are administered orally to the animals with the drinking water or feed. The dosages and formulations that are suitable depend on the species.

Before a pesticide can be used or sold commercially, such pesticide undergoes lengthy evaluation processes by various governmental authorities (local, regional, state, national, international). Voluminous data requirements are specified by regulatory authorities and must be addressed through data generation and submission by the product registrant or by another on the product registrant's behalf. These governmental authorities then review such data and if a determination of safety is concluded, provide the potential user or seller with product registration approval. Thereafter, in that locality where the product registration is granted and supported, such user or seller may use or sell such pesticide.

Combinations

In another embodiment of this invention, molecules of Formula A, Formula One, Formula Two or Formula Three may be used in combination (such as, in a compositional mixture, or a simultaneous or sequential application) with one or more active ingredients.

In another embodiment of this invention, molecules of Formula A, Formula One, Formula Two or Formula Three may be used in combination (such as, in a compositional mixture, or a simultaneous or sequential application) with one or more active ingredients each having a mode of action (MoA) that is the same as, similar to, but more likely—different from, the MoA of the molecules of Formula A, Formula One, Formula Two or Formula Three.

In another embodiment, molecules of Formula A, Formula One, Formula Two or Formula Three may be used in combination (such as, in a compositional mixture, or a simultaneous or sequential application) with one or more molecules having acaricidal, algicidal, avicidal, bactericidal, fungicidal, herbicidal, insecticidal, molluscicidal, nematicidal, rodenticidal, and/or virucidal properties.

In another embodiment, the molecules of Formula A, Formula One, Formula Two or Formula Three may be used in combination (such as, in a compositional mixture, or a simultaneous or sequential application) with one or more molecules that are antifeedants, bird repellents, chemosterilants, herbicide safeners, insect attractants, insect repellents, mammal repellents, mating disrupters, plant activators, plant growth regulators, and/or synergists.

TABLE A

Weight Ratios
Molecule of the Formula A, Formula One, Formula
Two or Formula Three: active ingredient 100:1 to 1:100
50:1 to 1:50
20:1 to 1:20
10:1 to 1:10
5:1 to 1:5
3:1 to 1:3
2:1 to 1:2
1:1

Weight ratios of a molecule of Formula A, Formula One, Formula Two or Formula Three to an active ingredient may also be depicted as X:Y; wherein X is the parts by weight of a molecule of Formula A, Formula One, Formula Two or Formula Three and Y is the parts by weight of active ingredient. The numerical range of the parts by weight for X is $0<X\le100$ and the parts by weight for Y is $0<Y\le100$ and is shown graphically in Table B. By way of non-limiting example, the weight ratio of a molecule of Formula A, Formula One, Formula Two or Formula Three to an active ingredient may be 20:1.

Ranges of weight ratios of a molecule of Formula A, Formula One, Formula Two or Formula Three to an active ingredient may be depicted as $X_1:Y_1$ to $X_2:Y_2$, wherein X and Y are defined as above.

TABLE B

| active ingredient (Y) Parts by weight | | | | | | | | | |
|---|---|---|---|---|---|---|---|---|---|
| 100 | X, Y | | X, Y | | | X, Y | | | |
| 50 | X, Y | X, Y | X, Y | | | X, Y | X, Y | | |
| 20 | X, Y | | X, Y | X, Y | | X, Y | | X, Y | |
| 15 | X, Y | X, Y | | | | | X, Y | X, Y | X, Y |
| 10 | X, Y | | X, Y | | | | | | |
| 5 | X, Y | X, Y | X, Y | | | X, Y | | | |
| 3 | X, Y | X, Y | | X, Y | X, Y | | X, Y | X, Y | X, Y |
| 2 | X, Y | | X, Y | X, Y | | X, Y | | X, Y | |
| 1 | X, Y | X, Y | X, Y | X, Y | X, Y | X, Y | X, Y | X, Y | X, Y |
| | 1 | 2 | 3 | 5 | 10 | 15 | 20 | 50 | 100 |
| | molecule of Formula A, Formula One, Formula Two or Formula Three (X) Parts by weight | | | | | | | | |

In another embodiment, molecules of Formula A, Formula One, Formula Two or Formula Three may also be used in combination (such as in a compositional mixture, or a simultaneous or sequential application) with one or more biopesticides.

In another embodiment, in a pesticidal composition combinations of a molecule of Formula A, Formula One, Formula Two or Formula Three and an active ingredient may be used in a wide variety of weight ratios. For example, in a two-component mixture, the weight ratio of a molecule of Formula A, Formula One, Formula Two or Formula Three to an active ingredient, the weight ratios in Table A may be used. However, in general, weight ratios less than about 10:1 to about 1:10 are preferred. It is also preferred sometimes to use a three, four, five, six, seven, or more, component mixture comprising a molecule of Formula A, Formula One, Formula Two or Formula Three and an additional two or more active ingredients.

In one embodiment, the range of weight ratios may be $X_1:Y_1$ to $X_2:Y_2$, wherein $X_1>Y_1$ and $X_2<Y_2$. By way of non-limiting example, the range of a weight ratio of a molecule of Formula A, Formula One, Formula Two or Formula Three to an active ingredient may be between 3:1 and 1:3, inclusive of the endpoints.

In another embodiment, the range of weight ratios may be $X_1:Y_1$ to $X_2:Y_2$, wherein $X_1>Y_1$ and $X_2>Y_2$. By way of non-limiting example, the range of weight ratio of a molecule of Formula A, Formula One, Formula Two or Formula Three to an active ingredient may be between 15:1 and 3:1, inclusive of the endpoints.

In another embodiment, the range of weight ratios may be $X_1:Y_1$ to $X_2:Y_2$, wherein $X<Y_1$ and $X_2<Y_2$. By way of non-limiting example, the range of weight ratios of a molecule of Formula A, Formula One, Formula Two or Formula Three to an active ingredient may be between about 1:3 and about 1:20, inclusive of the endpoints.

It is envisioned that certain weight ratios of a molecule of Formula A, Formula One, Formula Two or Formula Three to an active ingredient, as presented in Table A and B, may be synergistic.

EXAMPLES

The examples are for illustration purposes and are not to be construed as limiting the invention disclosed in this document to only the embodiments disclosed in these examples.

Starting materials, reagents and solvents which are obtained from commercial sources are used without further purification. Anhydrous solvents are purchased as Sure/Seal™ from Aldrich and are used as received. Melting points are obtained on a Thomas Hoover Unimelt capillary melting point apparatus or an OptiMelt Automated Melting Point System from Sanford Research Systems and are uncorrected. Examples using "room temperature" were conducted in climate controlled laboratories with temperatures ranging from about 20° C. to about 24° C. Molecules are given their known names, named according to naming programs within ISIS Draw, ChemDraw, or ACD Name Pro. If such programs are unable to name a molecule, such molecule is named using conventional naming rules. $^1$H Nuclear magnetic resonance (NMR) spectral data are in parts per million (ppm, δ) and were recorded at 300, 400, or 500; $^{13}$C NMR spectral data are in ppm (δ) and were recorded at 75, 100, or 150 MHz, and $^{19}$F NMR spectral data are in ppm (δ) and were recorded at 376 MHz, unless otherwise stated.

Example 1: Preparation of (Z)-1-(3-(2-isopropyl-5-methylphenyl)-4-oxothiazolidin-2-ylidene)-3-(4-((2-oxo-2-(4-(trifluoromethoxy)phenyl)ethyl)amino) phenethyl)urea (A1)

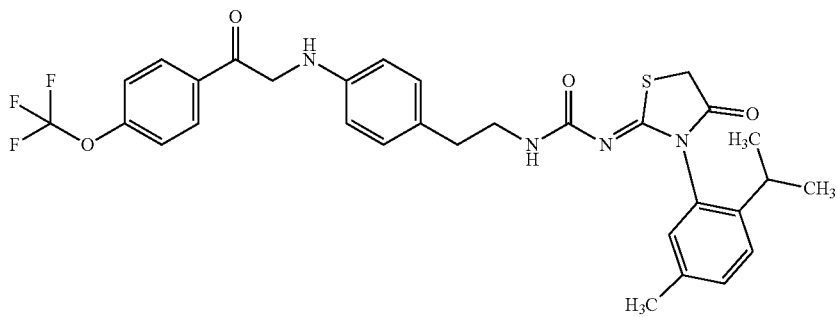 [SMILES: Cc1ccc(C(C)C)c(N2C(=O)CS/C2=N\C(=O)NCCc2ccc(NCC(=O)c3ccc(OC(F)(F)F)cc3)cc2)c1]

To a solution of (Z)-1-(4-aminophenethyl)-3-(3-(2-isopropyl-5-methylphenyl)-4-oxothiazolidin-2-ylidene)urea (C1; 0.1 g, 0.244 mmol) in methanol (6 mL) was added 2-bromo-1-(4-(trifluoromethoxy)phenyl)ethanone (0.069 g, 0.244 mmol). The reaction mixture was stirred at room temperature for 22.5 hours (h). The mixture was concentrated and adsorbed onto silica. Purification by reverse-phase high performance liquid chromatography (RP-HPLC) provided the title compound as a yellow oil (26 mg, 16%).

Example 2: Preparation of (Z)-1-(3-(5-methyl-2-(2,2,2-trifluoroethoxy)phenyl)-4-oxothiazolidin-2-ylidene)-3-(4-(2-(4-(trifluoromethoxy)phenyl)hydrazine-1-carbonyl)phenyl)urea (A3)

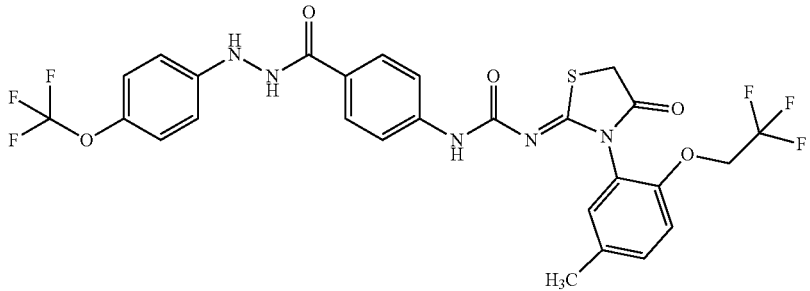 [SMILES: Cc1ccc(OCC(F)(F)F)c(N2C(=O)CS/C2=N\C(=O)Nc2ccc(C(=O)NNc3ccc(OC(F)(F)F)cc3)cc2)c1]

Step 1—Preparation of (Z)-4-(3-(3-(5-Methyl-2-(2,2,2-trifluoroethoxy)phenyl)-4-oxothiazolidin-2-ylidene)ureido) benzoic acid: tert-Butyl (Z)-4-(3-(3-(5-methyl-2-(2,2,2-trifluoroethoxy)phenyl)-4-oxothiazolidin-2-ylidene)ureido) benzoate (C4; 0.200 g, 0.382 mmol) was dissolved in hydrogen chloride (HCl, 4 molar (M); 1.91 mL, 7.64 mmol) in dioxane. After 10 minutes (min) stirring, the solution became cloudy and yellow. Only 20% conversion was observed by liquid chromatography. Additional HCl (2 mL) was added. After 1 h, conversion was better than 50%. Two additional aliquots were added over 2 h. The solvent was removed under a stream of nitrogen. The title compound was isolated as a light brown powder that was used without further purification (190 mg, 99%).

Step 2—Preparation of (Z)-1-(3-(5-methyl-2-(2,2,2-trifluoroethoxy)phenyl)-4-oxothiazolidin-2-ylidene)-3-(4-(2-(4-(trifluoromethoxy)phenyl)hydrazine-1-carbonyl)phenyl) urea (A3): (Z)-4-(3-(3-(5-Methyl-2-(2,2,2-trifluoroethoxy) phenyl)-4-oxothiazolidin-2-ylidene)ureido)benzoic acid (prepared as in Step 1; 0.220 g, 0.471 mmol) was combined in a vial with (benzotriazol-1-yloxy)tripyrrolidinophosphonium hexafluorophosphate (PyBOP; 0.490 g, 0.941 mmol) and (4-(trifluoromethoxy)phenyl)hydrazine hydrochloride (0.129 g, 0.490 mmol). To the solids were added dichloromethane (1.88 mL) followed by N,N-diisopropylethylamine (0.329 mL, 1.88 mmol). The reaction mixture became homogeneous and was stirred for 1 h. The mixture was concentrated. Purification by silica gel chromatography (eluting with 0-40% acetone in hexanes) afforded the title compound as a yellow foam (0.160 g, 53%).

The following compound was synthesized in a manner similar to that provided in Example 2.

(Z)-1-(3-(2-Isopropyl-5-methylphenyl)-4-oxothiazolidin-2-ylidene)-3-(4-(2-(4-(trifluoromethoxy)phenyl)hydrazine-1-carbonyl)phenyl)urea (A2)

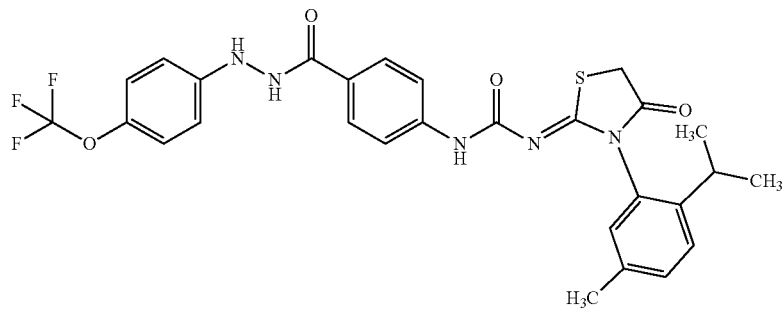 [SMILES: Cc1ccc(C(C)C)c(N2C(=O)CS/C2=N\C(=O)Nc2ccc(C(=O)NNc3ccc(OC(F)(F)F)cc3)cc2)c1]

The title compound was synthesized using the appropriate starting materials and isolated as a yellow foam (0.029 g, 30%).

Example 3: Preparation of (Z)-1-(3-(2-isopropyl-5-methylphenyl)-4-oxothiazolidin-2-ylidene)-3-(4-(2-(4-(trifluoromethoxy)benzoyl)hydrazinyl)phenyl) urea (A4)

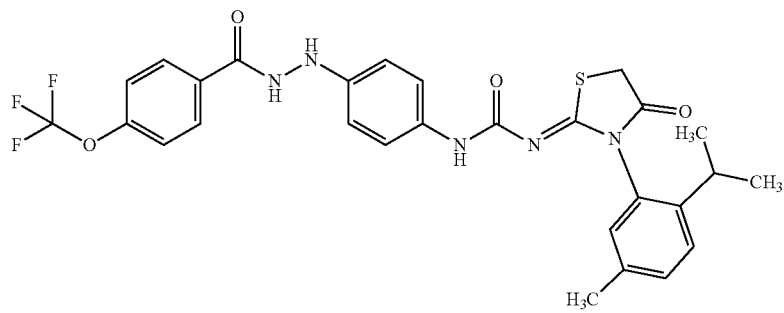 [SMILES: Cc1ccc(C(C)C)c(N2C(=O)CS/C2=N\C(=O)Nc2ccc(NNC(=O)c3ccc(OC(F)(F)F)cc3)cc2)c1]

N'-(4-Aminophenyl)-4-(trifluoromethoxy)benzohydrazide (C7; 0.100 g, 0.321 mmol) was stirred with N,N-diisopropylethylamine (0.112 mL, 0.643 mmol) and bis(2,5-dioxopyrrolidin-1-yl) carbonate (0.091 g, 0.353 mmol) in acetonitrile (3.21 mL) for 1 h. 2-Imino-3-(2-isopropyl-5-methylphenyl)thiazolidin-4-one (0.080 g, 0.321 mmol) was added, and the mixture was stirred for 1 h. The mixture was concentrated under a stream of nitrogen and the residue was purified by silica gel chromatography (eluting with 0-40% acetone in hexanes). The title compound was isolated as a red/brown amorphous solid (0.044 g, 23%).

The following compounds were synthesized in a manner similar to that provided in Example 3.

(Z)-1-(3-(5-Methyl-2-(2,2,2-trifluoroethoxy)phenyl)-4-oxothiazolidin-2-ylidene)-3-(4-(2-(4-(trifluoromethoxy)benzoyl)hydrazinyl)phenyl)urea (A5)

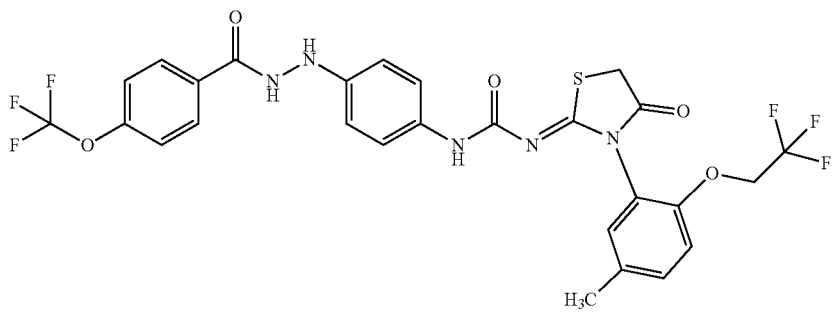 [SMILES: Cc1ccc(OCC(F)(F)F)c(N2C(=O)CS/C2=N\C(=O)Nc2ccc(NNC(=O)c3ccc(OC(F)(F)F)cc3)cc2)c1]

The title compound was synthesized using the appropriate starting materials and isolated as a brown solid (0.043 g, 21%).

(Z)-1-(3-(5-Chloro-2-(2,2,2-trifluoroethoxy)phenyl)-4-oxothiazolidin-2-ylidene)-3-(4-(2-(4-(trifluoromethoxy)benzoyl)hydrazinyl)phenyl)urea (A6)

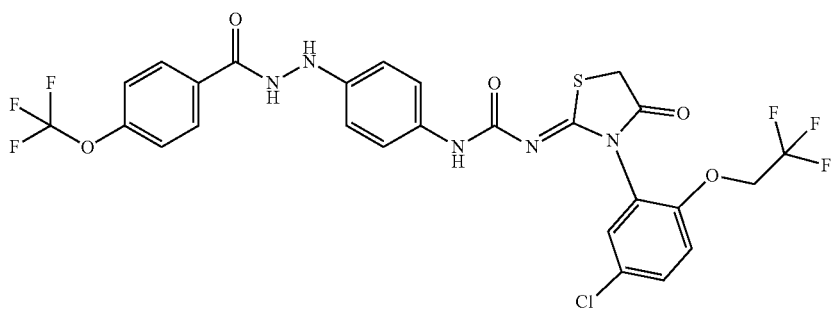 [SMILES: O=C(/N=C1\SCC(=O)N1c1cc(Cl)ccc1OCC(F)(F)F)Nc1ccc(NNC(=O)c2ccc(OC(F)(F)F)cc2)cc1]

The title compound was synthesized using the appropriate starting materials and isolated as a brown solid (0.043 g, 20%).

Example 4: Preparation of (Z)-1-(3-(2-isopropyl-5-methylphenyl)-4-oxothiazolidin-2-ylidene)-3-(4-(3-(4-(trifluoromethoxy)phenyl)ureido)phenyl)urea (A7)

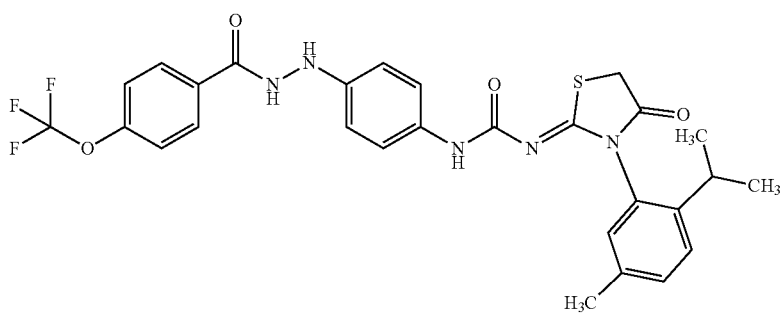 [SMILES: Cc1ccc(C(C)C)c(N2C(=O)CS/C2=N\C(=O)Nc2ccc(NNC(=O)c3ccc(OC(F)(F)F)cc3)cc2)c1]

To a solution of (Z)-1-(4-aminophenyl)-3-(3-(2-isopropyl-5-methylphenyl)-4-oxothiazolidin-2-ylidene)urea (C3; 64 mg, 0.167 mmol) in dry tetrahydrofuran (2 mL) in a 30 mL vial was added 1-isocyanato-4-(trifluoromethoxy)benzene (0.025 mL, 0.167 mmol). The reaction mixture was stirred at room temperature for 1 h. The solution was concentrated and dried under vacuum. The title compound was isolated as a tan solid (85 mg, 86%).

Example 5: Preparation of (Z)-1-(3-(2-isopropyl-5-methylphenyl)-4-oxothiazolidin-2-ylidene)-3-(4-(3-(4-(trifluoromethoxy)phenyl)ureido)phenethyl)urea (A8)

To 1-(4-(2-aminoethyl)phenyl)-3-(4-(trifluoromethyl)phenyl)urea hydrochloride (C11; 103 mg, 0.319 mmol) in acetonitrile (1593 µL) were added bis(2,5-dioxopyrrolidin-1-yl) carbonate (106 mg, 0.414 mmol) and pyridine (103 µL, 1.274 mmol). The reaction mixture was stirred at room temperature for 1 h. The acetonitrile was concentrated under nitrogen, and the yellow oil was dissolved in dichloromethane (0.5 mL) and water (0.5 mL). 2-Imino-3-(2-isopropyl-5-methylphenyl)thiazolidin-4-one (103 mg, 0.414 mmol) and sodium bicarbonate (268 mg, 3.19 mmol) were added. The reaction mixture was stirred overnight. The reaction was quenched with water, and the mixture was diluted with dichloromethane. The biphasic mixture was filtered through a phase separator onto a Celite® cartridge. Purification by

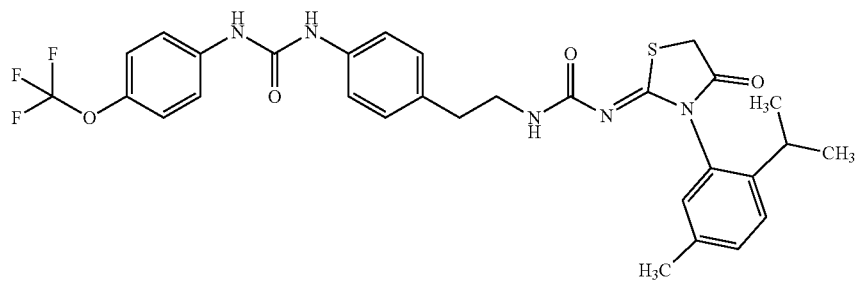 [SMILES: Cc1ccc(C(C)C)c(N2C(=O)CS/C2=N\C(=O)NCCc2ccc(NC(=O)Nc3ccc(OC(F)(F)F)cc3)cc2)c1]

To a solution of (Z)-1-(4-aminophenethyl)-3-(3-(2-isopropyl-5-methylphenyl)-4-oxothiazolidin-2-ylidene)urea (C1; 85 mg, 0.207 mmol) in dry tetrahydrofuran (3 mL) in a 30 mL vial was added 1-isocyanato-4-(trifluromethoxy)benzene (0.031 mL, 0.207 mmol) via syringe. The solution was stirred at room temperature. After 1 h, additional isocyanate (15 µL) was added, and the mixture was stirred for 3 h. The reaction mixture was diluted with ethyl acetate and washed with water. The organic layer was dried with magnesium sulfate, filtered, and concentrated to give an orange oil. The oil was diluted with ether and adsorbed onto silica gel. Purification by silica gel chromatography (eluting with ethyl acetate-hexanes (0-40%, 40% for 3 min, then 40-100%)) afforded the product as a yellow solid (79 mg, 61%).

Example 6: Preparation of (Z)-1-(4-(2-(3-(3-(2-isopropyl-5-methylphenyl)-4-oxothiazolidin-2-ylidene)ureido)ethyl)phenyl)-3-(4-(trifluoromethyl)phenyl)urea (A9)

silica gel flash chromatography (0-70% ethyl acetate/[1:1 dichloromethane/hexanes]) afforded the title compound as a tan foam (119 mg, 59%).

The following compounds were synthesized in a manner similar to that provided in Example 6.

(Z)-1-(4-(2-(3-(3-(4-Methoxy-2-methylphenyl)-4-oxothiazolidin-2-ylidene)ureido)ethyl)phenyl)-3-(4-(trifluoromethyl)phenyl)urea (A10)

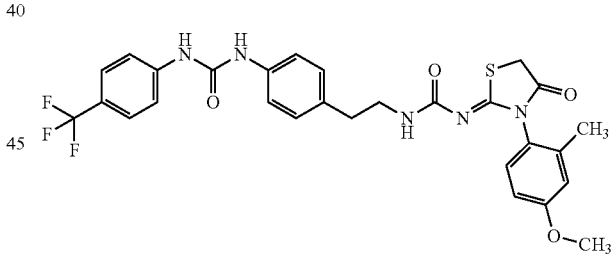

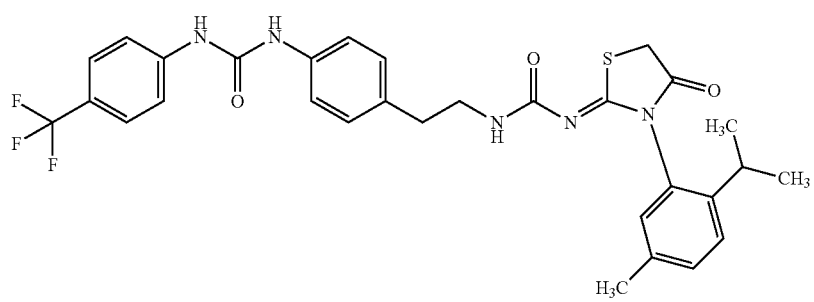 [SMILES: Cc1ccc(C(C)C)c(N2C(=O)CS/C2=N\C(=O)NCCc2ccc(NC(=O)Nc3ccc(C(F)(F)F)cc3)cc2)c1]

The title compound was synthesized using the appropriate starting materials and isolated as a yellow oil (63 mg, 66%).

(Z)-1-(4-(2-(3-(3-(2-Ethyl-6-methylphenyl)-4-oxothiazolidin-2-ylidene)ureido)ethyl)phenyl)-3-(4-(trifluoromethyl)phenyl)urea (A11)

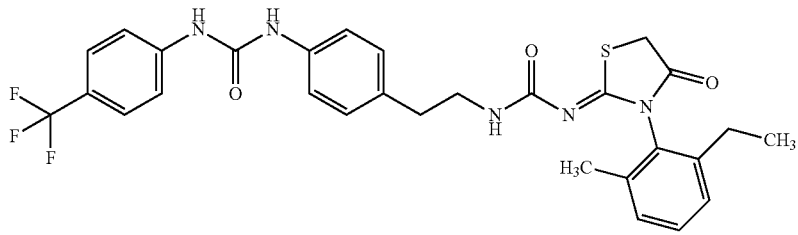 [SMILES: CCc1cccc(C)c1N1C(=O)CS/C1=N\C(=O)NCCc1ccc(NC(=O)Nc2ccc(C(F)(F)F)cc2)cc1]

The title compound was synthesized using the appropriate starting materials and isolated as a tan oily solid (69 mg, 73%).

(Z)-1-(4-(2-(3-(3-(2-Isopropylphenyl)-4-oxothiazolidin-2-ylidene)ureido)ethyl)phenyl)-3-(4-(trifluoromethyl)phenyl)urea (A12)

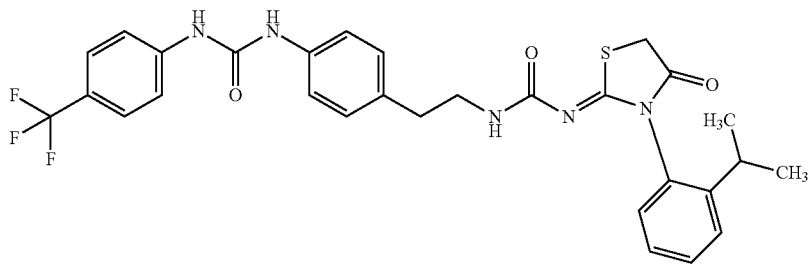 [SMILES: CC(C)c1ccccc1N1C(=O)CS/C1=N\C(=O)NCCc1ccc(NC(=O)Nc2ccc(C(F)(F)F)cc2)cc1]

The title compound was synthesized using the appropriate starting materials and isolated as a white solid (74 mg, 80%).

(Z)-1-(4-(2-(3-(3-(5-Chloro-2-isopropylphenyl)-4-oxothiazolidin-2-ylidene)ureido)ethyl)phenyl)-3-(4-(trifluoromethyl)phenyl)urea (A13)

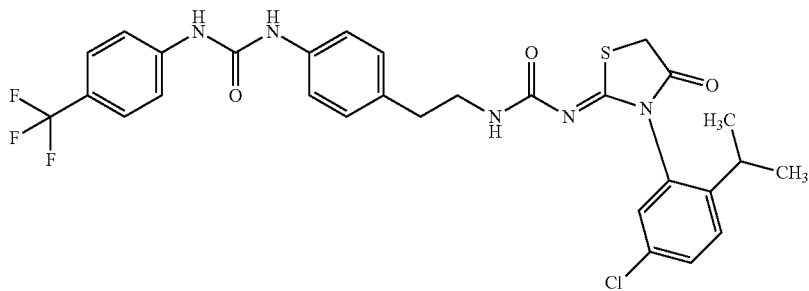 [SMILES: CC(C)c1ccc(Cl)cc1N1C(=O)CS/C1=N\C(=O)NCCc1ccc(NC(=O)Nc2ccc(C(F)(F)F)cc2)cc1]

The title compound was synthesized using the appropriate starting materials and isolated as a white solid (67 mg, 69%).

(Z)-1-(4-(2-(3-(3-(2-Isopropyl-5-methylphenyl)thiazol-2(3H)-ylidene)ureido)ethyl)phenyl)-3-(4-(trifluoromethyl)phenyl)urea (A14)

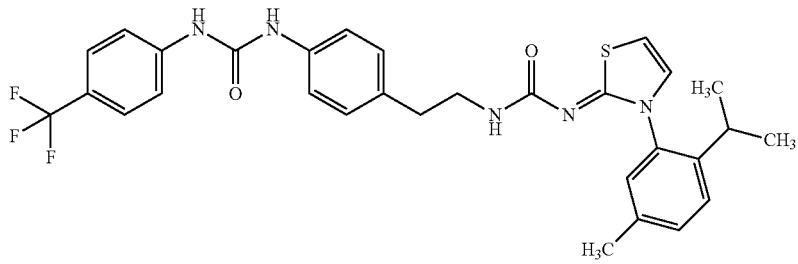 [SMILES: Cc1ccc(C(C)C)c(-n2ccs/c2=N\C(=O)NCCc2ccc(NC(=O)Nc3ccc(C(F)(F)F)cc3)cc2)c1]

The title compound was synthesized using the appropriate starting materials and isolated as a white solid (60 mg, 59%).

(Z)-1-(4-(2-(3-(3-(5-Chloro-2-isopropylphenyl)-4-oxothiazolidin-2-ylidene)ureido)ethyl)phenyl)-3-(4-(trifluoromethoxy)phenyl)urea (A15)

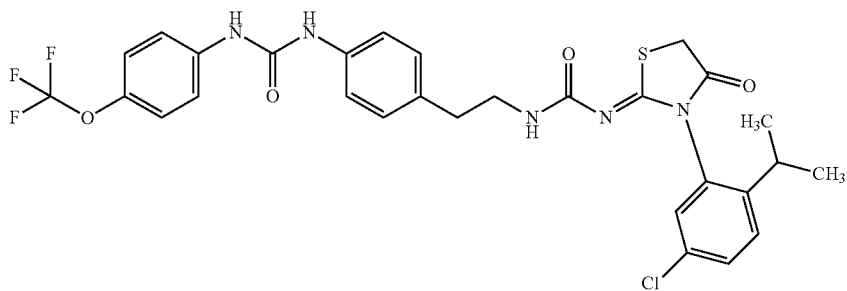 [SMILES: CC(C)c1ccc(Cl)cc1N1C(=O)CS/C1=N\C(=O)NCCc1ccc(NC(=O)Nc2ccc(OC(F)(F)F)cc2)cc1]

The title compound was synthesized using the appropriate starting materials and isolated as a yellow oil (56 mg, 57%).

(Z)-1-(4-(2-(3-(3-(2-Isopropylphenyl)-4-oxothiazolidin-2-ylidene)ureido)ethyl)phenyl)-3-(4-(trifluoromethoxy)phenyl)urea (A16)

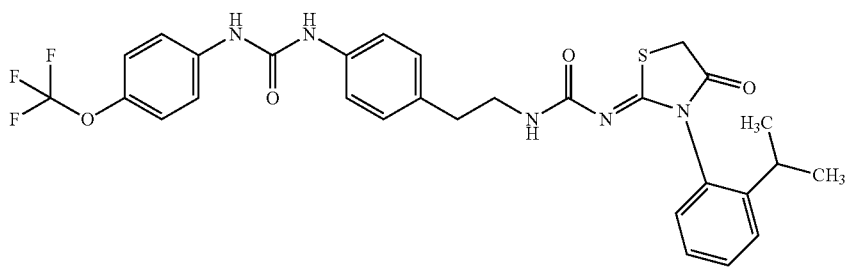 [SMILES: CC(C)c1ccccc1N1C(=O)CS/C1=N\C(=O)NCCc1ccc(NC(=O)Nc2ccc(OC(F)(F)F)cc2)cc1]

The title compound was synthesized using the appropriate starting materials and isolated as a white solid (41 mg, 44%).

(Z)-1-(4-(2-(3-(3-(5-Chloro-2-(2,2,2-trifluoroethoxy)phenyl)-4-oxothiazolidin-2-ylidene)ureido)ethyl)phenyl)-3-(4-(trifluoromethoxy)phenyl)urea (A17)

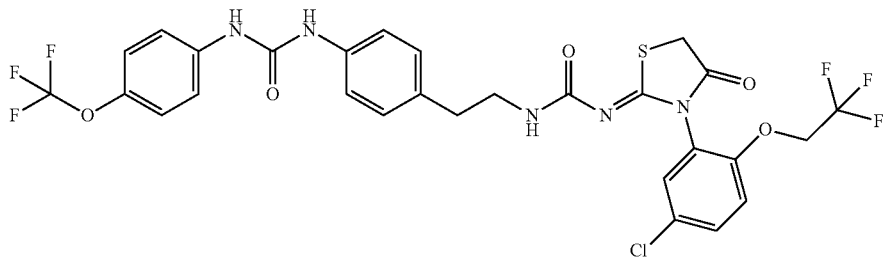 [SMILES: O=C(/N=C1\SCC(=O)N1c1cc(Cl)ccc1OCC(F)(F)F)NCCc1ccc(NC(=O)Nc2ccc(OC(F)(F)F)cc2)cc1]

The title compound was synthesized using the appropriate starting materials and isolated as a tan solid (60 mg, 56%).

(Z)-1-(4-(2-(3-(3-(5-Methoxy-2-propylphenyl)-4-oxothiazolidin-2-ylidene)ureido)ethyl)phenyl)-3-(4-(trifluoromethoxy)phenyl)urea (A18)

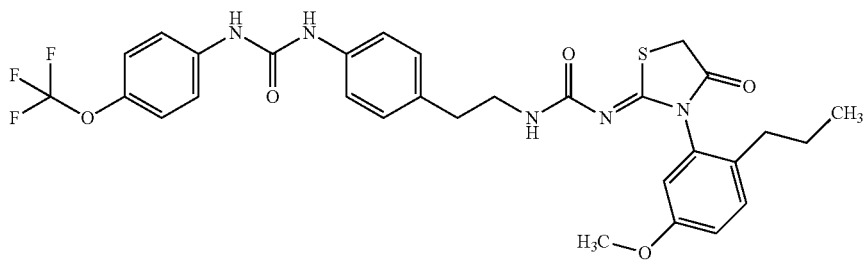 [SMILES: CCCc1ccc(OC)cc1N1C(=O)CS/C1=N\C(=O)NCCc1ccc(NC(=O)Nc2ccc(OC(F)(F)F)cc2)cc1]

The title compound was synthesized using the appropriate starting materials and isolated as a white solid (73 mg, 77%).

(Z)-1-(4-(2-(3-(3-(5-Methyl-2-(2,2,2-trifluoroethoxy)phenyl)-4-oxothiazolidin-2-ylidene)ureido)ethyl)phenyl)-3-(4-(trifluoromethoxy)phenyl)urea (A19)

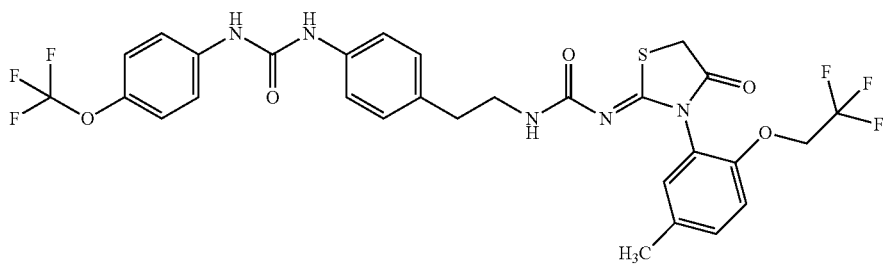 [SMILES: Cc1ccc(OCC(F)(F)F)c(N2C(=O)CS/C2=N\C(=O)NCCc2ccc(NC(=O)Nc3ccc(OC(F)(F)F)cc3)cc2)c1]

The title compound was synthesized using the appropriate starting materials and isolated as a white solid (70 mg, 70%).

(Z)-1-(4-(2-(3-(3-(2-(sec-Butoxy)-5-methylphenyl))-4-oxothiazolidin-2-ylidene)ureido)ethyl)phenyl)-3-(4-(trifluoromethoxy)phenyl)urea (A20)

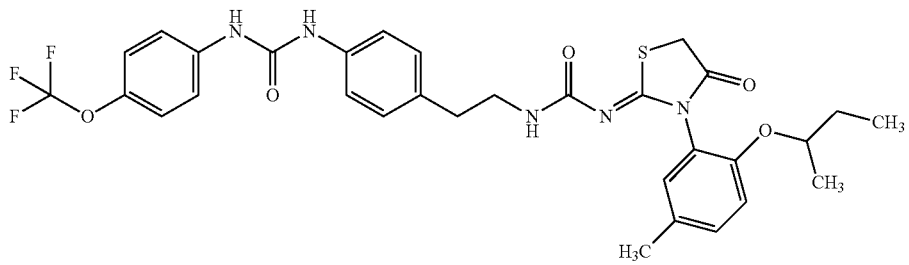 [SMILES: CCC(C)Oc1ccc(C)cc1N1C(=O)CS/C1=N\C(=O)NCCc1ccc(NC(=O)Nc2ccc(OC(F)(F)F)cc2)cc1]

The title compound was synthesized using the appropriate starting materials and isolated as a brown solid (56 mg, 560%).

(Z)-1-(4-(2-(3-(3-(4-methoxy-2-methylphenyl)-4-oxothiazolidin-2-ylidene)ureido)ethyl)phenyl)-3-(4-(trifluoromethoxy)phenyl)urea (A21)

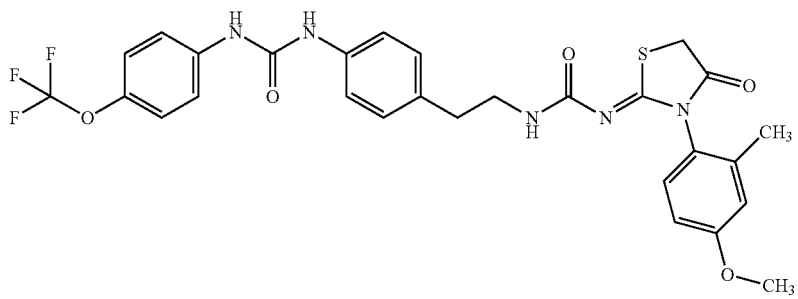 [SMILES: COc1ccc(N2C(=O)CS/C2=N\C(=O)NCCc2ccc(NC(=O)Nc3ccc(OC(F)(F)F)cc3)cc2)c(C)c1]

The title compound was synthesized using the appropriate starting materials and isolated as an orange solid (41 mg, 44%).

(Z)-1-(4-(2-(3-(3-(2-Isopropyl-5-methylphenyl)thiazol-2(3H)-ylidene)ureido)ethyl)phenyl)-3-(4-(trifluoromethoxy)phenyl)urea (A22)

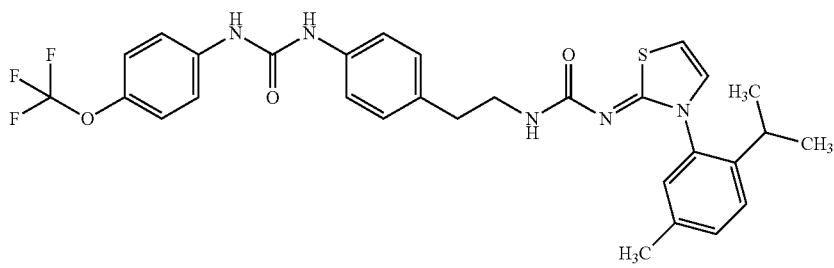 [SMILES: Cc1ccc(C(C)C)c(-n2ccs/c2=N\C(=O)NCCc2ccc(NC(=O)Nc3ccc(OC(F)(F)F)cc3)cc2)c1]

The title compound was synthesized using the appropriate starting materials and isolated as a white solid (68 mg, 76%).

(Z)-1-(4-(2-(3-(3-(2-Ethyl-6-methylphenyl)-4-oxothiazolidin-2-ylidene)ureido)ethyl)phenyl)-3-(4-(trifluoromethoxy)phenyl)urea (A23)

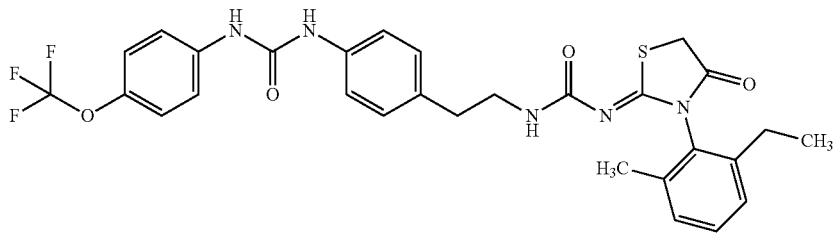 [SMILES: CCc1cccc(C)c1N1C(=O)CS/C1=N\C(=O)NCCc1ccc(NC(=O)Nc2ccc(OC(F)(F)F)cc2)cc1]

The title compound was synthesized using the appropriate starting materials and isolated as an off-white oily foam (39 mg, 42%).

(Z)-1-(4-(2-(3-(4-Oxo-3-(5,6,7,8-tetrahydronaphthalen-1-yl)thiazolidin-2-ylidene)ureido)ethyl)phenyl)-3-(4-(trifluoromethoxy)phenyl)urea (A24)

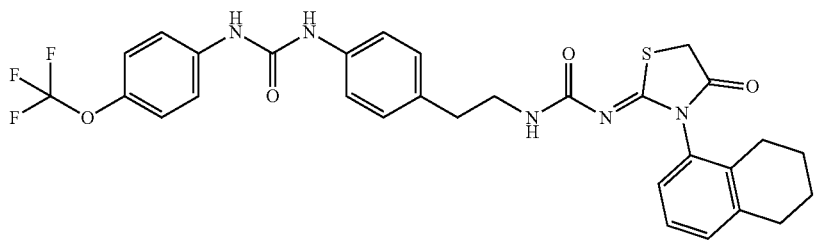 [SMILES: O=C(/N=C1\SCC(=O)N1c1cccc2c1CCCC2)NCCc1ccc(NC(=O)Nc2ccc(OC(F)(F)F)cc2)cc1]

The title compound was synthesized using the appropriate starting materials and isolated as a yellow oil (38 mg, 40%).

(Z)-1-(4-(2-(3-(3-(4-Fluoro-2-isopropyl-5-methylphenyl)-4-oxothiazolidin-2-ylidene)ureido)ethyl)phenyl)-3-(4-(trifluoromethoxy)phenyl)urea (A25)

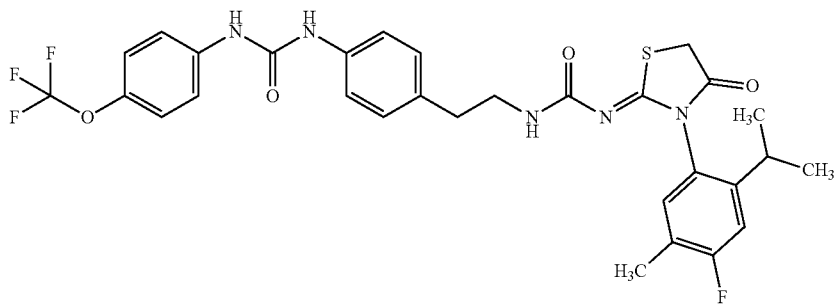 [SMILES: Cc1cc(N2C(=O)CS/C2=N\C(=O)NCCc2ccc(NC(=O)Nc3ccc(OC(F)(F)F)cc3)cc2)c(C(C)C)cc1F]

The title compound was synthesized using the appropriate starting materials and isolated as a white solid (44 mg, 46%).

(Z)-1-(3-(2-Isopropyl-5-methylphenyl)-4-oxothiazo-lidin-2-ylidene)-3-(1-(4-(3-(4-(trifluoromethoxy)phenyl)ureido)phenyl)propan-2-yl)urea (A26)

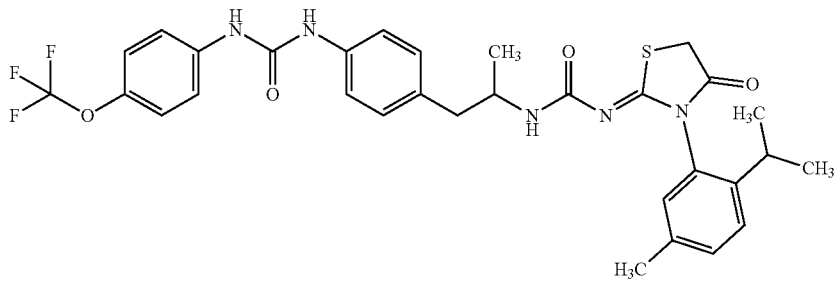 [SMILES: Cc1ccc(C(C)C)c(N2C(=O)CS/C2=N\C(=O)NC(C)Cc2ccc(NC(=O)Nc3ccc(OC(F)(F)F)cc3)cc2)c1]

The title compound was synthesized using the appropriate starting materials and isolated as a white solid (56 mg, 52%).

(Z)-1-(4-(2-(3-(3-(2-Isopropyl-5-methylphenyl)-4-oxothiazolidin-2-ylidene)ureido)propyl)phenyl)-3-(4-(trifluoromethyl)phenyl)urea (A27)

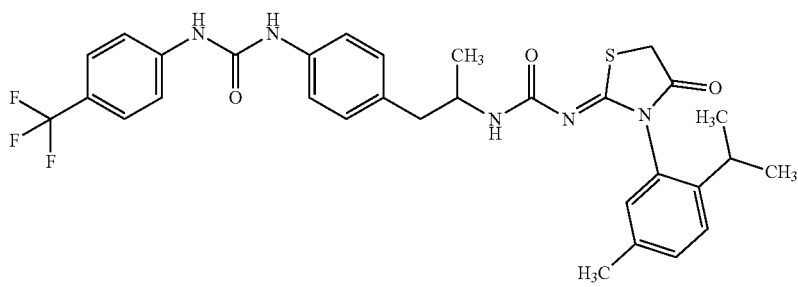 [SMILES: Cc1ccc(C(C)C)c(N2C(=O)CS/C2=N\C(=O)NC(C)Cc2ccc(NC(=O)Nc3ccc(C(F)(F)F)cc3)cc2)c1]

The title compound was synthesized using the appropriate starting materials and isolated as a tan solid (51 mg, 53%).

(Z)-1-(4-(2-(3-(3-(2-Isopropylphenyl)-4-oxothiazoli-din-2-ylidene)ureido)propyl)phenyl)-3-(4-(trifluoromethyl)phenyl)urea (A28)

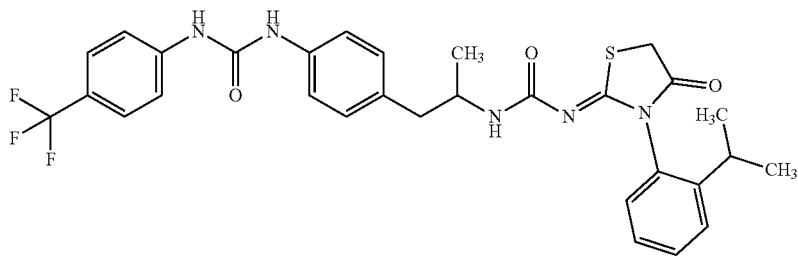 [SMILES: CC(Cc1ccc(NC(=O)Nc2ccc(C(F)(F)F)cc2)cc1)NC(=O)/N=C1\SCC(=O)N1c1ccccc1C(C)C]

The title compound was synthesized using the appropriate starting materials and isolated as a white solid (39 mg, 42%).

(Z)-1-(4-(2-(3-(3-(5-Chloro-2-isopropylphenyl)-4-oxothiazolidin-2-ylidene)ureido)propyl)phenyl)-3-(4-(trifluoromethyl)phenyl)urea (A29)

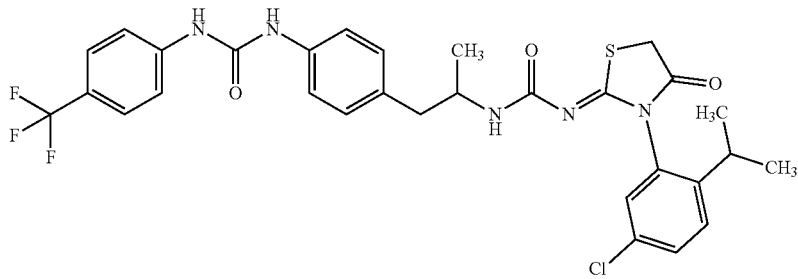 [SMILES: CC(Cc1ccc(NC(=O)Nc2ccc(C(F)(F)F)cc2)cc1)NC(=O)/N=C1\SCC(=O)N1c1cc(Cl)ccc1C(C)C]

The title compound was synthesized using the appropriate starting materials and isolated as a white solid (37 mg, 38%).

(Z)-1-(4-(2-(3-(3-(2-(sec-Butoxy)-5-methylphenyl)-4-oxothiazolidin-2-ylidene)ureido)propyl)phenyl)-3-(4-(trifluoromethyl)phenyl)urea (A30)

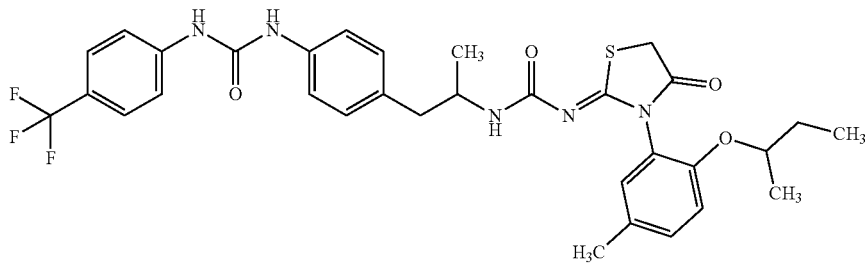 [SMILES: CCC(C)Oc1ccc(C)cc1N1C(=O)CS/C1=N\C(=O)NC(C)Cc1ccc(NC(=O)Nc2ccc(C(F)(F)F)cc2)cc1]

The title compound was synthesized using the appropriate starting materials and isolated as a yellow solid (47 mg, 47%).

(Z)-1-(4-(2-(3-(3-(4-Methoxy-2-methylphenyl)-4-oxothiazolidin-2-ylidene)ureido)propyl)phenyl)-3-(4-(trifluoromethyl)phenyl)urea (A31)

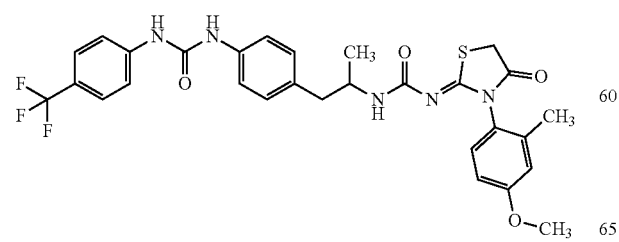

The title compound was synthesized using the appropriate starting materials and isolated as an orange solid (44 mg, 47%).

(Z)-1-(4-(2-(3-(3-(2-Ethyl-6-methylphenyl)-4-oxothiazolidin-2-ylidene)ureido)propyl)phenyl)-3-(4-(trifluoromethyl)phenyl)urea (A32)

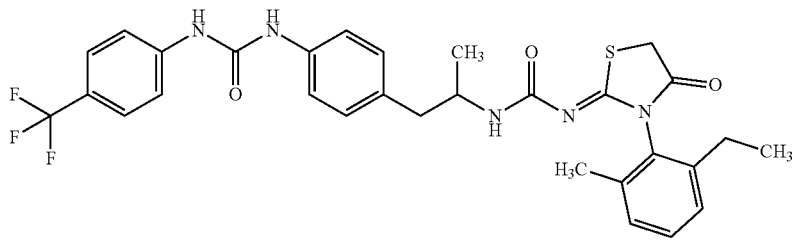 [SMILES: CCc1cccc(C)c1N1C(=O)CS/C1=N\C(=O)NC(C)Cc1ccc(NC(=O)Nc2ccc(C(F)(F)F)cc2)cc1]

The title compound was synthesized using the appropriate starting materials and isolated as a tan solid (15 mg, 16%).

(Z)-1-(4-(2-(3-(3-(2-Isopropyl-5-methylphenyl)thiazol-2(3H)-ylidene)ureido)propyl)phenyl)-3-(4-(trifluoromethoxy)phenyl)urea (A33)

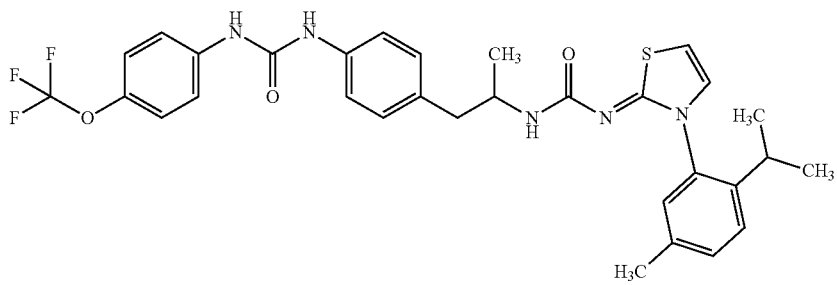 [SMILES: Cc1ccc(C(C)C)c(-n2ccs/c2=N\C(=O)NC(C)Cc2ccc(NC(=O)Nc3ccc(OC(F)(F)F)cc3)cc2)c1]

The title compound was synthesized using the appropriate starting materials and isolated as a white oily solid (36 mg, 41%).

(Z)-1-(4-(2-(3-(3-(2-Isopropylphenyl)-4-oxothiazolidin-2-ylidene)ureido)propyl)phenyl)-3-(4-(trifluoromethoxy)phenyl)urea (A34)

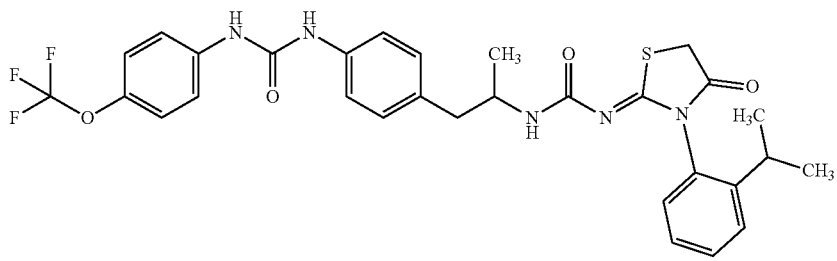 [SMILES: CC(Cc1ccc(NC(=O)Nc2ccc(OC(F)(F)F)cc2)cc1)NC(=O)/N=C1\SCC(=O)N1c1ccccc1C(C)C]

The title compound was synthesized using the appropriate starting materials and isolated as a white oily solid (27 mg, 30%).

(Z)-1-(4-(2-(3-(3-(5-Chloro-2-isopropylphenyl)-4-oxothiazolidin-2-ylidene)ureido)propyl)phenyl)-3-(4-(trifluoromethoxy)phenyl)urea (A35)

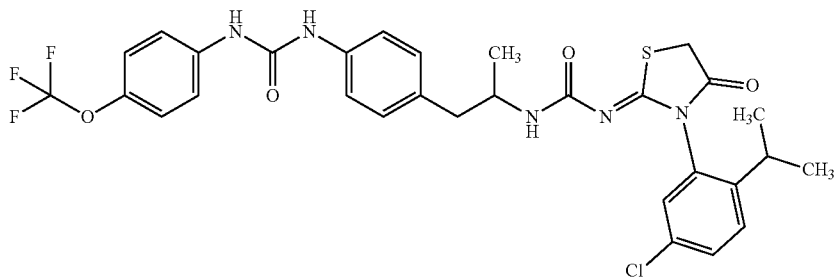 [SMILES: CC(Cc1ccc(NC(=O)Nc2ccc(OC(F)(F)F)cc2)cc1)NC(=O)/N=C1\SCC(=O)N1c1cc(Cl)ccc1C(C)C]

The title compound was synthesized using the appropriate starting materials and isolated as a white oily solid (28 mg, 29%).

(Z)-1-(4-(2-(3-(3-(5-Chloro-2-(trifluoromethoxy)phenyl)-4-oxothiazolidin-2-ylidene)ureido)propyl)phenyl)-3-(4-(trifluoromethoxy)phenyl)urea (A36)

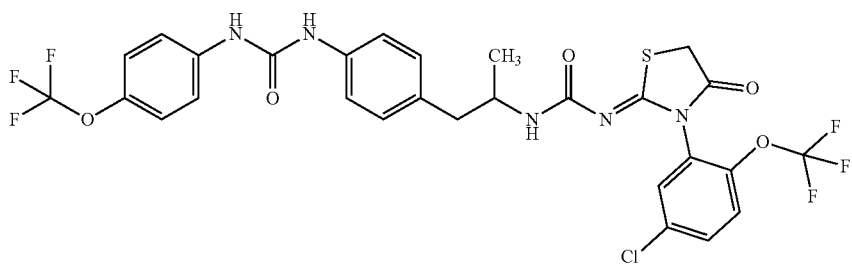 [SMILES: CC(Cc1ccc(NC(=O)Nc2ccc(OC(F)(F)F)cc2)cc1)NC(=O)/N=C1\SCC(=O)N1c1cc(Cl)ccc1OC(F)(F)F]

The title compound was synthesized using the appropriate starting materials and isolated as a white oily solid (34 mg, 33%).

(Z)-1-(4-(2-(3-(3-(5-Methoxy-2-propylphenyl)-4-oxothiazolidin-2-ylidene)ureido)propyl)phenyl)-3-(4-(trifluoromethoxy)phenyl)urea (A37)

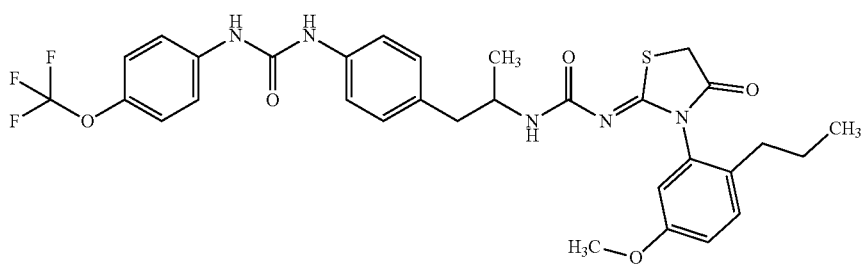 [SMILES: CCCc1ccc(OC)cc1N1C(=O)CS/C1=N\C(=O)NC(C)Cc1ccc(NC(=O)Nc2ccc(OC(F)(F)F)cc2)cc1]

The title compound was synthesized using the appropriate starting materials and isolated as a white oil (34 mg, 36%).

(Z)-1-(4-(2-(3-(3-(5-Methyl-2-(2,2,2-trifluoroethoxy)phenyl)-4-oxothiazolidin-2-ylidene)ureido)propyl)phenyl)-3-(4-(trifluoromethoxy)phenyl)urea (A38)

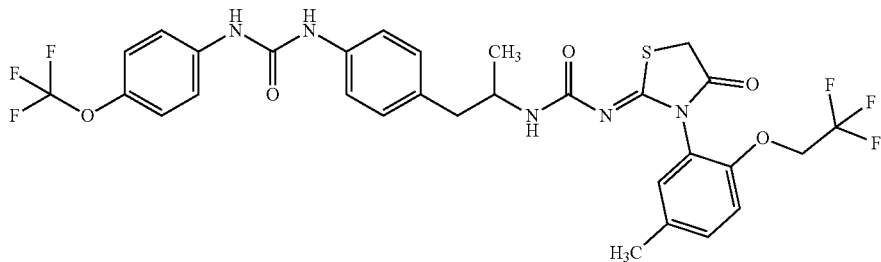 [SMILES: Cc1ccc(OCC(F)(F)F)c(N2C(=O)CS/C2=N\C(=O)NC(C)Cc2ccc(NC(=O)Nc3ccc(OC(F)(F)F)cc3)cc2)c1]

The title compound was synthesized using the appropriate starting materials and isolated as a white oily solid (39 mg, 38%).

(Z)-1-(4-(2-(3-(3-(2-(sec-Butoxy)-5-methylphenyl)-4-oxothiazolidin-2-ylidene)ureido)propyl)phenyl)-3-(4-(trifluoromethoxy)phenyl)urea (A39)

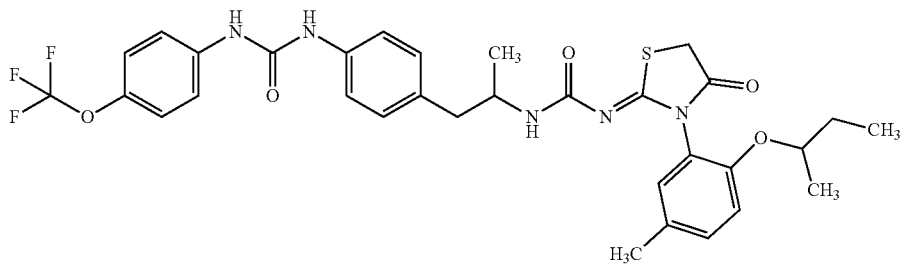 [SMILES: CCC(C)Oc1ccc(C)cc1N1C(=O)CS/C1=N\C(=O)NC(C)Cc1ccc(NC(=O)Nc2ccc(OC(F)(F)F)cc2)cc1]

The title compound was synthesized using the appropriate starting materials and isolated as an orange oily solid (33 mg, 34%).

(Z)-1-(4-(2-(3-(3-(2-Ethyl-6-methylphenyl)-4-oxothiazolidin-2-ylidene)ureido)propyl)phenyl)-3-(4-(trifluoromethoxy)phenyl)urea (A40)

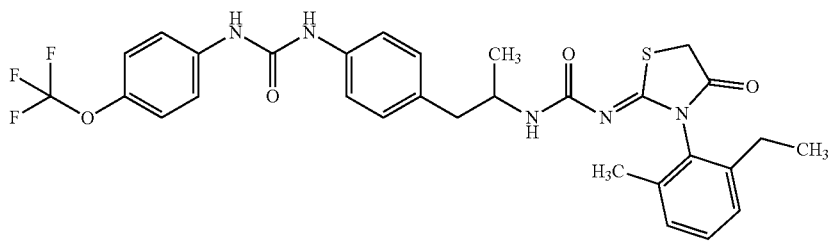 [SMILES: CCc1cccc(C)c1N1C(=O)CS/C1=N\C(=O)NC(C)Cc1ccc(NC(=O)Nc2ccc(OC(F)(F)F)cc2)cc1]

The title compound was synthesized using the appropriate starting materials and isolated as a tan semisolid (30 mg, 33%).

(Z)-1-(4-(2-(3-(3-(2-Chloro-4,5-dimethylphenyl)-4-oxothiazolidin-2-ylidene)ureido)propyl)phenyl)-3-(4-(trifluoromethoxy)phenyl)urea (A41)

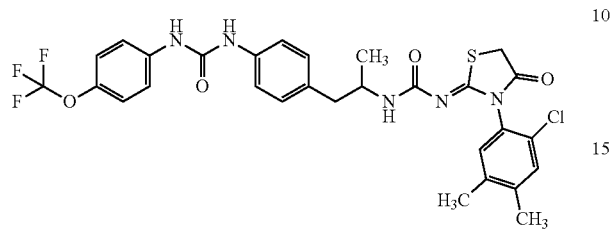

The title compound was synthesized using the appropriate starting materials and isolated as a yellow oil (33 mg, 35%).

(Z)-1-(4-(2-(3-(4-Oxo-3-(5,6,7,8-tetrahydronaphthalen-1-yl)thiazolidin-2-ylidene)ureido)propyl)phenyl)-3-(4-(trifluoromethoxy)phenyl)urea (A42)

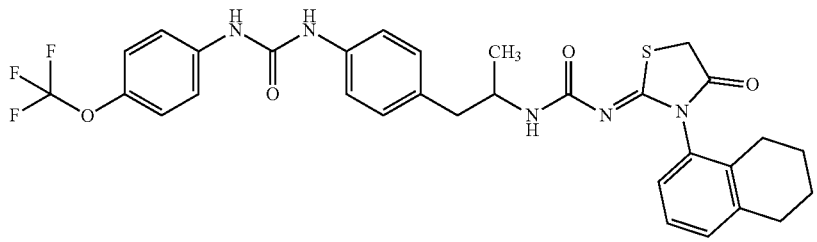 [SMILES: CC(Cc1ccc(NC(=O)Nc2ccc(OC(F)(F)F)cc2)cc1)NC(=O)/N=C1\SCC(=O)N1c1cccc2c1CCCC2]

The title compound was synthesized using the appropriate starting materials and isolated as a tan solid (37 mg, 40%).

Example 7: Preparation of (Z)-1-(4-(3-(3-(2-isopropyl-5-methylphenyl)-4-oxothiazolidin-2-ylidene)ureido)benzyl)-3-(4-(trifluoromethoxy)phenyl)urea (A43)

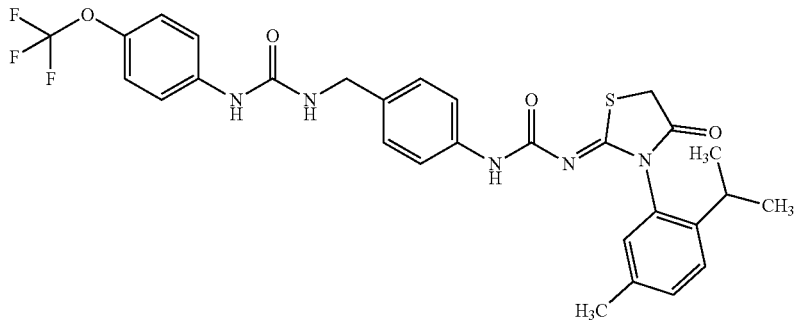 [SMILES: Cc1ccc(C(C)C)c(N2C(=O)CS/C2=N\C(=O)Nc2ccc(CNC(=O)Nc3ccc(OC(F)(F)F)cc3)cc2)c1]

To a solution of 4-nitrophenyl (4-((3-(4-(trifluoromethoxy)phenyl)ureido)methyl)phenyl)carbamate (C19; 84 mg, 0.171 mmol) in acetonitrile (4 mL) were added 2-imino-3-(2-isopropyl-5-methylphenyl)thiazolidin-4-one (42.5 mg, 0.171 mmol), cesium carbonate (11.2 mg, 0.034 mmol), and N,N-diisopropylethylamine (0.090 mL, 0.514 mmol). The reaction mixture was stirred at room temperature for 1 h, diluted with ethyl acetate, and poured onto water. The organic layer was dried and concentrated. Purification by silica gel chromatography (eluting with 0-100% ethyl acetate-hexanes) afforded the title compound as a cream solid (29 mg, 27%).

Example 8: Preparation of (Z)-1-(3-(2-isopropyl-5-methylphenyl)-4-oxothiazolidin-2-ylidene)-3-(4-(2-(3-(4-(trifluoromethoxy)phenyl)ureido)ethyl)phenyl) urea (A44)

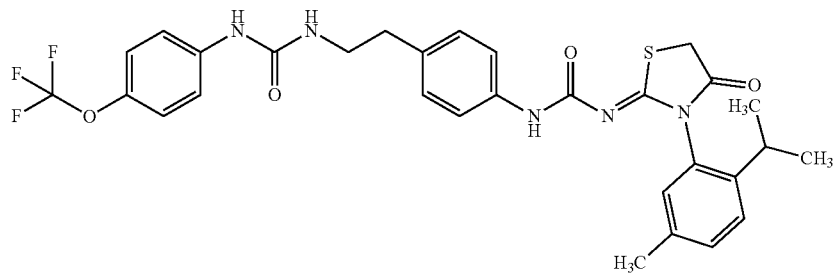 [SMILES: Cc1ccc(C(C)C)c(N2C(=O)CS/C2=N\C(=O)Nc2ccc(CCNC(=O)Nc3ccc(OC(F)(F)F)cc3)cc2)c1]

To a solution of (Z)-1-(4-(2-aminoethyl)phenyl)-3-(3-(2-isopropyl-5-methylphenyl)-4-oxothiazolidin-2-ylidene)urea (C21; 39 mg, 0.095 mmol) in dry acetonitrile (2 mL) was added 1-isocyanato-4-(trifluoromethoxy)benzene (0.014 mL, 0.095 mmol). The reaction mixture was stirred at room temperature. After 1 h, cesium carbonate (31.0 mg, 0.095 mmol) added. Stirring was continued for 4 h. RP-HPLC purification provided the title compound (3.8 mg, 6.5%).

Example 9: Preparation of (Z)-1-(3-(2-isopropyl-5-methylphenyl)-4-oxothiazolidin-2-ylidene)-3-(4-(3-(4-(trifluoromethoxy)phenyl)thioureido)phenyl)urea (A45)

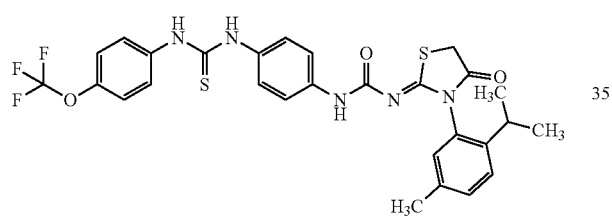

To a solution of (Z)-1-(4-aminophenyl)-3-(3-(2-isopropyl-5-methylphenyl)-4-oxothiazolidin-2-ylidene)urea (C3; 0.1 g, 0.261 mmol) in acetonitrile (5 mL) was added 1-isothiocyanato-4-(trifluoromethoxy)benzene (0.042 mL, 0.261 mmol). The reaction mixture was stirred at room temperature for 3 h. The solution was concentrated to 1/2 volume and adsorbed onto silica. Purification by silica gel chromatography (eluting with 0-40, 40 for 30 min, and 40-100% ethyl acetate-hexanes) afforded the title compound as an orange solid (60 mg, 36%).

Example 10: Preparation of (Z)-1-(3-(2-isopropyl-5-methylphenyl)-4-oxothiazolidin-2-ylidene)-3-(4-(3-(4-(trifluoromethoxy)phenyl)thioureido)phenethyl) urea (A46)

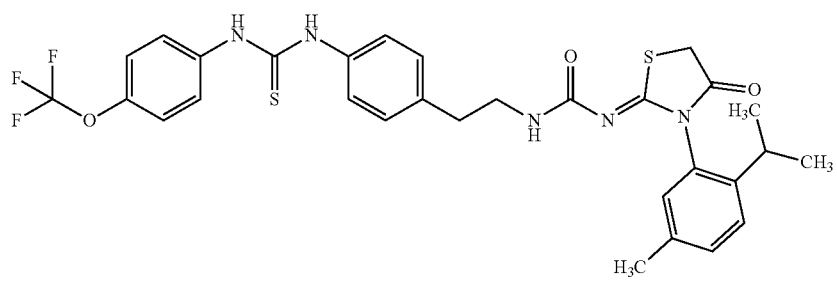 [SMILES: Cc1ccc(C(C)C)c(N2C(=O)CS/C2=N\C(=O)NCCc2ccc(NC(=S)Nc3ccc(OC(F)(F)F)cc3)cc2)c1]

To a solution of (Z)-1-(4-aminophenethyl)-3-(3-(2-isopropyl-5-methylphenyl)-4-oxothiazolidin-2-ylidene)urea (C1; 59 mg, 0.144 mmol) in acetonitrile (5 mL) was added 1-isothiocyanato-4-(trifluoromethoxy)benzene (0.023 mL, 0.144 mmol). After 3 h, the solution was concentrated to 1/2 volume and adsorbed onto silica. Purification by silica gel chromatography (eluting with 0-40, 40 for 30 min, and 40-100% ethyl acetate-hexanes) afforded the title compound as a yellow oil (26 mg, 29%).

Example 11: Preparation of (Z)-1-(3-(2-isopropyl-5-methylphenyl)-4-oxothiazolidin-2-ylidene)-3-(4-(2-(3-(4-(trifluoromethoxy)phenyl)thioureido)ethyl)phenyl)urea (A47)

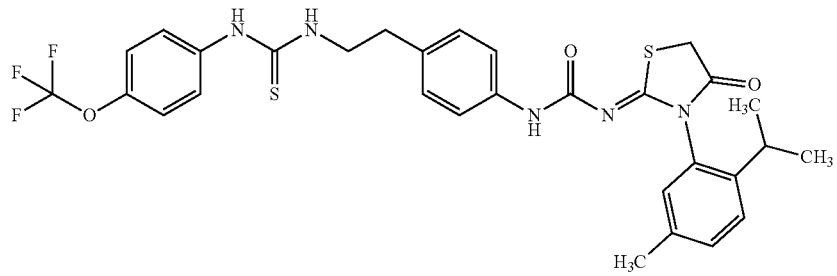 [SMILES: Cc1ccc(C(C)C)c(N2C(=O)CS/C2=N\C(=O)Nc2ccc(CCNC(=S)Nc3ccc(OC(F)(F)F)cc3)cc2)c1]

To a solution of (Z)-1-(4-(2-aminoethyl)phenyl)-3-(3-(2-isopropyl-5-methylphenyl)-4-oxothiazolidin-2-ylidene)urea (C21; 175 mg, 0.426 mmol) in dry tetrahydrofuran (5 mL) was added 1-isothiocyanato-4-(trifluoromethoxy)benzene (0.069 mL, 0.426 mmol) and N,N-diisopropylethylamine (0.2 mL, 1.145 mmol). The reaction mixture was stirred at room temperature for 18 h. The mixture was diluted with ethyl acetate and washed with water, and the organic layer was dried and concentrated. Purification by silica gel chromatography (eluting with 0-100% ethyl acetate-hexanes) afforded the title compound as a yellow solid (110 mg, 37%).

Example 12: Preparation of (Z)—N-(4-(3-(3-(2-isopropyl-5-methylphenyl)-4-oxothiazolidin-2-ylidene)ureido)phenyl)-4-(trifluoromethoxy)benzamide (A48)

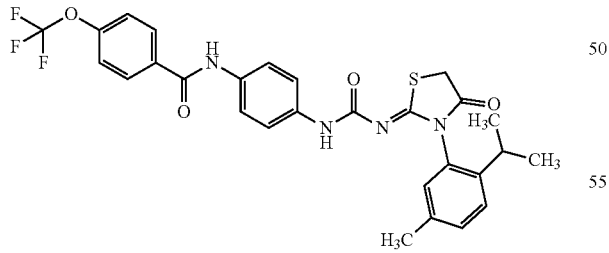

To a solution of (Z)-1-(4-aminophenyl)-3-(3-(2-isopropyl-5-methylphenyl)-4-oxothiazolidin-2-ylidene)urea (C3; 70 mg, 0.183 mmol) in dry acetonitrile (4 mL) was added 4-(trifluoromethoxy)benzoyl chloride (0.029 mL, 0.183 mmol). The reaction mixture was stirred at room temperature for 40 min. The volatiles were concentrated and the residue dried. The title compound was isolated as an orange oil (94 mg, 82%).

Example 13: Preparation of (Z)—N-(4-(2-(3-(3-(2-isopropyl-5-methylphenyl)-4-oxothiazolidin-2-ylidene)ureido)ethyl)phenyl)-4-(trifluoromethoxy)benzamide (A49)

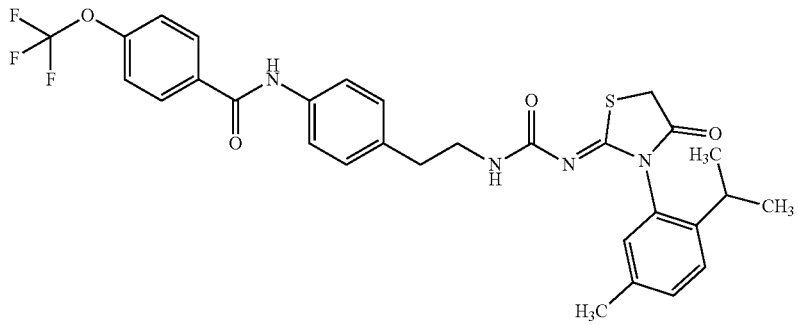 [SMILES: Cc1ccc(C(C)C)c(N2C(=O)CS/C2=N\C(=O)NCCc2ccc(NC(=O)c3ccc(OC(F)(F)F)cc3)cc2)c1]

To a solution of (Z)-1-(4-aminophenethyl)-3-(3-(2-isopropyl-5-methylphenyl)-4-oxothiazolidin-2-ylidene)urea (C1; 80 mg, 0.195 mmol) in tetrahydrofuran (4 mL) was added 4-(trifluoromethoxy)benzoyl chloride (0.030 mL, 0.195 mmol). The reaction mixture was stirred at room temperature for 20 min. The solution was concentrated and dried. Purification by silica gel chromatography (eluting with 0-50% ethyl acetate-hexanes) afforded the title compound as a yellow solid (44 mg, 38%).

Example 14: Preparation of (Z)—N-(4-(3-(3-(2-isopropyl-5-methylphenyl)-4-oxothiazolidin-2-ylidene)ureido)phenethyl)-4-(trifluoromethoxy)benzamide (A50)

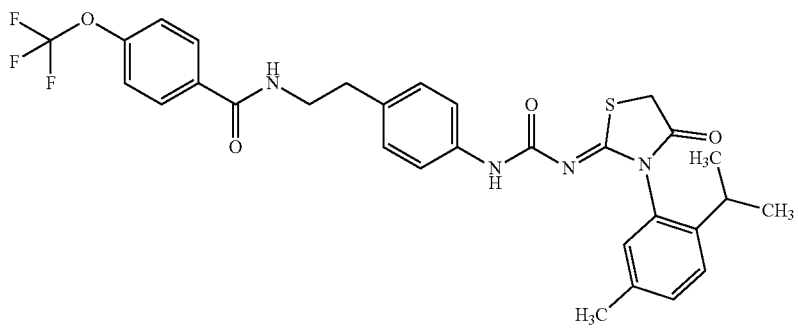 [SMILES: Cc1ccc(C(C)C)c(N2C(=O)CS/C2=N\C(=O)Nc2ccc(CCNC(=O)c3ccc(OC(F)(F)F)cc3)cc2)c1]

To a solution of 4-nitrophenyl (4-(2-(4-(trifluoromethoxy)benzamido)ethyl)phenyl)carbamate (C23; 89 mg, 0.182 mmol) in dry acetonitrile (5 mL) were added 2-imino-3-(2-isopropyl-5-methylphenyl)thiazolidin-4-one (45.2 mg, 0.182 mmol), cesium carbonate (11.9 mg, 0.036 mmol), and N,N-diisopropylethylamine (0.095 mL, 0.546 mmol). The reaction mixture was stirred at room temperature for 30 min. The solution was concentrated under nitrogen. Purification by silica gel chromatography (eluting with 0-40, 40, and 40-100% ethyl acetate-hexanes) afforded the title compound as a yellow oil (89 mg, 82%).

Example 15: Preparation of (Z)—N-(4-(3-(3-(2-isopropyl-5-methylphenyl)-4-oxothiazolidin-2-ylidene)ureido)phenyl)-4-(trifluoromethoxy)benzenesulfonamide (A51)

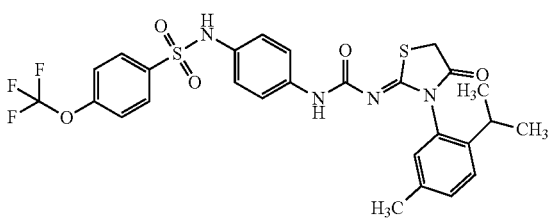 [SMILES: Cc1ccc(C(C)C)c(N2C(=O)CS/C2=N\C(=O)Nc2ccc(NS(=O)(=O)c3ccc(OC(F)(F)F)cc3)cc2)c1]

To a solution of (Z)-1-(4-aminophenyl)-3-(3-(2-isopropyl-5-methylphenyl)-4-oxothiazolidin-2-ylidene)urea (C3; 120 mg, 0.314 mmol) in acetonitrile (6 mL) was added 4-(trifluoromethoxy)benzene-1-sulfonyl chloride (0.053 mL, 0.314 mmol). The reaction mixture was stirred at room temperature for 3 days (d). The solution was concentrated. Purification by silica gel chromatography (eluting with 0-40, 40 for 2 min, and 40-100% ethyl acetate-hexanes) afforded the title compound as a dark red oil (94 mg, 49%).

Example 16: Preparation of (Z)-4-(3-(3-(2-isopropyl-5-methylphenyl)-4-oxothiazolidin-2-ylidene)ureido)phenethyl (4-(trifluoromethoxy)phenyl)carbamate (A52)

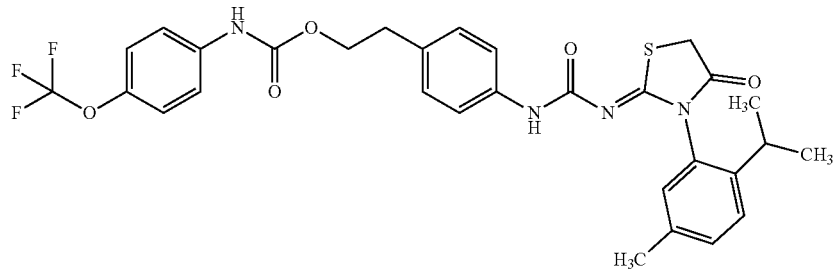 [SMILES: Cc1ccc(C(C)C)c(N2C(=O)CS/C2=N\C(=O)Nc2ccc(CCOC(=O)Nc3ccc(OC(F)(F)F)cc3)cc2)c1]

A solution of 4-(azidocarbonyl)phenethyl (4-(trifluoromethoxy)phenyl)carbamate (C25; 145 mg, 0.368 mmol) in acetonitrile (5 mL) was stirred and heated at 79° C. for 1.5 h. The solution was cooled to room temperature, and 1-(2-isopropyl-5-methylphenyl)thiourea (77 mg, 0.368 mmol) and cesium carbonate (132 mg, 0.405 mmol) were added. The reaction mixture was stirred at room temperature for 3 h. Methyl bromoacetate (0.068 mL, 0.735 mmol), ethanol (5.0 mL) and sodium acetate (91 mg, 1.10 mmol) were added. The reaction mixture was heated at 60° C. for 0.5 h. The solution was concentrated, and the residue was dissolved and adsorbed onto silica. Purification by silica gel chromatography (eluting with 0-50, 50, and 50-100% ethyl acetate-hexanes) afforded an orange oil. Purification of the orange oil by silica gel chromatography (eluting with 0-100% ethyl acetate-hexanes) afforded the title compound as an orange oil (30 mg, 13%).

Example 17: Preparation of 4-(trifluoromethoxy)phenyl (Z)-(4-(2-(3-(3-(2-isopropyl-5-methylphenyl)-4-oxothiazolidin-2-ylidene)ureido)ethyl)phenyl)carbamate (A53)

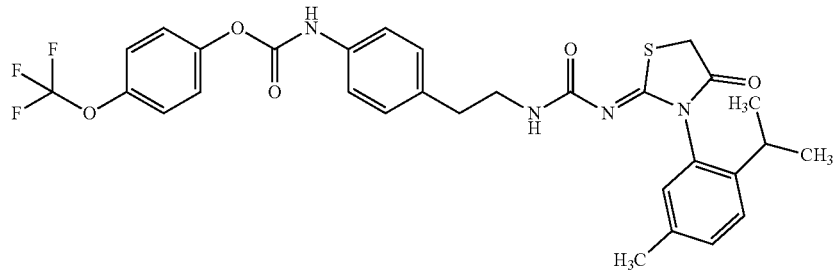 [SMILES: Cc1ccc(C(C)C)c(N2C(=O)CS/C2=N\C(=O)NCCc2ccc(NC(=O)Oc3ccc(OC(F)(F)F)cc3)cc2)c1]

To a solution of 4-nitrophenyl (Z)-(4-(2-(3-(3-(2-isopropyl-5-methylphenyl)-4-oxothiazolidin-2-ylidene)ureido)ethyl)phenyl)carbamate (C2; 162 mg, 0.281 mmol) in acetonitrile (4 mL) were added 4-(trifluoromethoxy)phenol (0.036 mL, 0.281 mmol), N,N-diisopropylethylamine (0.147 mL, 0.844 mmol), and cesium carbonate (18.3 mg, 0.056 mmol). The reaction mixture was stirred at room temperature for 15 min. The solution was adsorbed onto silica gel. Purification by silica gel chromatography (eluting with 0-40, 40 for 3 min, and 40-100% ethyl acetate-hexanes) afforded the title compound as a yellow oil (65 mg, 36%).

Example 18: Preparation of 1-((Z)-3-(2-isopropylphenyl)-4-oxothiazolidin-2-ylidene)-3-(4-(2-((E)-4-(trifluoromethoxy)benzylidene)hydrazinyl)phenyl)urea (A54)

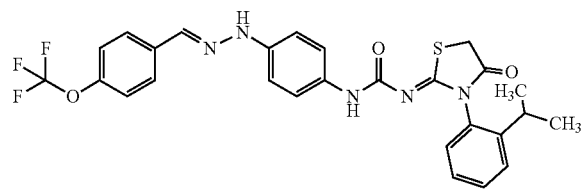 [SMILES: CC(C)c1ccccc1N1C(=O)CS/C1=N\C(=O)Nc1ccc(N/N=C/c2ccc(OC(F)(F)F)cc2)cc1]

A solution of (E)-4-(2-(4-(trifluoromethoxy)benzylidene)hydrazinyl)benzoyl azide (C26; 150 mg, 0.429 mmol) in dry acetonitrile (8 mL) was heated to 78° C. and stirred for 2 h. The solution was cooled to room temperature, and 2-imino-3-(2-isopropylphenyl)thiazolidin-4-one (101 mg, 0.429 mmol) was added. The reaction mixture was stirred for 20 min. The solvent was concentrated under a stream of nitrogen overnight. The title compound was isolated as a brown solid (145 mg, 56%).

The following compound was synthesized in a manner similar to that provided in Example 18.

1-((Z)-3-(2-Isopropyl-5-methylphenyl)-4-oxothiazolidin-2-ylidene)-3-(4-(2-((E)-4-(trifluoromethoxy)benzylidene)hydrazinyl)phenyl)urea (A55)

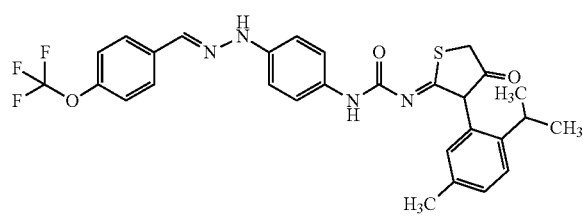 [SMILES: Cc1ccc(C(C)C)c(C2C(=O)CS/C2=N\C(=O)Nc2ccc(N/N=C/c3ccc(OC(F)(F)F)cc3)cc2)c1]

The title compound was synthesized from C26 and 2-imino-3-(2-isopropyl-5-methylphenyl)thiazolidin-4-one and isolated as a light brown solid (187 mg, 76%).

Example 19: Preparation of (Z)-1-(4-aminophenethyl)-3-(3-(2-isopropyl-5-methylphenyl)-4-oxothiazolidin-2-ylidene)urea (C1)

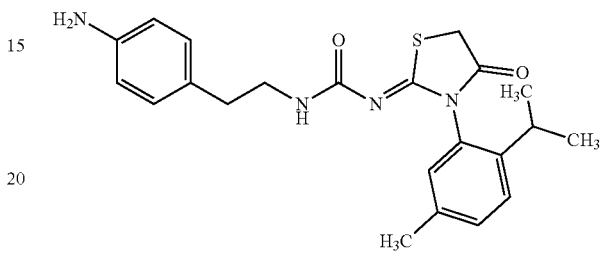

To a solution of (Z)-4-nitrophenyl-(3-(2-isopropyl-5-methylphenyl)-4-oxothiazolidin-2-ylidene)carbamate (prepared as in Fischer, L. G. et al., U. S. Patent Application Publication 2014/0274688; 120 mg, 0.290 mmol) in dry tetrahydrofuran (5 mL) was added 2-(4-aminophenyl)ethylamine (0.037 mL, 0.290 mmol) via syringe. The reaction mixture was stirred for 1 h at room temperature. The mixture was concentrated and dried under vacuum. The title compound was isolated as a red oil (85 mg, 70%): $^1$H NMR (400 MHz, CDCl$_3$) δ 8.20-8.03 (m, 2H), 6.89-6.79 (m, 3H), 6.62-6.51 (m, 2H), 5.52 (t, J=6.1 Hz, 1H), 3.92 (d, J=1.8 Hz, 2H), 3.54-3.27 (m, 3H), 2.66 (tq, J=13.7, 6.7 Hz, 4H), 2.33 (t, J=0.7 Hz, 3H), 1.15 (dd, J=6.9, 3.7 Hz, 6H); $^{13}$C NMR (101 MHz, CDCl$_3$) δ 172.55, 161.76, 144.48, 142.98, 136.63, 132.23, 130.96, 129.37, 128.40, 126.49, 125.99, 115.48, 115.23, 41.81, 34.68, 32.83, 28.14, 23.68, 23.45, 20.60; ESIMS m/z 410 ([M+1]$^+$).

Example 20: Preparation of 4-nitrophenyl (Z)-(4-(2-(3-(3-(2-isopropyl-5-methylphenyl)-4-oxothiazolidin-2-ylidene)ureido)ethyl)phenyl)carbamate (C$_2$)

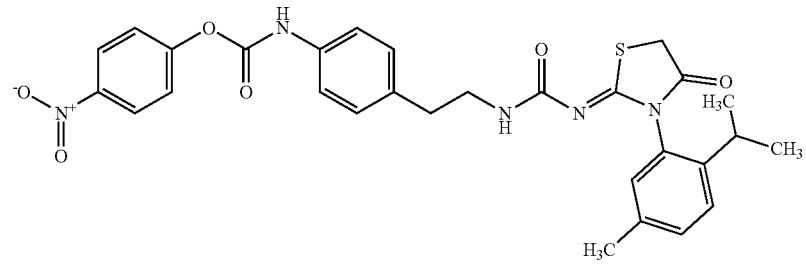

To a solution of (Z)-1-(4-aminophenethyl)-3-(3-(2-isopropyl-5-methylphenyl)-4-oxothiazolidin-2-ylidene)urea (C1; 142 mg, 0.346 mmol) in tetrahydrofuran (4 mL) was added 4-nitrophenyl carbonochloridate (69.7 mg, 0.346 mmol). The reaction mixture was stirred at room temperature for 3 min. The solution was diluted with ethyl acetate and poured onto water. The organic layer was dried and concentrated. The title compound was isolated as a yellow foam, which was used without further purification (162 mg, 58%): $^1$H NMR (400 MHz, CDCl$_3$) δ 8.15 (d, J=9.1 Hz, 3H), 7.43-7.35 (m, 2H), 7.13 (d, J=8.4 Hz, 2H), 7.01-6.95 (m, 1H), 6.93-6.84 (m, 4H), 5.54 (t, J=6.4 Hz, 1H), 3.93 (d, J=1.8 Hz, 2H), 3.62-3.29 (m, 2H), 2.78 (t, J=7.1 Hz, 2H), 2.66-2.57 (m, 1H), 2.32 (s, 3H), 1.15 (dd, J=6.9, 3.2 Hz, 6H); ESIMS m/z 576 ([M+1]$^+$).

Example 21: Preparation of (Z)-1-(4-aminophenyl)-3-(3-(2-isopropyl-5-methylphenyl)-4-oxothiazolidin-2-ylidene)urea (C3)

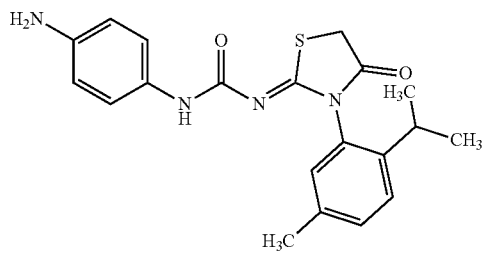 [SMILES: Cc1ccc(C(C)C)c(N2C(=O)CS/C2=N\C(=O)Nc2ccc(N)cc2)c1]

To a solution of (Z)-4-nitrophenyl (3-(2-isopropyl-5-methylphenyl)-4-oxothiazolidin-2-ylidene)carbamate (prepared as in Fischer, L. G. et al., U. S. Patent Application Publication 2014/0274688; 100 mg, 0.242 mmol) and benzene-1,4-diamine (26.2 mg, 0.242 mmol) in dry tetrahydrofuran (4 mL) was added cesium carbonate (87 mg, 0.266 mmol). The reaction mixture was stirred at room temperature for 19 h and was diluted with ether. The mixture washed with water, and the organic layer was dried and concentrated to give an orange oil. Purification by silica gel chromatography (eluting with 0-55% ethyl acetate-hexanes) afforded the title compound as a red oil (64 mg, 66%): $^1$H NMR (400 MHz, CDCl$_3$) δ 7.37 (d, J=8.0 Hz, 1H), 7.30 (dd, J=8.1, 1.8 Hz, 1H), 7.25 (d, 2H), 7.10 (s, 1H), 6.90 (dd, J=1.8, 0.9 Hz, 1H), 6.70-6.53 (m, 2H), 3.94 (d, J=2.7 Hz, 2H), 3.56 (s, 2H), 2.67 (p, J=6.9 Hz, 1H), 2.37 (t, J=0.7 Hz, 3H), 1.18 (dd, J=6.9, 5.0 Hz, 6H); $^{13}$C NMR (101 MHz, CDCl$_3$) δ 172.45, 169.02, 159.28, 143.12, 142.79, 136.71, 131.00, 129.09, 128.43, 126.54, 125.98, 120.69, 115.33, 32.85, 30.77, 28.19, 23.65, 20.65; ESIMS m/z 382 ([M+1]$^+$).

Example 22: Preparation of tert-butyl (Z)-4-(3-(3-(5-methyl-2-(2,2,2-trifluoroethoxy)phenyl)-4-oxothiazolidin-2-ylidene)ureido)benzoate (C4)

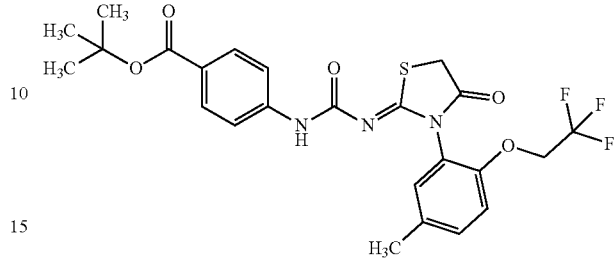

tert-Butyl 4-aminobenzoate (0.100 g, 0.517 mmol) was dissolved in dichloromethane (2.59 mL), and triphosgene (0.061 g, 0.207 mmol) and N,N-diisopropylethylamine (0.271 mL, 1.552 mmol) were added. The mixture was stirred for 1 h. 2-Imino-3-(5-methyl-2-(2,2,2-trifluoroethoxy)phenyl)thiazolidin-4-one (0.173 g, 0.569 mmol) was added, and the mixture was stirred at room temperature overnight. The solvent was concentrated. Purification by silica gel chromatography (eluting with 0-30% acetone in hexanes) provided the title compound as a sticky white foam (225 mg, 83%): $^1$H NMR (300 MHz, CDCl$_3$) δ 7.92 (d, J=8.7 Hz, 2H), 7.53 (d, J=8.6 Hz, 2H), 7.34-7.25 (m, 3H), 7.06 (d, J=2.3 Hz, 1H), 6.98 (d, J=8.5 Hz, 1H), 4.50-4.24 (m, 2H), 3.94 (d, J=3.0 Hz, 2H), 2.39 (s, 3H), 1.57 (s, 9H); HRMS-ESI (m/z) [M+H]$^+$ calcd for C$_{24}$H$_{24}$F$_3$N$_3$O$_5$S, 524.1462; found, 524.1462.

Example 23: Preparation of tert-butyl (Z)-4-(3-(3-(2-isopropyl-5-methylphenyl)-4-oxothiazolidin-2-ylidene)ureido)benzoate (C5)

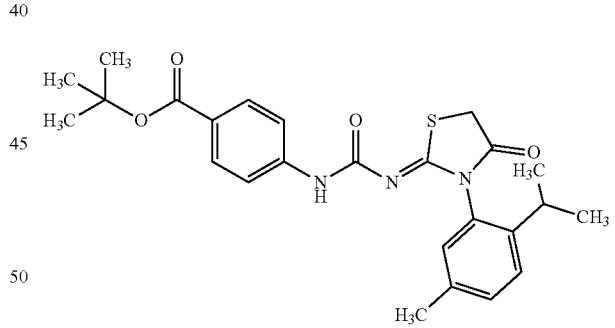

tert-Butyl 4-aminobenzoate (0.200 g, 1.035 mmol) was stirred in acetonitrile (5.17 mL) with N,N-diisopropylethylamine (0.542 mL, 3.10 mmol) and bis(2,5-dioxopyrrolidin-1-yl) carbonate (0.318 g, 1.242 mmol) for 20 min. 2-Imino-3-(2-isopropyl-5-methylphenyl)thiazolidin-4-one (0.283 g, 1.138 mmol) was then added, and the mixture was stirred at room temperature overnight. The solvent was concentrated under a stream of nitrogen, and the residue was partitioned between dichloromethane and aqueous sodium bicarbonate solution. The layers were passed through a phase separator, and the dichloromethane was removed. Purification of the resulting material by silica gel chromatography (eluting with 0-35% acetone in hexanes) provided the title compound as a yellow foam and as a mixture of rotational isomers (200 mg, 41%): $^1$H NMR (400 MHz, CDCl$_3$) δ 7.93 (dd, J=15.3, 8.7 Hz, 2H), 7.48 (dd, J=33.0, 8.7 Hz, 2H), 7.40-7.29 (m, 2H), 7.10-6.93 (m, 1H), 6.87 (d, J=26.4 Hz, 1H), 4.13-3.84 (m, 2H), 2.67 (dq, J=13.3, 6.8 Hz, 1H), 2.41-2.30 (m, 3H), 1.56 (d, J=10.2 Hz, 9H), 1.19 (dd, J=6.9, 3.8 Hz, 6H); ESIMS m/z 468.1 ([M+H]$^+$).

Example 24: Preparation of N'-(4-nitrophenyl)-4-(trifluoromethoxy)benzohydrazide (C6)

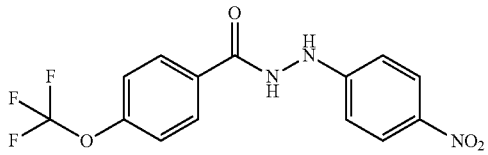

To a solution of pyridine (1.08 mL, 13.4 mmol) in dichloromethane was added (4-nitrophenyl)hydrazine hydrochloride (0.929 g, 4.90 mmol). The mixture was stirred for 10 min. 4-(Trifluoromethoxy)benzoyl chloride (0.702 mL, 4.45 mmol) was added dropwise, with a small amount of bubbling (exotherm). The mixture was stirred for 30 minutes, at which point a large amount of precipitate had formed. The mixture was poured into water and sodium bicarbonate, and more dichloromethane was added. A strong emulsion resulted. After washing and filtration, the organic layer showed no product by LCMS, while the solid was shown to be the desired product. The filtrates were collected, washed with dichloromethane, and dried under vacuum before being used in the next step without further manipulation. The title compound was isolated as an orange solid (1.35 g, 89%): $^1$H NMR (400 MHz, DMSO-d$_6$) δ 10.77 (s, 1H), 9.29 (s, 1H), 8.15-8.03 (m, 4H), 7.54 (d, J=8.3 Hz, 2H), 6.91-6.82 (m, 2H); $^{19}$F NMR (376 MHz, DMSO-d$_6$) δ −56.65; HRMS-ESI (m/z) [M+H]$^+$ calcd for C$_{14}$H$_{10}$F$_3$N$_3$O$_4$, 342.0696; found, 342.07.

Example 25: Preparation of N'-(4-aminophenyl)-4-(trifluoromethoxy)benzohydrazide (C7)

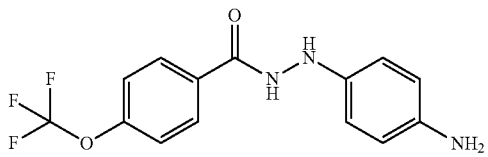 [SMILES: O=C(NNc1ccc([N+](=O)[O-])cc1)c1ccc(OC(F)(F)F)cc1]

N-(4-Nitrophenyl)-4-(trifluoromethoxy)benzohydrazide (C6; 1.34 g, 3.93 mmol) was dissolved in ethyl acetate (7.85 mL) and ethanol (7.85 mL). 10% Palladium on carbon (0.209 g, 0.196 mmol) was added and the mixture was placed under a balloon of hydrogen. The reaction mixture was stirred vigorously overnight. The mixture was filtered and concentrated to a red oil that solidified. There was low recovery due to the material solidifying on the Celite® column during attempted purification. The columns were flushed with methanol and the solvent concentrated. The title compound was isolated as a pale yellow solid (710 mg, 58%): $^1$H NMR (400 MHz, DMSO-d$_6$) δ 10.40 (d, J=4.1 Hz, 1H), 8.06-8.00 (m, 2H), 7.52-7.47 (m, 2H), 7.24 (d, J=4.1 Hz, 1H), 6.63-6.57 (m, 2H), 6.46 (d, J=2.2 Hz, 2H), 4.54 (s, 2H); $^{19}$F NMR (376 MHz, DMSO-d$_6$) δ −56.67; ESIMS m/z 312 ([M+H]$^+$).

Example 26: Preparation of tert-butyl (4-aminophenethyl)carbamate (C8)

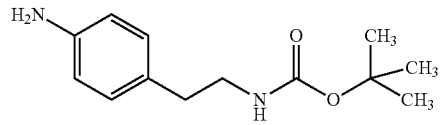 [SMILES: CC(C)(C)OC(=O)NCCc1ccc(N)cc1]

Method A: To a solution of 4-(2-aminoethyl)aniline (10 g, 73.5 mmol) in dichloromethane (750 mL) was added sequentially triethylamine (8.2 g, 88.2 mmol) and di-tert-butyl dicarbonate (19.2 g, 88.23 mmol), and the reaction mixture was stirred at room temperature for 16 h. The reaction mixture was poured into water, the layers were separated and the aqueous layer was extracted with dichloromethane (2×500 mL). The organic layer was dried over anhydrous sodium sulfate, filtered and concentrated under reduced pressure. The residue was triturated with n-pentane to afford the title compound as an off-white solid (15.5 g, 98%): $^1$H NMR (300 MHz, DMSO-d$_6$) δ 6.83-6.75 (m, 3H), 6.47 (d, J=8.4 Hz, 2H), 4.83 (s, 2H), 3.01-2.95 (m, 2H), 2.51-2.46 (m, 2H), 1.39 (s, 9H); ESIMS m/z 236.2 ([M]$^+$).

Method B: To a solution of di-tert-butyl dicarbonate (1.06 mL, 4.58 mmol) in dioxane (12 mL) was added 4-(2-aminoethyl)aniline (1.181 mL, 9.16 mmol) slowly over −15 min. The reaction mixture was stirred at room temperature for 22 h. The solvent was concentrated. Purification of the residue by silica gel chromatography (eluting with 0-70% ethyl acetate-hexanes) afforded the title compound as a yellow solid (888 mg, 82%). $^1$H NMR (400 MHz, CDCl$_3$) δ 7.06-6.90 (m, 2H), 6.72-6.50 (m, 2H), 4.53 (s, 1H), 3.59 (s, 2H), 3.30 (t, J=6.7 Hz, 2H), 2.67 (t, J=7.0 Hz, 2H), 1.43 (s, 9H); ESIMS m/z 237 ([M]$^+$).

Example 27: Preparation of tert-butyl (4-(3-(4-(trifluoromethyl)phenyl)ureido)phenethyl)carbamate (C9)

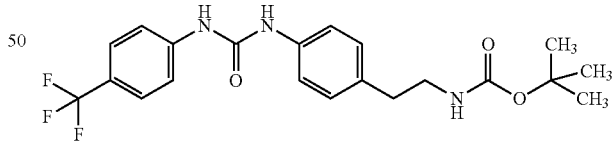

To a solution of tert-butyl (4-aminophenethyl)carbamate (C8; 3 g, 12.71 mmol) in toluene (120 mL) was added 1-isocyanato-4-(trifluoromethyl)benzene (2.4 g, 12.71 mmol), and the reaction mixture was stirred at room temperature for 4 h. The reaction mixture was concentrated under reduced pressure. The residue was triturated with diethyl ether to afford the title compound as an off-white solid (3.3 g, 61%): $^1$H NMR (300 MHz, DMSO-d$_6$) δ 9.06 (s, 1H), 8.72 (s, 1H), 7.67-7.60 (m, 4H), 7.37 (d, J=8.4 Hz, 2H), 7.10 (d, J=8.4 Hz, 2H), 6.86 (t, J=5.1 Hz, 1H), 3.05-2.96 (m, 2H), 2.63 (t, J=6.9 Hz, 2H), 1.37 (s, 9H); ESIMS m/z 424 ([M+H]$^+$).

The following compound was synthesized in a manner similar to that provided in Example 27.

tert-butyl (4-(3-(4-(trifluoromethoxy)phenyl)ureido)phenethyl)carbamate (C10)

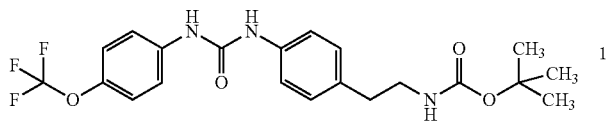

The title compound was synthesized from compound C8 and 1-isocyanato-4-(trifluoromethoxy)benzene and isolated as an off-white solid (3.2 g, 57%): $^1$H NMR (300 MHz, DMSO-$d_6$) δ 8.83 (s, 1H), 8.62 (s, 1H), 7.56-7.52 (m, 2H), 7.36 (d, J=8.4 Hz, 2H), 7.27 (d, J=8.4 Hz, 2H), 7.10 (d, J=8.4 Hz, 2H), 6.85 (t, J=5.1 Hz, 1H), 3.07-2.94 (m, 2H), 2.63 (t, J=7.2 Hz, 2H), 1.37 (s, 9H); ESIMS m/z 440 ([M+H]$^+$).

Example 28: Preparation of 1-(4-(2-aminoethyl)phenyl)-3-(4-(trifluoromethyl)phenyl)urea hydrochloride (C11)

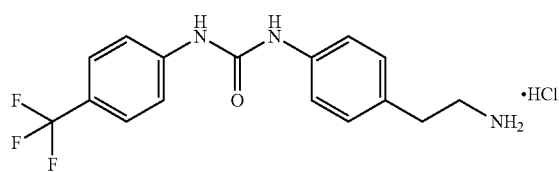 [SMILES: NCCc1ccc(NC(=O)Nc2ccc(C(F)(F)F)cc2)cc1 ; Cl]

To a solution of tert-butyl (4-(3-(4-(trifluoromethyl)phenyl)ureido)phenethyl)carbamate (C9; 3.2 g, 7.56 mmol) in dichloromethane (50 mL) was added HCl in dioxane (4 M; 15 mL, 60 mmol) at 0° C., and the reaction mixture was stirred at room temperature for 16 h. The reaction mixture was concentrated under reduced pressure. The residue was triturated with diethyl ether to afford the title compound as an off-white solid (2.2 g, 81%): mp 279-281° C.; $^1$H NMR (400 MHz, DMSO-$d_6$) δ 9.58 (s, 1H), 9.21 (s, 1H), 7.84 (br s, 3H), 7.68-7.61 (m, 4H), 7.43 (d, J=8.4 Hz, 2H), 7.18 (d, J=8.4 Hz, 2H), 3.04-2.98 (m, 2H), 2.81 (t, J=7.6 Hz, 2H); $^{19}$F NMR (376 MHz, DMSO-$d_6$) δ −60.04; ESIMS m/z 324 ([M+H]$^+$).

The following compound was synthesized in a manner similar to that provided in Example 28.

1-(4-(2-Aminoethyl)phenyl)-3-(4-(trifluoromethoxy)phenyl)urea hydrochloride (C12)

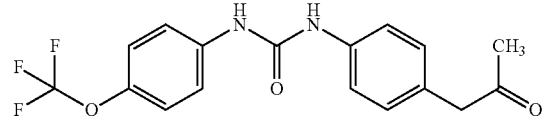

The title compound was synthesized from compound C10 and isolated as an off-white solid (1.9 g, 73%): mp 337-339° C.; $^1$H NMR (400 MHz, DMSO-$d_6$) δ 9.21 (s, 1H), 9.02 (s, 1H), 7.83 (br s, 3H), 7.55 (d, J=9.2 Hz, 2H), 7.42 (d, J=8.4 Hz, 2H), 7.28 (d, J=8.8 Hz, 2H), 7.17 (d, J=8.4 Hz, 2H), 3.04-2.98 (m, 2H), 2.80 (t, J=7.2 Hz, 2H); $^{19}$F NMR (376 MHz, DMSO-$d_6$) δ −57.13; ESIMS m/z 340.24 ([M+H]$^+$).

Example 29: Preparation of 1-(4-aminophenyl)propan-2-one (C13)

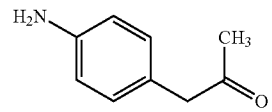

To a solution of 1-(4-nitrophenyl)-2-propanone (4.5 g, 2.51 mmol) in ethyl acetate (100 mL) was added 10% palladium on carbon (1 g), and the reaction mixture was stirred under hydrogen (30 pounds per square inch (psi)) at room temperature for 4 h. The reaction mixture was filtered through a pad of Celite®, and the filter pad was washed with ethyl acetate. The filtrate was concentrated under reduced pressure. The title compound was isolated as a colorless liquid (3.2 g, 85%): $^1$H NMR (300 MHz, DMSO-$d_6$) δ 6.82 (d, J=8.1 Hz, 2H), 6.50 (d, J=8.4 Hz, 2H), 4.95 (s, 2H), 3.48 (s, 2H), 2.04 (s, 3H); ESIMS m/z 149.83 ([M+H])$^+$.

Example 30: Preparation of 1-(4-(2-oxopropyl)phenyl)-3-(4-(trifluoromethyl)phenyl)urea (C14)

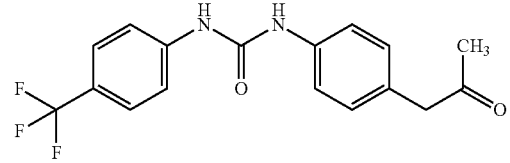 [SMILES: CC(=O)Cc1ccc(NC(=O)Nc2ccc(C(F)(F)F)cc2)cc1]

To a solution of 1-(4-aminophenyl)propan-2-one (C13; 2 g, 13.4 mmol) in toluene (80 mL) was added 1-isocyanato-4-(trifluoromethyl)benzene (2.5 g, 13.4 mmol), and the reaction mixture was stirred at room temperature for 4 h. The reaction mixture was concentrated under reduced pressure, and the residue was triturated with diethyl ether. The title compound was isolated as an off-white solid (3.1 g, 68%): $^1$H NMR (300 MHz, DMSO-$d_6$) δ 9.07 (s, 1H), 8.76 (s, 1H), 7.67-7.60 (m, 4H), 7.40 (d, J=8.6 Hz, 2H), 7.10 (d, J=8.4 Hz, 2H), 3.69 (s, 2H), 2.11 (s, 3H); ESIMS m/z 336.96 ([M+H]$^+$).

The following compound was synthesized in a manner similar to that provided in Example 30.

1-(4-(2-Oxopropyl)phenyl)-3-(4-(trifluoromethoxy)phenyl)urea (C15)

The title compound was synthesized from compound C13 and 1-isocyanato-4-(trifluoromethoxy)benzene and isolated as an off-white solid (3.4 g, 72%): ESIMS m/z 353 ([M+H]$^+$).

Example 31: Preparation of 1-(4-(2-aminopropyl) phenyl)-3-(4-(trifluoromethyl)phenyl)urea (C16)

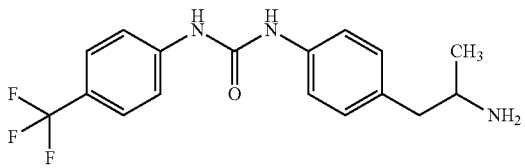 [SMILES: CC(N)Cc1ccc(NC(=O)Nc2ccc(C(F)(F)F)cc2)cc1]

To a solution of 1-(4-(2-oxopropyl)phenyl)-3-(4-(trifluoromethyl)phenyl)urea (C14; 2.6 g, 7.73 mmol) in methanol (20 mL) was added ammonium acetate (4.8 g, 61.9 mmol), and the reaction mixture was stirred at room temperature for 3 h. The reaction mixture was cooled to 0° C., sodium cyanoborohydride (0.53 g, 8.51 mmol) was added, and the reaction mixture was stirred at room temperature for 3 h. The reaction mixture was concentrated under reduced pressure. The residue was partitioned between saturated potassium carbonate (100 mL) and ethyl acetate (200 mL). The organic layer was separated, dried over anhydrous sodium sulfate, filtered and concentrated under reduced pressure. Purification by preparative HPLC afforded the title compound as an off-white solid (0.55 g, 22%): mp 163-165° C.; $^1$H NMR (400 MHz, DMSO-$d_6$) δ 9.78 (s, 1H), 9.39 (s, 1H), 7.68 (d, J=8.8 Hz, 2H), 7.58 (d, J=8.8 Hz, 2H), 7.40 (d, J=8.4 Hz, 2H), 7.07 (d, J=8.4 Hz, 2H), 2.96 (q, J=6.8 Hz, 1H), 2.46 (d, J=6.0 Hz, 2H), 0.94 (d, J=6.4 Hz, 3H); $^{19}$F NMR (376 MHz, DMSO-$d_6$) δ −59.99; ESIMS m/z 338.27 ([M+H]$^+$).

The following compound was synthesized in a manner similar to that provided in Example 31.

1-(4-(2-Aminopropyl)phenyl)-3-(4-(trifluoromethoxy)phenyl)urea (C17)

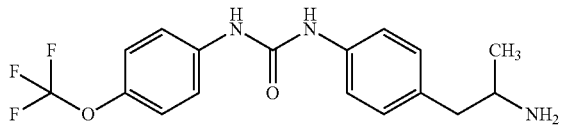 [SMILES: CC(N)Cc1ccc(NC(=O)Nc2ccc(OC(F)(F)F)cc2)cc1]

The title compound was synthesized from compound C15 and isolated as an off-white solid (1.4 g, 61%): mp 118-120° C.; $^1$H NMR (400 MHz, DMSO-$d_6$) δ 10.31 (s, 1H), 10.10 (s, 1H), 7.61 (d, J=8.8 Hz, 2H), 7.47 (d, J=8.8 Hz, 2H), 7.24 (d, J=8.4 Hz, 2H), 7.10 (d, J=8.4 Hz, 2H), 3.28 (q, J=6.4 Hz, 1H), 2.82-2.76 (m, 1H), 2.59-2.54 (m, 1H), 1.07 (d, J=8.0 Hz, 3H); $^{19}$F NMR (376 MHz, DMSO-$d_6$) δ −57.11; ESIMS m/z 354 ([M+H]$^+$).

Example 32: Preparation of 1-(4-aminobenzyl)-3-(4-(trifluoromethoxy)phenyl)urea (C18)

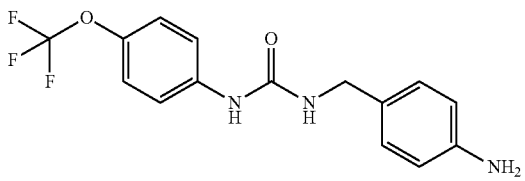 [SMILES: Nc1ccc(CNC(=O)Nc2ccc(OC(F)(F)F)cc2)cc1]

To a solution of 4-(aminomethyl)aniline (0.139 mL, 1.228 mmol) in tetrahydrofuran (4 mL) was added 1-isocyanato-4-(trifluoromethoxy)benzene (0.185 mL, 1.228 mmol). The mixture was stirred at room temperature for 20 min, which by liquid chromatography-mass spectrometry (LC-MS) was mostly the desired product and a little diacylated material. The solution was concentrated and dried. The title compound was isolated as a white solid (184 mg, 45%): $^1$H NMR (400 MHz, methanol-$d_4$) δ 7.48-7.39 (m, 2H), 7.20-7.11 (m, 2H), 7.10-7.03 (m, 2H), 6.75-6.65 (m, 2H), 4.24 (s, 2H); $^{19}$F NMR (376 MHz, methanol-$d_4$) δ −59.86; $^{13}$C NMR (101 MHz, methanol-$d_4$) δ 157.44, 147.47, 144.58, 139.88, 129.64, 129.08, 122.23, 120.49, 116.28, 100.97, 43.96; ESIMS m/z 325 ([M]$^+$).

Example 33: Preparation of 4-nitrophenyl (4-((3-(4-(trifluoromethoxy)phenyl)ureido)methyl)phenyl) carbamate (C19)

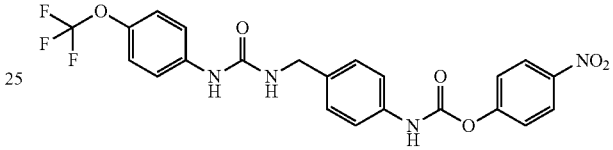

To a solution of 1-(4-aminobenzyl)-3-(4-(trifluoromethoxy)phenyl)urea (C18; 53 mg, 0.163 mmol) in dry acetonitrile (4 mL) was added 4-nitrophenyl carbonochloridate (32.8 mg, 0.163 mmol). The reaction mixture was stirred at room temperature for 3 min. The solvent was concentrated under vacuum. The title compound was isolated as a yellow solid (83 mg, 88%): $^1$H NMR (400 MHz, DMSO-$d_6$) δ 10.29 (s, 1H), 8.76-8.60 (m, 1H), 8.29-8.04 (m, 2H), 7.41-7.29 (m, 4H), 7.15-7.09 (m, 2H), 7.09-7.01 (m, 2H), 6.82-6.71 (m, 2H), 6.61-6.41 (m, 1H), 4.15-3.98 (m, 2H); $^{19}$F NMR (376 MHz, DMSO-$d_6$) δ −57.13.

Example 34: Preparation of tert-butyl (Z)-(4-(3-(3-(2-isopropyl-5-methylphenyl)-4-oxothiazolidin-2-ylidene)ureido)phenethyl)carbamate (C20)

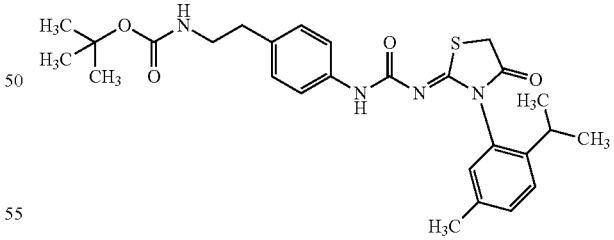

A solution of 2-imino-3-(2-isopropyl-5-methylphenyl)thiazolidin-4-one (61.9 mg, 0.249 mmol), tert-butyl (4-aminophenethyl)carbamate (C8; 100 mg, 0.249 mmol), and cesium carbonate (89 mg, 0.274 mmol) in dry acetonitrile (3 mL) and methanol (3 mL) was stirred at room temperature for 1 h. The solvent was concentrated to 1/2 volume and adsorbed onto silica. Purification (eluting with 0-100% acetonitrile-water) afforded the title compound as a yellow solid (86 mg, 68%): $^1$H NMR (400 MHz, CDCl$_3$) δ 7.43-7.35 (m, 3H), 7.12 (t, J=8.7 Hz, 4H), 6.93-6.87 (m, 1H), 6.73

(s, 1H), 3.96 (d, J=2.6 Hz, 2H), 3.34 (s, 2H), 2.76 (t, J=7.2 Hz, 2H), 2.67 (p, J=6.9 Hz, 1H), 2.38 (d, J=0.7 Hz, 3H), 1.43 (d, J=4.1 Hz, 9H), 1.27-1.05 (m, 6H); ESIMS m/z 510 ([M]+).

Example 35: Preparation of (Z)-2-(4-(3-(3-(2-isopropyl-5-methylphenyl)-4-oxothiazolidin-2-ylidene)ureido)phenylethan-1-aminium 2,2,2-trifluoroacetate (C21)

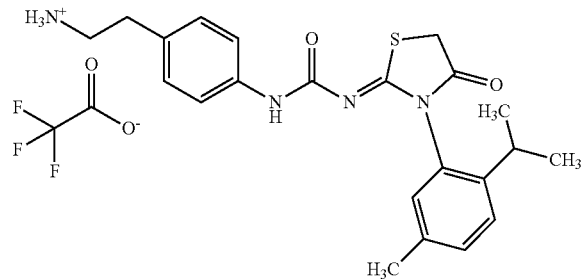 [SMILES: O=C([O-])C(F)(F)F ; Cc1ccc(C(C)C)c(N2C(=O)CS/C2=N\C(=O)Nc2ccc(CC[NH3+])cc2)c1]

To a solution of tert-butyl (Z)-(4-(3-(3-(2-isopropyl-5-methylphenyl)-4-oxothiazolidin-2-ylidene)ureido)phenethyl)carbamate (C20; 86 mg, 0.168 mmol) in dry dichloromethane (3 mL) was added trifluoroacetic acid (0.013 mL, 0.168 mmol). The mixture was stirred at room temperature for 1.5 h. Additional TFA (26 µL) was added and the mixture was stirred at room temperature. Another aliquot of TFA (13 µL) was added after 26 h. The mixture was stirred for 4 h more. The solution was concentrated. The title compound was isolated as a red oil (39 mg, 56%): $^1$H NMR (400 MHz, CDCl$_3$) δ 9.41 (s, 2H), 7.44 (s, 1H), 7.35 (d, J=4.8 Hz, 2H), 7.23-7.17 (m, 2H), 7.14-7.05 (m, 2H), 6.90 (dd, J=1.7, 1.0 Hz, 1H), 3.98 (d, J=2.0 Hz, 2H), 3.25 (s, 2H), 2.92 (t, J=6.5 Hz, 2H), 2.70-2.55 (m, 1H), 2.37 (s, 3H), 1.24-1.04 (m, 6H); $^{13}$C NMR (101 MHz, CDCl3) δ 172.93, 171.73, 163.47, 161.20, 161.06, 143.67, 137.53, 136.69, 132.58, 132.41, 131.88, 130.37, 128.94, 127.29, 121.72, 41.21, 33.46, 33.14, 28.88, 28.06, 24.29, 21.22; ESIMS m/z 410 ([M]+).

Example 36: Preparation of N-(4-aminophenethyl)-4-(trifluoromethoxy)benzamide (C22)

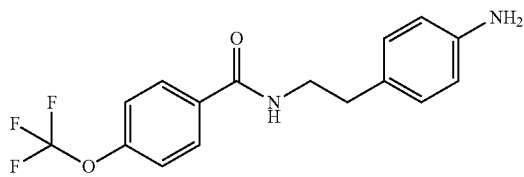 [SMILES: Nc1ccc(CCNC(=O)c2ccc(OC(F)(F)F)cc2)cc1]

4-(Trifluoromethoxy)benzoyl chloride (0.487 mL, 3.12 mmol) was added dropwise to a solution of 4-(2-aminoethyl)aniline (2.01 mL, 15.6 mmol) in dry tetrahydrofuran (10 mL). The reaction mixture was stirred at room temperature. A white precipitate formed immediately. After 30 min, the precipitate was removed by filtration and rinsed with ether. The filtrate was poured onto brine and extracted with ether (2×). The organic extracts were dried and concentrated. The filtrate was dissolved and adsorbed onto silica. Purification (eluting with 0-100% acetonitrile-water) provided the title compound as a yellow solid (152 mg, 15%): $^1$H NMR (400 MHz, DMSO-d$_6$) δ 8.61 (t, J=5.6 Hz, 1H), 7.98-7.85 (m, 2H), 7.51-7.33 (m, 2H), 6.94-6.80 (m, 2H), 6.55-6.39 (m, 2H), 4.84 (s, 2H), 3.45-3.33 (m, 2H), 2.64 (dd, J=8.6, 6.6 Hz, 2H); $^{19}$F NMR (376 MHz, DMSO-d$_6$) δ −56.68; ESIMS m/z 324 ([M]+).

Example 37: Preparation of 4-nitrophenyl (4-(2-(4-(trifluoromethoxy)benzamido)ethyl)phenyl)carbamate (C23)

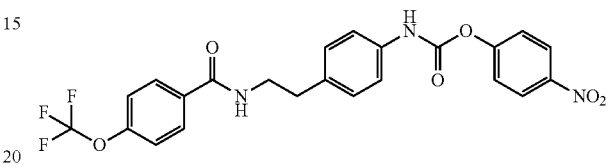

To a solution of N-(4-aminophenethyl)-4-(trifluoromethoxy)benzamide (C22; 152 mg, 0.469 mmol) in dry acetonitrile (3 mL) was added 4-nitrophenyl carbonochloridate (94 mg, 0.469 mmol). The reaction mixture was stirred at room temperature for 10 min. The solution was diluted with ethyl acetate and poured onto water. The organic layer was separated, dried, and concentrated. The title compound was isolated as an orange solid (198 mg, 85%): $^1$H NMR (400 MHz, CDCl$_3$) δ 10.39 (s, 1H), 8.66 (t, J=5.6 Hz, 1H), 8.33-8.25 (m, 2H), 7.97-7.87 (m, 2H), 7.55-7.47 (m, 2H), 7.47-7.38 (m, 4H), 7.25-7.15 (m, 2H), 3.46 (q, J=6.8 Hz, 2H), 2.80 (t, J=7.4 Hz, 2H); $^{19}$F NMR (376 MHz, CDCl3) δ −51.93; ESIMS m/z 490 ([M+1]+).

Example 38: Preparation of 4-(2-(((4-(trifluoromethoxy)phenyl)carbamoyl)oxy)ethyl)benzoic acid (C24)

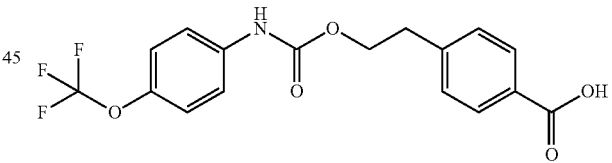

A suspension of 4-(2-hydroxyethyl)benzoic acid (0.25 g, 1.504 mmol) and 1-isocyanato-4-(trifluoromethoxy)benzene (0.227 mL, 1.504 mmol) in acetonitrile (7 mL) was stirred at room temperature for 1 h. Ethanol (5 mL) was added after 3 h to aid with solubility. N,N-Diisopropylethylamine (0.263 mL, 1.50 mmol) was added after 21.5 h. Cesium carbonate (0.490 g, 1.50 mmol) added after 25 h. After 26 h total, the solution was poured onto water and extracted with ethyl acetate. The organic extracts were dried, concentrated, and dried under vacuum. The title compound was isolated as a white solid (479 mg, 59%): $^1$H NMR (400 MHz, DMSO-d$_6$) δ 9.84 (s, 1H), 7.85 (d, J=8.1 Hz, 1H), 7.68-7.45 (m, 4H), 7.39-7.09 (m, 5H), 4.32 (t, J=6.7 Hz, 2H), 2.98 (td, J=6.6, 4.5 Hz, 2H); $^{19}$F NMR (376 MHz, DMSO-d$_6$) δ −57.13; ESIMS m/z 369 ([M]+).

Example 39: Preparation of 4-(azidocarbonyl)phenethyl (4-(trifluoromethoxy)phenyl)carbamate (C25)

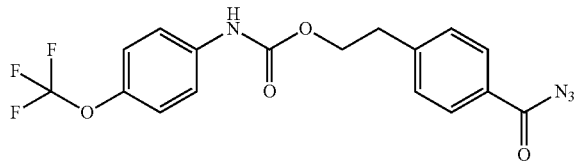 [SMILES: [N-]=[N+]=NC(=O)c1ccc(CCOC(=O)Nc2ccc(OC(F)(F)F)cc2)cc1]

To a suspension of 4-(2-(((4-(trifluoromethoxy)phenyl) carbamoyl)oxy)ethyl)benzoic acid (C24; 479 mg, 1.30 mmol) in toluene (25 mL) were added triethylamine (0.181 mL, 1.30 mmol) followed by diphenylphosphoryl azide (0.279 mL, 1.30 mmol). The reaction mixture was stirred at room temperature for 2 h. The mixture was concentrated and adsorbed onto silica gel. Purification (eluting with 0-100% acetonitrile-water) afforded the title compound as a yellow solid (145 mg, 25%): $^1$H NMR (400 MHz, CDCl$_3$) δ 8.01-7.95 (m, 2H), 7.42-7.31 (m, 4H), 7.19-7.11 (m, 2H), 6.61 (s, 1H), 4.42 (t, J=6.7 Hz, 2H), 3.06 (t, J=6.7 Hz, 2H); $^{19}$F NMR (376 MHz, CDCl$_3$) δ -58.21; ESIMS m/z 379 ([M-15]$^+$).

Example 40: Preparation of (E)-4-(2-(4-(trifluoromethoxy)benzylidene)hydrazinyl)benzoyl azide (C26)

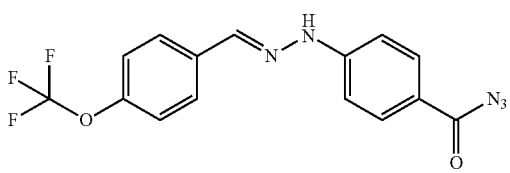 [SMILES: [N-]=[N+]=NC(=O)c1ccc(N/N=C/c2ccc(OC(F)(F)F)cc2)cc1]

To a solution of 4-hydrazinylbenzoic acid (1 g, 6.57 mmol) in acetonitrile (5 mL) was added 4-(trifluoromethoxy)benzaldehyde (1.04 mL, 7.30 mmol). The reaction mixture was stirred at room temperature for 4 h. The suspension was further diluted in toluene (10.0 mL). Triethylamine (1.02 mL, 7.30 mmol) and diphenylphosphoryl azide (1.57 mL, 7.30 mmol) were added sequentially, and the reaction mixture was stirred at room temperature for 1 h. The mixture was concentrated and adsorbed onto silica. Purification (eluting with 0-100% acetonitrile-water) afforded the title compound as a yellow solid (2.176 g, 76%): $^1$H NMR (400 MHz, CDCl$_3$) δ 7.96 (d, J=8.8 Hz, 3H), 7.75 (d, J=1.1 Hz, 1H), 7.71 (d, J=8.8 Hz, 2H), 7.24 (t, J=1.0 Hz, 2H), 7.14-7.03 (m, 2H); $^{19}$F NMR (376 MHz, CDCl$_3$) δ -57.77; ESIMS m/z 348 ([M]$^+$).

Example 41: Preparation of tert-butyl (4-(((4-nitrophenoxy)carbonyl)amino)phenethyl)carbamate (C27)

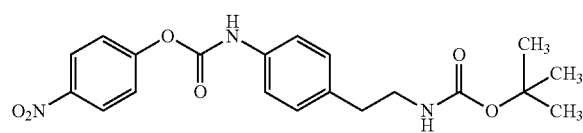 [SMILES: CC(C)(C)OC(=O)NCCc1ccc(NC(=O)Oc2ccc([N+](=O)[O-])cc2)cc1]

tert-Butyl (4-aminophenethyl)carbamate (C8; 0.1 g, 0.423 mmol) and 4-nitrophenyl carbonochloridate (0.085 g, 0.423 mmol) were partially dissolved in dry acetonitrile (7 mL). The suspension was stirred at room temperature for 2 h and the solvent was concentrated. The title compound was isolated as a yellow solid (150 mg, 87%): $^1$H NMR (400 MHz, CDCl$_3$) δ 8.37-8.21 (m, 2H), 7.39 (dd, J=9.8, 2.8 Hz, 3H), 7.20 (d, J=8.2 Hz, 2H), 6.96 (s, 1H), 4.53 (s, 1H), 3.37 (d, J=7.1 Hz, 2H), 2.79 (t, J=7.1 Hz, 2H), 1.44 (s, 9H); ESIMS m/z 401 ([M]$^+$) 401.

Example 42: Preparation of 4-chloro-2-nitro-1-(2,2,2-trifluoroethoxy)benzene (C28)

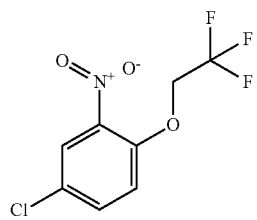

To 4-chloro-2-nitrophenol (2 g, 11.5 mmol) in acetone (25 mL) were added sequentially potassium carbonate (3.19 g, 23.1 mmol) and 2,2,2-trifluoroethyl trifluoromethanesulfonate (2.5 mL, 17.3 mmol). The reaction mixture was stirred overnight under nitrogen then warmed to 60° C. for 3 h. The mixture was cooled to room temperature and diluted with ethyl acetate and water. The organic layer was separated and washed with brine, dried over sodium sulfate, filtered and concentrated. The title compound was isolated as a red solid (2.8 g, 90%): mp 59-61° C.; $^1$H NMR (400 MHz, CDCl$_3$) δ 7.90 (d, J=2.6 Hz, 1H), 7.55 (dd, J=8.9, 2.6 Hz, 1H), 7.09 (d, J=8.9 Hz, 1H), 4.48 (q, J=7.9 Hz, 2H); $^{19}$F NMR (376 MHz, CDCl$_3$) δ -73.74; EIMS m/z 255.

Example 43: Preparation of 1-allyl-4-methoxy-2-nitrobenzene (C29)

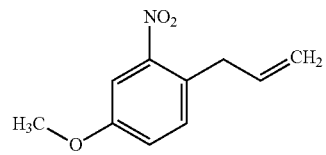

1-Chloro-4-methoxy-2-nitrobenzene (3 g, 15.99 mmol), allyltributylstannane (6.36 g, 19.19 mmol) and bis(triphenylphosphine)palladium(II) dichloride (1.123 g, 1.599 mmol) in 1,2-dichloroethane (30 mL) in three microwave reaction vials were allowed to react in the microwave at 120° C. for 45 min. The reaction mixture was adsorbed onto Celite© cartridge. Purification by silica gel flash chromatography (eluting with 0-20% ethyl acetate-hexanes) provided the title compound as a yellow liquid (3.0 g, 95%): $^1$H NMR (300 MHz, CDCl$_3$) δ 7.44 (d, J=2.7 Hz, 1H), 7.26 (d, J=8.5 Hz, 1H), 7.09 (dd, J=8.5, 2.7 Hz, 1H), 5.96 (ddt, J=16.6, 10.2, 6.4 Hz, 1H), 5.19-4.89 (m, 2H), 3.86 (s, 3H), 3.62 (dt, J=6.4, 1.5 Hz, 2H); $^{13}$C NMR (126 MHz, CDCl$_3$)

δ 158.37, 149.56, 135.51, 132.74, 126.80, 119.82, 116.65, 109.20, 55.80, 36.34; EIMS m/z 193.

Example 44: Preparation of 5-chloro-2-(2,2,2-trifluoroethoxy)aniline (C30)

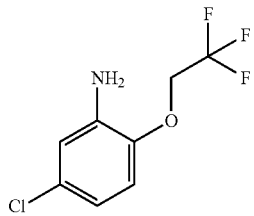 [SMILES: Nc1cc(Cl)ccc1OCC(F)(F)F]

To 4-chloro-2-nitro-1-(2,2,2-trifluoroethoxy)benzene (C28; 2.75 g, 10.8 mmol) and ammonium chloride (0.288 g, 5.38 mmol) in ethanol (20 mL) and water (5 mL) was added iron (3.00 g, 53.8 mmol). The reaction mixture was heated to 70° C. for 3 h under nitrogen. The mixture was cooled to room temperature and filtered through Celite©. The filtrate was diluted with ethyl acetate and water. The organic layer was separated and washed with brine, dried over sodium sulfate, filtered and concentrated. The title compound was isolated as a brown oil (2.63 g, 100%): $^1$H NMR (400 MHz, CDCl$_3$) δ 6.78-6.61 (m, 3H), 4.33 (q, J=8.1 Hz, 2H), 3.91 (s, 2H); $^{19}$F NMR (376 MHz, CDCl$_3$) δ −74.13; ESIMS m/z 226 ([M+H]$^+$).

Example 45: Preparation of 5-methoxy-2-propylaniline (C31)

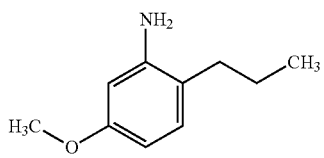

A mixture of 1-allyl-4-methoxy-2-nitrobenzene (C29; 3.0 g, 15.5 mmol) and 10% palladium on carbon (1.65 g, 1.55 mmol) in ethyl acetate (30 mL) was placed on a Parr shaker under hydrogen for 20 min. The reaction mixture was flushed with nitrogen, was filtered through Celite® and was concentrated. The title compound was isolated as a golden yellow liquid (2.27 g, 84%): $^1$H NMR (300 MHz, CDCl$_3$) δ 6.94 (d, J=8.2 Hz, 1H), 6.30 (dd, J=8.2, 2.6 Hz, 1H), 6.26 (d, J=2.5 Hz, 1H), 3.75 (s, 3H), 3.63 (s, 2H), 2.46-2.33 (m, 2H), 1.71-1.52 (m, 2H), 0.98 (t, J=7.3 Hz, 3H); $^{13}$C NMR (126 MHz, CDCl$_3$) δ 158.84, 145.06, 130.23, 119.36, 103.75, 101.41, 55.14, 32.70, 22.20, 14.12; EIMS m/z 165.

Example 46: Preparation of 2-chloro-N-(5-chloro-2-(2,2,2-trifluoroethoxy)phenyl)acetamide (C32)

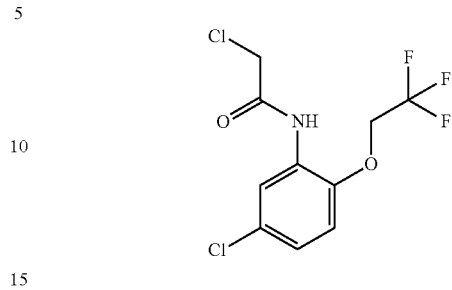

To 5-chloro-2-(2,2,2-trifluoroethoxy)aniline (C30; 2.6 g, 11.5 mmol) in acetone (30 mL) were added sequentially sodium bicarbonate (2.42 g, 28.8 mmol) and 2-chloroacetyl chloride (1.06 mL, 13.3 mmol). The cloudy off-white reaction mixture was stirred under nitrogen at room temperature overnight. The reaction mixture was diluted with ethyl acetate and water. The organic layer was separated, washed with brine, dried over sodium sulfate, and filtered. The title compound was isolated as a tan solid (3.45 g, 97%): mp 116-118° C.; $^1$H NMR (400 MHz, CDCl$_3$) δ 8.97 (s, 1H), 8.46 (d, J=2.6 Hz, 1H), 7.09 (dd, J=8.7, 2.5 Hz, 1H), 6.82 (d, J=8.8 Hz, 1H), 4.43 (q, J=7.8 Hz, 2H), 4.21 (s, 2H); $^{19}$F NMR (376 MHz, CDCl$_3$) δ −74.09; ESIMS m/z 302 ([M+H]$^+$).

The following compounds were synthesized in a manner similar to that provided in Example 46.

2-Chloro-N-(5-methoxy-2-propylphenyl)acetamide (C33)

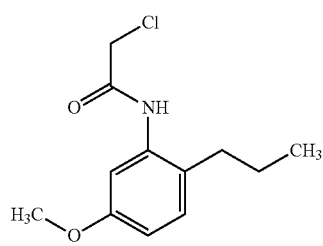 [SMILES: CCCc1ccc(OC)cc1NC(=O)CCl]

The title compound was prepared from compound C31 and isolated as a white solid, which was used as is: $^1$H NMR (300 MHz, CDCl$_3$) δ 8.35 (s, 1H), 7.65 (d, J=2.7 Hz, 1H), 7.09 (d, J=8.5 Hz, 1H), 6.70 (dd, J=8.5, 2.7 Hz, 1H), 4.24 (s, 2H), 3.80 (s, 3H), 2.62-2.37 (m, 2H), 1.72-1.51 (m, 2H), 0.98 (t, J=7.3 Hz, 3H); $^{13}$C NMR (126 MHz, CDCl$_3$) δ 163.61, 158.39, 135.03, 130.43, 124.58, 111.57, 107.49, 55.41, 43.27, 32.82, 23.25, 13.88; EIMS m/z 241.

2-Imino-3-(5,6,7,8-tetrahydronaphthalen-1-yl)thiazolidin-4-one (C34)

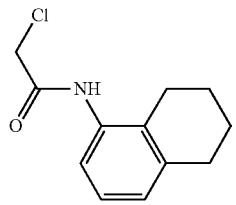 [SMILES: O=C(CCl)Nc1cccc2c1CCCC2]

The title compound was prepared from commercially available starting materials and isolated as a tan solid (1.91 g, 82%): mp 102-106° C.; $^1$H NMR (400 MHz, CDCl$_3$) δ 9.19 (s, 1H), 7.25-7.07 (m, 2H), 6.92 (dd, J=7.3, 1.7 Hz, 1H), 4.28-4.09 (m, 2H), 2.77 (d, J=5.5 Hz, 2H), 2.39 (q, J=5.5, 3.9 Hz, 2H), 1.69 (d, J=7.0 Hz, 4H); $^{13}$C NMR (101 MHz, CDCl$_3$) δ 131.14, 126.63, 125.92, 29.50, 24.21, 22.46, 22.36; ESIMS m/z 247 ([M+H]$^+$).

2-Chloro-N-(5-chloro-2-(trifluoromethoxy)phenyl)acetamide (C35)

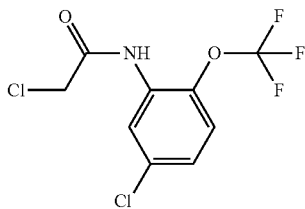 [SMILES: O=C(CCl)Nc1cc(Cl)ccc1OC(F)(F)F]

The title compound was prepared from commercially available starting materials and isolated as a light pink solid (4.3 g, 96%): mp 72-74° C.; $^1$H NMR (400 MHz, CDCl$_3$) δ 8.74 (s, 1H), 8.50 (d, J=2.5 Hz, 1H), 7.23 (dq, J=8.8, 1.5 Hz, 1H), 7.15 (dd, J=8.8, 2.5 Hz, 1H), 4.23 (s, 2H); $^{19}$F NMR (376 MHz, CDCl$_3$) δ −58.01; ESIMS m/z 288 ([M+H]$^+$).

2-Chloro-N-(2-chloro-4,5-dimethylphenyl)acetamide (C36)

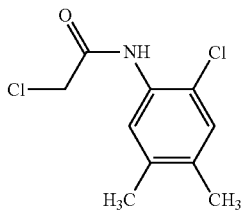

The title compound was prepared from commercial starting materials and isolated as a brown solid (2.77 g, 93%): mp 124-128° C.; $^1$H NMR (400 MHz, CDCl$_3$) δ 8.77 (s, 1H), 8.10 (s, 1H), 7.16 (s, 1H), 4.22 (s, 2H), 2.25 (s, 3H), 2.22 (s, 3H); $^{13}$C NMR (101 MHz, CDCl$_3$) δ 163.66, 136.42, 134.44, 131.01, 129.65, 122.41, 120.50, 43.13, 19.65, 19.21; EIMS m/z 232.

Example 47: Preparation of 3-(5-chloro-2-(2,2,2-trifluoroethoxy)phenyl)-2-iminothiazolidin-4-one (C37)

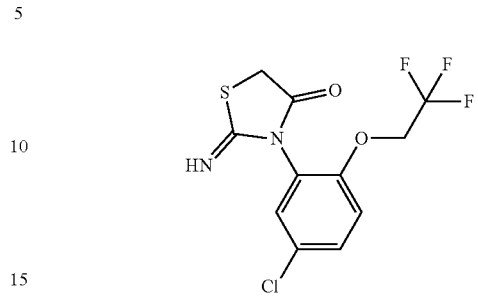

To a solution of 2-chloro-N-(5-chloro-2-(2,2,2-trifluoroethoxy)phenyl)acetamide (C32; 3.0 g, 9.93 mmol) in acetone (30 mL) was added potassium thiocyanate (1.93 g, 19.9 mmol) in portions. The reaction mixture was stirred at reflux for 3 h and was cooled to room temperature. Cesium carbonate (0.324 g, 0.993 mmol) was added slowly, and the reaction mixture was stirred at room temperature overnight. The solution was filtered through Celite® and the filtrate was concentrated. Purification by flash chromatography (eluting with 0-60% ethyl acetate/hexanes) provided the title compound as a yellow solid (3.12 g, 92%): mp 114-116° C.; $^1$H NMR (400 MHz, CDCl$_3$) δ 7.84 (s, 1H), 7.43 (dd, J=9.0, 2.5 Hz, 1H), 7.29 (d, J=2.6 Hz, 1H), 7.00 (d, J=8.9 Hz, 1H), 4.39-4.30 (m, 2H), 4.07 (d, J=6.0 Hz, 2H); $^{19}$F NMR (376 MHz, CDCl$_3$) δ −74.16; ESIMS m/z 325 ([M+H]$^+$).

The following compounds were synthesized in a manner similar to that provided in Example 47.

2-Imino-3-(5-methoxy-2-propylphenyl)thiazolidin-4-one (C38)

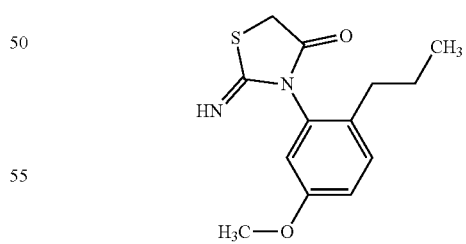

The title compound was prepared from compound C33 and isolated as an orange oil (2.50 g, 41%): $^1$H NMR (300 MHz, CDCl$_3$) δ 7.87 (s, 1H), 7.29 (d, J=8.8 Hz, 1H), 6.99 (s, 1H), 6.63 (d, J=8.0 Hz, 1H), 4.09 (s, 2H), 3.79 (s, 3H), 2.34 (s, 2H), 1.55 (q, J=7.4 Hz, 2H), 0.91 (td, J=7.3, 3.5 Hz, 3H); ESIMS m/z 265 ([M+H]$^+$).

2-Imino-3-(5,6,7,8-tetrahydronaphthalen-1-yl)thiazolidin-4-one (C39)

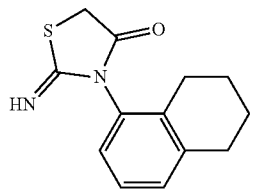

The title compound was prepared from compound C34 and isolated as a tan solid (1.91 g, 82%): mp 102-106° C.; $^1$H NMR (400 MHz, CDCl$_3$) δ 9.19 (s, 1H), 7.25-7.07 (m, 2H), 6.92 (dd, J=7.3, 1.7 Hz, 1H), 4.28-4.09 (m, 2H), 2.77 (d, J=5.5 Hz, 2H), 2.39 (q, J=5.5, 3.9 Hz, 2H), 1.69 (d, J=7.0 Hz, 4H); $^{13}$C NMR (101 MHz, CDCl$_3$) δ 131.14, 126.63, 125.92, 29.50, 24.21, 22.46, 22.36; ESIMS m/z 247 ([M+H]$^+$).

3-(5-Chloro-2-(trifluoromethoxy)phenyl)-2-iminothiazolidin-4-one (C40)

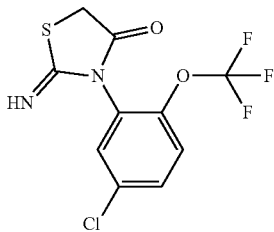 [SMILES: N=C1SCC(=O)N1c1cc(Cl)ccc1OC(F)(F)F]

The title compound was prepared from compound C35 and isolated as a light pink solid (2.49 g, 52%): mp 109-111° C.; $^1$H NMR (400 MHz, CDCl$_3$) δ 7.94 (s, 1H), 7.51-7.45 (m, 1H), 7.36 (q, J=3.4 Hz, 2H), 4.19-4.02 (m, 2H); $^{19}$F NMR (376 MHz, CDCl$_3$) δ −57.42; ESIMS m/z 311 ([M+H]$^+$).

3-(2-Chloro-4,5-dimethylphenyl)-2-iminothiazolidin-4-one (C41)

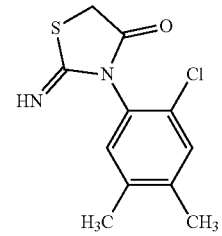

The title compound was prepared from compound C36 and isolated as a brown oil (2.62 g, 82%): $^1$H NMR (400 MHz, DMSO-d$_6$) δ 9.28 (s, 1H), 7.39 (s, 1H), 7.15-7.12 (m, 1H), 4.25-4.14 (m, 2H), 2.25 (s, 3H), 2.22 (s, 3H); $^{13}$C NMR (101 MHz, DMSO-d$_6$) δ 170.99, 156.80, 139.50, 136.47, 131.52, 130.07, 130.01, 128.53, 33.63, 18.82, 18.62; ESIMS m/z 255 ([M+H]$^+$).

TABLE 2

Analytical Data for Compounds in Table 1

| Cmpd. No. | mp (° C.) | IR (cm$^{-1}$) | MASS SPEC | NMR |
|---|---|---|---|---|
| A1 | | | ESIMS m/z 612 ([M]$^+$) | $^1$H NMR (400 MHz, CDCl$_3$) δ 8.14-8.00 (m, 2H), 7.39-7.29 (m, 3H), 7.24 (dd, J = 8.1, 1.8 Hz, 1H), 7.04-6.95 (m, 2H), 6.84 (dd, J = 1.8, 0.9 Hz, 1H), 6.65-6.52 (m, 2H), 5.50 (t, J = 6.2 Hz, 1H), 4.57 (s, 2H), 3.90 (d, J = 1.8 Hz, 2H), 3.48 (q, J = 7.0 Hz, 2H), 3.44-3.25 (m, 1H), 2.66 (dt, J = 25.8, 7.0 Hz, 3H), 2.33 (d, J = 0.7 Hz, 3H), 1.15 (dd, J = 6.9, 3.2 Hz, 6H); $^{13}$C NMR (101 MHz, CDCl$_3$) δ 194.17, 173.14, 168.82, 162.25, 153.60, 145.98, 143.64, 137.17, 133.55, 133.00, 131.50, 130.30, 130.15, 128.98, 128.52, 127.06, 121.12, 113.68, 66.30, 51.01, 42.42, 35.37, 28.75, 24.31, 21.24, 15.73; $^{19}$F NMR (376 MHz, CDCl$_3$) δ −57.58 |
| A2 | | | HRMS-ESI (m/z) [M + H]$^+$ calcd for C$_{28}$H$_{26}$F$_3$N$_5$O$_4$S, 586.173; found, 586.1735 | $^1$H NMR (400 MHz, CDCl$_3$) δ 7.79 (d, J = 8.6 Hz, 2H), 7.61 (d, J = 8.5 Hz, 2H), 7.49-7.41 (m, 1H), 7.39 (d, J = 8.1 Hz, 1H), 7.33 (d, J = 7.8 Hz, 1H), 7.12-7.07 (m, 2H), 6.94-6.87 (m, 3H), 3.99 (d, J = 3.3 Hz, 2H), 2.71-2.60 (m, 1H), 2.38 (s, 3H), 1.19 (dd, J = 6.8, 4.1 Hz, 6H); $^{19}$F NMR (376 MHz, CDCl$_3$) δ −58.32 |
| A3 | | | HRMS-ESI (m/z) [M + H]$^+$ calcd for | $^1$H NMR (400 MHz, CDCl$_3$) δ 7.79 (d, J = 8.7 Hz, 4H), 7.61 (d, J = 8.5 Hz, 2H), 7.48-7.43 (m, 1H), 7.36 (s, 1H), 7.30 (d, J = 8.3 |

TABLE 2-continued

Analytical Data for Compounds in Table 1

| Cmpd. No. | mp (° C.) | IR (cm⁻¹) | MASS SPEC | NMR |
|---|---|---|---|---|
| | | | C₂₇H₂₁F₆N₅O₅S, 642.124; found, 642.1251 | Hz, 1H), 7.10 (d, J = 8.6 Hz, 2H), 6.99 (d, J = 8.4 Hz, 1H), 6.94-6.89 (m, 2H), 4.45-4.27 (m, 2H), 4.03-3.88 (m, 2H), 2.39 (s, 3H); ¹⁹F NMR (376 MHz, CDCl₃) δ −58.32, −74.12 |
| A4 | | | HRMS-ESI (m/z) [M + H]⁺ calcd for C₂₈H₂₆F₃N₅O₄S, 586.173; found, 586.1726 | ¹H NMR (400 MHz, CDCl₃) δ 7.88 (d, J = 8.6 Hz, 2H), 7.78 (s, 1H), 6.92-6.84 (m, 2H), 7.42-7.25 (m, 8H), 6.25 (s, 1H), 3.95 (d, J = 2.7 Hz, 2H), 2.73-2.60 (m, 1H), 2.38 (s, 3H), 1.18 (dd, J = 6.9, 4.1 Hz, 6H); ¹⁹F NMR (376 MHz, CDCl₃) δ −57.70 |
| A5 | | (thin film) 3296, 2949, 1709, 1655, 1510, 1215 | HRMS-ESI (m/z) [M + H]⁺ calcd for C₂₇H₂₁F₆N₅O₅S, 642.124; found, 642.1278 | ¹H NMR (400 MHz, CDCl₃) δ 8.24 (s, 1H), 7.92 (d, J = 8.5 Hz, 2H), 7.39-7.22 (m, 7H), 7.10-7.05 (m, 1H), 6.97 (d, J = 8.4 Hz, 1H), 6.87 (d, J = 8.7 Hz, 2H), 4.44-4.28 (m, 2H), 3.98-3.85 (m, 2H), 2.38 (s, 3H); ¹⁹F NMR (376 MHz, CDCl₃) δ −57.68, −74.11 |
| A6 | | (thin film) 3297, 1739, 1714, 1654, 1603, 1497 | HRMS-ESI (m/z) [M + H]⁺ calcd for C₂₆H₁₈ClF₆N₅O₅S, 662.0694; found, 662.0683 | ¹H NMR (400 MHz, CDCl₃) δ 7.94-7.84 (m, 3H), 7.44 (dd, J = 8.8, 2.6 Hz, 1H), 7.36 (d, J = 8.8 Hz, 2H), 7.32 (d, J = 8.3 Hz, 2H), 7.28 (d, J = 2.5 Hz, 1H), 7.15 (s, 1H), 6.99 (d, J = 8.9 Hz, 1H), 6.91-6.83 (m, 2H), 6.26 (d, J = 4.1 Hz, 1H), 4.34 (qq, J = 11.6, 7.9 Hz, 2H), 3.97-3.83 (m, 2H); ¹⁹F NMR (376 MHz, CDCl₃) δ −57.69, −73.99 |
| A7 | | | ESIMS m/z 586 ([M + H]⁺) | ¹H NMR (400 MHz, CDCl₃) δ 7.41-7.28 (m, 6H), 7.25 (s, 1H), 7.21-7.16 (m, 2H), 7.12 (d, J = 8.5 Hz, 2H), 6.98-6.86 (m, 2H), 6.77 (s, 1H), 3.96 (d, J = 3.1 Hz, 2H), 3.83-3.64 (m, 1H), 2.66 (p, J = 6.9 Hz, 1H), 2.38 (s, 3H), 1.94-1.80 (m, 1H), 1.19 (dd, J = 6.9, 4.8 Hz, 6H); ¹⁹F NMR (376 MHz, CDCl₃) δ −58.17 |
| A8 | | | ESIMS m/z 614 ([M + H]⁺) | ¹H NMR (400 MHz, CDCl₃) δ 7.47 (s, 1H), 7.39-7.29 (m, 3H), 7.26 (m, 3H), 7.16-7.12 (m, 2H), 7.12-7.07 (m, 2H), 7.02-6.93 (m, 2H), 6.87-6.82 (m, 1H), 5.63 (t, J = 6.2 Hz, 1H), 3.88 (d, J = 1.7 Hz, 2H), 3.43 (dp, J = 16.6, 6.6 Hz, 2H), 2.70 (t, J = 7.2 Hz, 2H), 2.61 (p, J = 6.9 Hz, 1H), 2.32 (s, 3H), 1.15 (d, J = 6.9 Hz, 6H); ¹⁹F NMR (376 MHz, CDCl₃) δ −58.17 |
| A9 | | | ESIMS m/z 598 ([M + H]⁺) | ¹H NMR (400 MHz, CDCl₃) δ 7.53 (q, J = 8.8 Hz, 5H), 7.32 (d, J = 8.0 Hz, 1H), 7.22 (d, J = 8.0 Hz, 2H), 7.11 (d, J = 7.9 Hz, 2H), 7.00 (s, 1H), 6.85 (s, 1H), 6.67 (s, 1H), 5.55 (s, 1H), 3.97-3.85 (m, 2H), 3.49 (ddd, J = 27.3, 13.5, 6.8 Hz, 2H), 2.77 (t, J = 7.0 Hz, 2H), 2.69-2.58 (m, 1H), 2.34 (s, 3H), 1.16 (dd, J = 6.8, 1.3 Hz, 6H); ¹⁹F NMR (376 MHz, CDCl₃) δ −61.98 |
| A10 | | | ESIMS m/z 586 ([M + H]⁺) | ¹H NMR (400 MHz, CDCl₃) δ 7.56-7.48 (m, 4H), 7.29 (s, 1H), 7.19 (d, J = 8.4 Hz, 2H), 7.08 (d, J = 8.4 Hz, 2H), 6.99 (d, J = 8.3 Hz, 1H), 6.95 (s, 1H), 6.80 (d, J = 8.9 Hz, 2H), 5.63 (t, J = 6.1 Hz, 1H), 3.93-3.83 (m, 2H), 3.79 (s, 3H), 3.49 (q, J = 6.8 Hz, 2H), 2.76 (t, J = 7.0 Hz, 2H), 2.10 (s, 3H); ¹⁹F NMR (376 MHz, CDCl₃) δ −61.93 |
| A11 | | | ESIMS m/z 584 ([M + H]⁺) | ¹H NMR (400 MHz, CDCl₃) δ 7.57-7.46 (m, 4H), 7.32 (t, J = 7.6 Hz, 1H), 7.22-7.12 (m, 5H), 7.08 (d, J = 8.3 Hz, 2H), 6.81 (s, 1H), 5.59 (t, J = 6.2 Hz, 1H), 3.92 (s, 2H), 3.47 (qd, J = 7.0, 2.7 Hz, 2H), 2.77 (t, J = 7.1 Hz, 2H), 2.41 (qd, J = 7.5, 2.7 Hz, 2H), 2.11 (s, 3H), 1.16 (t, J = 7.6 Hz, 3H); ¹⁹F NMR (376 MHz, CDCl₃) δ −61.95 |
| A12 | | | ESIMS m/z 584 ([M + H]⁺) | ¹H NMR (400 MHz, CDCl₃) δ 7.57-7.42 (m, 6H), 7.30 (ddd, J = 7.8, 6.1, 2.8 Hz, 1H), 7.21 (d, J = 8.4 Hz, 2H), 7.15-7.07 (m, 3H), 7.06-7.02 (m, 1H), 6.80 (s, 1H), 5.55 (t, J = 6.2 Hz, 1H), 3.99-3.84 (m, 2H), 3.47 (dh, J = 20.5, 6.8 Hz, 2H), 2.76 (t, J = 7.0 Hz, 2H), 2.67 (p, J = 6.8 Hz, 1H), 1.18 (dd, J = 6.8, 2.8 Hz, 6H); ¹⁹F NMR (376 MHz, CDCl₃) δ −61.96 |

TABLE 2-continued

Analytical Data for Compounds in Table 1

| Cmpd. No. | mp (° C.) | IR (cm$^{-1}$) | MASS SPEC | NMR |
|---|---|---|---|---|
| A13 | | | ESIMS m/z 619 ([M + H]$^+$) | $^1$H NMR (400 MHz, CDCl$_3$) δ 7.55-7.46 (m, 4H), 7.42 (dd, J = 8.5, 2.2 Hz, 1H), 7.39-7.31 (m, 2H), 7.19 (d, J = 8.4 Hz, 2H), 7.06 (dd, J = 5.3, 3.1 Hz, 3H), 6.98 (s, 1H), 5.60 (t, J = 6.3 Hz, 1H), 3.90 (d, J = 1.6 Hz, 2H), 3.54-3.42 (m, 2H), 2.75 (t, J = 7.0 Hz, 2H), 2.63 (p, J = 6.8 Hz, 1H), 1.16 (t, J = 6.5 Hz, 6H); $^{19}$F NMR (376 MHz, CDCl$_3$) δ −61.94 |
| A14 | | | ESIMS m/z 582 ([M + H]$^+$) | $^1$H NMR (400 MHz, CDCl$_3$) δ 8.13 (s, 1H), 7.79 (s, 1H), 7.57-7.46 (m, 5H), 7.32 (d, J = 8.0 Hz, 1H), 7.11 (d, J = 8.1 Hz, 2H), 6.99-6.92 (m, 3H), 6.77 (d, J = 4.8 Hz, 1H), 6.50 (d, J = 4.8 Hz, 1H), 5.29 (q, J = 5.9, 4.7 Hz, 1H), 3.50 (q, J = 6.8 Hz, 2H), 2.69 (t, J = 7.1 Hz, 2H), 2.61 (p, J = 7.0 Hz, 1H), 2.33 (s, 3H), 1.20 (d, J = 6.8 Hz, 3H), 1.11 (d, J = 6.9 Hz, 3H); $^{19}$F NMR (376 MHz, CDCl$_3$) δ −61.79 |
| A15 | | | ESIMS m/z 634 ([M]$^+$) | $^1$H NMR (400 MHz, CDCl$_3$) δ 7.44-7.32 (m, 4H), 7.18 (dd, J = 21.1, 8.3 Hz, 4H), 7.12-7.00 (m, 3H), 6.93 (s, 1H), 6.73 (s, 1H), 5.54 (t, J = 6.3 Hz, 1H), 3.91 (d, J = 1.6 Hz, 2H), 3.46 (h, J = 6.7 Hz, 2H), 2.77 (t, J = 7.0 Hz, 2H), 2.63 (p, J = 6.8 Hz, 1H), 1.15 (dd, J = 8.4, 6.8 Hz, 6H); $^{19}$F NMR (376 MHz, CDCl$_3$) δ −58.16 |
| A16 | | | ESIMS m/z 600 ([M + H]$^+$) | $^1$H NMR (400 MHz, CDCl$_3$) δ 7.47-7.42 (m, 2H), 7.42-7.36 (m, 2H), 7.30 (ddd, J = 7.9, 6.1, 2.8 Hz, 1H), 7.21 (d, J = 8.4 Hz, 2H), 7.16 (d, J = 8.6 Hz, 2H), 7.09 (d, J = 8.3 Hz, 2H), 7.05-7.01 (m, 1H), 6.85 (s, 1H), 6.66 (s, 1H), 5.52 (t, J = 6.2 Hz, 1H), 3.91 (d, J = 1.5 Hz, 2H), 3.47 (ddq, J = 20.2, 13.6, 6.8 Hz, 2H), 2.76 (t, J = 7.0 Hz, 2H), 2.67 (p, J = 6.8 Hz, 1H), 1.17 (dd, J = 6.9, 4.2 Hz, 6H); $^{19}$F NMR (376 MHz, CDCl$_3$) δ −58.17 |
| A17 | 178-183 | | ESIMS m/z 690 ([M + H]$^+$) | $^1$H NMR (400 MHz, CDCl$_3$) δ 7.40 (d, J = 8.7 Hz, 3H), 7.24-7.19 (m, 3H), 7.16 (d, J = 8.6 Hz, 2H), 7.11 (d, J = 8.5 Hz, 2H), 6.97 (d, J = 8.9 Hz, 1H), 6.83 (s, 1H), 6.64 (s, 1H), 5.52 (s, 1H), 4.32 (dd, J = 7.9, 3.9 Hz, 2H), 3.88 (d, J = 4.6 Hz, 2H), 3.56-3.38 (m, 2H), 2.79 (t, J = 7.1 Hz, 2H); $^{19}$F NMR (376 MHz, CDCl$_3$) δ −58.17, −74.00 |
| A18 | | | ESIMS m/z 630 ([M + H]$^+$) | $^1$H NMR (400 MHz, CDCl$_3$) δ 7.42-7.35 (m, 2H), 7.24 (d, J = 8.6 Hz, 1H), 7.16 (dd, J = 14.8, 8.4 Hz, 4H), 7.06 (m, 3H), 6.93 (dd, J = 8.6, 2.7 Hz, 1H), 6.87 (s, 1H), 6.59 (d, J = 2.6 Hz, 1H), 5.60 (t, J = 6.1 Hz, 1H), 3.90 (d, J = 2.3 Hz, 2H), 3.76 (s, 3H), 3.47 (q, J = 6.8 Hz, 2H), 2.75 (t, J = 7.1 Hz, 2H), 2.30 (td, J = 7.5, 3.5 Hz, 2H), 1.52 (q, J = 7.5 Hz, 2H), 0.88 (t, J = 7.3 Hz, 3H); $^{19}$F NMR (376 MHz, CDCl$_3$) δ −58.17 |
| A19 | | | ESIMS m/z 670 ([M + H]$^+$) | $^1$H NMR (400 MHz, CDCl$_3$) δ 7.42-7.37 (m, 2H), 7.24-7.19 (m, 2H), 7.14 (td, J = 6.5, 3.1 Hz, 4H), 7.03 (d, J = 8.4 Hz, 2H), 7.01-6.97 (m, 2H), 6.90 (d, J = 8.4 Hz, 1H), 5.58 (t, J = 6.1 Hz, 1H), 4.28 (qt, J = 8.2, 4.0 Hz, 2H), 3.95-3.80 (m, 2H), 3.47 (qd, J = 7.0, 2.3 Hz, 2H), 2.74 (t, J = 7.1 Hz, 2H), 2.30 (s, 3H); $^{19}$F NMR (376 MHz, CDCl$_3$) δ −58.18, −74.12 |
| A20 | | | ESIMS m/z 644 ([M + H]$^+$) | $^1$H NMR (400 MHz, CDCl$_3$) δ 7.41-7.37 (m, 2H), 7.16 (q, J = 8.4 Hz, 5H), 7.07 (d, J = 8.3 Hz, 2H), 6.98 (s, 1H), 6.95-6.92 (m, 1H), 6.88 (d, J = 8.5 Hz, 1H), 6.79 (s, 1H), 5.56 (d, J = 6.4 Hz, 1H), 4.27 (q, J = 6.0 Hz, 1H), 3.91-3.80 (m, 2H), 3.47 (d, J = 6.6 Hz, 2H), 2.76 (t, J = 6.8 Hz, 2H), 2.28 (s, 3H), 1.66-1.57 (m, 2H), 1.17 (dd, J = 17.5, 6.1 Hz, 3H), 0.86 (dt, J = 10.5, 7.4 Hz, 3H); $^{19}$F NMR (376 MHz, CDCl$_3$) δ −58.17 |

TABLE 2-continued

Analytical Data for Compounds in Table 1

| Cmpd. No. | mp (° C.) | IR (cm$^{-1}$) | MASS SPEC | NMR |
|---|---|---|---|---|
| A21 | | | ESIMS m/z 602 ([M + H]$^+$) | $^1$H NMR (400 MHz, CDCl$_3$) δ 7.39 (d, J = 9.0 Hz, 2H), 7.19 (d, J = 8.4 Hz, 2H), 7.15 (d, J = 8.3 Hz, 2H), 7.09 (d, J = 8.3 Hz, 2H), 6.99 (d, J = 8.2 Hz, 1H), 6.94 (s, 1H), 6.81 (s, 2H), 6.73 (s, 1H), 5.59 (t, J = 6.2 Hz, 1H), 3.96-3.82 (m, 2H), 3.79 (s, 3H), 3.48 (q, J = 6.9 Hz, 2H), 2.77 (t, J = 7.1 Hz, 2H), 2.10 (s, 3H); $^{19}$F NMR (376 MHz, CDCl$_3$) δ −58.17 |
| A22 | | | ESIMS m/z 598 ([M + H]$^+$) | $^1$H NMR (400 MHz, CDCl$_3$) δ 7.84 (s, 1H), 7.62 (s, 1H), 7.46-7.39 (m, 2H), 7.32 (d, J = 8.0 Hz, 1H), 7.26-7.23 (m, 1H), 7.14-7.08 (m, 4H), 6.96 (d, J = 8.4 Hz, 3H), 6.76 (d, J = 4.8 Hz, 1H), 6.50 (d, J = 4.8 Hz, 1H), 5.27 (t, J = 6.0 Hz, 1H), 3.49 (d, J = 7.3 Hz, 2H), 2.70 (t, J = 7.1 Hz, 2H), 2.61 (p, J = 6.9 Hz, 1H), 2.32 (s, 3H), 1.19 (d, J = 6.8 Hz, 3H), 1.10 (d, J = 6.9 Hz, 3H); $^{19}$F NMR (376 MHz, CDCl$_3$) δ −58.17 |
| A23 | | | ESIMS m/z 600 ([M + H]$^+$) | $^1$H NMR (400 MHz, CDCl$_3$) δ 7.38 (dd, J = 8.9, 1.6 Hz, 2H), 7.31 (t, J = 7.6 Hz, 1H), 7.22-7.10 (m, 7H), 7.04 (d, J = 8.2 Hz, 2H), 6.96 (s, 1H), 5.59 (s, 1H), 3.91 (s, 2H), 3.45 (q, J = 7.2 Hz, 2H), 2.79-2.67 (m, 2H), 2.41 (qd, J = 7.6, 2.6 Hz, 2H), 2.10 (s, 3H), 1.15 (t, J = 7.6 Hz, 3H); $^{19}$F NMR (376 MHz, CDCl$_3$) δ −58.17 |
| A24 | | | ESIMS m/z 612 ([M + H]$^+$) | $^1$H NMR (400 MHz, CDCl$_3$) δ 7.38 (d, J = 8.6 Hz, 3H), 7.23-7.08 (m, 6H), 7.05-6.99 (m, 3H), 6.90 (dd, J = 7.0, 2.1 Hz, 1H), 5.65 (s, 1H), 3.88 (s, 2H), 3.45 (p, J = 6.7 Hz, 2H), 2.80 (s, 2H), 2.73 (t, J = 7.2 Hz, 2H), 2.43 (s, 2H), 1.80-1.69 (m, 4H); $^{19}$F NMR (376 MHz, CDCl$_3$) δ −58.17 |
| A25 | | | ESIMS m/z 632 ([M + H]$^+$) | $^1$H NMR (400 MHz, CDCl$_3$) δ 7.43-7.35 (m, 2H), 7.22 (d, J = 8.4 Hz, 2H), 7.19-7.14 (m, 2H), 7.11 (d, J = 8.3 Hz, 2H), 7.04 (d, J = 10.6 Hz, 1H), 6.87 (d, J = 7.1 Hz, 1H), 6.75 (s, 1H), 6.57 (s, 1H), 5.52 (t, J = 6.2 Hz, 1H), 3.90 (d, J = 1.8 Hz, 2H), 3.48 (dp, J = 26.9, 6.6 Hz, 2H), 2.78 (t, J = 7.0 Hz, 2H), 2.67-2.51 (m, 1H), 2.24 (d, J = 1.9 Hz, 3H), 1.14 (dd, J = 6.8, 3.9 Hz, 6H); $^{19}$F NMR (376 MHz, CDCl$_3$) δ −58.17, −114.62 |
| A26 | | | ESIMS m/z 628 ([M + H]$^+$) | $^1$H NMR (400 MHz, CDCl$_3$) δ 7.75 (s, 1H), 7.44-7.37 (m, 2H), 7.35 (d, J = 8.1 Hz, 1H), 7.29 (d, J = 8.4 Hz, 1H), 7.18-7.09 (m, 5H), 7.01 (d, J = 12.3 Hz, 2H), 6.88 (d, J = 20.9 Hz, 1H), 5.51 (t, J = 9.7 Hz, 1H), 4.09 (d, J = 19.8 Hz, 1H), 3.92-3.75 (m, 2H), 2.61 (m, 3H), 2.36 (d, J = 6.2 Hz, 3H), 1.23-1.01 (m, 9H); $^{19}$F NMR (376 MHz, CDCl$_3$) δ −58.18 |
| A27 | | | ESIMS m/z 612 ([M + H]$^+$) | $^1$H NMR (400 MHz, CDCl$_3$) δ 7.54 (s, 4H), 7.35 (d, J = 7.9 Hz, 1H), 7.30 (d, J = 8.6 Hz, 1H), 7.19 (dd, J = 8.3, 6.4 Hz, 2H), 7.07 (dd, J = 15.7, 8.2 Hz, 2H), 7.00 (s, 1H), 6.97 (s, 1H), 6.88 (d, J = 23.0 Hz, 1H), 5.46 (t, J = 10.2 Hz, 1H), 4.09 (s, 1H), 3.90-3.83 (m, 2H), 2.78-2.56 (m, 3H), 2.37 (d, J = 8.6 Hz, 3H), 1.16 (dq, J = 9.5, 6.4 Hz, 9H); $^{19}$F NMR (376 MHz, CDCl$_3$) δ −61.91 |
| A28 | 235-240 | | ESIMS m/z 598 ([M + H]$^+$) | $^1$H NMR (400 MHz, CDCl$_3$) δ 7.54 (d, J = 2.2 Hz, 4H), 7.48 (d, J = 6.6 Hz, 2H), 7.33 (d, J = 8.4 Hz, 2H), 7.20 (t, J = 7.8 Hz, 2H), 7.10 (dd, J = 12.2, 8.0 Hz, 3H), 6.76 (s, 1H), 5.40 (d, J = 9.3 Hz, 1H), 4.09 (d, J = 7.5 Hz, 1H), 3.89 (d, J = 1.8 Hz, 2H), 2.81-2.58 (m, 3H), 1.24-1.08 (m, 9H); $^{19}$F NMR (376 MHz, CDCl$_3$) δ −61.95 |
| A29 | | | ESIMS m/z 632 ([M + H]$^+$) | $^1$H NMR (400 MHz, CDCl$_3$) δ 7.54 (d, J = 2.0 Hz, 5H), 7.47-7.36 (m, 2H), 7.21 (dd, J = 12.4, 8.3 Hz, 2H), 7.15-7.09 (m, 2H), 7.09-7.04 (m, 1H), 6.79 (s, 1H), 5.40 (d, J = 9.0 Hz, 1H), 4.09 (dd, J = 14.4, 7.5 Hz, |

TABLE 2-continued

Analytical Data for Compounds in Table 1

| Cmpd. No. | mp (° C.) | IR (cm$^{-1}$) | MASS SPEC | NMR |
|---|---|---|---|---|
| | | | | 1H), 3.90-3.82 (m, 2H), 2.82-2.55 (m, 3H), 1.21-1.11 (m, 9H); $^{19}$F NMR (376 MHz, CDCl$_3$) δ −61.94 |
| A30 | | | ESIMS m/z 642 ([M + H]$^+$) | $^1$H NMR (400 MHz, CDCl$_3$) δ 7.76-7.63 (m, 2H), 7.57-7.50 (m, 4H), 7.18 (d, J = 8.6 Hz, 3H), 7.09-7.02 (m, 2H), 7.01-6.86 (m, 2H), 5.47 (d, J = 8.1 Hz, 1H), 4.29 (p, J = 6.0 Hz, 1H), 4.19-4.03 (m, 1H), 3.82 (d, J = 2.9 Hz, 2H), 2.65 (qd, J = 13.7, 7.8 Hz, 2H), 2.32 (t, J = 2.4 Hz, 3H), 1.64-1.54 (m, 2H), 1.24-1.08 (m, 6H), 0.93-0.79 (m, 3H); $^{19}$F NMR (376 MHz, CDCl$_3$) δ −61.88 |
| A31 | | | ESIMS m/z 600 ([M + H]$^+$) | $^1$H NMR (400 MHz, CDCl$_3$) δ 7.81 (s, 1H), 7.54 (s, 4H), 7.18 (dd, J = 9.8, 3.3 Hz, 3H), 7.10-6.96 (m, 3H), 6.91-6.71 (m, 2H), 5.50 (d, J = 9.1 Hz, 1H), 4.10 (d, J = 10.3 Hz, 1H), 3.92-3.76 (m, 5H), 2.73-2.56 (m, 2H), 2.12 (d, J = 3.4 Hz, 3H), 1.15 (d, J = 6.6 Hz, 3H); $^{19}$F NMR (376 MHz, CDCl$_3$) δ −61.87 |
| A32 | 215-220 | | ESIMS m/z 598 ([M + H]$^+$) | $^1$H NMR (400 MHz, DMSO-d$_6$) δ 9.05 (s, 1H), 8.70 (s, 1H), 7.64 (d, J = 3.4 Hz, 4H), 7.51 (d, J = 8.3 Hz, 1H), 7.31 (dd, J = 15.7, 8.0 Hz, 2H), 7.21 (d, J = 7.7 Hz, 2H), 7.06 (d, J = 7.6 Hz, 2H), 4.18 (d, J = 5.8 Hz, 1H), 4.13 (d, J = 4.7 Hz, 2H), 3.79 (d, J = 7.2 Hz, 1H), 2.74-2.65 (m, 2H), 2.35 (q, J = 6.9, 6.4 Hz, 2H), 2.04 (s, 3H), 1.08 (t, J = 7.6 Hz, 3H), 0.98 (d, J = 6.4 Hz, 3H); $^{19}$F NMR (376 MHz, DMSO) δ −60.01 |
| A33 | | | ESIMS m/z 612 ([M + H]$^+$) | $^1$H NMR (400 MHz, CDCl$_3$) δ 8.25 (s, 1H), 7.68 (s, 1H), 7.48 (d, J = 9.0 Hz, 2H), 7.38-7.32 (m, 1H), 7.29 (s, 1H), 7.15-7.06 (m, 4H), 6.99 (dd, J = 14.7, 9.0 Hz, 3H), 6.73 (d, J = 4.7 Hz, 1H), 6.45 (dd, J = 4.8, 3.0 Hz, 1H), 5.17 (dd, J = 9.2, 4.0 Hz, 1H), 4.12 (t, J = 7.6 Hz, 1H), 2.75-2.47 (m, 3H), 2.36 (s, 3H), 1.24-1.06 (m, 9H); $^{19}$F NMR (376 MHz, CDCl$_3$) δ −58.18 |
| A34 | | | ESIMS m/z 614 ([M + H]$^+$) | $^1$H NMR (400 MHz, DMSO-d$_6$) δ 8.82 (d, J = 5.7 Hz, 1H), 8.60 (d, J = 5.2 Hz, 1H), 7.57-7.51 (m, 2H), 7.51-7.38 (m, 3H), 7.35-7.24 (m, 5H), 7.17 (dt, J = 8.1, 1.3 Hz, 1H), 7.04 (t, J = 8.3 Hz, 2H), 4.15-3.85 (m, 2H), 3.79 (dp, J = 14.7, 7.3 Hz, 1H), 2.78-2.59 (m, 2H), 2.50 (p, J = 1.9 Hz, 1H), 1.11 (ddd, J = 22.5, 6.8, 2.6 Hz, 6H), 0.99 (dd, J = 10.5, 6.6 Hz, 3H); $^{19}$F NMR (376 MHz, DMSO-d$_6$) δ −52.35 |
| A35 | | | ESIMS m/z 648 ([M + H]$^+$) | $^1$H NMR (400 MHz, DMSO-d$_6$) δ 8.84 (d, J = 6.9 Hz, 1H), 8.62 (d, J = 7.1 Hz, 1H), 7.57-7.47 (m, 4H), 7.41 (d, J = 2.1 Hz, 1H), 7.36-7.23 (m, 4H), 7.04 (dd, J = 12.2, 8.4 Hz, 2H), 4.08 (dd, J = 17.9, 14.8 Hz, 1H), 3.92 (dd, J = 17.9, 2.2 Hz, 1H), 3.77 (s, 1H), 2.77-2.56 (m, 2H), 1.12 (d, J = 6.8 Hz, 3H), 1.07 (dd, J = 6.8, 3.8 Hz, 3H), 0.99 (dd, J = 13.8, 6.5 Hz, 3H); $^{19}$F NMR (376 MHz, DMSO-d$_6$) δ −52.35 |
| A36 | | | ESIMS m/z 690 ([M + H]$^+$) | $^1$H NMR (400 MHz, DMSO-d$_6$) δ 8.83 (d, J = 4.7 Hz, 1H), 8.61 (d, J = 3.8 Hz, 1H), 7.79 (dd, J = 4.0, 2.6 Hz, 1H), 7.71 (dd, J = 8.9, 2.6 Hz, 1H), 7.66-7.51 (m, 4H), 7.39-7.20 (m, 4H), 7.06 (t, J = 8.8 Hz, 2H), 4.19-3.92 (m, 2H), 3.80 (dt, J = 16.8, 7.3 Hz, 1H), 2.77-2.50 (m, 2H), 0.99 (dd, J = 6.6, 2.7 Hz, 3H); $^{19}$F NMR (376 MHz, DMSO-d$_6$) δ −51.64, −51.72, −52.35 |
| A37 | | | ESIMS m/z 644 ([M + H]$^+$) | $^1$H NMR (400 MHz, DMSO-d$_6$) δ 8.82 (d, J = 5.1 Hz, 1H), 8.60 (d, J = 3.3 Hz, 1H), 7.58-7.43 (m, 3H), 7.35-7.21 (m, 5H), 7.05 (t, J = 8.3 Hz, 2H), 6.96 (ddd, J = 8.6, 2.8, 1.2 Hz, 1H), 6.83 (dd, J = 2.8, 0.9 Hz, 1H), 4.03 (m, 2H), 3.73 (d, J = 1.0 Hz, 3H), 2.74-2.50 (m, 3H), 2.25 (td, J = 9.8, 5.0 Hz, 2H), 1.45 (h, J = 7.1 Hz, 2H), 0.99 (dd, J = 6.6, |

TABLE 2-continued

Analytical Data for Compounds in Table 1

| Cmpd. No. | mp (° C.) | IR (cm$^{-1}$) | MASS SPEC | NMR |
|---|---|---|---|---|
| A38 | | | ESIMS m/z 684 ([M + H]$^+$) | 2.9 Hz, 3H), 0.87-0.78 (m, 3H); $^{19}$F NMR (376 MHz, CDCl$_3$) δ −52.35<br>$^1$H NMR (400 MHz, DMSO-d$_6$) δ 8.83 (d, J = 3.4 Hz, 1H), 8.61 (d, J = 3.7 Hz, 1H), 7.57-7.44 (m, 3H), 7.36-7.21 (m, 6H), 7.12 (d, J = 3.3 Hz, 1H), 7.06 (dd, J = 8.4, 4.4 Hz, 2H), 4.82-4.52 (m, 2H), 4.02-3.93 (m, 2H), 3.80 (dp, J = 21.8, 7.2 Hz, 1H), 2.70 (dt, J = 13.4, 6.6 Hz, 1H), 2.49-2.42 (m, 1H), 2.29 (s, 3H), 0.97 (d, J = 6.6 Hz, 3H); $^{19}$F NMR (376 MHz, DMSO-d$_6$) δ −52.35, −68.19, −68.26 |
| A39 | | | ESIMS m/z 658 ([M + H]$^+$) | $^1$H NMR (400 MHz, DMSO-d$_6$) δ 8.82 (d, J = 6.5 Hz, 1H), 8.60 (d, J = 4.9 Hz, 1H), 7.57-7.51 (m, 2H), 7.43 (dd, J = 12.8, 8.1 Hz, 1H), 7.30 (dt, J = 13.1, 8.0 Hz, 4H), 7.17 (d, J = 8.3 Hz, 1H), 7.04 (dd, J = 15.6, 6.8 Hz, 4H), 4.33 (q, J = 5.9 Hz, 1H), 3.96 (d, J = 2.1 Hz, 2H), 3.82 (s, 1H), 2.76-2.50 (m, 2H), 2.25 (s, 3H), 1.48 (d, J = 12.0 Hz, 2H), 1.17-1.07 (m, 2H), 1.05-0.93 (m, 4H), 0.87-0.70 (m, 3H); $^{19}$F NMR (376 MHz, DMSO-d$_6$) δ −52.35 |
| A40 | | | ESIMS m/z 614 ([M + H]$^+$) | $^1$H NMR (400 MHz, DMSO-d$_6$) δ 8.82 (d, J = 1.9 Hz, 1H), 8.60 (d, J = 3.1 Hz, 1H), 7.58-7.45 (m, 3H), 7.30 (ddd, J = 10.8, 8.4, 6.7 Hz, 5H), 7.25-7.15 (m, 2H), 7.04 (dd, J = 8.3, 5.6 Hz, 2H), 4.21-4.05 (m, 2H), 3.78 (p, J = 7.0 Hz, 1H), 2.72-2.50 (m, 2H), 2.40-2.28 (m, 2H), 2.04 (s, 3H), 1.08 (t, J = 7.5 Hz, 3H), 0.99 (dd, J = 6.6, 4.9 Hz, 3H); $^{19}$F NMR (376 MHz, DMSO-d$_6$) δ −52.35 |
| A41 | | | ESIMS m/z 634 ([M + H]$^+$) | $^1$H NMR (400 MHz, DMSO-d$_6$) δ 8.83 (d, J = 2.5 Hz, 1H), 8.61 (s, 1H), 7.54 (dd, J = 9.0, 2.2 Hz, 3H), 7.42 (d, J = 2.8 Hz, 1H), 7.33 (d, J = 8.2 Hz, 2H), 7.31-7.22 (m, 3H), 7.09-7.02 (m, 2H), 4.13-3.96 (m, 2H), 3.80 (dq, J = 13.6, 7.1 Hz, 1H), 2.79-2.63 (m, 1H), 2.48-2.41 (m, 1H), 2.26 (s, 3H), 2.23 (s, 3H), 0.98 (t, J = 6.0 Hz, 3H); $^{19}$F NMR (376 MHz, DMSO-d$_6$) δ −52.35 |
| A42 | | | ESIMS m/z 626 ([M + H]$^+$) | $^1$H NMR (400 MHz, DMSO-d$_6$) δ 8.83 (d, J = 2.9 Hz, 1H), 8.61 (s, 1H), 7.52 (dd, J = 16.3, 8.6 Hz, 3H), 7.36-7.25 (m, 4H), 7.23-7.11 (m, 2H), 7.09-6.97 (m, 3H), 4.11-3.92 (m, 2H), 3.79 (q, J = 8.1 Hz, 1H), 2.82-2.50 (m, 4H), 2.35 (dd, J = 13.7, 4.1 Hz, 2H), 1.79-1.59 (m, 4H), 0.99 (d, J = 6.6 Hz, 3H); $^{19}$F NMR (376 MHz, DMSO-d$_6$) δ −52.35 |
| A43 | | | ESIMS m/z 600 ([M + 1]$^+$) | $^1$H NMR (400 MHz, CDCl$_3$) δ 7.40-7.26 (m, 6H), 7.17 (d, J = 8.3 Hz, 2H), 7.10-7.02 (m, 3H), 6.92-6.84 (m, 1H), 5.34 (s, 1H), 4.30-4.28 (m, 2H), 4.00-3.85 (m, 2H), 2.74-2.58 (m, 2H), 2.37 (s, 3H), 1.22-1.08 (m, 6H); $^{19}$F NMR (376 MHz, CDCl$_3$) δ −58.19 |
| A44 | | | ESIMS m/z 613 ([M]$^+$) | $^1$H NMR (500 MHz, DMSO-d$_6$) δ 9.69 (s, 1H), 8.84 (s, 1H), 7.59-7.52 (m, 2H), 7.50-7.44 (m, 2H), 7.38 (d, J = 8.0 Hz, 1H), 7.26 (dd, J = 8.3, 1.8 Hz, 1H), 7.20 (dt, J = 9.0, 2.3 Hz, 2H), 7.13-7.08 (m, 2H), 7.04 (dd, J = 1.9, 0.9 Hz, 1H), 6.29 (t, J = 5.7 Hz, 1H), 4.23-3.94 (m, 2H), 3.28 (q, J = 6.8 Hz, 2H), 2.66 (q, J = 7.2 Hz, 3H), 2.30 (s, 3H), 1.19-1.04 (m, 6H);<br>$^{13}$C NMR (126 MHz, DMSO-d$_6$) δ 172.56, 169.36, 158.94, 154.40, 142.34, 141.26, 139.33, 136.80, 135.39, 133.35, 132.48, 129.85, 128.25, 128.06, 125.88, 120.94, 118.52, 117.93, 40.06, 34.53, 32.08, 27.05, 23.03, 22.79, 19.65 |
| A45 | | | ESIMS m/z 601 ([M]$^+$) | $^1$H NMR (400 MHz, DMSO-d$_6$) δ 9.80 (s, 1H), 9.77 (d, J = 6.6 Hz, 2H), 7.62-7.52 (m, 4H), 7.38 (d, J = 8.0 Hz, 1H), 7.34-7.23 (m, 5H), 7.09-6.99 (m, 1H), 4.23-4.00 (m, 2H), 2.71-2.60 (m, 1H), 2.30 (s, 3H), 1.15 (d, J = 6.8 Hz, 3H), 1.08 (d, J = 6.9 Hz, 3H); $^{19}$F NMR (376 MHz, DMSO-d$_6$) δ −56.95 |

TABLE 2-continued

Analytical Data for Compounds in Table 1

| Cmpd. No. | mp (° C.) | IR (cm$^{-1}$) | MASS SPEC | NMR |
|---|---|---|---|---|
| A46 | | | ESIMS m/z 629 ([M]$^+$) | $^1$H NMR (400 MHz, CDCl$_3$) δ 7.91 (s, 1H), 7.70 (s, 1H), 7.48-7.40 (m, 2H), 7.29 (d, J = 8.0 Hz, 1H), 7.25-7.17 (m, 7H), 6.86-6.81 (m, 1H), 5.53 (t, J = 6.3 Hz, 1H), 3.89 (d, J = 1.4 Hz, 2H), 3.59-3.30 (m, 2H), 2.81 (td, J = 7.0, 1.9 Hz, 2H), 2.61 (p, J = 6.9 Hz, 1H), 2.41-2.25 (m, 3H), 1.13 (t, J = 6.8 Hz, 6H); $^{13}$C NMR (101 MHz, CDCl$_3$) δ 180.55, 173.01, 169.28, 162.32, 147.68, 143.60, 139.05, 137.25, 136.57, 135.18, 132.92, 131.56, 130.77, 128.95, 127.08, 127.01, 126.10, 122.16, 119.55, 41.93, 35.87, 33.38, 28.75, 24.26, 24.12, 21.23; $^{19}$F NMR (376 MHz, CDCl$_3$) δ −57.97 |
| A47 | | | ESIMS m/z 629 ([M]$^+$) | $^1$H NMR (400 MHz, CDCl$_3$) δ 7.61 (s, 1H), 7.42-7.35 (m, 3H), 7.35-7.29 (m, 1H), 7.24 (s, 1H), 7.19-7.13 (m, 2H), 7.10-7.04 (m, 2H), 7.02 (d, J = 8.8 Hz, 2H), 6.91 (dd, J = 1.7, 0.9 Hz, 1H), 5.85 (s, 1H), 3.96 (d, J = 2.5 Hz, 2H), 3.86 (q, J = 6.4 Hz, 2H), 2.88 (t, J = 6.7 Hz, 2H), 2.75-2.59 (m, 1H), 2.38 (s, 3H), 1.23-1.11 (m, 6H); $^{19}$F NMR (376 MHz, CDCl$_3$) δ −57.96 |
| A48 | | | ESIMS m/z 571 ([M + H]$^+$) | $^1$H NMR (400 MHz, CDCl$_3$) δ 8.16 (dd, J = 24.4, 9.0 Hz, 1H), 7.96-7.84 (m, 2H), 7.78 (d, J = 8.4 Hz, 2H), 7.59-7.46 (m, 2H), 7.39 (d, J = 8.1 Hz, 1H), 7.37-7.28 (m, 3H), 6.94-6.79 (m, 2H), 3.99 (d, J = 2.0 Hz, 2H), 2.65 (p, J = 6.8 Hz, 1H), 2.38 (s, 3H), 1.20 (dd, J = 12.6, 6.8 Hz, 6H); $^{19}$F NMR (376 MHz, CDCl$_3$) δ −57.70 |
| A49 | | | ESIMS m/z 598 ([M]$^+$) | $^1$H NMR (400 MHz, CDCl$_3$) δ 7.97-7.86 (m, 2H), 7.74 (s, 1H), 7.57-7.46 (m, 2H), 7.32 (ddd, J = 8.1, 2.6, 1.6 Hz, 4H), 7.16 (d, J = 8.4 Hz, 2H), 6.91-6.79 (m, 1H), 5.51 (t, J = 6.2 Hz, 1H), 3.91 (d, J = 1.9 Hz, 2H), 3.62-3.27 (m, 2H), 2.79 (t, J = 7.1 Hz, 2H), 2.62 (p, J = 6.8 Hz, 1H), 2.33 (t, J = 0.7 Hz, 3H), 1.15 (dd, J = 6.9, 1.8 Hz, 6H); $^{13}$C NMR (101 MHz, CDCl$_3$) δ 173.13, 171.13, 169.09, 164.79, 162.32, 143.63, 143.33, 137.23, 136.47, 135.89, 133.84, 132.96, 131.56, 129.89, 129.40, 128.97, 127.11, 121.32, 120.98, 42.16, 35.77, 33.44, 28.78, 24.32, 24.11, 21.27 |
| A50 | | | ESIMS m/z 599 ([M + H]$^+$) | $^1$H NMR (400 MHz, CDCl$_3$) δ 7.73-7.67 (m, 2H), 7.45-7.40 (m, 2H), 7.37 (d, J = 8.0 Hz, 1H), 7.33-7.27 (m, 2H), 7.25-7.19 (m, 2H), 7.14 (d, J = 8.5 Hz, 2H), 6.90 (dd, J = 1.7, 0.9 Hz, 1H), 6.22-6.11 (m, 1H), 3.94 (d, J = 2.7 Hz, 2H), 3.65 (q, J = 6.5 Hz, 2H), 2.87 (t, J = 6.8 Hz, 2H), 2.71-2.58 (m, 1H), 2.37 (s, 3H), 1.17 (dd, J = 6.9, 4.2 Hz, 6H); $^{13}$C NMR (101 MHz, CDCl$_3$) δ 207.43, 172.94, 171.60, 166.62, 159.99, 151.86, 143.72, 137.36, 136.99, 134.76, 133.48, 132.94, 131.66, 129.75, 129.14, 129.02, 127.18, 121.07, 119.73, 41.65, 35.40, 33.43, 31.36, 28.82, 24.19, 21.48; $^{19}$F NMR (376 MHz, DMSO-d$_6$) δ −56.67 |
| A51 | | | ESIMS m/z 606 ([M]$^+$) | $^1$H NMR (400 MHz, CDCl$_3$) δ 7.78-7.68 (m, 2H), 7.41-7.34 (m, 3H), 7.31 (dd, J = 8.1, 1.8 Hz, 1H), 7.24-7.19 (m, 3H), 6.99 (d, J = 8.9 Hz, 2H), 6.88 (dd, J = 2.0, 0.9 Hz, 1H), 6.73 (s, 1H), 3.95 (d, J = 2.9 Hz, 2H), 2.64 (p, J = 6.8 Hz, 1H), 2.36 (s, 3H), 1.17 (d, J = 6.9 Hz, 6H); $^{13}$C NMR (101 MHz, CDCl$_3$) δ 172.92, 159.95, 152.77, 143.70, 137.67, 137.39, 136.71, 132.88, 131.81, 131.70, 129.84, 129.01, 127.20, 124.29, 121.16, 120.13, 33.45, 31.39, 28.83, 24.23; $^{19}$F NMR (376 MHz, CDCl$_3$) δ −57.66 |

TABLE 2-continued

Analytical Data for Compounds in Table 1

| Cmpd. No. | mp (° C.) | IR (cm$^{-1}$) | MASS SPEC | NMR |
|---|---|---|---|---|
| A52 | | | ESIMS m/z 614 ([M]$^+$) | $^1$H NMR (400 MHz, CDCl$_3$) δ 7.83 (d, J = 6.0 Hz, 1H), 7.63 (d, J = 5.8 Hz, 1H), 7.45-7.36 (m, 4H), 7.32 (dd, J = 8.1, 5.5 Hz, 1H), 7.24 (d, J = 2.3 Hz, 1H), 7.15-7.02 (m, 4H), 6.86 (t, J = 2.9 Hz, 1H), 4.29 (q, J = 6.4 Hz, 2H), 3.89 (dd, J = 5.8, 2.9 Hz, 2H), 2.88 (q, J = 6.3 Hz, 2H), 2.70-2.54 (m, 1H), 2.32 (d, J = 5.2 Hz, 3H), 1.21-0.93 (m, 6H); $^{19}$F NMR (376 MHz, CDCl$_3$) δ −58.19 |
| A53 | | | ESIMS m/z 614 ([M]$^+$) | $^1$H NMR (400 MHz, CDCl$_3$) δ 8.13-8.06 (m, 1H), 7.32 (dd, J = 8.2, 5.7 Hz, 3H), 7.25-7.20 (m, 3H), 7.12 (d, J = 8.5 Hz, 2H), 6.92 (d, J = 7.8 Hz, 1H), 6.86-6.81 (m, 1H), 6.75 (d, J = 9.2 Hz, 1H), 5.49 (t, J = 6.2 Hz, 1H), 3.91 (d, J = 1.7 Hz, 2H), 3.61-3.29 (m, 2H), 2.77 (t, J = 7.1 Hz, 2H), 2.67-2.57 (m, 1H), 2.33 (s, 3H), 1.19-1.10 (m, 6H); $^{19}$F NMR (376 MHz, CDCl$_3$) δ −58.13 |
| A54 | | | ESIMS m/z 555 ([M]$^+$) | $^1$H NMR (400 MHz, CDCl$_3$) δ 7.67 (d, J = 8.4 Hz, 1H), 7.66-7.61 (m, 2H), 7.52-7.45 (m, 3H), 7.41-7.36 (m, 2H), 7.35-7.31 (m, 1H), 7.22-7.17 (m, 2H), 7.15 (s, 1H), 7.12-7.07 (m, 1H), 7.05-7.00 (m, 2H), 3.96 (d, J = 2.6 Hz, 2H), 2.81-2.62 (m, 1H), 1.28-1.15 (m, 6H); $^{19}$F NMR (376 MHz, CDCl$_3$) δ −57.81 |
| A55 | | | ESIMS m/z 569 ([M]$^+$) | $^1$H NMR (400 MHz, CDCl$_3$) δ 7.71-7.59 (m, 4H), 7.39 (dd, J = 8.7, 7.2 Hz, 3H), 7.35-7.28 (m, 1H), 7.23-7.16 (m, 3H), 7.07-6.99 (m, 2H), 6.93-6.86 (m, 1H), 3.95 (d, J = 3.0 Hz, 2H), 2.74-2.58 (m, 1H), 2.38 (s, 3H), 1.19 (t, J = 6.7 Hz, 6H); $^{19}$F NMR (376 MHz, CDCl$_3$) δ −57.81 |

EXAMPLE: BIOASSAYS

Insecticidal Test for Beet Armyworm (*Spodoptera exigua*, LAPHEG) ("BAW")

Bioassays on beet armyworm (BAW; *Spodoptera exigua*: Lepidoptera) are conducted using a 128-well diet tray assay. One to five second instar BAW larvae are placed in each well (3 mL) of the diet tray that had been previously filled with 1 mL of artificial diet to which 50 μg/cm$^2$ of the test compound (dissolved in 50 μL of 90:10 acetone-water mixture) had been applied (to each of eight wells) and then allowed to dry. Trays are covered with a clear self-adhesive cover, vented to allow gas exchange, and held at 25° C., 14:10 light-dark for five to seven days. Percent mortality is recorded for the larvae in each well; activity in the eight wells is then averaged.

Insecticidal Test for Cabbage Looper (*Trichloplusia Ni*, TRIPNI) ("CL")

Bioassays on cabbage looper (CL; *Trichloplusia ni*: Lepidoptera) are conducted using a 128-well diet tray assay. One to five second instar CL larvae are placed in each well (3 mL) of the diet tray that had been previously filled with 1 mL of artificial diet to which 50 μg/cm$^2$ of the test compound (dissolved in 50 μL of 90:10 acetone-water mixture) had been applied (to each of eight wells) and then allowed to dry. Trays are covered with a clear self-adhesive cover, vented to allow gas exchange, and held at 25° C., 14:10 light-dark for five to seven days. Percent mortality is recorded for the larvae in each well; activity in the eight wells is then averaged.

Insecticidal Test for Yellow Fever Mosquito (*Aedes aegypti*, AEDSAE) ("YFM")

Master plates containing 400 μg of a molecule dissolved in 100 μL of dimethyl sulfoxide (DMSO) (equivalent to a 4000 ppm solution) are used. A master plate of assembled molecules contains 15 μL per well. To this plate, 135 μL of a 90:10 water/acetone mixture is added to each well. A robot (Biomek® NXP Laboratory Automation Workstation) is programmed to dispense 15 μL aspirations from the master plate into an empty 96-well shallow plate ("daughter" plate). There are 6 reps ("daughter" plates) created per master. The created "daughter" plates are then immediately infested with YFM larvae.

The day before plates are to be treated, mosquito eggs are placed in Millipore water containing liver powder to begin hatching (4 g. into 400 mL). After the "daughter" plates are created using the robot, they are infested with 220 μL of the liver powder/larval mosquito mixture (about 1 day-old larvae). After plates are infested with mosquito larvae, a non-evaporative lid is used to cover the plate to reduce drying. Plates are held at room temperature for 3 days prior to grading. After 3 days, each well is observed and scored based on mortality.

BAW & CL Rating Table

| % Control (or Mortality) | Rating |
|---|---|
| 50-100 | A |
| More than 0-Less than 50 | B |
| Not Tested | C |
| No activity noticed in this bioassay | D |

YFM Rating Table

| % Control (or Mortality) | Rating |
|---|---|
| 80-100 | A |
| More than 0-Less than 80 | B |
| Not Tested | C |
| No activity noticed in this bioassay | D |

TABLE 3

Biological Data for Compounds in Table 1

| Cmpd. No. | BAW | CL | YFM |
|---|---|---|---|
| A1 | A | A | A |
| A2 | A | A | A |
| A3 | A | A | D |
| A4 | A | A | A |
| A5 | B | B | B |
| A6 | D | D | D |
| A7 | A | A | A |
| A8 | A | A | A |
| A9 | A | A | A |
| A10 | A | A | A |
| A11 | A | A | A |
| A12 | A | A | A |
| A13 | A | A | A |
| A14 | A | A | A |
| A15 | A | A | A |
| A16 | A | A | A |
| A17 | A | A | A |
| A18 | A | A | B |
| A19 | A | A | B |
| A20 | A | A | B |
| A21 | A | A | A |
| A22 | A | A | A |
| A23 | A | A | A |
| A24 | A | A | B |
| A25 | A | A | A |
| A26 | A | A | A |
| A27 | A | A | A |
| A28 | A | A | A |
| A29 | A | A | A |
| A30 | A | A | B |
| A31 | B | A | A |
| A32 | A | A | C |
| A33 | A | A | A |
| A34 | A | A | A |
| A35 | A | A | A |
| A36 | A | A | A |
| A37 | A | A | B |
| A38 | A | A | B |
| A39 | A | A | D |
| A40 | A | A | A |
| A41 | A | A | B |
| A42 | A | A | A |
| A43 | A | A | A |
| A44 | C | C | C |
| A45 | A | A | A |
| A46 | A | A | A |
| A47 | A | A | A |
| A48 | A | A | A |
| A49 | A | D | A |
| A50 | A | A | A |
| A51 | D | A | B |
| A52 | A | A | A |
| A53 | A | A | A |
| A54 | A | A | A |
| A55 | A | A | A |

We claim:

1. The molecule having the structure of Formula One, Formula Two, or Formula Three:

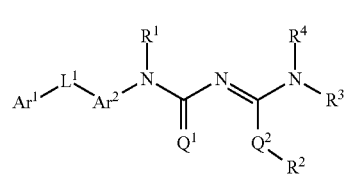

Formula One

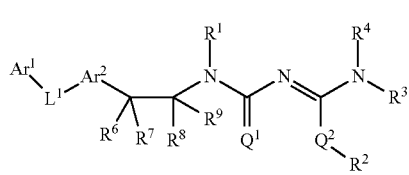

Formula Two

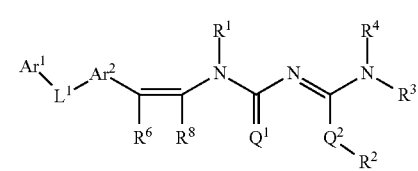

Formula Three wherein:

(A) $AR^1$ is a substituted phenyl having one or more substituents independently selected from $C_1$-$C_6$ haloalkyl and $C_1$-$C_6$ haloalkoxy;

(B) $L^1$ is selected from the group consisting of:

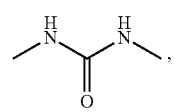

$L^1$-1

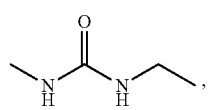

$L^1$-2

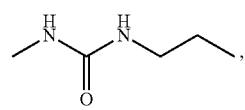

$L^1$-3

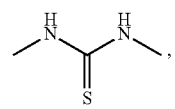

$L^1$-4

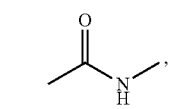

$L^1$-5

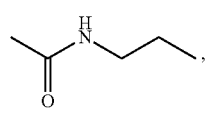

$L^1$-6

-continued

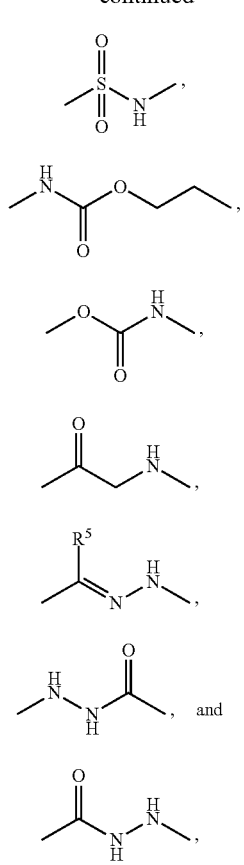

wherein R⁵ is selected from H, $C_1$-$C_8$ alkyl, $C_1$-$C_8$ haloalkyl, $C_1$-$C_8$ alkoxy, $C_1$-$C_8$ haloalkoxy, phenyl, or substituted phenyl, wherein said substituted phenyl has one or more substituents selected from H, F, Cl, Br, I, CN, $NO_2$, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_3$-$C_8$ halocycloalkenyl, and $C_2$-$C_8$ alkynyl;
(C) $Ar^2$ is a phenyl;
(D) each $R^6$, $R^7$, $R^8$, and $R^9$ is selected from H, F, Cl, Br, and $C_1$-$C_6$ alkyl;
(E) $Q^1$ is O or S;
(F) $Q^2$ is O or S;
(G) $R^2$ and $R^3$ is a 1- to 4-membered saturated or unsaturated, hydrocarbyl link, and together with $(Q^2)(C)(N)$ forms a 4- to 7-membered cyclic structure, wherein said hydrocarbyl link may optionally be substituted with one or more substituents independently selected from H, F, Cl, Br, I, CN, OH, SH, $NO_2$, $NR^xR^y$, $C_1$-$C_6$ alkyl, $C_1$-$C_6$ haloalkyl, $C_1$-$C_6$ alkoxy, $C_1$-$C_6$ haloalkoxy, $S(=O)_n(C_1$-$C_6$ alkyl), $S(=O)_n(C_1$-$C_6$ haloalkyl), phenyl, and oxo;
(H) $R^4$ is phenyl, wherein the phenyl may be optionally substituted with one or more substituents independently selected from H, F, Cl, Br, I, CN, OH, SH, $NO_2$, $NR^xR^y$, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ haloalkenyl, $(C_1$-$C_6$ alkyl)O($C_1$-$C_8$ alkyl), $(C_1$-$C_8$ alkyl)O($C_1$-$C_8$ haloalkyl), $(C_1$-$C_6$ alkyl)S$(=O)_n(C_1$-$C_6$ alkyl), $C_1$-$C_6$ alkoxy, $C_1$-$C_6$ haloalkoxy, $S(=O)_n(C_1$-$C_6$ alkyl), $S(=O)_n(C_1$-$C_6$ haloalkyl), phenyl, and oxo, or wherein two adjacent substituents form a 5- or 6-membered saturated or unsaturated, hydrocarbyl link, which may contain one or more heteroatoms selected from nitrogen, sulfur, and oxygen, and wherein said hydrocarbyl link may optionally be substituted with one or more substituents independently selected from H, F, Cl, Br, I, CN, OH, SH, $NO_2$, $NR^xR^y$, $C_1$-$C_6$ alkyl, $C_1$-$C_6$ haloalkyl, $C_1$-$C_6$ alkoxy, $C_1$-$C_6$ haloalkoxy, $S(=O)_n(C_1$-$C_6$ alkyl), and $S(=O)_n(C_1$-$C_6$ haloalkyl);
(I) $R^x$ and $R^y$ are independently selected from H, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ alkynyl, and phenyl; and
(J) n is each individually 0, 1, or 2.

2. The molecule of claim 1, wherein $R^2$ and $R^3$ is 1- to 4-membered saturated or unsaturated, hydrocarbyl link and together with $(Q^2)(C)(N)$ forms a 5-membered cyclic structure, wherein said hydrocarbyl link is optionally substituted with H, OH, F, Cl, Br, I, $C_1$-$C_6$ alkyl, $C_1$-$C_6$ haloalkyl, $C_1$-$C_6$ alkoxy, or $C_1$-$C_6$ haloalkoxy.

3. The molecule of claim 1, wherein $AR^1$ is a substituted phenyl having one or more substituents independently selected from $OCF_3$, $OCF_2CF_3$, and $CF_3$.

4. The molecule of claim 1, wherein $L^1$ is selected from the group consisting of:

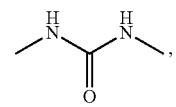

L¹-1

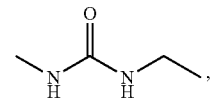

L¹-2

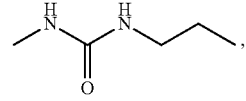

L¹-3

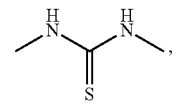

L¹-4

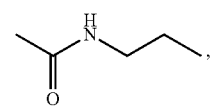

L¹-6

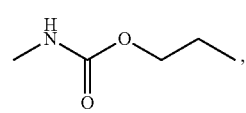

L¹-8

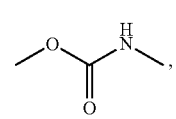

L¹-9

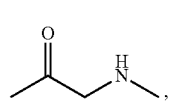

L¹-10

-continued

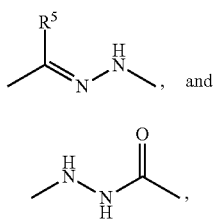

wherein R⁵ is selected from H, $C_1$-$C_8$ alkyl, $C_1$-$C_8$ haloalkyl, $C_1$-$C_8$ alkoxy, $C_1$-$C_8$ haloalkoxy, phenyl, and substituted phenyl, wherein said substituted phenyl has one or more substituents selected from H, F, Cl, Br, I, CN, $NO_2$, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_3$-$C_8$ halocycloalkenyl, and $C_2$-$C_8$ alkynyl.

5. The molecule of claim 1, wherein each of R⁶, R⁷, R⁸, and R⁹ is independently H, F, Cl, or a $C_1$-$C_6$ alkyl.

6. The molecule of claim 1, wherein R⁴ is a substituted phenyl with one or more H, F, Cl, Br, I, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, ($C_1$-$C_6$ alkyl)O($C_1$-$C_6$ alkyl), $C_1$-$C_6$ alkoxy, or $C_1$-$C_6$ haloalkoxy, or wherein two adjacent substituents form a 5- or 6-membered saturated or unsaturated, hydrocarbyl link, which may contain one or more heteroatoms selected from nitrogen, sulfur, and oxygen, and wherein said hydrocarbyl link may optionally be substituted with one or more substituents independently selected from H, F, Cl, Br, I, CN, OH, SH, $NO_2$, $NR^xR^y$, $C_1$-$C_6$ alkyl, $C_1$-$C_6$ haloalkyl, $C_1$-$C_6$ alkoxy, $C_1$-$C_6$ haloalkoxy, S(=O)$_n$($C_1$-$C_6$ alkyl), and S(=O)$_n$($C_1$-$C_6$ haloalkyl).

7. The molecule of claim 1 having a structure selected from compounds listed in Table 1

TABLE 1

Structures for Compounds

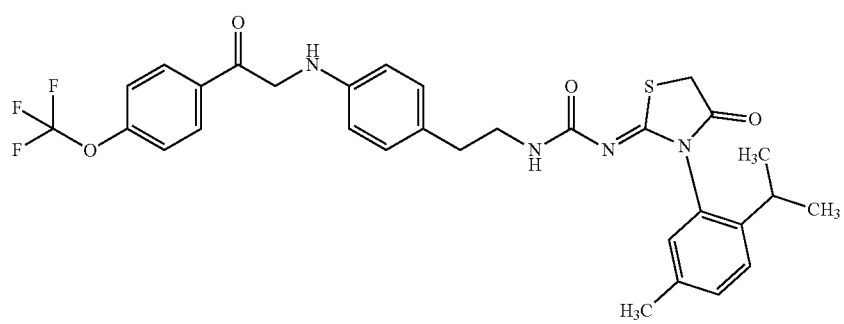 [SMILES: Cc1ccc(C(C)C)c(N2C(=O)CS/C2=N\C(=O)NCCc2ccc(NCC(=O)c3ccc(OC(F)(F)F)cc3)cc2)c1]

A1

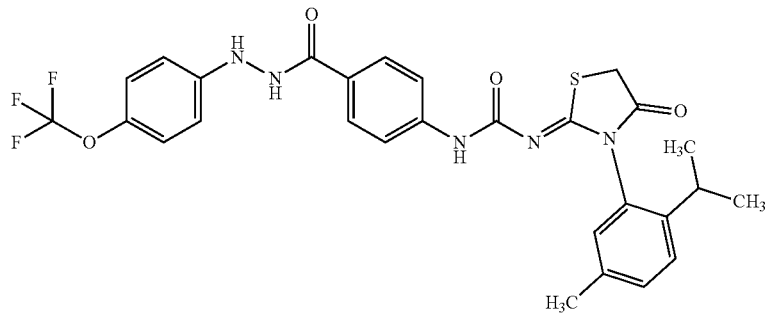 [SMILES: Cc1ccc(C(C)C)c(N2C(=O)CS/C2=N\C(=O)Nc2ccc(C(=O)NNc3ccc(OC(F)(F)F)cc3)cc2)c1]

A2

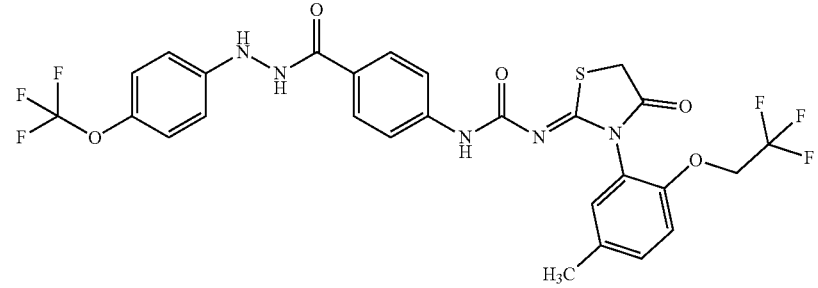 [SMILES: Cc1ccc(OCC(F)(F)F)c(N2C(=O)CS/C2=N\C(=O)Nc2ccc(C(=O)NNc3ccc(OC(F)(F)F)cc3)cc2)c1]

A3

TABLE 1-continued
Structures for Compounds
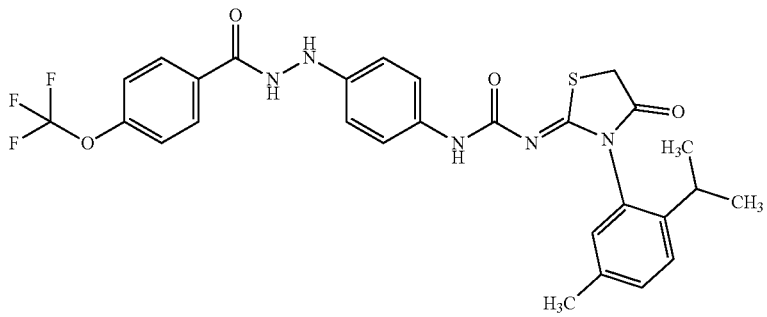 [SMILES: Cc1ccc(C(C)C)c(N2C(=O)CS/C2=N\C(=O)Nc2ccc(NNC(=O)c3ccc(OC(F)(F)F)cc3)cc2)c1]
A4
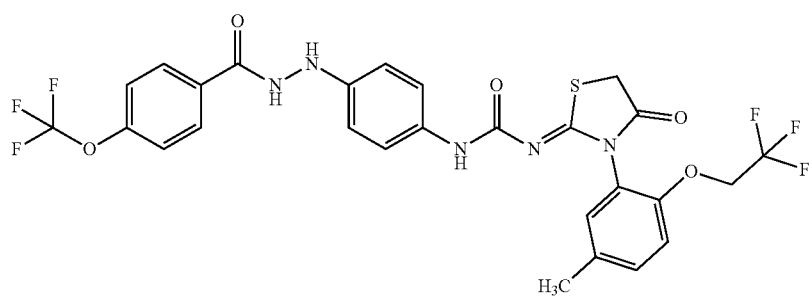 [SMILES: Cc1ccc(OCC(F)(F)F)c(N2C(=O)CS/C2=N\C(=O)Nc2ccc(NNC(=O)c3ccc(OC(F)(F)F)cc3)cc2)c1]
A5
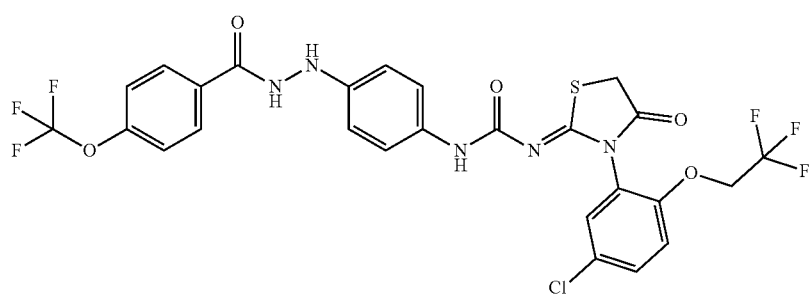 [SMILES: O=C(/N=C1\SCC(=O)N1c1cc(Cl)ccc1OCC(F)(F)F)Nc1ccc(NNC(=O)c2ccc(OC(F)(F)F)cc2)cc1]
A6
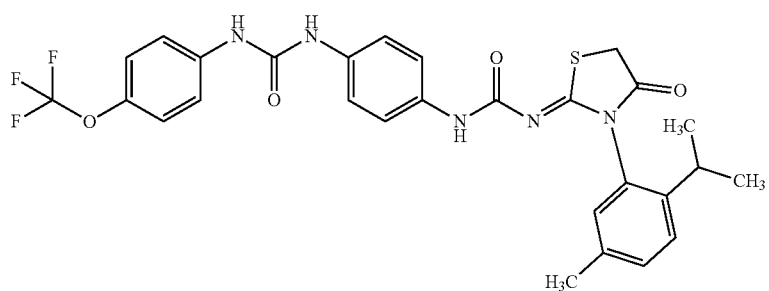 [SMILES: Cc1ccc(C(C)C)c(N2C(=O)CS/C2=N\C(=O)Nc2ccc(NC(=O)Nc3ccc(OC(F)(F)F)cc3)cc2)c1]
A7
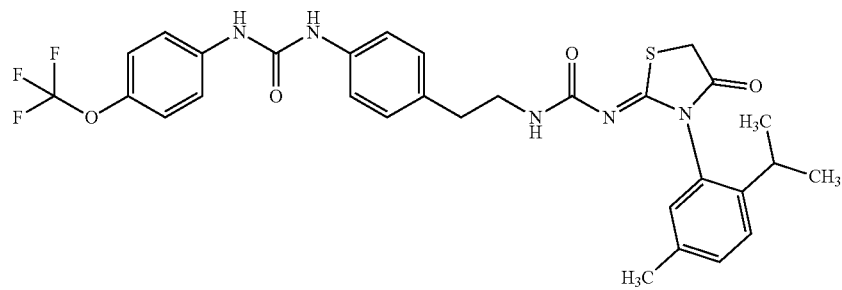 [SMILES: Cc1ccc(C(C)C)c(N2C(=O)CS/C2=N\C(=O)NCCc2ccc(NC(=O)Nc3ccc(OC(F)(F)F)cc3)cc2)c1]
A8

TABLE 1-continued
Structures for Compounds
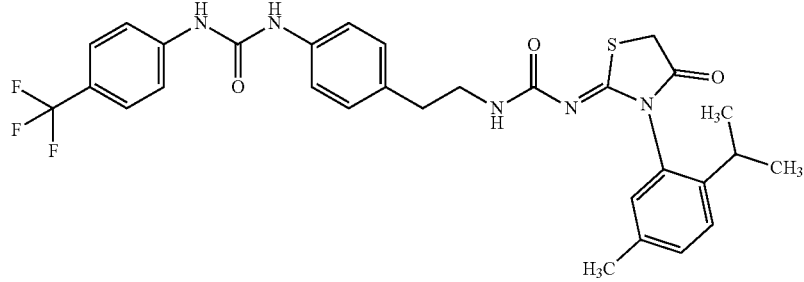 [SMILES: Cc1ccc(C(C)C)c(N2C(=O)CS/C2=N\C(=O)NCCc2ccc(NC(=O)Nc3ccc(C(F)(F)F)cc3)cc2)c1]
A9
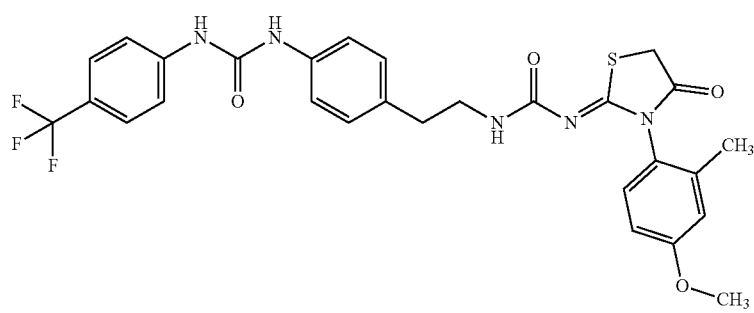 [SMILES: COc1ccc(N2C(=O)CS/C2=N\C(=O)NCCc2ccc(NC(=O)Nc3ccc(C(F)(F)F)cc3)cc2)c(C)c1]
A10
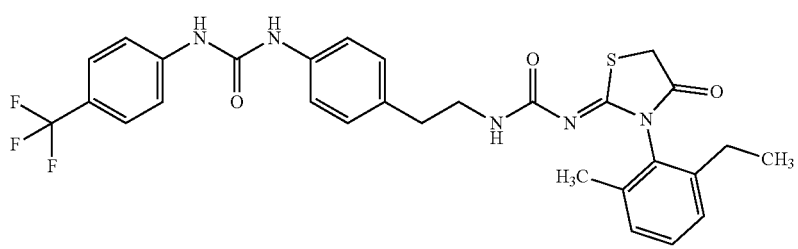 [SMILES: CCc1cccc(C)c1N1C(=O)CS/C1=N\C(=O)NCCc1ccc(NC(=O)Nc2ccc(C(F)(F)F)cc2)cc1]
A11
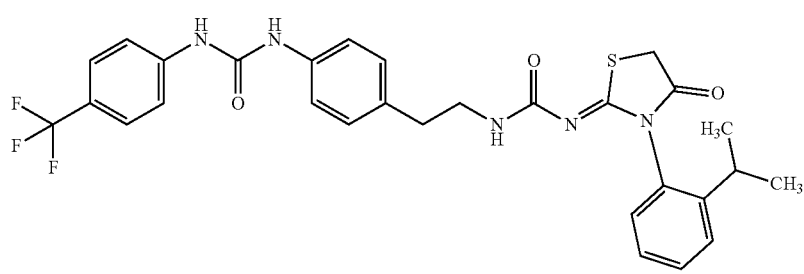 [SMILES: CC(C)c1ccccc1N1C(=O)CS/C1=N\C(=O)NCCc1ccc(NC(=O)Nc2ccc(C(F)(F)F)cc2)cc1]
A12
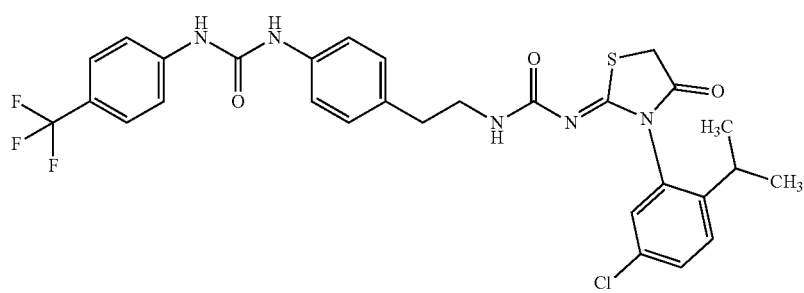 [SMILES: CC(C)c1ccc(Cl)cc1N1C(=O)CS/C1=N\C(=O)NCCc1ccc(NC(=O)Nc2ccc(C(F)(F)F)cc2)cc1]
A13

TABLE 1-continued
Structures for Compounds
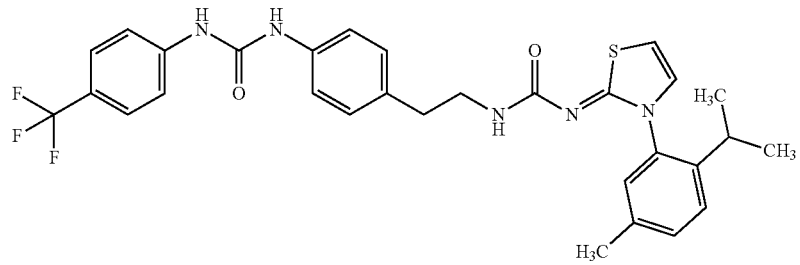 [SMILES: Cc1ccc(C(C)C)c(-n2ccs/c2=N\C(=O)NCCc2ccc(NC(=O)Nc3ccc(C(F)(F)F)cc3)cc2)c1]
A14
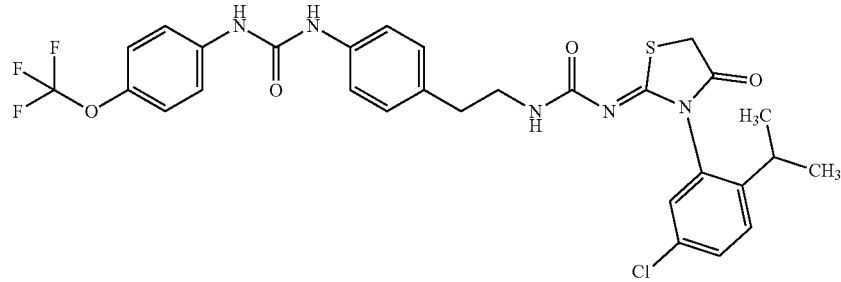 [SMILES: CC(C)c1ccc(Cl)cc1N1C(=O)CS/C1=N\C(=O)NCCc1ccc(NC(=O)Nc2ccc(OC(F)(F)F)cc2)cc1]
A15
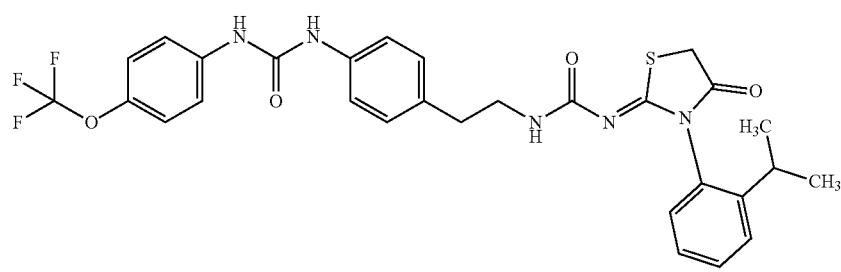 [SMILES: CC(C)c1ccccc1N1C(=O)CS/C1=N\C(=O)NCCc1ccc(NC(=O)Nc2ccc(OC(F)(F)F)cc2)cc1]
A16
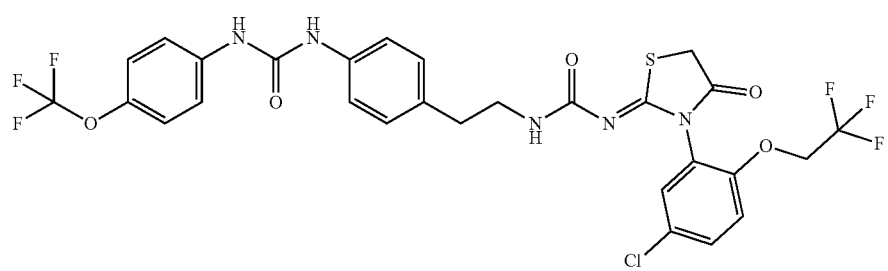 [SMILES: O=C(/N=C1\SCC(=O)N1c1cc(Cl)ccc1OCC(F)(F)F)NCCc1ccc(NC(=O)Nc2ccc(OC(F)(F)F)cc2)cc1]
A17
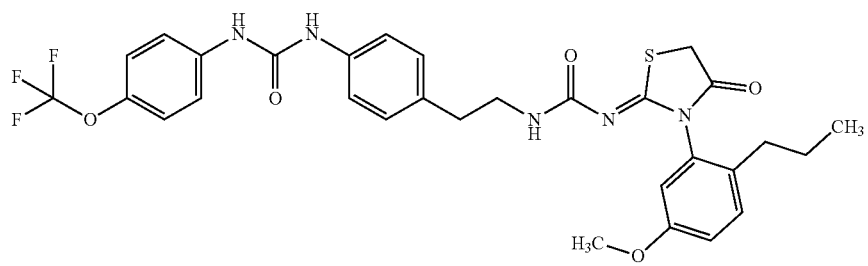 [SMILES: CCCc1ccc(OC)cc1N1C(=O)CS/C1=N\C(=O)NCCc1ccc(NC(=O)Nc2ccc(OC(F)(F)F)cc2)cc1]
A18

TABLE 1-continued
Structures for Compounds
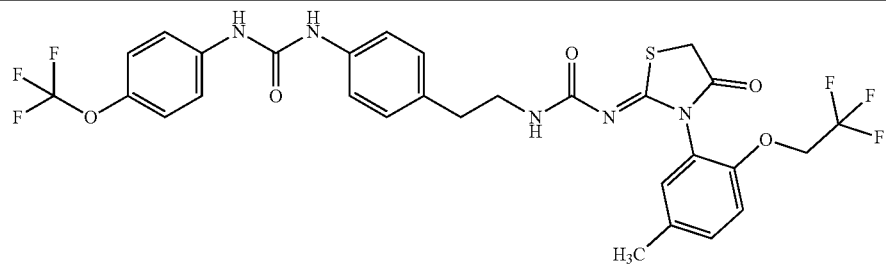
A19
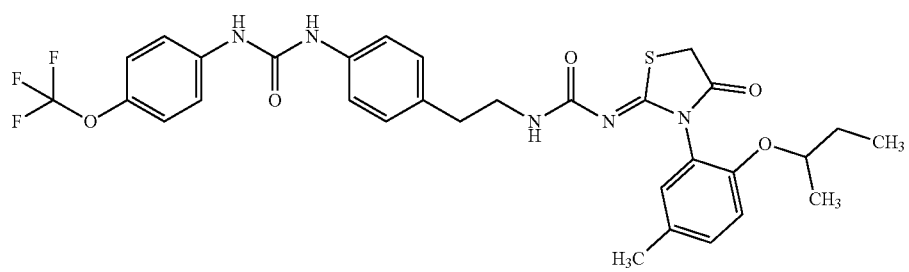 [SMILES: CCC(C)Oc1ccc(C)cc1N1C(=O)CS/C1=N\C(=O)NCCc1ccc(NC(=O)Nc2ccc(OC(F)(F)F)cc2)cc1]
A20
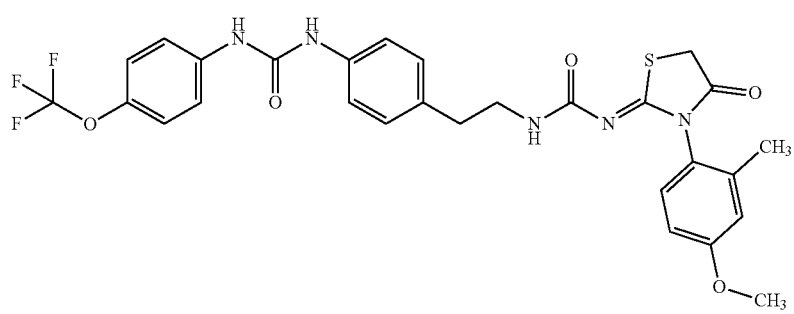 [SMILES: COc1ccc(N2C(=O)CS/C2=N\C(=O)NCCc2ccc(NC(=O)Nc3ccc(OC(F)(F)F)cc3)cc2)c(C)c1]
A21
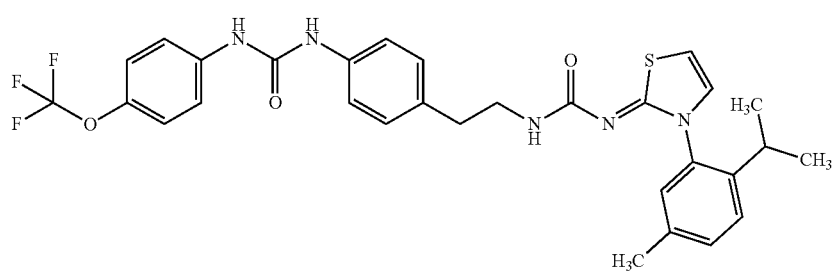 [SMILES: Cc1ccc(C(C)C)c(-n2ccs/c2=N\C(=O)NCCc2ccc(NC(=O)Nc3ccc(OC(F)(F)F)cc3)cc2)c1]
A22
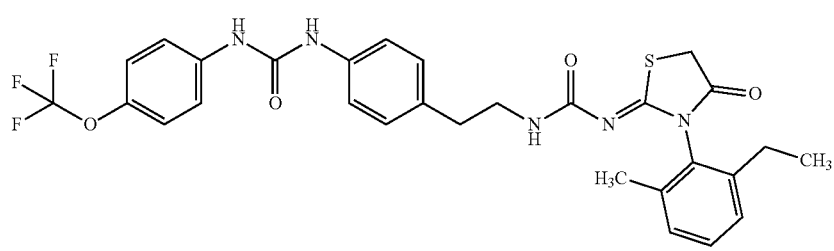 [SMILES: CCc1cccc(C)c1N1C(=O)CS/C1=N\C(=O)NCCc1ccc(NC(=O)Nc2ccc(OC(F)(F)F)cc2)cc1]
A23
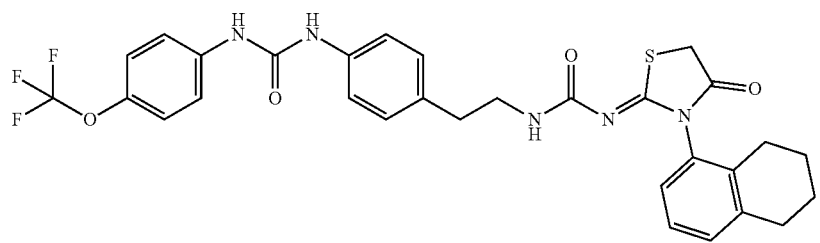 [SMILES: O=C(/N=C1\SCC(=O)N1c1cccc2c1CCCC2)NCCc1ccc(NC(=O)Nc2ccc(OC(F)(F)F)cc2)cc1]
A24

TABLE 1-continued
Structures for Compounds
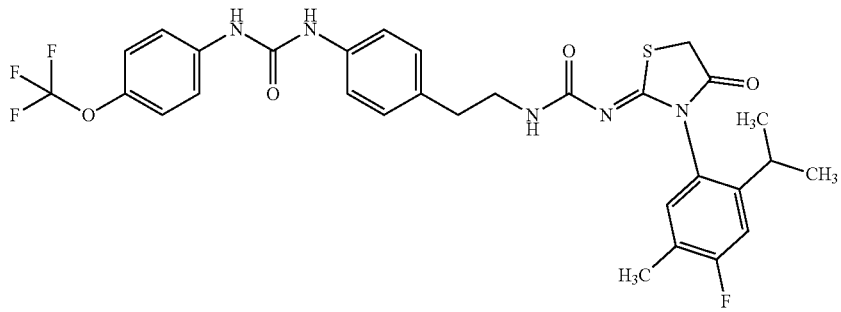 [SMILES: Cc1cc(N2C(=O)CS/C2=N\C(=O)NCCc2ccc(NC(=O)Nc3ccc(OC(F)(F)F)cc3)cc2)c(C(C)C)cc1F]
A25
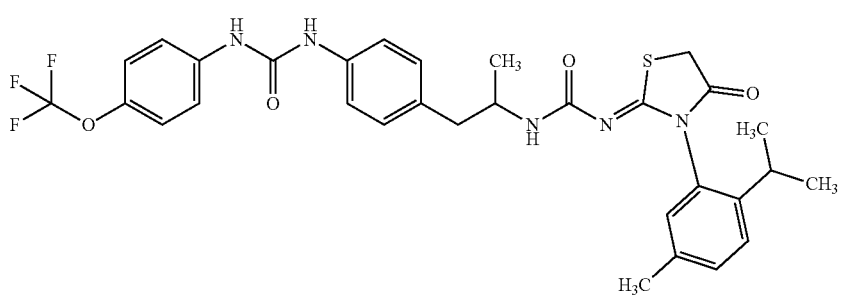 [SMILES: Cc1ccc(C(C)C)c(N2C(=O)CS/C2=N\C(=O)NC(C)Cc2ccc(NC(=O)Nc3ccc(OC(F)(F)F)cc3)cc2)c1]
A26
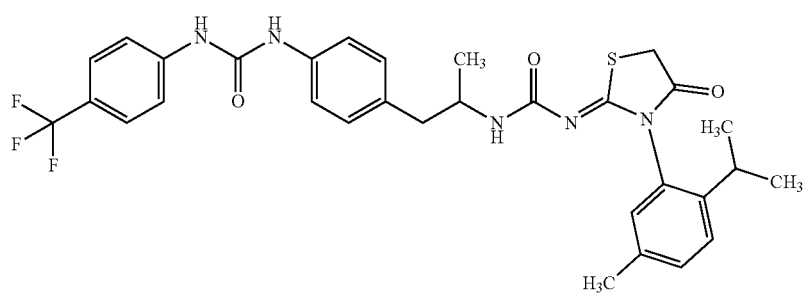
A27
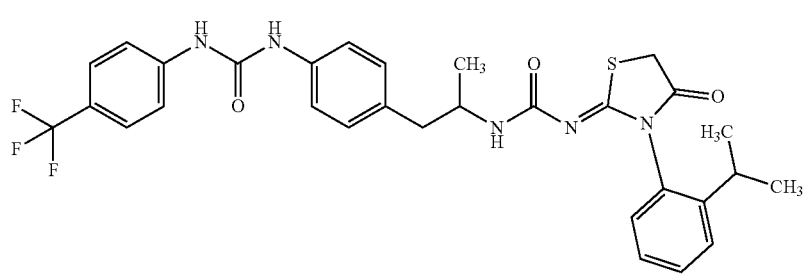 [SMILES: CC(Cc1ccc(NC(=O)Nc2ccc(C(F)(F)F)cc2)cc1)NC(=O)/N=C1\SCC(=O)N1c1ccccc1C(C)C]
A28
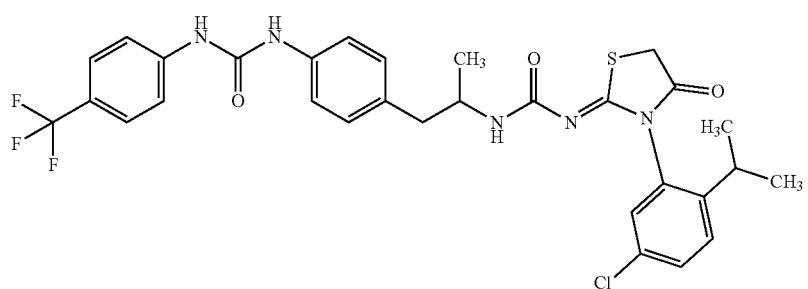 [SMILES: CC(Cc1ccc(NC(=O)Nc2ccc(C(F)(F)F)cc2)cc1)NC(=O)/N=C1\SCC(=O)N1c1cc(Cl)ccc1C(C)C]
A29

TABLE 1-continued
Structures for Compounds
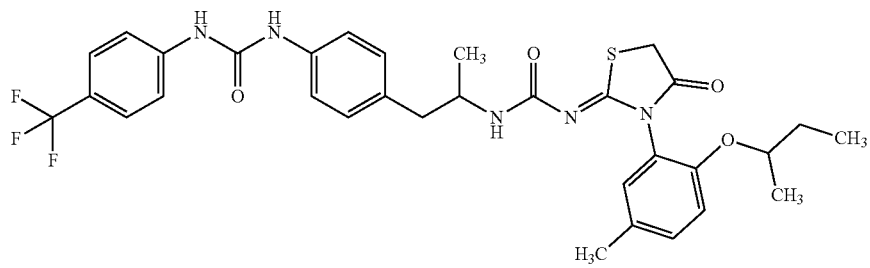 [SMILES: CCC(C)Oc1ccc(C)cc1N1C(=O)CS/C1=N\C(=O)NC(C)Cc1ccc(NC(=O)Nc2ccc(C(F)(F)F)cc2)cc1]
A30
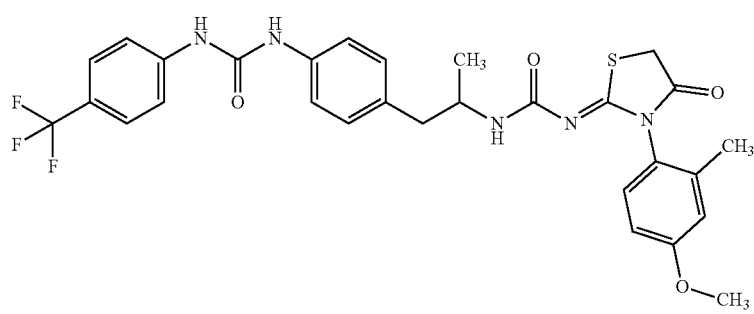 [SMILES: COc1ccc(N2C(=O)CS/C2=N\C(=O)NC(C)Cc2ccc(NC(=O)Nc3ccc(C(F)(F)F)cc3)cc2)c(C)c1]
A31
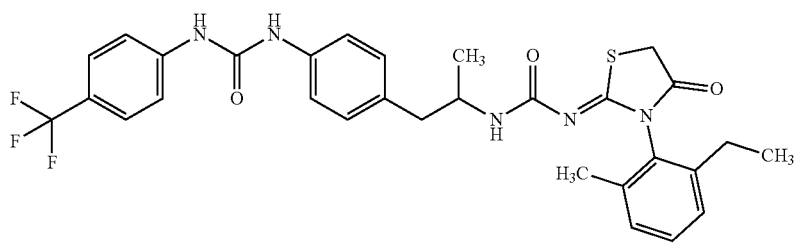 [SMILES: CCc1cccc(C)c1N1C(=O)CS/C1=N\C(=O)NC(C)Cc1ccc(NC(=O)Nc2ccc(C(F)(F)F)cc2)cc1]
A32
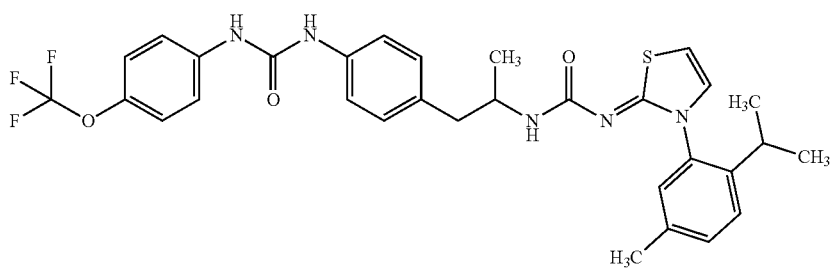 [SMILES: Cc1ccc(C(C)C)c(-n2ccs/c2=N\C(=O)NC(C)Cc2ccc(NC(=O)Nc3ccc(OC(F)(F)F)cc3)cc2)c1]
A33
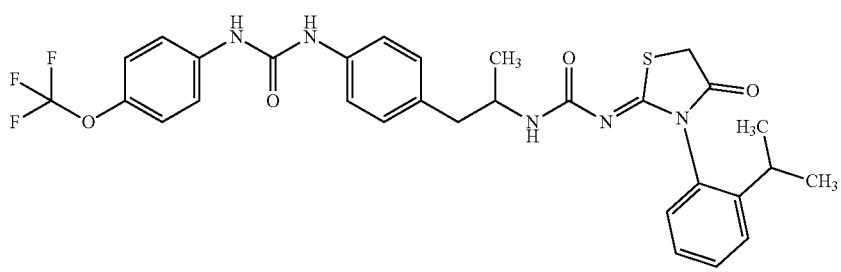 [SMILES: CC(Cc1ccc(NC(=O)Nc2ccc(OC(F)(F)F)cc2)cc1)NC(=O)/N=C1\SCC(=O)N1c1ccccc1C(C)C]
A34

TABLE 1-continued
Structures for Compounds
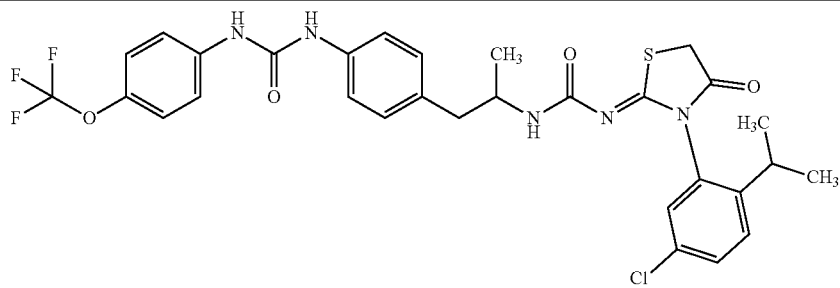
A35
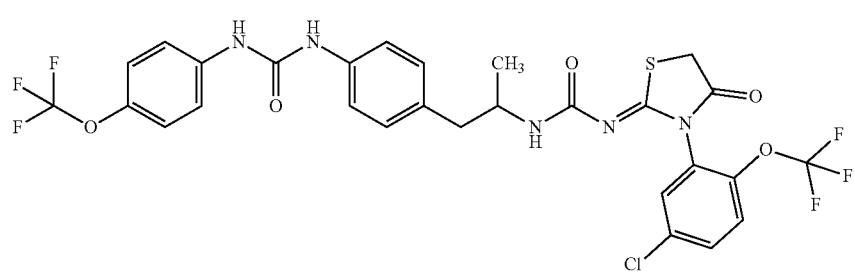 [SMILES: CC(Cc1ccc(NC(=O)Nc2ccc(OC(F)(F)F)cc2)cc1)NC(=O)/N=C1\SCC(=O)N1c1cc(Cl)ccc1OC(F)(F)F]
A36
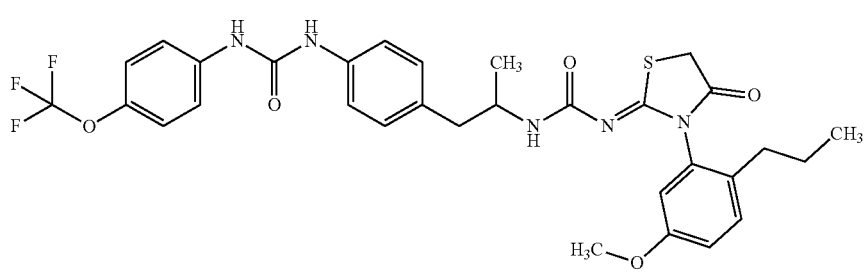 [SMILES: CCCc1ccc(OC)cc1N1C(=O)CS/C1=N\C(=O)NC(C)Cc1ccc(NC(=O)Nc2ccc(OC(F)(F)F)cc2)cc1]
A37
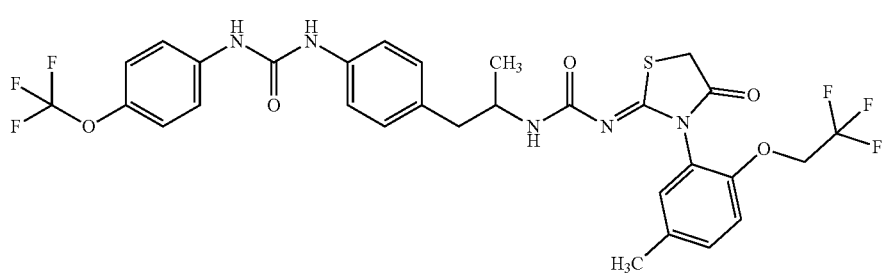 [SMILES: Cc1ccc(OCC(F)(F)F)c(N2C(=O)CS/C2=N\C(=O)NC(C)Cc2ccc(NC(=O)Nc3ccc(OC(F)(F)F)cc3)cc2)c1]
A38
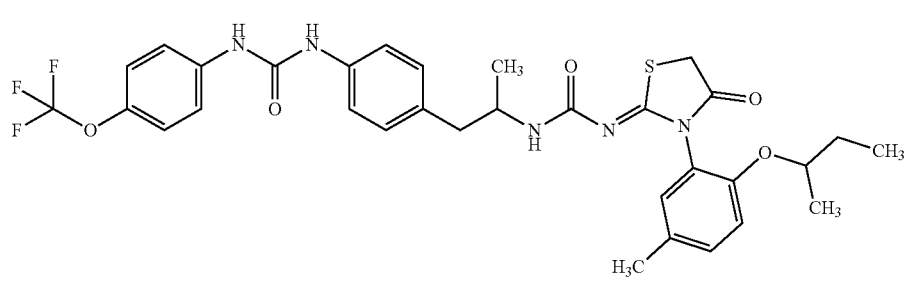 [SMILES: CCC(C)Oc1ccc(C)cc1N1C(=O)CS/C1=N\C(=O)NC(C)Cc1ccc(NC(=O)Nc2ccc(OC(F)(F)F)cc2)cc1]
A39
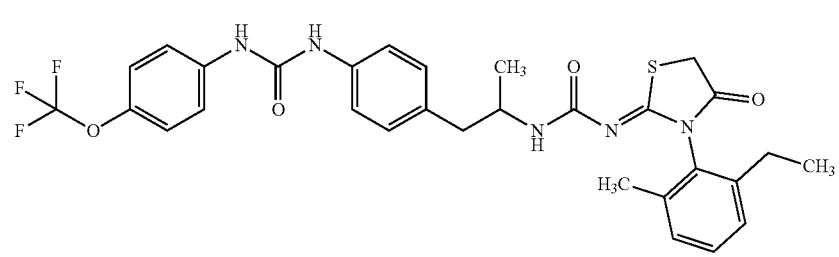 [SMILES: CCc1cccc(C)c1N1C(=O)CS/C1=N\C(=O)NC(C)Cc1ccc(NC(=O)Nc2ccc(OC(F)(F)F)cc2)cc1]
A40

TABLE 1-continued
Structures for Compounds
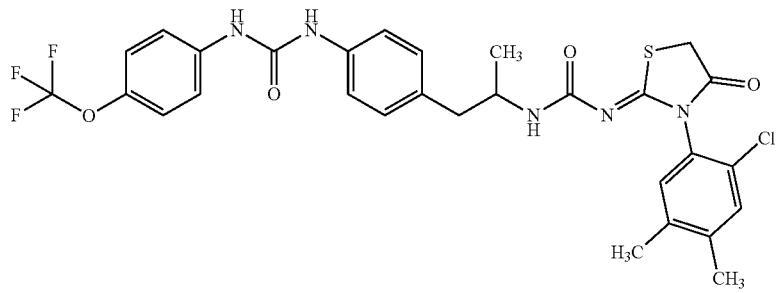 [SMILES: Cc1cc(Cl)c(N2C(=O)CS/C2=N\C(=O)NC(C)Cc2ccc(NC(=O)Nc3ccc(OC(F)(F)F)cc3)cc2)cc1C]
A41
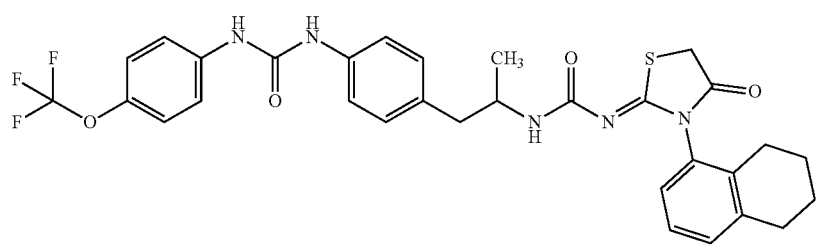 [SMILES: CC(Cc1ccc(NC(=O)Nc2ccc(OC(F)(F)F)cc2)cc1)NC(=O)/N=C1\SCC(=O)N1c1cccc2c1CCCC2]
A42
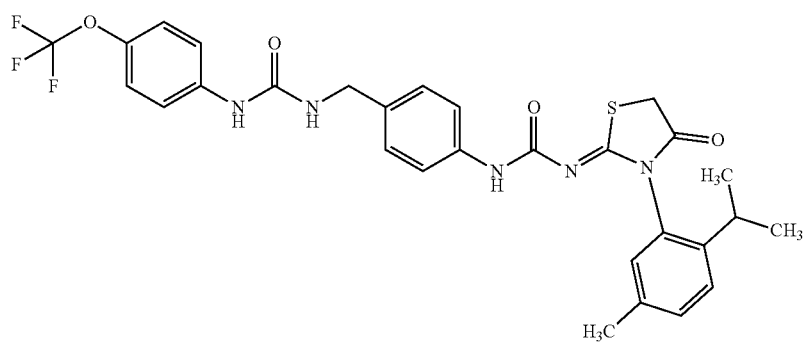 [SMILES: Cc1ccc(C(C)C)c(N2C(=O)CS/C2=N\C(=O)Nc2ccc(CNC(=O)Nc3ccc(OC(F)(F)F)cc3)cc2)c1]
A43
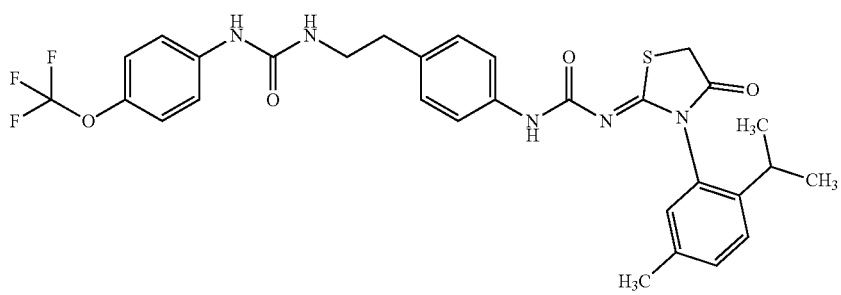
A44
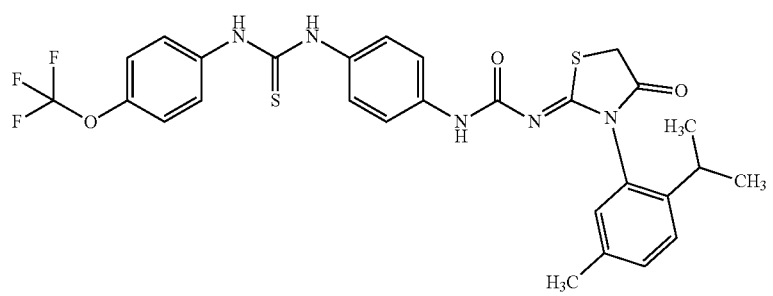 [SMILES: Cc1ccc(C(C)C)c(N2C(=O)CS/C2=N\C(=O)Nc2ccc(NC(=S)Nc3ccc(OC(F)(F)F)cc3)cc2)c1]
A45

TABLE 1-continued
Structures for Compounds
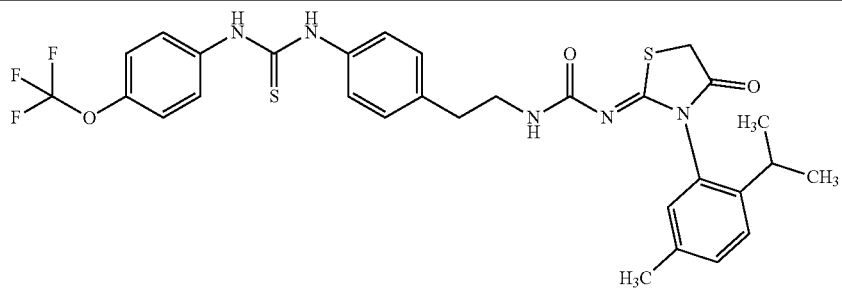
A46
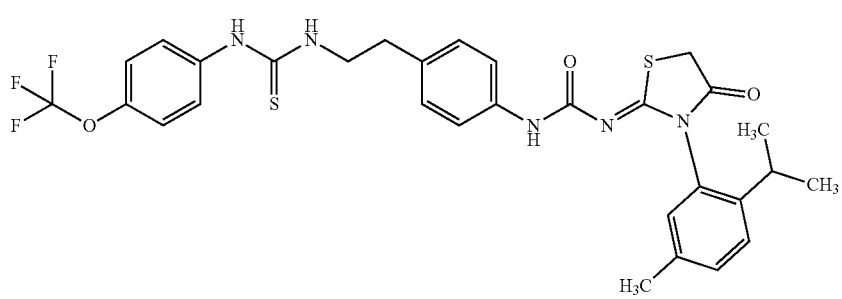 [SMILES: Cc1ccc(C(C)C)c(N2C(=O)CS/C2=N\C(=O)Nc2ccc(CCNC(=S)Nc3ccc(OC(F)(F)F)cc3)cc2)c1]
A47
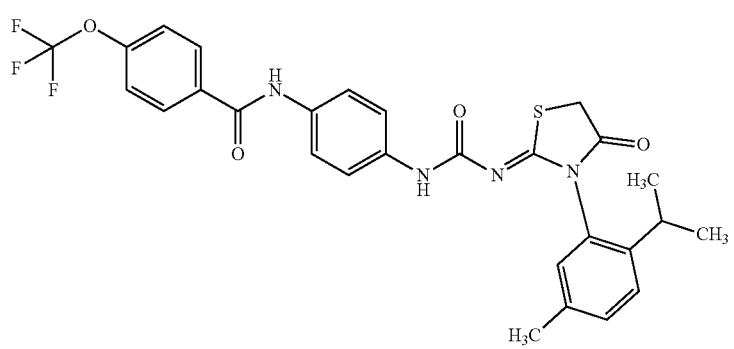 [SMILES: Cc1ccc(C(C)C)c(N2C(=O)CS/C2=N\C(=O)Nc2ccc(NC(=O)c3ccc(OC(F)(F)F)cc3)cc2)c1]
A48
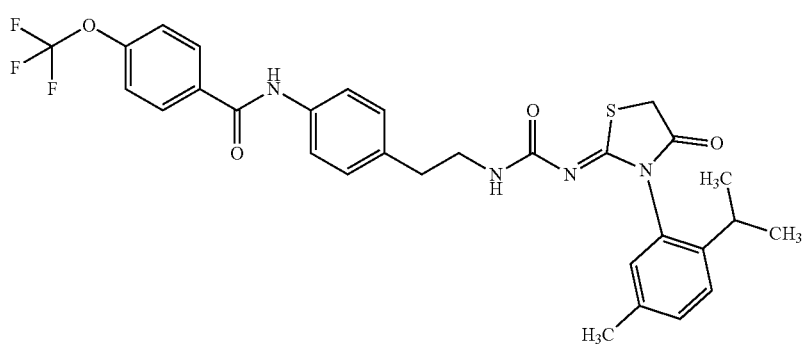 [SMILES: Cc1ccc(C(C)C)c(N2C(=O)CS/C2=N\C(=O)NCCc2ccc(NC(=O)c3ccc(OC(F)(F)F)cc3)cc2)c1]
A49
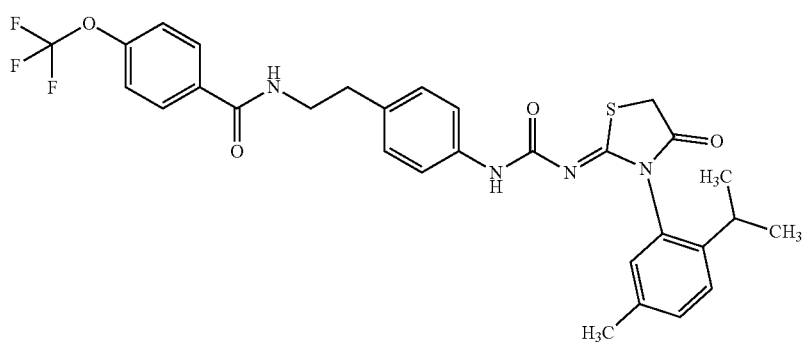 [SMILES: Cc1ccc(C(C)C)c(N2C(=O)CS/C2=N\C(=O)Nc2ccc(CCNC(=O)c3ccc(OC(F)(F)F)cc3)cc2)c1]
A50

TABLE 1-continued
Structures for Compounds
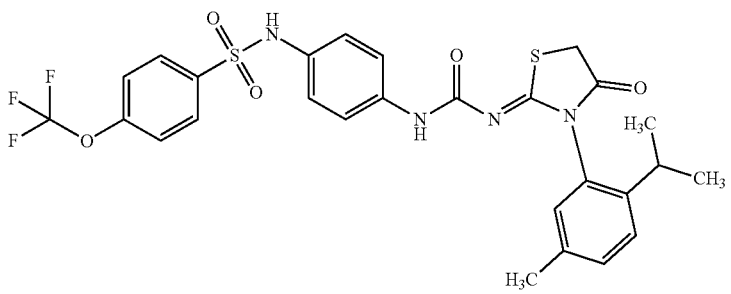 [SMILES: Cc1ccc(C(C)C)c(N2C(=O)CS/C2=N\C(=O)Nc2ccc(NS(=O)(=O)c3ccc(OC(F)(F)F)cc3)cc2)c1]
A51
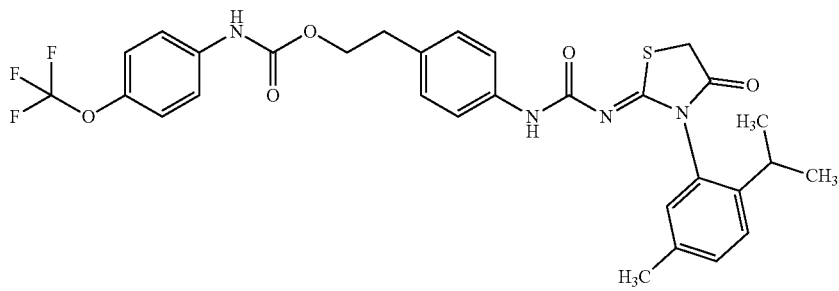 [SMILES: Cc1ccc(C(C)C)c(N2C(=O)CS/C2=N\C(=O)Nc2ccc(CCOC(=O)Nc3ccc(OC(F)(F)F)cc3)cc2)c1]
A52
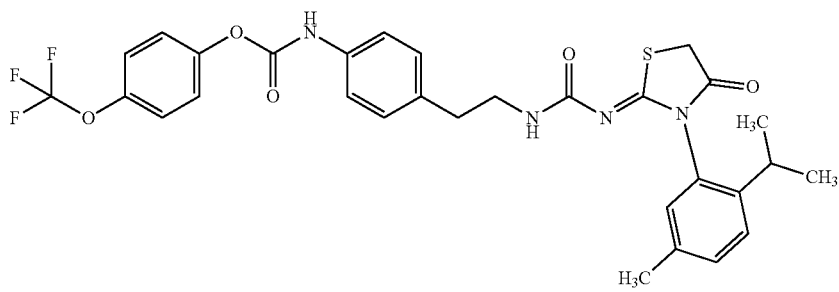 [SMILES: Cc1ccc(C(C)C)c(N2C(=O)CS/C2=N\C(=O)NCCc2ccc(NC(=O)Oc3ccc(OC(F)(F)F)cc3)cc2)c1]
A53
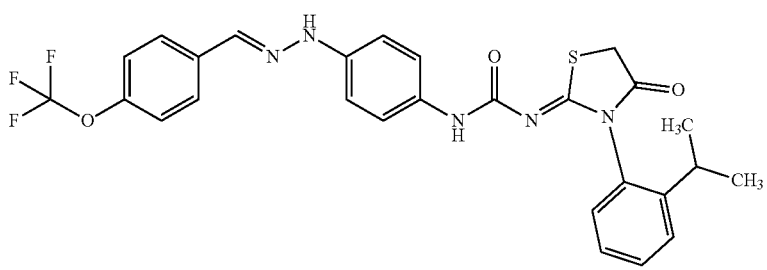 [SMILES: CC(C)c1ccccc1N1C(=O)CS/C1=N\C(=O)Nc1ccc(N/N=C/c2ccc(OC(F)(F)F)cc2)cc1]
A54
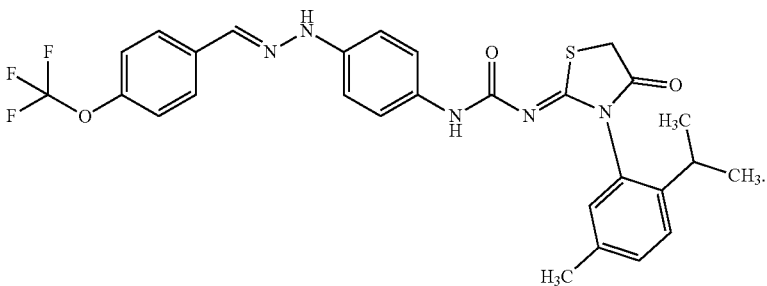 [SMILES: Cc1ccc(C(C)C)c(N2C(=O)CS/C2=N\C(=O)Nc2ccc(N/N=C/c3ccc(OC(F)(F)F)cc3)cc2)c1]
A55
* * * * *